(12) United States Patent
Tran et al.

(10) Patent No.: US 10,789,590 B2
(45) Date of Patent: Sep. 29, 2020

(54) BLOCKCHAIN

(71) Applicants: Bao Tran, Saratoga, CA (US); Ha Tran, Saratoga, CA (US)

(72) Inventors: Bao Tran, Saratoga, CA (US); Ha Tran, Saratoga, CA (US)

( * ) Notice: Subject to any disclaimer, the term of this patent is extended or adjusted under 35 U.S.C. 154(b) by 4 days.

(21) Appl. No.: 16/213,943

(22) Filed: Dec. 7, 2018

(65) Prior Publication Data
US 2019/0358515 A1 Nov. 28, 2019

Related U.S. Application Data

(63) Continuation of application No. 15/989,484, filed on May 25, 2018, now Pat. No. 10,195,513.

(51) Int. Cl.
*G06Q 20/32* (2012.01)
*G06Q 20/38* (2012.01)
(Continued)

(52) U.S. Cl.
CPC ........... *G06Q 20/389* (2013.01); *G06F 1/163* (2013.01); *G06Q 20/382* (2013.01); *H04L 9/321* (2013.01);
(Continued)

(58) Field of Classification Search
CPC ....... A63B 71/145; A63B 69/38; A63B 60/16; A63B 60/46; A63B 43/004; A63B 71/06; A63B 5/0022; A63B 21/0724; A63B 71/085; A63B 2220/803; A63B 2220/806; A63B 2220/807; A63B 2220/833; A63B 2220/836; A63B 2225/30; A63B 2225/50; A63B 2225/54; A63B 2230/06; A63B 2230/60; A63B 2230/70; A63B 2243/0025; A63B 2243/0037; A63B 2243/0054; A63B 2243/0066; A63B 2243/007; A63B 2243/0095; A63B 2244/102; A63B 2244/18; A63B 2244/19; A63B 2244/20; A63B 2244/203; A63B 21/072; A63B 21/0726; A63B 2071/1283; A63B 69/0002; A63B 69/0026; A63B 69/0028; A63B 69/0048; A63B 69/0071; A63B 69/02; A63B 96/06; A63B 69/16; A63B 69/36; A63B 69/3632; A63B 71/10; A63B 71/1216; A63B 71/1291; A63B 71/141; A63B 2071/1233; A63B 2071/125; A63B 2207/02; A63B 2220/12; A63B 2220/13; A63B 2220/16; A63B 2220/20; A63B 2220/24; A63B 2220/30; A63B 2220/40; A63B 2220/51; A63B 2220/53; A63B 2220/56; A63B 2220/72; A63B 2220/74; A63B 2220/75; A63B 2220/76;
(Continued)

(56) References Cited

U.S. PATENT DOCUMENTS

| | | | |
|---|---|---|---|
| 5,892,900 A * | 4/1999 | Ginter | ...................... G06F 21/10 726/26 |
| 10,521,780 B1 * | 12/2019 | Hopkins, III | .......... G06Q 20/10 |

(Continued)

*Primary Examiner* — Calvin L Hewitt, II
*Assistant Examiner* — Vincent Idiake
(74) *Attorney, Agent, or Firm* — Patent Law Office PC; Bao Tran

(57) ABSTRACT

An Internet of Thing (IoT) device includes a transceiver coupled to a processor. Blockchain smart contracts can be used with the device to facilitate secure operation.

18 Claims, 28 Drawing Sheets

| |
|---|
| (20) Buyer requests to obtain the service or item from the service or item provider |
| (24) Item provider utilizes the blockchain and generates a cryptographic key pair |
| (26) Service or item provider embeds the key data in the service or item using the embedding module |
| (28) Service or service or item provider stores the private key in association with an entity credential in the database |
| (30) Third party validates the terms of the smart contract with the private key |
| (32) Shared ledger is analyzed to determine if key data was used and if contractual terms are satisfied according to contract law expert system and if so mark the satisfaction of the contract terms |
| (34) Seller/provider is paid based on smart contract and service or item is then made available to the buyer |

(51) Int. Cl.
*G06F 1/16* (2006.01)
*H04L 9/32* (2006.01)
*A63B 71/12* (2006.01)
*G09B 19/00* (2006.01)
*G06K 9/00* (2006.01)
*A61B 5/11* (2006.01)
*A63B 71/14* (2006.01)
*A63B 71/10* (2006.01)
*A63B 71/08* (2006.01)
*A63B 69/36* (2006.01)
*A63B 69/16* (2006.01)
*A63B 69/06* (2006.01)
*A63B 69/02* (2006.01)
*A63B 69/00* (2006.01)
*H04W 84/18* (2009.01)
*G01L 5/00* (2006.01)
*A63B 21/072* (2006.01)
*G16H 20/30* (2018.01)
*A61B 5/00* (2006.01)
*G16H 40/60* (2018.01)
*A63B 43/00* (2006.01)
*A63B 60/46* (2015.01)
*A63B 69/38* (2006.01)

(52) U.S. Cl.
CPC .......... H04L 9/3236 (2013.01); H04L 9/3247 (2013.01); *A61B 5/0022* (2013.01); *A61B 5/11* (2013.01); *A63B 21/072* (2013.01); *A63B 21/0724* (2013.01); *A63B 21/0726* (2013.01); *A63B 43/004* (2013.01); *A63B 60/46* (2015.10); *A63B 69/0002* (2013.01); *A63B 69/0026* (2013.01); *A63B 69/0028* (2013.01); *A63B 69/0048* (2013.01); *A63B 69/0071* (2013.01); *A63B 69/02* (2013.01); *A63B 69/06* (2013.01); *A63B 69/16* (2013.01); *A63B 69/36* (2013.01); *A63B 69/3632* (2013.01); *A63B 69/38* (2013.01); *A63B 71/085* (2013.01); *A63B 71/10* (2013.01); *A63B 71/1216* (2013.01); *A63B 71/1291* (2013.01); *A63B 71/141* (2013.01); *A63B 71/145* (2013.01); *A63B 2071/125* (2013.01); *A63B 2071/1233* (2013.01); *A63B 2071/1283* (2013.01); *A63B 2207/02* (2013.01); *A63B 2220/12* (2013.01); *A63B 2220/13* (2013.01); *A63B 2220/16* (2013.01); *A63B 2220/20* (2013.01); *A63B 2220/24* (2013.01); *A63B 2220/30* (2013.01); *A63B 2220/40* (2013.01); *A63B 2220/51* (2013.01); *A63B 2220/53* (2013.01); *A63B 2220/56* (2013.01); *A63B 2220/72* (2013.01); *A63B 2220/74* (2013.01); *A63B 2220/75* (2013.01); *A63B 2220/76* (2013.01); *A63B 2220/803* (2013.01); *A63B 2220/806* (2013.01); *A63B 2220/807* (2013.01); *A63B 2220/833* (2013.01); *A63B 2220/836* (2013.01); *A63B 2225/30* (2013.01); *A63B 2225/50* (2013.01); *A63B 2225/54* (2013.01); *A63B 2230/06* (2013.01); *A63B 2230/60* (2013.01); *A63B 2230/70* (2013.01); *A63B 2243/007* (2013.01); *A63B 2243/0025* (2013.01); *A63B 2243/0037* (2013.01); *A63B 2243/0054* (2013.01); *A63B 2243/0066* (2013.01); *A63B 2243/0095* (2013.01); *A63B 2244/102* (2013.01); *A63B 2244/18* (2013.01); *A63B 2244/19* (2013.01); *A63B 2244/20* (2013.01); *A63B 2244/203* (2013.01); *G01L 5/0052* (2013.01); *G06K 9/00342* (2013.01); *G09B 19/0038* (2013.01); *G16H 20/30* (2018.01); *G16H 40/60* (2018.01); *H04L 2209/38* (2013.01); *H04L 2209/56* (2013.01); *H04W 84/18* (2013.01)

(58) Field of Classification Search
CPC ..... H04L 9/3247; H04L 9/3236; H04L 9/321; H04L 2209/56; H04L 2209/38; G16H 40/60; G16H 20/30; B33Y 10/00; G06F 1/163; G06F 3/00; G01L 5/0052; G06K 9/00342; G09B 19/0038; H04W 84/18; A61B 5/11; A61B 5/6804
See application file for complete search history.

(56) References Cited

U.S. PATENT DOCUMENTS

| | | | |
|---|---|---|---|
| 2016/0330034 A1* | 11/2016 | Back | G06Q 20/06 |
| 2017/0132621 A1* | 5/2017 | Miller | G06Q 20/3829 |
| 2017/0287090 A1* | 10/2017 | Hunn | G06F 40/166 |
| 2018/0350451 A1* | 12/2018 | Ohnemus | G06F 19/3418 |
| 2019/0208414 A1* | 7/2019 | Roennow | G06F 16/1824 |

* cited by examiner

| |
|---|
| 2 - user logs into the system to author a smart contract. |
| 4 - user enters the information that is requested by the user interface based on the attributes displayed, the user interface is rendered as a mark-up language such as XML showing the structure of the requirements of the contract. The user interface can be rendered as an Excel worksheet, Word document, or other application compatible format that can be read by the contracting parties, lawyers, judges, and jury. |
| 6 - the contract is generated based on the user input to the user interface. The contract can be in the form of bytecodes for machine interpretation or can be the markup language for human consumption. If there are other contracts that are incorporated by reference, the other contracts are formed in a nested hierarchy similar to program language procedures/subroutines and then embedded inside the contract. |
| 8 - smart contract is inserted into block chain with a unique block chain ID number. |
| 10 - smart contract is sent to one or more recipients, which open the payload and execute the terms of the contract and if specified contractual conditions are met, the smart contract automatically sends or authorizes payment or obligations to offeror or offeree machines. |
| 12 - if dispute arise, a contract management system (CMS) can graphically display the contract terms in the smart contract for a judge, jury, or lawyer to apply legal analysis and determine the parties' obligations. |

| |
|---|
| (20) Buyer requests to obtain the service or item from the service or item provider |
| (24) Item provider utilizes the blockchain and generates a cryptographic key pair |
| (26) Service or item provider embeds the key data in the service or item using the embedding module |
| (28) Service or service or item provider stores the private key in association with an entity credential in the database |
| (30) Third party validates the terms of the smart contract with the private key |
| (32) Shared ledger is analyzed to determine if key data was used and if contractual terms are satisfied according to contract law expert system and if so mark the satisfaction of the contract terms |
| (34) Seller/provider is paid based on smart contract and service or item is then made available to the buyer |

FIG. 13D

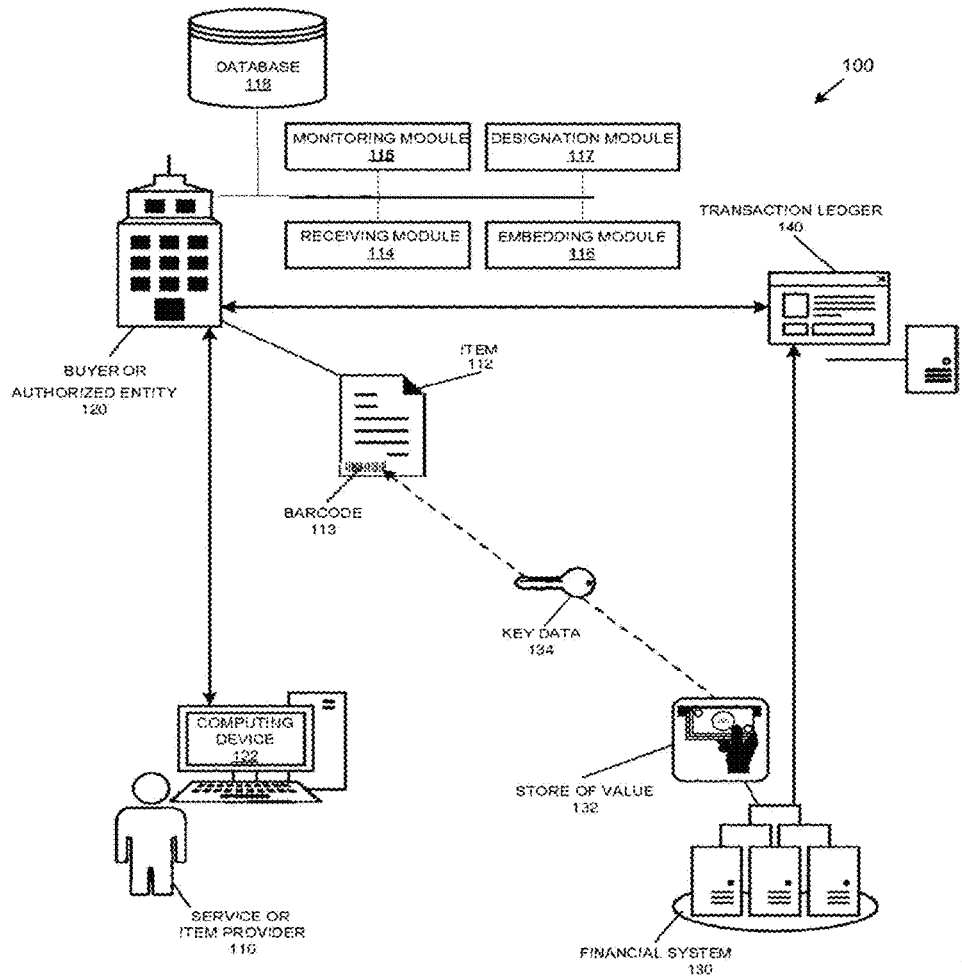

FIG. 13E

BLOCKCHAIN

BACKGROUND

The emergence of smart devices such as Internet of Things (IOT) devices has provided intelligence to many common appliances and gears for sports.

IOT devices have appeared with features of autonomous operation. For example, smart sport gears monitor the users' behavior and improve or aid user performance. Smart cars can drive autonomously. Many other convenient and time-saving features are appearing in IOT devices.

In a parallel trend, the wealth of data generated by IOT devices can overwhelm the Internet cloud. Moreover, fraudulent and harmful activities arising from hacked IOT devices have potential to cause major disruptions to the Internet.

SUMMARY

In one aspect, an Internet of Thing (IoT) device includes a processor, sensor(s), and a wireless transceiver coupled to the processor.

These and other features of the present invention will become readily apparent upon further review of the following specification and drawings.

BRIEF DESCRIPTION OF THE DRAWINGS

FIG. 2A is a block diagram of an electronic circuit for a smart device, while

FIG. 11A shows exemplary smart rackets while

FIG. 12A-12B show exemplary protective gears, while

FIGS. 13A-13I show exemplary blockchain smart contract processes.

FIG. 16A-16C shows exemplary coaching system for skiing, bicycling, and weightlifting/free style exercise, respectively, while

Similar reference characters denote corresponding features consistently throughout the attached drawings.

DETAILED DESCRIPTION

The reader should appreciate that the present application describes several inventions. Rather than separating those inventions into multiple isolated patent applications, applicants have grouped these inventions into a single document because their related subject matter lends itself to economies in the application process. But the distinct advantages and aspects of such inventions should not be conflated. In some cases, embodiments address all of the deficiencies noted herein, but it should be understood that the inventions are independently useful, and some embodiments address only a subset of such problems or offer other, unmentioned benefits that will be apparent to those of skill in the art reviewing the present disclosure. Due to costs constraints, some inventions disclosed herein may not be presently claimed and may be claimed in later filings, such as continuation applications or by amending the present claims. Similarly, due to space constraints, neither the Abstract nor the Summary of the Invention sections of the present document should be taken as containing a comprehensive listing of all such inventions or all aspects of such inventions.

Figure 1A:
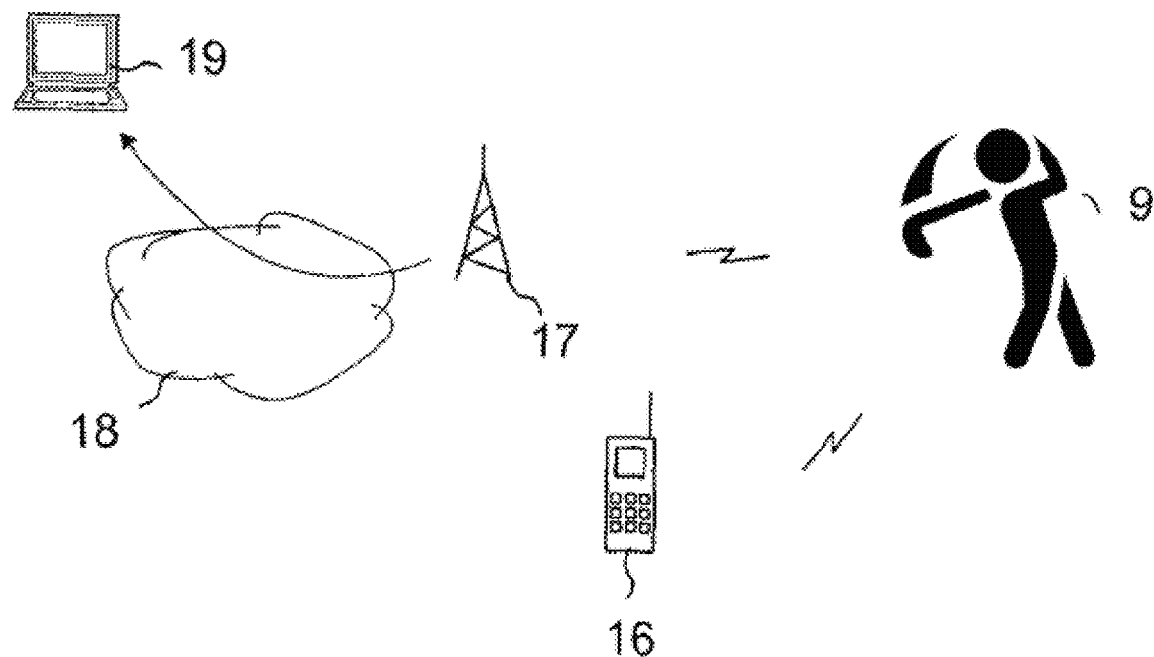
FIG. 1A illustrates an exemplary environment for communicating data from a monitoring device to external computers.

FIG. 1A illustrates an exemplary environment for communicating data from a monitoring device to external computers. In FIG. 1A, the monitoring device used for a sport device 9 includes an interface with a radio transmitter for forwarding the result of the comparison to a remote device. In one example, the monitoring device may include an additional switch and user interface. The user interface may be used by the user in order to trigger transmission of the comparison of the hand or foot pattern reference data with the stroke patterns data to the remote device. Alternatively, the transmission may occur automatically each time the device has been used, or may be triggered by placing the sport device in a cradle or base. All parts of the monitoring device may be encapsulated with each other and/or may be integrated into or attached to the body of the sport device 9. Alternatively, a radio transmitter may be arranged separately from the other parts, for instance, in a battery charger, cradle or base of the sport device 9. In that example, the interface 7 may include contact terminals in the sport device 9, which are connected to the corresponding terminals in the battery charger for forwarding the result of the comparison via a wired connection to the transmitter in the battery charger or may be connected by induction or short range wireless communications. The radio transmitter in the battery charger then transmits this comparison result further via the wireless radio connection to the remote device. In FIG. 1A, the remote device may be a mobile phone 16, PDA or computer 19, which receives the information directly from the monitoring device via a short range radio connection, as one example of a transmitter, such as a Bluetooth or a Wifi or a Zigbee connection. In one example, the user of the remote device may receive information about how thoroughly the sport device 9 has been used or the need to provide a replacement sport device. FIG. 1A also illustrates an alternate example of a transmitter, using an intermediate receiver 17 and a network 18, such as a cellular radio system. Also in this example, the radio transmitter may be located in connection with the sport device 9 or alternatively in connection, with a charger, cradle or base station of the sport device 9. In such an example, the comparison result may be transmitted via an intermediate receiver 17 and the network 18 to a remote device 19, 16 located further away than the range of a short range radio system, for example. The remove device 19, 16 may be any device suitable for receiving the signals from the network 18 and providing feedback on an output device. The transmission of information via a cellular radio system to the remote device may allow an advertiser provide an advertisement. For example, an advertisement may be added to the comparison result using network elements in the cellular radio system. The user may receive an advertisement with the comparison result. An advantage with such a solution is that the advertiser may provide revenue offsetting all or a portion of the cost for the transmission of the comparison result from the sport device 9 to the remote device 19, 16.

Figure 1B:
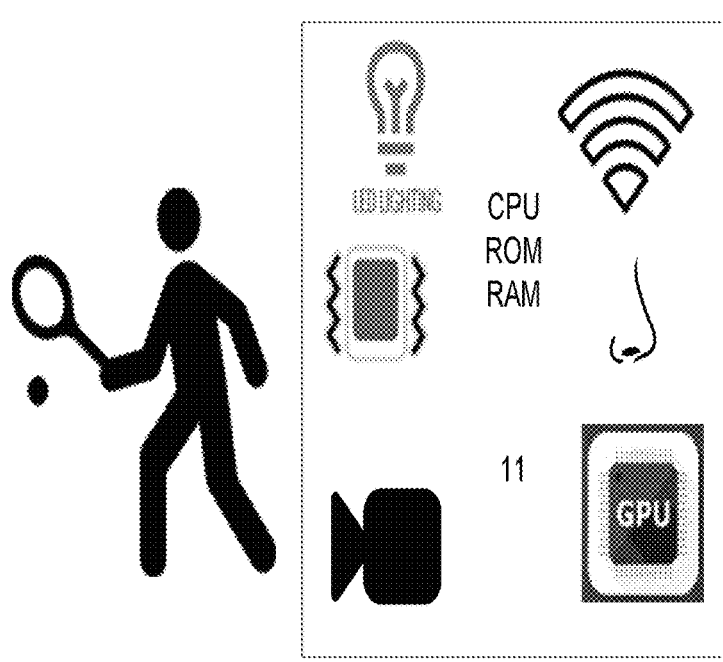
FIG. 1B is a schematic view of an exemplary IoT sport device system.

FIG. 1B shows a block diagram of the unit 9 with processor/RAM/ROM 11. The unit 9 includes a motion sensor, a multi-axis accelerometer, and a strain gage 42. The multi-axis accelerometer may be a two-axis or three-axis accelerometer. Strain gage 21 is mounted in the neck of the racket, and measures force applied to the ball, i.e., force in a z direction. Acceleration and force data are acquired by the microprocessor at a data acquisition rate (sampling rate) of from about 10 to 50 samples/second, e.g., about 20 samples/second. The acceleration data is used to infer motion, using an algorithm discussed below; it is not converted to position data. In this embodiment, because the sensors and strain gage are not in the head region, the head can be removable and replaceable, e.g., by threaded engagement with the handle (not shown), so that the sport device can continue to be used after instrument wear has occurred. Any desired type of removable head or cartridge can be used.

The unit 11 also includes a camera, which can be a 360 degree camera. Alternatively, the camera can be a 3D camera such as the Kinect camera or the Intel RealSense camera for ease of generating 3D models and for detecting distance of objects. To reduce image processing load, each camera has a high performance GPU to perform local processing, and the processed images, sound, and odor data are uploaded to a cloud storage for subsequent analysis.

The unit 11 includes an electronic nose to detect odor. The electronic nose can simply be a MEMS device acting as a particle counter. An embodiment of the electronic nose can be used that includes a fan module, a gas molecule sensor module, a control unit and an output unit. The fan module is used to pump air actively to the gas molecule sensor module. The gas molecule sensor module detects the air pumped into by the fan module. The gas molecule sensor module at least includes a gas molecule sensor which is covered with a compound. The compound is used to combine preset gas molecules. The control unit controls the fan module to suck air into the electronic nose device. Then the fan module transmits an air current to the gas molecule sensor module to generate a detected data. The output unit calculates the detected data to generate a calculation result and outputs an indicating signal to an operator or compatible host computer according to the calculation result.

An electronic tongue sensor can be provided to sense quality of sweat or liquid. The tongue includes a liquid molecule sensor module, a control unit and an output unit. Body liquid is applied or swiped on to the liquid molecule sensor module. The molecule sensor module detects the liquid molecules pumped into by the stirring module. The liquid molecule sensor module at least includes a molecule sensor which is covered with a compound. The compound is used to combine preset liquid molecules. The control unit controls the stirring module to pump liquid to be "tasted" into the electronic tongue device. Then the module transmits a flow current to the liquid molecule sensor module to generate a detected data. The output unit calculates the detected data to generate a calculation result and outputs an indicating signal to an operator or compatible host computer according to the calculation result. Such electronic tongue can detect quality of fog or liquid, among others.

In one embodiment for analyzing tooth structure, restorative materials within a tooth structure, and disease states of a tooth, the unit 11 includes a probe 20 which may be attached to a variety of sport probes, and instruments to afford adaptability to a variety of situations in providing diagnostic information on an object such as a naturally occurring structure, man-made materials placed or found within the structure, diseased or otherwise affected, infected or effected structure, as well as structure that has been eroded, worn by attrition, abraded, abfracted, fractured, crazed, broken or otherwise compromised through sport enthusiast use, misuse, fatigue or longevity of use. The probe 20 generates electrical outputs which are interpreted by a smart phone or computer.

In one embodiment, the probe 20 can be a vibratory transducer that sends out vibrations at known frequency and amplitude. The probe 20 also includes a receiver which can be an accelerometer, for example. The accelerometer is attached to the teeth and connected to a computer. The accelerometer digitizes the received vibrations and provides them into the phone or computer. The transducer can be a single piezoelectric transducer or an array with elements arranged to fit in a mouthpiece or an appliance to be worn over the oral arch. The transducer elements can be mounted in silicone rubber or other material suitable for damping mechanical coupling between the elements. Other materials may also be used for the array construction. For example, the transducer may be formed from one or more pieces of piezocomposite material, or any material that converts electrical energy to acoustic energy. The receiver can also be positioned to fit in the mouthpiece or appliance. One embodiment of the receiver is an accelerometer, but a suitable piezoelectric transducer can serve as the receiver as well.

The software in the computer compares these inputs to known vibration responses corresponding to striking states on a ball or sport object. The computer 30 displays a response on the computer screen for that user.

Figure 1C:
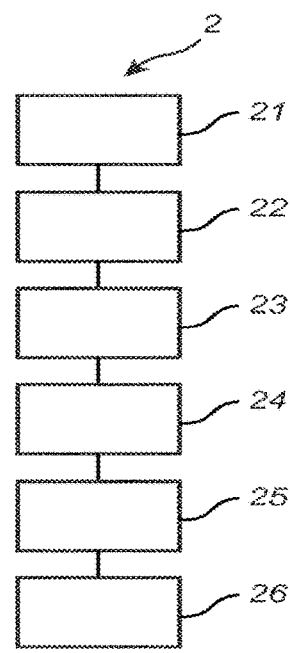
FIG. 1C is an exemplary process supported by the IoT device.

FIG. 1C schematically shows a method or app 2 which may be implemented by the computing unit 11 shown in FIG. 1B. For example, the app 2 may be a computer implemented method. A computer program may be provided for executing the app 2. The app 2 includes code for:

(21) capture user motion with accelerometer or gyroscope
(22) capture VR views through camera and process using GPU
(23) capture user emotion using facial recognition or GSR
(24) model user action using kinematic model
(25) compare user action with idea action
(26) coach user on improvement to user sport techniques.

The device can negotiate and enforce agreements with others blockchain smart contracts. The system may include one or more of the following:

code to determine trade settlement amounts and transfers funds automatically, code to automatically pay coupon payments and returns principal upon bond expiration, code to determine payout based on claim type and policy coverage, code to collect insurance based on usage and upon a claim submission, code to determine payout based on claim type and policy coverage, code to transfer electronic medical record from a source to a destination based on patient consent, code to anonymously store wearable health data from wearable devices for public health monitoring, a secured content and code to determine and distributes royalty to an author, code for storing a stock certificate number with stock quantity, code to determine a share registry or a capitalization table from each stock certificate number and stock quantity, code to distribute shareholder communication from a share registry or a capitalization table, code to collect secure shareholder votes from a share registry or a capitalization table for transparent corporate governance, code to provide financial information to shareholder a share registry or a capitalization table for corporate governance, code to enforce majority or supermajority shareholder votes from a share registry or a capitalization table for corporate governance, code for supply chain management, code for tracking chain of custody for an item, or code for peer-to-peer transactions for between two computers.

Figure 2A:
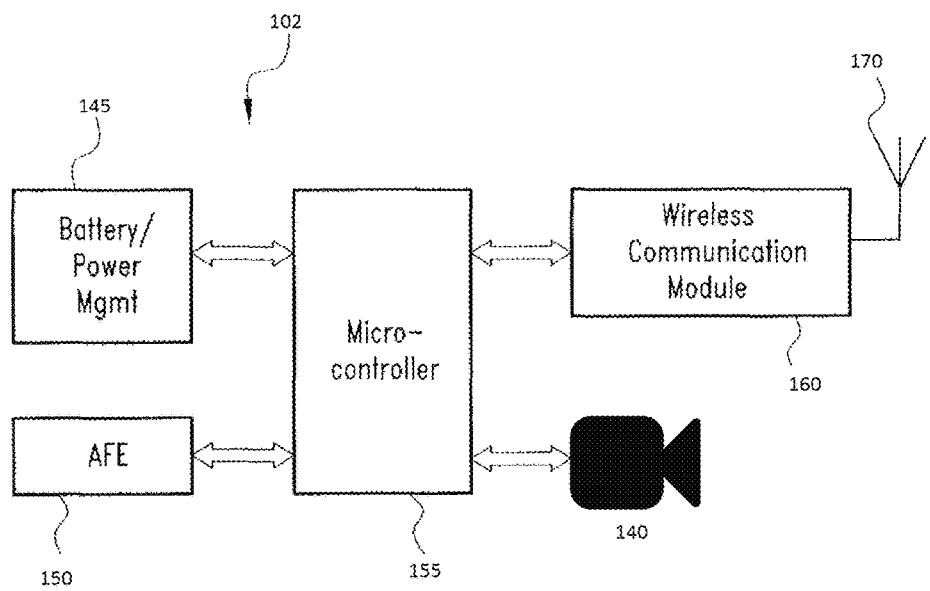

As shown in FIG. 2A, a microcontroller 155 receives and processes signals from the sensor 112-114, and converts those signals into an appropriate digital electronic format. The microcontroller 155 wirelessly transmits tension information in the appropriate digital electronic format, which may be encoded or encrypted for secure communications, corresponding to the sensed traffic and/or crime indication through a wireless communication module or transceiver 160 and antenna 170. Optionally, a camera 140 can be provided to visually detect traffic and/or crime and movement of the structure. While monitoring of the smart device 100 traffic and/or crime is continuous, transmission of tension information can be continuous, periodic or event-driven, such as when the tension enters into a warning or emergency level. Typically the indicated tension enters a warning level, then an emergency level as tension drops below the optimal range, but corresponding warning and emergency levels above the optimal range can also be used if supported by the smart device 100. The microcontroller 155 is programmed with the appropriate warning and emergency levels, as well as internal damage diagnostics and self-recovery features.

The tension information can take any form, including a simple warning/emergency indication that the tension is approaching or exceeding tension specifications, respectively. While under-tension is known to be the primary cause of structural or mechanical problems associated with devices, over-tension can also be a problem and can also be reported by the smart device 100.

The sensors can detect force, load, tension and compression forces on the device such as the device. Other data includes Acceleration; Velocity; Global absolute displacement; Local relative displacement; Rotation; Strain; Stress; Force; and Static-position video. Wind speed/direction; External temperature; weather parameters (rainfall, humidity, solar radiation, etc.); Internal or structural temperature; Mass loading (occupant count, etc.); Static tilt; Fatigue damage; Corrosion; Acoustic emission; and Moving-position video. A force is simply a push or pull to an object and can be detected by a load cell, pressure cell or strain sensor. A Load: Is simply a force applied to a structure. Ex: weight of vehicles or pedestrians, weight of wind pushing on sides. Tension & Compression are internal forces that make a member longer or shorter. Tension stretches a member and Compression pushes the member closer together. Acceleration can also be detected by Force-Balance (Servo) Piezoelectric Piezoresistive MEMS. Velocity can be measured by force-balance (servo) MEMS, or Mechanical Doppler Heated wire. A local Displacement sensor can be LVDT/Cable potentiometer Acoustic Optical/laser Temperature Electrical Optical fiber. A rotation sensor can be Gyro MEMS Gyro Tilt Electro-mechanical MEMS. A strain sensor can be a resistance gauge Vibrating wire Optical fiber Corrosion Electrical Chemical sensors. A traffic and/or crime sensor can be a microphone listening to acoustic emission, or Piezoelectric MEMS, for example, and sonar sound processing can be used to detect where crime activity is coming from.

The sensor 112-114, transceiver 160/antenna 170, and microcontroller 155 are powered by and suitable power source, which may optionally include an electromagnetic field (EMF) scavenging device 145, such as those known in the art, that convert ambient EMF (such as that emitted by radio station broadcasts) into small amounts of electrical power. The EMF scavenging device 145 includes a battery to buffer and store energy for the microcontroller 155, sensor 112-114, camera 140 and wireless communications 160/170, among others.

The circuit of FIG. 2A contains an analog front-end ("AFE") transducer 150 for interfacing signals from the sensor 112-114 to the microcontroller 155. The AFE 150 electrically conditions the signals coming from the sensor 112-114 prior to their conversion by the microcontroller 155 so that the signals are electrically compatible with the specified input ranges of the microcontroller 155. The microcontroller 155 can have a CPU, memory and peripheral circuitry. The microcontroller 155 is electrically coupled to a wireless communication module 160 using either a standard or proprietary communication standard. Alternatively, the microcontroller 155 can include internally any or all circuitry of the smart device 100, including the wireless communication module 160. The microcontroller 155 preferably includes power savings or power management circuitry 145 and modes to reduce power consumption significantly when the microcontroller 155 is not active or is less active. The microcontroller 155 may contain at least one Analog-to-Digital Converter (ADC) channel for interfacing to the AFE 150.

The battery/power management module 145 preferably includes the electromagnetic field (EMF) scavenging device, but can alternatively run off of previously stored electrical power from the battery alone. The battery/power management module 145 powers all the circuitry in the smart device 100, including the camera 140, AFE 150, microcontroller 155, wireless communication module 160, and antenna 170. Even though the smart device 100 is preferably powered by continuously harvesting RF energy, it is beneficial to minimize power consumption. To minimize power consumption, the various tasks performed by the circuit should be repeated no more often than necessary under the circumstances.

Stress information from the smart device 100 and other information from the microcontroller 155 is preferably transmitted wirelessly through a wireless communication module 160 and antenna 170. As stated above, the wireless communication component can use standard or proprietary communication protocols. Smart lids 100 can also communicate with each other to relay information about the current status of the structure or machine and the smart device 100 themselves. In each smart device 100, the transmission of this information may be scheduled to be transmitted periodically. The smart lid 100 has a data storage medium (memory) to store data and internal status information, such as power levels, while the communication component is in an OFF state between transmission periods. On the other hand, once the communication commences in the ON state, the microcontroller 155 can execute the following tasks:

1. Neighbor discovery: in this task each smart device 100 sends a beacon identifying its location, capabilities (e.g. residual energy), status. 2. Cluster formation: cluster head will be elected based on the findings in (1). The cluster children communicate directly with their cluster head (CH). 3. Route discovery: this task interconnects the elected cluster heads together and finds the route towards the sink smart device (node) so that minimum energy is consumed. 4. Data transmission: the microcontroller processes the collected color data and based on the adopted data dissemination approach, the smart device 100 will do one of the following. (a) Transmit the data as is without considering the previous status; or (b) transmit the data considering the previous status. Here we can have several scenarios, which include: (i) transmitting the data if the change in reported tension exceeds the warning or emergency levels; and (ii) otherwise, do not transmit.

Figure 2B:
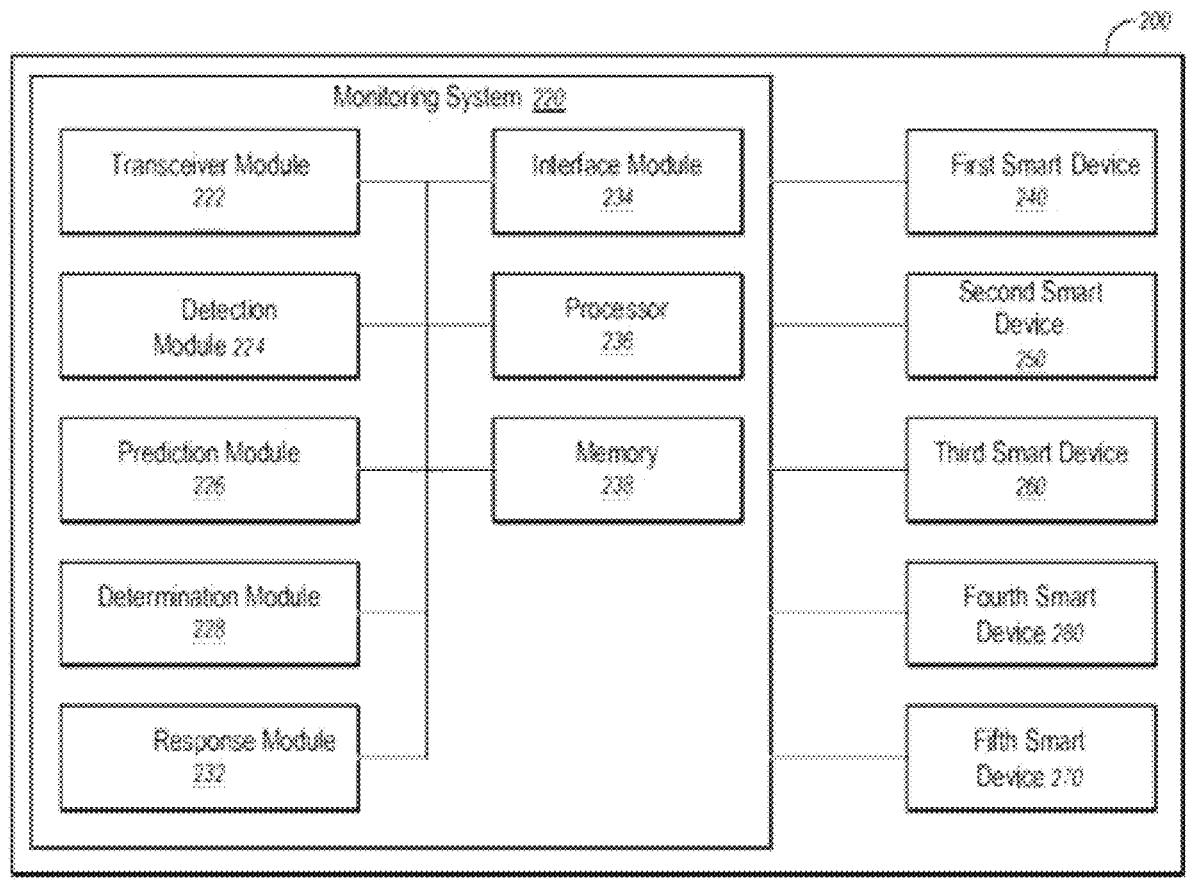
FIG. 2B is a block diagram of a big data system for predicting stress experienced by a structural unit such as a bridge, a building, or a plane, for example.

The electronic of FIG. 2A operates with a big data discovery system of FIG. 2B that determines events that may lead to failure. FIG. 2B is a block diagram of an example stress monitoring system 200 that may be process the stress detected by the smart device 100 of FIG. 1, arranged in accordance with at least some embodiments described herein. Along with the stress monitoring system 220, a first smart device such as a smart device 240, a second smart device 250, a third smart device 260, a fourth smart device 280, and additional sensors 270 may also be associated with the unit 200. The stress monitoring system 220 may include, but is not limited to, a transceiver module 222, a stress detection module 224, a stress prediction module 226, a determination module 228, a stress response module 232, an interface module 234, a processor 236, and a memory 238.

The transceiver module 222 may be configured to receive a stress report from each of the first, second, and third sport smart devices 240, 250, 260. In some embodiments, the transceiver module 222 may be configured to receive the stress reports over a wireless network. For example, the transceiver module 222 and the first, second, and third smart devices 240, 250, 260 may be connected over a wireless network using the IEEE 802.11 or IEEE 802.15 standards, for example, among potentially other standards. Alternately or additionally, the transceiver module 222 and the first, second, and third smart devices 240, 250, 260 may communicate by sending communications over conductors used to carry electricity to the first, second, and third smart devices 240, 250, 260 and to other electrical devices in the unit 200. The transceiver module 222 may send the stress reports from the first, second, and third smart devices 240, 250, 260 to the prediction module 226, the stress detection module 224, and/or the determination module 228.

The stress module 224 may be configured to detect stress on the sport object as detected by the devices 100. The signal sent by the devices 100 collectively may indicate the amount of stress being generated and/or a prediction of the amount of stress that will be generated. The stress detection module 224 may further be configured to detect a change in stress of non-smart devices associated with the unit 200.

The prediction module 226 may be configured to predict future stress based on past stress history as detected, environmental conditions, forecasted stress loads, among other factors. In some embodiments, the prediction module 226 may predict future stress by building models of usage and weight being transported. For example, the prediction module 226 may build models using machine learning based on support vector machines, artificial neural networks, or using other types of machine learning. For example, stress may correlate with the load carried by a bridge or an airplane structure. In other example, stress may correlate with temperature cycling when a structure is exposed to constant changes (such as that of an airplane).

The prediction module 226 may gather data for building the model to predict stress from multiple sources. Some of these sources may include, the first, second, and third smart devices 240, 250, 260; the stress detection module 224; networks, such as the World Wide Web; the interface module 234; among other sources. For example, the first, second, and third smart devices 240, 250, 260 may send information regarding human interactions with the first, second, and third smart devices 240, 250, 260. The human interactions with the first, second, and third smart devices 240, 250, 260 may indicate a pattern of usage for the first, second, and third smart devices 240, 250, 260 and/or other human behavior with respect to stress in the unit 200.

In some embodiments, the first, second, and third smart devices 240, 250, 260 may perform predictions for their own stress based on history and send their predicted stress in reports to the transceiver module 222. The prediction module 226 may use the stress reports along with the data of human interactions to predict stress for the system 200. Alternately or additionally, the prediction module 226 may make predictions of stress for the first, second, and third smart devices 240, 250, 260 based on data of human interactions and passed to the transceiver module 222 from the first, second, and third smart devices 240, 250, 260. A discussion of predicting stress for the first, second, and third smart devices 240, 250, 260 is provided below with respect to FIGS. 5 and 6.

The prediction module 224 may predict the stress for different amounts of time. For example, the prediction module 224 may predict stress of the system 200 for 1 hour, 2 hours, 12 hours, 1 day, or some other period. The prediction module 224 may also update a prediction at a set interval or when new data is available that changes the prediction. The prediction module 224 may send the predicted stress of the system 200 to the determination module 228. In some embodiments, the predicted stress of the system 200 may contain the entire stress of the system 200 and may incorporate or be based on stress reports from the first, second, and third smart devices 240, 250, 260. In other embodiments, the predicted stress of the system 200 may not incorporate or be based on the stress reports from the first, second, and third smart devices 240, 250, 260.

The determination module 228 may be configured to generate a unit stress report for the system 200. The determination module 228 may use the current stress of the system 200, the predicted stress of the system 200 received from the prediction module 224; stress reports from the first, second, and/or third smart devices 240, 250, 260, whether incorporated in the predicted stress of the system 200 or separate from the predicted stress of the system 200; and an amount of stress generated or the predicted amount of stress, to generate a unit stress report.

In some embodiments, one or more of the stress reports from the first, second, and/or third smart device 240, 250, 260 may contain an indication of the current operational profile and not stress. In these and other embodiments, the determination module 228 may be configured to determine the stress of a smart device for which the stress report indicates the current operational profile but not the stress. The determination module 228 may include the determined amount of stress for the smart device in the unit stress report. For example, both the first and second smart device 240, 250 may send stress report. The stress report from the first smart device 240 may indicate stress of the first smart device 240. The stress report from the second smart device 250 may indicate the current operational profile but not the stress of the second smart device 250. Based on the current operational profile of the second smart device 250, the determination module 228 may calculate the stress of the second smart device 250. The determination module 228 may then generate a unit stress report that contains the stress of both the first and second smart devices 240, 250.

In some embodiments, the stress monitoring system 220 may not include the prediction module 226. In these and other embodiments, the determination module 228 may use stress reports from the first, second, and/or third smart devices 240, 250, 260, with the received amount of stress inferred on non-smart devices, if any, to generate the unit stress report. The determination module 228 may send the unit stress report to the transceiver module 222.

In some embodiments, the processor 236 may be configured to execute computer instructions that cause the stress monitoring system 220 to perform the functions and operations described herein. The computer instructions may be loaded into the memory 238 for execution by the processor 236 and/or data generated, received, or operated on during performance of the functions and operations described herein may be at least temporarily stored in the memory 238.

Although the stress monitoring system 220 illustrates various discrete components, such as the prediction module 226 and the determination module 228, various components may be divided into additional components, combined into fewer components, or eliminated, depending on the desired implementation. In some embodiments, the unit 200 may be associated with more or less smart devices than the three smart devices 240, 250, 260 illustrated in FIG. 2.

Figure 3:
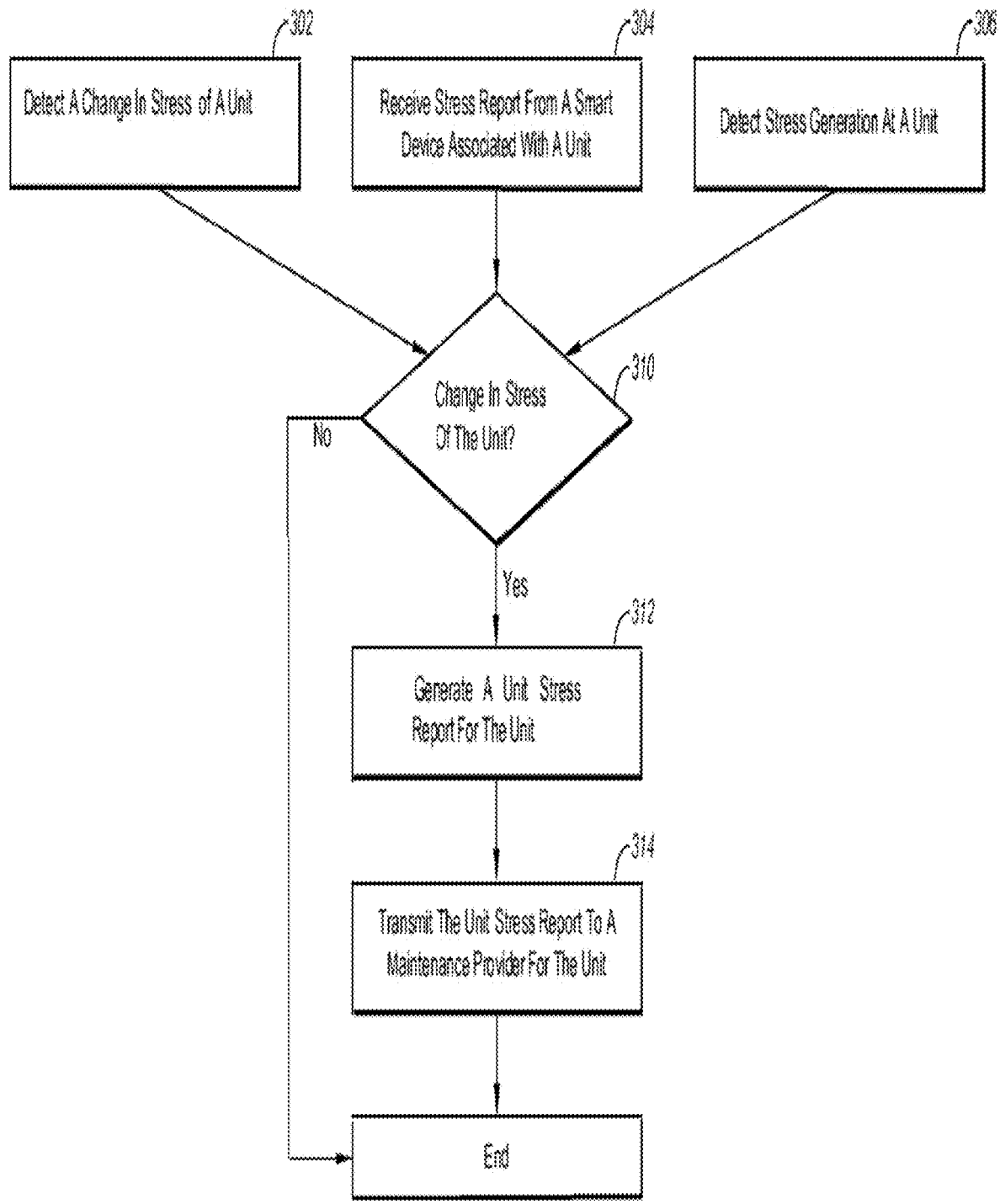
FIG. 3 is a flowchart illustrating one operation of the system of FIG. 2A-2B in detecting stress on a unit.

FIG. 3 is a flow chart of an example method 300 of monitoring stress of a sport or game unit, arranged in accordance with at least some embodiments described herein. The method 300 may be implemented, in some embodiments, by an stress monitoring system, such as the stress monitoring system 220 of FIG. 2. For instance, the processor 236 of FIG. 2B may be configured to execute computer instructions to perform operations for monitoring stress as represented by one or more of blocks 302, 304, 306, 310, 312, and/or 314 of the method 300. Although illustrated as discrete blocks, various blocks may be divided into additional blocks, combined into fewer blocks, or eliminated, depending on the desired implementation.

The method 300 may begin at one or more of blocks 302, 304, and/or 306. The blocks 302, 304, and/or 306 may occur at the same time or at different times and may or may not depend on one another. Furthermore, one or more of the block 302, 304, 306 may occur during the method 300. For example, the method 300 may complete when blocks 304, 310, and 312 occurs and without the occurrence of block 302 and 306.

In block 302, a change in stress of a device (device or beam) associated with a unit may be detected. A non-smart device may by any device that receives stress and does not generate an stress report indicating its stress, for example a legacy racket without IoT electronics. A change in the stress of a non-smart device may be detected using an stress detection module and/or usage meter associated with the unit, such as the stress detection module 224 and/or the smart device 100. For example, non-smart device stress can be estimated by the load the unit carries, the temperature cycling experienced by the unit, for example.

After a change in stress of the non-smart device is detected, the method 300 proceeds to block 310. In block 304, a stress report from a smart device such as the smart device 100 associated with the unit may be received. A smart device may be a device that detects stress and generates and transmits an stress report indicating the stress on the smart device. The stress report may indicate predicted future stress of the smart device. In some embodiments, a stress report may be received at set intervals from the smart device regardless of a change in the stress report. Alternately or additionally, a stress report may be received after a change in the stress of the smart device results in a change to the stress report. After a stress report is received from the smart device, the method 300 proceeds to block 310.

In block 306, stress experienced at the unit may be detected. Stress at the unit may be detected using a stress detection module, such as the stress detection module 224 of FIG. 2B. After detecting stress at the unit, the method proceeds to block 310. At block 310, it is determined if a change in the stress occurred. For example, if an increase in stress occurs at the same time and at the same amount as an increase in the stress of a non-smart device, a change in the stress may not occur. If a change in the stress occurs, the method 300 proceeds to block 312. If no change occurs, the method 300 ends.

At block 312, a unit stress report is generated for the unit. In some embodiments, the unit stress report may indicate the current stress of the unit. Alternately or additionally, the unit stress report may indicate a current and predicted future stress of the unit. At block 314, the unit stress report is transmitted to a maintenance provider. In some embodiments, the unit stress report may be transmitted when the unit stress report indicates a change in stress for the unit that is greater than a predetermined threshold. If the unit stress report indicates a change in stress for the unit that is less than the predetermined threshold, the unit stress report may not be transmitted to the provider of maintenance services.

Figure 5:
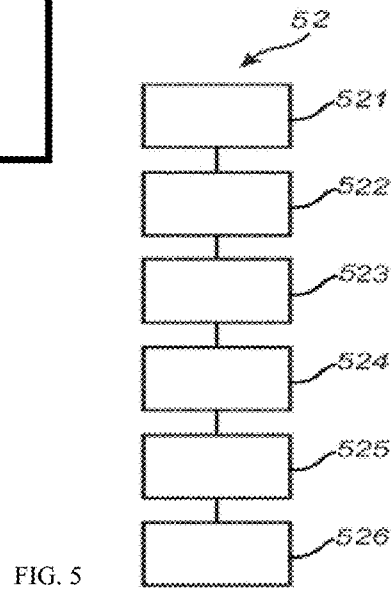
FIG. 5 shows an exemplary process for augmented and/or virtual reality for viewers participating in a game.

FIG. 5 shows in more details the computer 30 and the interface to the probe 20. An amplifier 90 amplifies vibratory output from a transducer 92. A pick up unit having an accelerometer (or an array) 96 receives reflected vibrations from user arm or leg 94, among others. A computer 98 includes a digital converter to digitize output from the pick-up unit and software on the computer 98 can process the captured diagnostic data. Diagnostic software 100 can include a database of known restorations, diseases, and tissue conditions whose signatures can be matched against the capture diagnostic data, and the result can be displayed on a screen for review by the athlete.

Included in one embodiment of the instrumentation is the transmitter or transducer, which will emit the vibrations that will be imparted to the teeth and jaws. This will be connected to a power supply and amplifier, which will allow for a frequency range. On electrical excitation, the transducer emits an outgoing vibration. That vibration will then travel into the arm or leg and down is root into the soft tissues and out into the bones or jaws. The accelerometer or detector will be placed on the bone of interest. It will receive the vibrations from the emitter. The effect of the vibrations on the muscle of interest will generate a pattern of frequency vibrations. Those vibrations will be digitally converted and analyzed against known dental states in the software of the computer. As the data is collected various linear samplings and comparisons will be made against the database. Software will make these comparisons as the data is received from the teeth.

FIG. 5 schematically shows a method or app 52 to perform collaborative VR/AR gaming. The app 52 includes code for:

(51) capture 360 degree view of the live event

(52) detect head position of the viewer

(53) adjust viewing angle on screen based on head position and user posture

(54) render view to simulate action based on user control rather than what the professional is doing

(55) augment view with a simulated object that is powered by viewer action as detected by sensors on viewer body

(56) compare professional result with simulated result and show result to a crowd of enthusiasts for social discussion.

Figure 6:
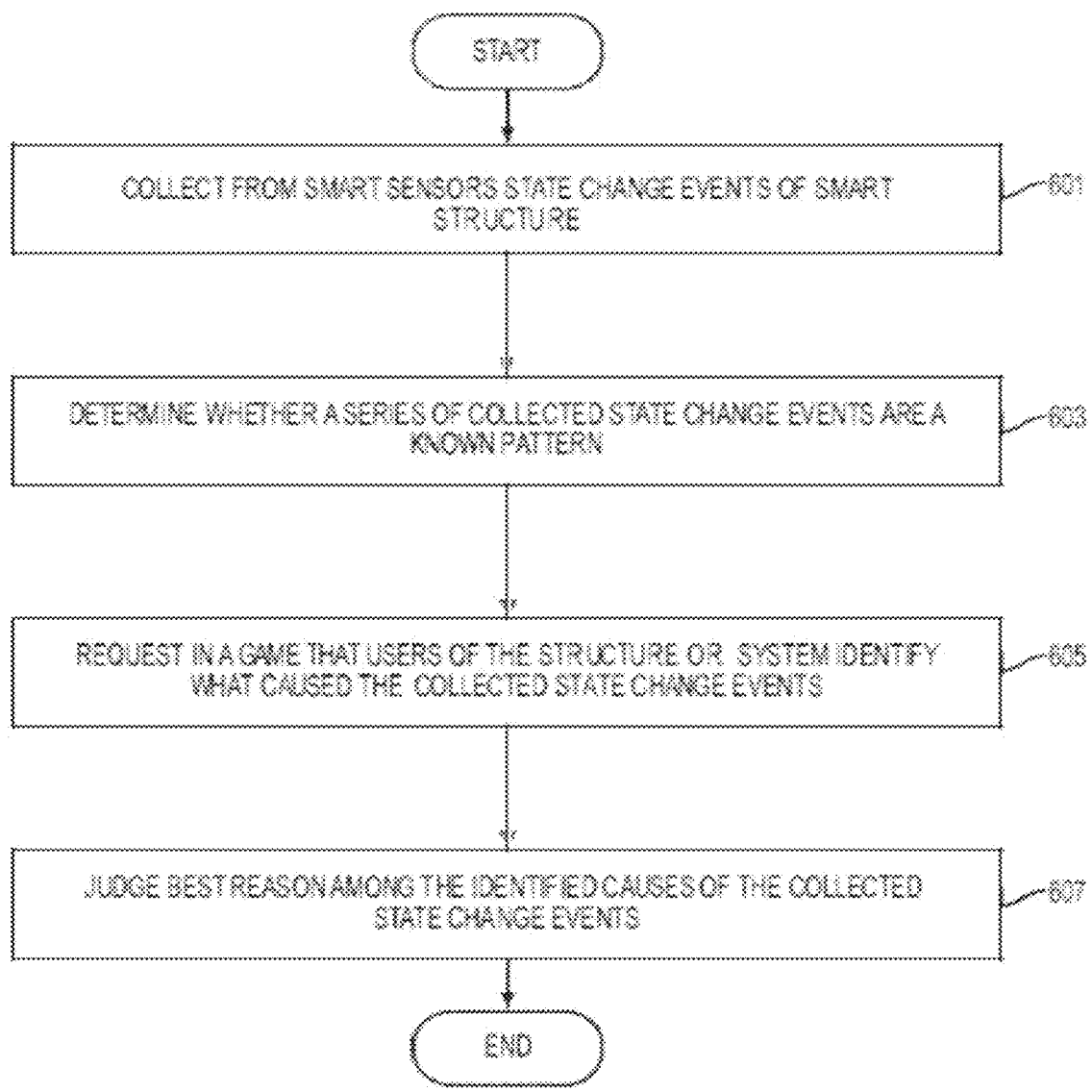
FIG. 6 shows an exemplary process to identify reasons for sensor data changes using a gaming process.

FIG. 6 is a flowchart of a method of an embodiment of the present disclosure. Referring to FIG. 6, a smart system may collect from smart devices state change events of a smart system in operation 601. That is, the smart system of FIG. 4 collects information on each of the group of devices, the smart devices, the smart appliances, the security devices, the lighting devices, the energy devices, and the like. The state change events indicate when there is a change in the state of the device or the surrounding environment. The state change events are stored by the smart system. In operation 603, the system may determine whether a series of the collected state change events are a known pattern. That is, the gateway determines whether there are events which have been correlated or identified in the past. If the collected state change events have been identified in the past, it may be necessary to determine that the smart system trusts the identification the collected state change events. The trust factor of the identification of the collected state change events may be determined by the number of users who have identified the collected state change events or the number of time collected state change events have been repeated and identified. In operation 605, when the series of the collected state change events is an unknown pattern, request users of the smart system to identify what caused the collected state change events request. That is, the system transmits to a gamification application (hereinafter app) on the user's mobile device a request to identify the collected state change events. The gamification app displays the information and request the user enter information identifying the collected state change events. Each of the mobile devices transmits this information back to the system to the gamification module. In operation 605, the system transmits the user's identified collected state change events to the other user's of the smart home system and they each vote on the best identification of the collected state change events. Thus, the identified collected change state events that have been repeatedly identified over a period of weeks increases, the trustworthiness of the identification increases. Likewise, if every user of the smart system makes the same identification of the collected change state events, the identified collected change state events may be considered trustworthy at point. Such a determination of a threshold for when the identified collected change state events are considered trustworthy and therefore need not be repeated, is made by a system administrator. However, it will be understood that such a trustworthiness of this type only gives higher confidence of this particular dataset at that point in time. As such further repetition is required, since the sensor data may have noise, the more datasets to be identified to the pattern, the more robust the trustworthiness will be. Until the robustness reaches a threshold, then the system can confirm this is a known trustworthy pattern.

The system can use gaming to help sport enthusiasts improve dental care or maintain teeth hygiene. This may involve use of virtual tools, corresponding to such tools used in normal dental hygiene: sport device, tooth picks, dental floss, gum massaging aids, etc. In this embodiment, the game may, for example, have the object of fighting tooth or gum decay, damage or infection which may be caused by carries or other infectious agents. The user is presented with a library of tools and has to select a tool to treat a certain developing virtual condition, e.g. carries or a gum infection. The game rules determine a certain continuous progress of infection which if not properly "treated" by the user will cause decay of one or more teeth, gum infection, potential bleeding, loss of teeth, etc. In step 13, the user may score points depending on his ability to choose the right tools to treat a particular condition or in avoiding a condition from developing. Next, it is determined whether the condition of the teeth is satisfactory. If yes, the process terminates. If no, then the user is prompted whether he wishes to select another tool. If no, the process terminates. If yes, the process restarts. Here again, the game, in addition to being amusing and providing an insight of the user into his own teeth, may be educational, particularly for children, on teeth oral hygiene methods and on the importance of maintaining oral hygiene.

In accordance with another embodiment of the invention the game may involve use of a variety of virtual imaginary tools such as virtual guns, wands, etc. in order to fight infectious agents of the teeth or gums.

Smart Sport Glove

Figure 7:
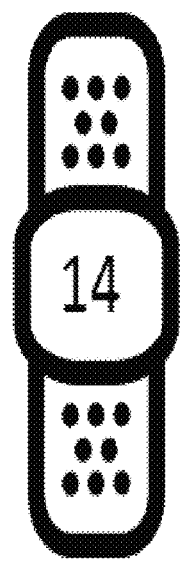
FIG. 7 shows an exemplary smart band.

FIG. 7 shows an exemplary glove which can be thin to provide touch sensitivity or thick to provide shock protection for boxers. A body 12 of the boxing glove 10 includes an impact measuring device 14 is embedded within the glove 12 in an area protected from direct impact. Such an area includes the cuff 15 of the glove 12 or that portion of the glove 12 adjacent a user's palm, or adjacent an inside surface of a user's fingers. Placement of the impact measuring device 14 into the lining of the glove in such an area allows for the force of a blow to be measured without presenting a hazard to the recipient of the blow. Under the embodiment, an impact measuring device 14 would be included in the right glove 12 for a right handed fighter, or the left glove 12 for a left handed fighter. For fighters that are equally effective with both hands, or to improve monitoring accuracy, an impact measuring device 14 would be included in both gloves 12. Theimpact measuring system 20. The impact measuring system 20 includes an impact measuring device 14 and impact display unit 16. The impact measuring device 14 is linked to the impact display 28 via a radio frequency (rf) link 32. Under the embodiment, the impact measuring device 14 includes at least one 3-axis accelerometer. A thin version of the glove can be worn to detect a golf stroke or a tennis stroke with legacy clubs or rackets that lacks IoT intelligence.

Smart Sport Band

Figure 8:
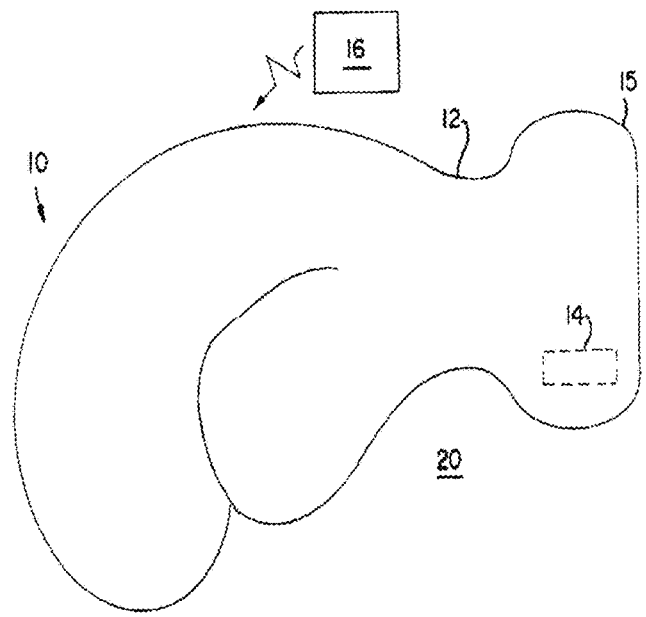
FIG. 8 shows an exemplary glove.

FIG. 8 shows an exemplary stick on wearable monitoring device for sports and fitness applications. The wireless sensor electronics 14 is mounted on a band-aid in the example of FIG. 8. The band-aid can be removed upon completion of the sports event. The central patch can be recycled, and the adhesive portion can be disposed. While the embodiment is shown as a band-aid, the inventors contemplate that any suitable bands, straps, attachments can be used in lieu of the band-aid to attach the sensors to the body. For example, in Virtual Reality (VR) sports applications, sensors including gyroscopes and cameras can be positioned on various body portions to capture motion as well as eye tracking, mouth tracking, speech recognition, among others.

One embodiment uses Samsung's Bio-Processor which is an all-in-one health solution chip. By integrating not only Analog Front Ends (AFE), but also microcontroller unit (MCU), power management integrated circuit (PMIC), digital signal processor (DSP), and eFlash memory, it is able to process the bio-signals it measures without the need of external processing parts. Even with its integrated design, the Bio-Processor is particularly innovative thanks to its incredibly small size. When compared to the total area of the discrete parts, the Bio-Processor is only about one fourth of the total combined size, which is ideal for small wearable devices, offering a bounty of options when designing new devices. The Bio-Processor has five AFEs including bio-electrical impedance analysis (BIA), photoplethysmogram (PPG), electrocardiogram (ECG), skin temperature, and galvanic skin response (GSR) into a single chip solution that measures body fat, and skeletal muscle mass, heart rate, heart rhythm, skin temperature and stress level, respectively.

One embodiment provides a flexible and stretchable electronic patch that monitors impact or other events whereby a flexible substrate is geometrically patterned to allow the substrate to undergo substantial stretching and flexing while large regions of the substrate material experiences local strains much lower than the macroscopic applied strain. The geometric patterning of the substrate facilitates continuous low strain domains (LSDs) throughout the substrate—where low strain domains are defined as regions that experience strain levels (magnitude) lower than the macroscopic applied strain. Conventional electronic components can be mounted to the LSDs, and conventional metal traces can be routed through the LSDs, dramatically reducing the stresses transmitted to the components and traces by the substrate during stretching and flexing, and therefore reducing the potential for component debonding, trace cracking, and circuit failure. The geometrically patterned strain relief features (SRFs) are dispersed either regularly or irregularly throughout the substrate. The geometrically patterned SRF regions form "hinge-like" domains. During macroscopic deformation, the SRFs rotate, translate, open, close, or otherwise change shape, causing the "hinge-like" regions to deform, and the remaining larger LSD substrate regions to primarily rotate and translate. The SRFs are designed such that the "hinge-like" regions also exhibit relatively small strain compared to the macroscopic applied strain and thus enable conductive traces, such as copper or gold, to run through the hinges and maintain function during stretching, flexing and twisting of the patch. The substrate can be multilayered to enable miming conductive traces, ground layers, vias, and/or components on/in multiple layers through the thickness of the overall substrate. The geometric patterning can be designed to enable different stretching, flexing and twisting, providing uniaxial, biaxial, and multi-axial stretchability or flexibility, and the ability to conform to a variety of surface curvatures. The geometrically patterned substrate offers a means of packaging complex multilayered electronics designs for monitoring impact (and other) events onto a stretchable and flexible substrate enabling the device to dynamically stretch, bend, twist, and conform to arbitrary shapes. The stretchable, flexible geometrically structure electronics can be fabricated using the same technologies for conventional flexible circuit boards where the stretch-enabling patterning can be imparted at different stages in the fabrication process and can also be fabricated using emerging materials and fabrication methods. The Stretchable bandaid has the stretchable, flexible substrate described above with multiple LSDs for placement of electronic components (e.g., accelerometers, gyroscopes, pressure temperature, gas and fluid sensors, microprocessors, transceivers, GPS, clocks, actuators, vias, and batteries (or other energy source)) and multiple patterned hinge-like regions bridging the LSDs which enable the routing of conducting interconnecting traces. The SEHIM patch can take the form factor of a bandaid or bandage or other such wearable form factor. The geometric patterning provides stretch, flex and twist to conform to a body and stretch, flex and twist to move or deform with a body. The bandaid detects impact accelerations, using a 3-axis accelerometer and processes the raw acceleration data in the microprocessor. The processed data is stored in the microprocessor and later (or potentially in real time) transmitted via the Bluetooth to a smart phone, tablet or computer. This embodiment encompasses wireless communication but wired communication may be desirable in some applications and can be accommodated by this invention. The bandaid can be stretched, bent and twisted with the traces and components at low strains to maintain electrical function. In all cases there was effectively no strain on the components and solder joints. The bandaid can also possess an adhesive backing for direct adhesion to the head, body or object. The band can also be coated to provide both added comfort and protection against moisture, water, and other environmental factors. The band can also contain other sensors including gyroscopes, temperature and pressure sensors, moisture sensors, clocks, chemical and/or biological sensors, etc. Features of the smart band can include:

Smart Clothing

Figure 9:
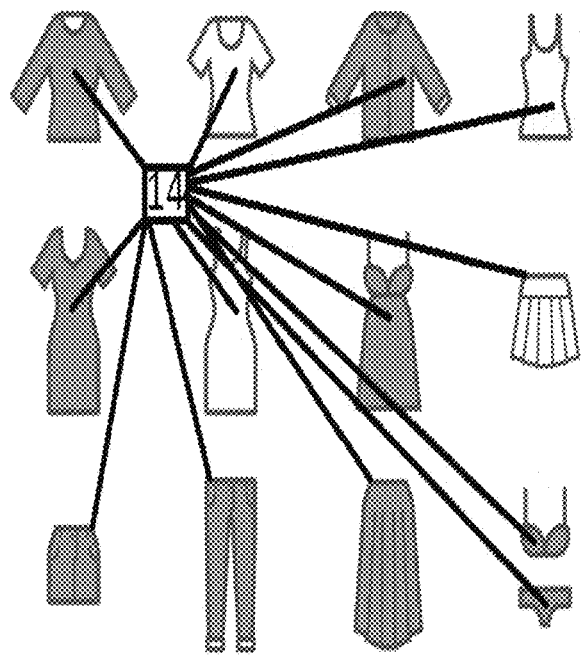
FIG. 9 shows exemplary smart clothing.
Figure 10:
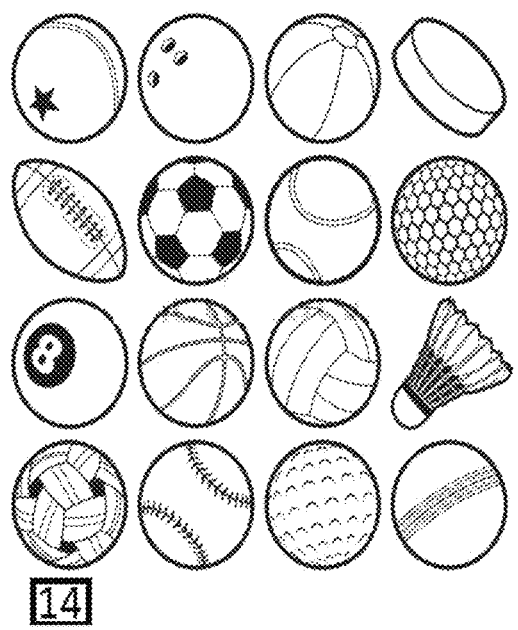
FIG. 10 shows exemplary smart balls.

FIG. 9 shows an exemplary shirt based embodiment where sensors can be positioned anywhere on the shirt and when worn, can capture position, video, and vital signs. One embodiment uses Samsung's Bio-Processor to process the bio-signals it measures without the need of external processing parts with five AFEs including bioelectrical impedance analysis (BIA), photoplethysmogram (PPG), electrocardiogram (ECG), skin temperature, and galvanic skin response (GSR) into a single chip solution that measures body fat, and skeletal muscle mass, heart rate, heart rhythm, skin temperature and stress level, respectively. Features of the smart clothe can include:

Smart Handle

Figure 11A:
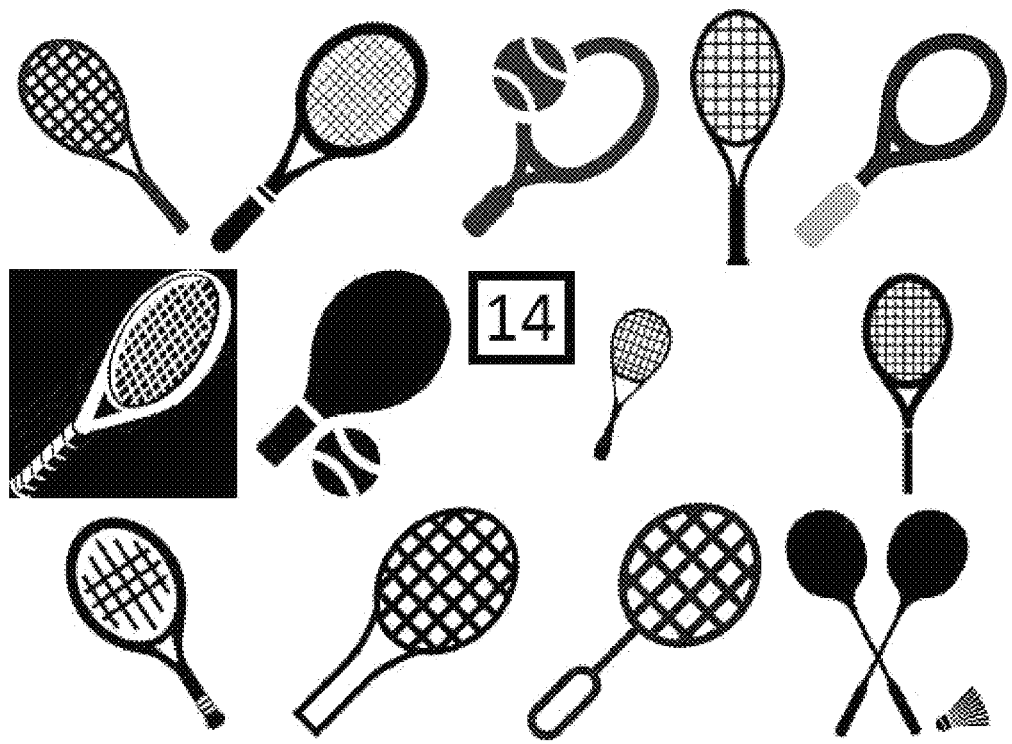
Figure 11B:
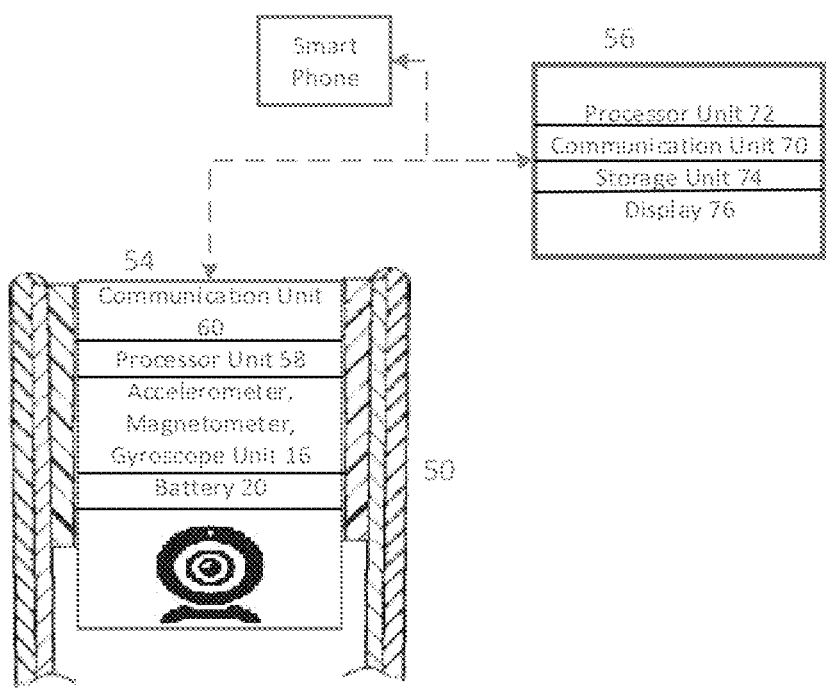
FIG. 11B shows electronics in the handle for golf clubs, rackets, or kung fu sticks.

FIGS. 11A-11B show an exemplary smart handle for sports such as tennis, badminton, table tennis, and golf, among others. The wireless sensor electronics 14 is mounted on a handle in the example of FIG. 11B. The handle can be embedded or can be removed upon completion of the sports event. The sports event does not have to be real, for example, in Virtual Reality (VR) sports applications, sensors including gyroscopes and cameras can be positioned on various body portions to capture motion as well as eye tracking, mouth tracking, speech recognition, among others.

The handle includes a swing analyzer measurement portion 54 in the grip end 52 of the handle of a golf club or a tennis/badminton racket, and a remote or handheld unit 56. The swing analyzer measurement portion 54 includes an accelerometer 16 of combination accelerometer and gyroscope or magnetometer unit, a processor unit 58 coupled to the accelerometer 16, and a battery 20 that is electrically coupled to and provides power to the accelerometer 16 and processor unit 58. A camera is included to capture videos of the swing and also the game in progress for future reference. A communications unit 60 is also housed in the grip end 52 of the golf club 50, receives power from the battery 20, and is coupled to the processor unit 58. Swing analyzer measurement portion 54, with or without the communications unit 60, may be assembled as an integral unit and inserted into a hollow portion of the handle of the golf club or tennis/racket handle 50 at the grip end 52 thereof. Processor unit 58 may be an integrated device that includes hardware and software components capable of processing acceleration measured by the accelerometer(s) 16 and converting the measured acceleration into data about the force on the shaft and position of the face of the club at impact at a set distance. If the measured force exceeds a threshold the measured force or a signal derived therefrom is transmitted via the communications unit 60 to the handheld unit 56. If not, acceleration and face position at impact of the golf club or tennis racket handle 50 is obtained again. The threshold is set so that only acceleration or force measurements arising from actual swings of the golf club 50 are transmitted to the handheld unit 56. Handheld or remote unit 56 includes an application or computer program embodied on a non-transitory computer-readable medium that performs the golf ball carrying distance estimation or prediction steps, as well as manages the training stage described above. Importantly, the handheld unit 56 receives acceleration measurement data from the golf clubs/tennis rackets equipped with a swing analyzer measurement portion 54 and the club face angle in relation to the swing plane, and manages the carrying distance estimation steps for all golf clubs equipped with the swing analyzer measurement portion 54 that are designed to communicate therewith. Handheld or remote unit 56 may be a standalone unit for use only with the golf clubs equipped with the swing analyzer measurement portion 54, and incorporating the application thereon, or may be a smartphone or similar device with the application embodied thereon or downloaded thereto and that can be used for other purposes. Handheld or remote unit 56 includes a communications unit 70 that communicates with the communications unit 60 on each golf club or tennis racket handle 50, i.e., with the communications units present on all of the golf clubs 50 equipped with swing analyzer measurement portions 54 and which have been designated to communicate therewith. Communications unit 70 may be an integral part of the handheld unit 56 as is the case when the handheld unit 56 is a smartphone. Communications unit 70 may also communicate with another device such as a Smartphone, to perform more data manipulations relating to the golf swing and/or swing results to provide more information to the user. The data and the calculation/manipulation results can be stored in the Smartphone and displayed when desired. Currently usable Smartphones are Apple iOS iPhones and Android operating system phones. Handheld or remote unit 56 also includes a processor unit 72, a storage unit 74 and a display 76. When the handheld unit 56 is a smartphone or similar device, all of the processor unit 72, storage unit 74 and display 76 may be integral components thereof. Processor unit 72 performs functions similar to those performed by the processor unit 18 described above, e.g., calculates an estimated carrying distance for the golf ball based on the acceleration measured by the accelerometer(s) 16 and transmitted via the communications units 60, 70, and the type of club provided to the application or computer program in the processor unit 72. Storage unit 74 receives and stores information about the carrying distance of each club as a function of clock or swing position, e.g., in the form of a virtual table associating the type of club, the swing or swing position and the estimated carrying distance.

Other sensors can be used as well. For example, the handle can contain conductive ink to capture biometric. One embodiment uses Samsung's Bio-Processor which is an all-in-one health solution chip to measure bioelectrical impedance analysis (BIA), photoplethysmogram (PPG), electrocardiogram (ECG), skin temperature, and galvanic skin response (GSR) into a single chip solution that measures body fat, and skeletal muscle mass, heart rate, heart rhythm, skin temperature and stress level, respectively. The handle can also contain other sensors including gyroscopes, temperature and pressure sensors, moisture sensors, clocks, chemical and/or biological sensors, etc. Features of the smart handle can include:

Smart Protective Gear

Figure 12A:
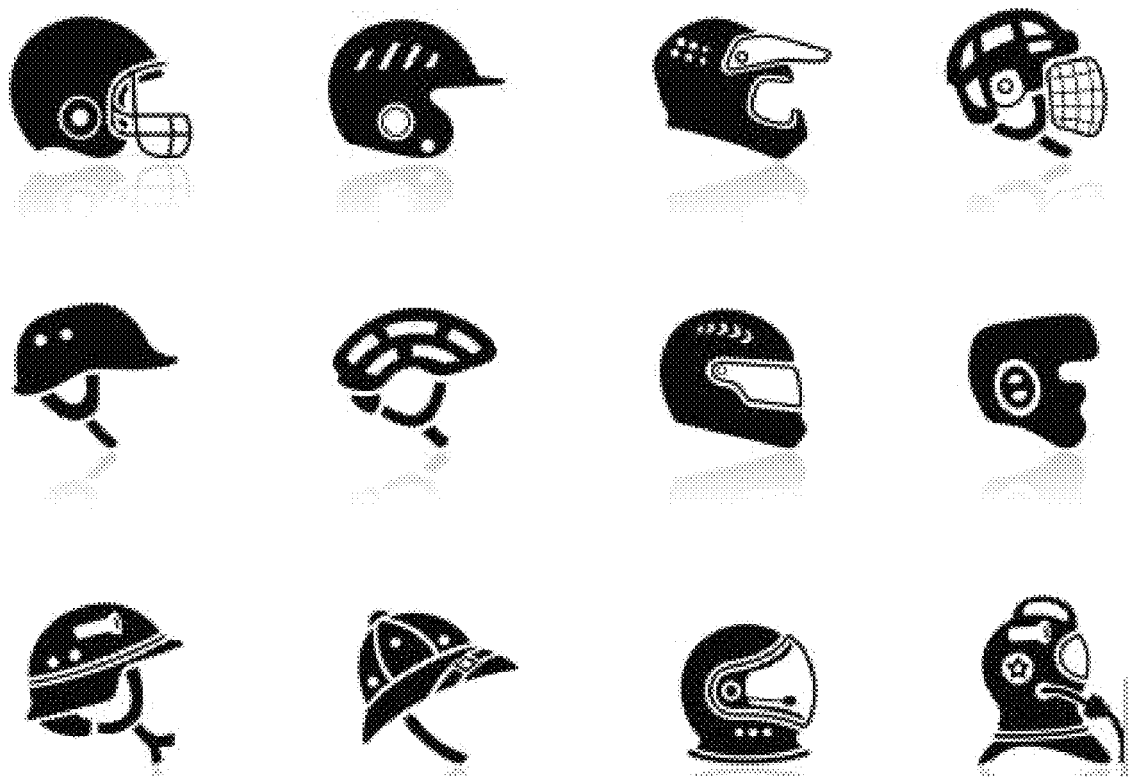
Figure 12C:
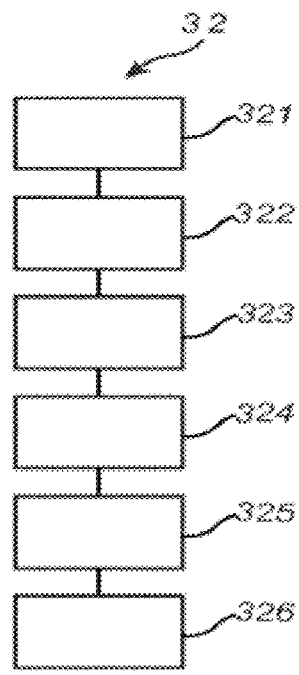
FIG. 12C shows an exemplary process to fabricate mass-customized protective gear.
Figure 12B:
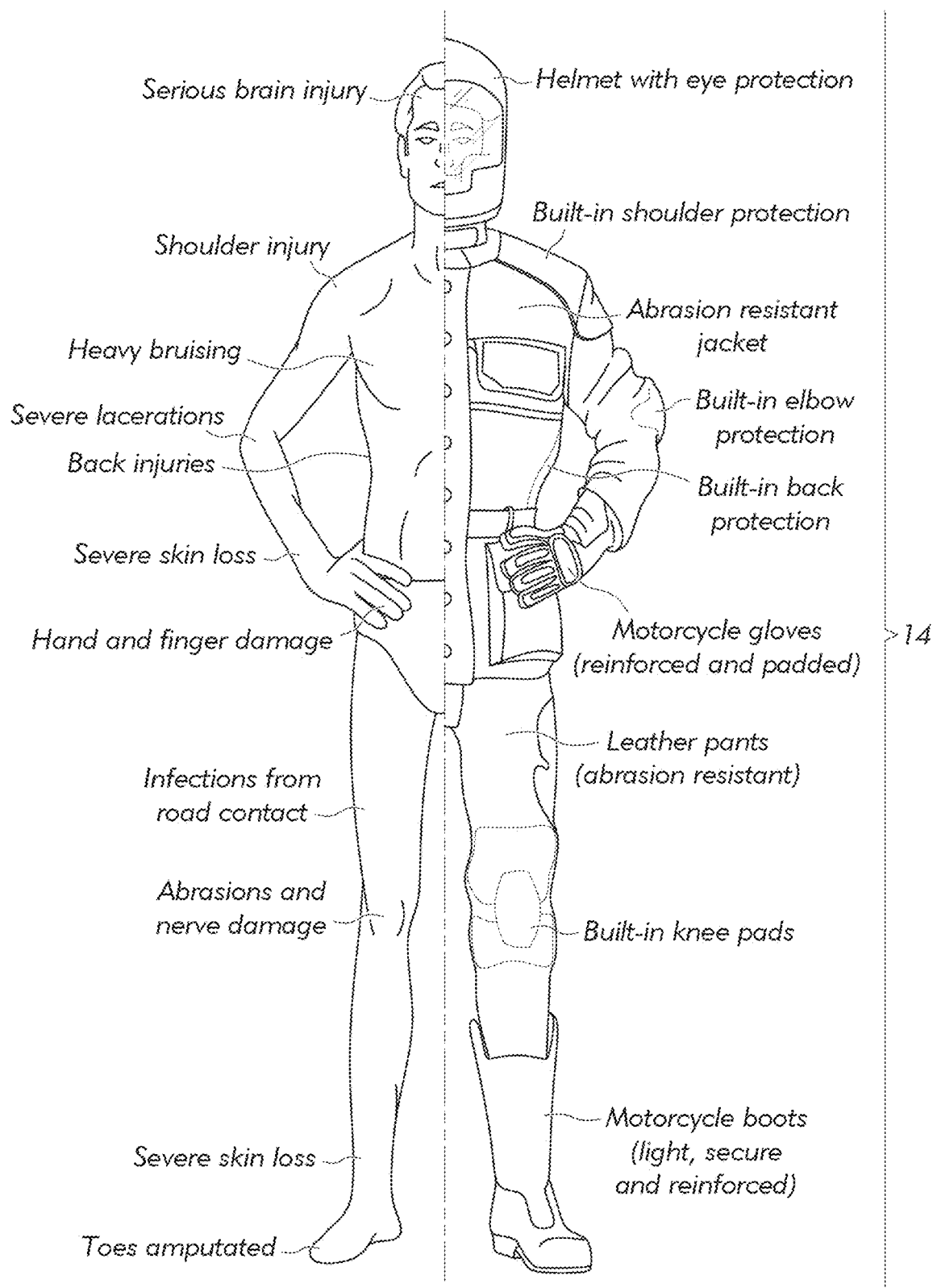

FIGS. 12A-12C illustrate smart protective gears embedded with the IoT sensors and instrumentations to report potential health issues. For soccer, the protection includes shin guards. For football, the protection includes Helmets, Chin Straps & Chin Shields, Cups & Athletic Supporters, Elbow Sleeves & Arm Pads, Back Plates & Rib Protection, Facemasks, Girdles, Helmet Visors, Shoulder Pads, Hip & Tail Pads, Mouthguards, Neck Rolls. For motorcycling, the protection includes helmet, should pads, jacket with back protection, padded gloves, leather pants, knee pads, and boots. For rock climbing, the protection includes shoes, carabiners, webbing, harnesses, among others.

The wireless sensor electronics 14 is mounted on the helmet or shoulder pad in the example of FIG. 12A or 12C. The electronics 14 can be embedded or can be removed upon completion of the sports event. The sports event does not have to be real, for example, in Virtual Reality (VR) sports applications, sensors including gyroscopes and cameras can be positioned on various body portions to capture motion as well as eye tracking, mouth tracking, speech recognition, among others.

The protection gear includes an impact sensor such as an accelerometer to indicate if concussion has occurred. Other sensors can be used as well. For example, the handle can contain conductive ink to capture biometric. One embodiment uses Samsung's Bio-Processor which is an all-in-one health solution chip to measure bioelectrical impedance analysis (BIA), photoplethysmogram (PPG), electrocardiogram (ECG), skin temperature, and galvanic skin response (GSR) into a single chip solution that measures body fat, and skeletal muscle mass, heart rate, heart rhythm, skin temperature and stress level, respectively. The handle can also contain other sensors including gyroscopes, temperature and pressure sensors, moisture sensors, clocks, chemical and/or biological sensors, etc.

Impact sensors, or accelerometers, measure in real time the force and even the number of impacts that players sustain. Data collected is sent wirelessly via Bluetooth to a dedicated monitor on the sidelines, while the impact prompts a visual light or audio alert to signal players, coaches, officials, and the training or medical staff of the team. One such sensor example is the ADXL377 from Analog Devices, a small, thin and low-power 3-axis accelerometer that measures acceleration from motion, shock, or vibration. It features a full-scale range of ±200 g, which would encompass the full range of impact acceleration in sports, which typically does not exceed 150 g's. Specifically designed for concussion and head-trauma detection, at 3 mm×3 mm×1.45 mm, the device is small enough to be designed into a helmet. Sensitivity, listed at 6.5 mV/g with −3 dB bandwidth at 1.6 kHz, is sufficiently high for the application. When a post-impact player is removed from a game and not allowed to return until cleared by a concussion-savvy healthcare professional, most will recover quickly. If the injury is undetected, however, and an athlete continues playing, concussion recovery often takes much longer. In addition, the industry is finding that long-term problems from delayed or unidentified injury can include: Early dementia, Depression, Rapid brain aging, and Death. The cumulative effects of repetitive head impacts (RHI) increases the risk of long-term neuro-degenerative diseases, such as Parkinson's disease, Alzheimer's, Mild Cognitive Impairment, and ALS or Lou Gehrig's disease. The sensors' most important role is to alert to dangerous concussions. Yet, the act of real-time monitoring brings these players to the attention of their coaches not only to monitor serious impacts but, based on the data provided by the sensors, also help to modify a player's technique so that they are not, for example, keeping their head low where they can sustain injury to the front and top of the skull. In the NFL there also has been an aggressive crackdown against hits to the head and neck—a response to the ongoing concussion crisis—resulting in immediate penalty to players using their helmets as a "weapon". Customized mouthguards also have sensors therein. A customized mouthguard has tested to be 99 percent accurate in predicting serious brain injury after near-concussive force, according to an Academy of General Dentistry study2. Teeth absorb and scatter infrared light, which shows how much force is taking place at the moment of impact.

Custom Gear

In one aspect, the protective gear is custom formed to the athlete's body. This is done in FIG. 12C as follows:
321) perform 3D scan of person and create 3D model
322) form positive mold from the 3D model
323) place mold into 2 phase 3D printer to form a negative
324) put composite material into mold and form composite protection gear
325) embed IoT electronics into one or more locations into the composite protection gear
326) link IoT electronics with mobile devices and cloud based storage and process impact data and warn user if impact is unsafe.

The protection gear or footwear can be custom produced at the request of a customer, who can specify the nature of the customization for one or more pairs of helmet, protective gear, or footwear. Each helmet of the footwear may have a different design, message or message portion designed into it and rendered using the bed of pins described below to make the custom helmet or shoe design messages or shapes, and then the bottom sole can be fabricated using the reformable bed described below. Once the negative is fixed in the reformable bed, suitable materials for the bottom sole can be deposited and cured and can include rubber, plastic, or foam. Further customization can be done by a Computerized Numerical Control (CNC) where component design can be integrated with computer-aided design (CAD) and computer-aided manufacturing (CAM) programs. The device can be programmed to use a number of different tools-drills, saws, and so on. Alternatively a number of different machines can be used with an external controller and human or robotic operators that move the component from machine to machine. Regardless, a series of steps needed to produce a part can produce a part that closely matches the original CAD design in a highly automated fashion. In accordance with aspects of the subject matter disclosed herein through the use of reformable bed and a suitably programmed CNC tools, customized footwear with custom cut sole designs, can cost effectively be created in small quantities and yet scalable for mass-customization.

Shock Protection

In one embodiment, the sole is not completely filled with material, but is formed as a lattice structure. The system generates triangulated surfaces for export to additive manufacturing (AM) processes. Implementing a process that coverts a CAD object into an image, known as voxelisation, the company uses an image-based method which allows designers to generate implicitly defined periodic lattice structures suitable for additive manufacturing applications and finite element analysis (FEA). The system generates robust lattice structures can overcome the problems faced with hollowing out a part to reduce weight and optimize designs prior to 3D printing. Cellular lattice structures can be used to replace the volume of CAD and image-based parts, reducing weight whilst maintaining optimal performance. In this way, the shoes can be light weight yet strong and provide shock impact absorption during running for the wearer.

Topology optimization can be used to drive the material layout including the lattice regions. From this new topology optimization implementation, the system can identify void regions in the design space, where the material can be removed, regions where solid material is needed, and regions where lattice structure is required. This allows the system to generate the optimal hybrid or blended solid-lattice design based on desired functionality of the part.

Lattice structures can be considered as porous structures. In the case of topology optimization, the semi-dense elements are like the porous media. To refine the design, a second-phase involves a detailed sizing optimization where the end diameters of each lattice cell member are optimized. This allows for further weight reduction while meeting design requirements, such as buckling, stress, and displacement.

A piezo material can be actuated to generate a vibration that cancels incoming shock on the wearer. In one embodiment, the system tracks the shock such as the foot contact patterns and generates an anti-vibration signal to cancel the shock generated when the foot contacts the ground. In this embodiment, a processor receives foot ground contact using an accelerometer. The stride pattern is determined, and the next foot ground contact is detected, and the piezo material is actuated with a counter signal to cancel the expected shock. This is similar to the noise cancellation, except the vibration/shock is canceled.

In one hybrid embodiment, the shoes incorporate passive and active isolation elements. The passive component consists of springs which support the load weight and provide isolation over a broad spectrum. These springs provide a basic level of isolation in the lower frequencies and excellent isolation in the higher frequencies (above 200 Hz). They also support the load while allowing for travel of the actuators in the active component. The performance of the springs is augmented and corrected by an active isolation component. The active isolation component consists of vibration sensors, control electronics, and actuators. The vibration sensors are piezo accelerometers. A plurality of sensors in each isolation system are positioned in different orientations to sense in all six degrees of freedom. The piezo accelerometers convert kinetic vibration energy into electrical signals which are transmitted to the control electronics. The electronics reconcile and process the signals from the various sensors using a processor. The electronics then send a cancellation signal to the actuators. The actuators generate vibrations that are equal to the incoming vibrations but out of phase in relation to the incoming vibrations. This results in cancellation of the incoming vibrational noise, leaving the wearer undisturbed. This process occurs within 5-20 milliseconds of a vibration entering the system.

Blockchain Authentication

The IoT machines can negotiate contracts on their own (without human) and exchange items of value by presenting an open transaction on the associated funds in their respective wallets. Blockchain token ownership is immediately transferred to a new owner after authentication and verification, which are based on network ledgers within a peer-to-peer network, guaranteeing nearly instantaneous execution and settlement.

A similar process is used to provide secure communications between IoT devices, which is useful for edge IoT devices. The industrial world is adding billions of new IoT devices and collectively these devices generate many petabytes of data each day. Sending all of this data to the cloud is not only very cost prohibitive but it also creates a greater security risk. Operating at the edge ensures much faster response times, reduced risks, and lower overall costs. Maintaining close proximity to the edge devices rather than sending all data to a distant centralized cloud, minimizes latency allowing for maximum performance, faster response times, and more effective maintenance and operational strategies. In addition to being highly secure, the system also significantly reduces overall bandwidth requirements and the cost of managing widely distributed networks.

In some embodiments, the described technology provides a peer-to-peer cryptographic currency trading method for initiating a market exchange of one or more Blockchain tokens in a virtual wallet for purchasing an asset (e.g., a security) at a purchase price. The system can determine, via a two-phase commit, whether the virtual wallet has a sufficient quantity of Blockchain tokens to purchase virtual assets (such as electricity only from renewable solar/wind/ . . . sources, weather data or location data) and physical asset (such as gasoline for automated vehicles) at the purchase price. In various embodiments, in response to verifying via the two-phase commit that the virtual wallet has a sufficient quantity of Blockchain tokens, the IoT machine purchases (or initiates a process in furtherance of purchasing) the asset with at least one of the Blockchain tokens. In one or more embodiments, if the described technology determines that the virtual wallet has insufficient Blockchain tokens for purchasing the asset, the purchase is terminated without exchanging Blockchain tokens.

The present system provides smart contract management with modules that automates the entire lifecycle of a legally enforceable smart contract by providing tools to author the contract so that it is both judge/arbitrator/lawyer readable and machine readable, and ensuring that all contractual obligations are met by integrating with appropriate execution systems, including traditional court system, arbitration system, or on-line enforcement system. Different from the blockchain/bitcoin contract system where payment is made in advance and released when the conditions are electronically determined to be satisfied, this embodiment creates smart contracts that are verifiable, trustworthy, yet does not require advance payments that restrict the applicability of smart contracts. The system has a contract management system (CMS) that helps users in creating smart contracts for deployment. After template creation, FIG. 13A shows a flow diagram of the functionality of system in accordance with one embodiment when authoring a contract using one of the smart contract templates. In one embodiment, the functionality of the flow diagram of FIG. 13A is implemented by software stored in memory and executed by a processor. In other embodiments, the functionality can be performed by hardware, or any combination of hardware and software.

A smart contract is a computerized transaction protocol that executes the terms of a contract. A smart contract can have the following fields: object of agreement, first party blockchain address, second party blockchain address, essential content of contract, signature slots and blockchain ID associated with the contract. Turning now to FIG. 13A, at 2, the user logs into the system to author a smart contract. The system then retrieves the appropriate contract template for the user, and a user interface renderer displays the corresponding deal sheet user interface to the user. The selection of the appropriate contract template can be based on many factors, including the role of the user, the intended parties to the contract, the type of contract desired, etc. At 4, the user enters the information that is requested by the user interface based on the attributes displayed. Because the user interface is tailored specifically to the desired type of contract, the required contract terms information for that type of contract will be entered by the user as guided by the attributes of the template. The user may interact with the user interface through a single page or through multiple pages in a particular sequence with a forms wizard, or through the selection of tabs. In one embodiment, the user interface is rendered as a mark-up language such as XML showing the structure of the requirements of the contract. In other embodiments, the user interface is rendered as an Excel worksheet, Word document, or other application compatible format that can be read by the contracting parties, lawyers, judges, and jury. At 6, the contract is generated based on the user input to the user interface. The contract can be in the form of bytecodes for machine interpretation or can be the markup language for human consumption. If there are other contracts that are incorporated by reference, the other contracts are formed in a nested hierarchy similar to program language procedures/subroutines and then embedded inside the contract. At 8, the smart contract is assigned a unique block chain number and inserted into block chain. At 10, the smart contract is sent to one or more recipients, which open the payload and execute the terms of the contract and if specified contractual conditions are met, the smart contract can authorize payment. At 12, if dispute arise, the CMS can graphically decode the contract terms in the smart contract for a judge, jury, or lawyer to apply legal analysis and determine the parties' obligations.

Cloud Storage Security

In another aspect, a distributed file storage system includes nodes are incentivized to store as much of the entire network's data as they can. Blockchain currency is awarded for storing files, and is transferred in Bitcoin or Ether transactions, as in. Files are added to the network by spending currency. This produces strong monetary incentives for individuals to join and work for the network. In the course of ordinary operation of the storage network, nodes contribute useful work in the form of storage and distribution of valuable data.

In another aspect, a method for providing electronic content retrieval with cloud computing is provided. A first request message is received in real-time on the first cloud application stored on the cloud server network device with the one or more processors from a second cloud application. The first request message includes a request for desired cloud electronic content stored in the plural cloud storage objects stored on the selected ones of the plural other different cloud server network devices located on one or more of the networks comprising the cloud communications network. The plural different cloud storage objects function as a single secure storage object for electronic content on the cloud communications network. A cloud content location map is retrieved securely on the first cloud application on the cloud server network device. The cloud content location map includes address locations of the selected ones of the plural other different cloud server network devices on the cloud communications network. The first cloud application on the cloud server network device sends plural second request messages for the desired cloud electronic content to the selected ones of the plural other different cloud server network devices identified in the retrieved cloud content location map and located on one or more of the public communication networks, the one or more private networks, community networks and hybrid networks comprising the cloud communications network. The first cloud application on the first server network device combines the one or more individual components of the desired cloud electronic content from the plural cloud storage objects from the received plural response messages into a final desired electronic cloud content component. The first cloud application on the cloud server network device securely sends in real-time the final desired cloud electronic content component as the request desired cloud electronic content to the target network device via the cloud communications network. The second cloud application on the target network device cannot determine the desired cloud electronic content was split and was stored in plural cloud storage objects and cannot determine which of plural selected ones of the other different cloud server network devices on which ones of the public, private, community or hybrid networks on the cloud communications network may have stored portions of the final desired cloud electronic content, thereby providing a second and/or fourth layer of security and privacy for the desired cloud electronic content on the cloud communications network.

To enable an IOT device such as a car or a robot to access cloud data securely, and to grant access right to agents of the IOT device such as media players in the car, for example, the following methods can be used:

1. A method for accessing data, content, or application stored in a cloud storage, comprising: authorizing a first client device; receiving an authorization request from the first client device; generating an authorization key for accessing the cloud server and storing the key in a blockchain; providing the authorization key to the first client device; receiving the authorization key from an IOT device as a second client device working as an agent of the first client device; granting access to the second client device based on the authorization key; receiving a map of storage locations of cloud objects associated with an application or content, each storage location identified in a blockchain; and reassembling the application or content from the storage locations.

2. The method of claim 1 wherein the blockchain is decentralized and does not require a central authority for creation, processing or verification and comprises a public digital ledger of all transactions that have ever been executed on the blockchain and wherein new blocks are added to the blockchain in a linear, chronological order.

3. The method of claim 2 wherein the public digital ledger of the blockchain comprises transactions and blocks.

4. The method of claim 3 wherein blocks in the blockchain record and confirm when and in what sequence transactions are entered and logged into the blockchain.

5. The method of claim 3 wherein transactions comprise desired electronic content stored in the blockchain.

6. The method of claim 5 wherein the desired electronic content includes a financial transaction.

7. The method of claim 5 wherein the financial transaction includes a cryptocurrency transaction, wherein the cryptocurrency transaction includes a BITCOIN or an ETHEREUM transaction.

8. The method of claim 1 wherein an identifier for the received one or more blocks in the blockchain includes a private encryption key.

9. The method of claim 1 wherein the modified Galois field GF(pn) provides a secure digital wallet for the one or more received blocks in the blockchain.

10. The method of claim 1, comprising determining a plurality of address locations includes determining a plurality of virtual cloud communication network addresses, a plurality of Internet Protocol (IP) addresses, a plurality of Medium Access Control (MAC) addresses, Transmission Control Protocol (TCP) port designations, User Datagram Protocol (UDP) port designations, other networking protocol port designations or a combination thereof, of the selected ones of the plurality of other cloud server network devices on the cloud communications network.

11. The method of claim 1 wherein the one or more cloud storage object include one or more of a REpresentational State Transfer (REST) or Simple Object Access Protocol (SOAP), Lightweight Directory Access Protocol (LDAP) cloud storage objects, portions thereof, or combinations thereof.

12. The method of claim 1 comprising securely storing the received one or more blocks in the blockchain in one or more cloud storage objects, in an encrypted format including using a Discrete Logarithm Integrated Encryption Scheme (DUES), a Elliptic Curve Integrated Encryption Scheme (ECIES), a user generated biometric encryption method, or a Homomorphic encryption method.

13. The method of claim 1 comprising sending securely with the cloud application the one or more cloud storage object includes securely sending using a Wireless Encryption Protocol (WEP), Wireless-Wi-Fi Protected Access (WPA), Robust Security Network (RSN), Advanced Encryption Standard (AES), Data Encryption Standard (DES), Triple Data Encryption Standard (3DES), Secure Hash Algorithm (SHA), Message Digest-5 (MD-5), Electronic Code Book (ECB), Diffie and Hellman (DH), HyperText Transport Protocol Secure, (HTTPs), Secure Sockets Layer (SSL), one-time pad (OTP), Transport Layer Security (TLS) security method, Discrete Logarithm Integrated Encryption Scheme (DUES), a Elliptic Curve Integrated Encryption Scheme (ECIES), biometric or a Homomorphic encryption method.

14. The method of claim 1 wherein the target network device, cloud server network device and one or more other cloud server network devices communicating with the cloud server network device include one or more wireless communications interfaces comprising: cellular telephone, 802.11a, 802.11b, 802.11g, 802.11n, 802.15.4 (ZigBee), Wireless Fidelity (Wi-Fi), Wi-Fi Aware, Worldwide Interoperability for Microwave Access (WiMAX), ETSI High Performance Radio Metropolitan Area Network (HIPERMAN), Near Field Communications (NFC), Machine-to-Machine (M2M), Bluetooth or Infra DAta (IrDA) wireless communication interfaces.

15. The method of claim 1 wherein the target network device includes a mobile network device, smart network device or a wearable network device.

16. The method of claim 1 wherein the cloud application offers a cloud computing Infrastructure as a Service (IaaS), a cloud Platform as a Service (PaaS) and offers a Specific cloud software service as a Service (SaaS) including a specific cloud software service for storage and retrieval of the one or more received blocks in the blockchain.

17. The method of claim 1 wherein the cloud application, the cloud network server, the cloud target application and the target network devices and the cloud communications network are replaced with a peer-to-peer (P2P) applications, P2P network devices and a P2P communications network.

18. The method of claim 1 further comprising: the blockchain defining cryptocurrency transactions, wherein a valid cryptocurrency transaction in the blockchain is digitally signed, electronically spends one or more unspent outputs of previous cryptocurrency transactions, and the sum of cryptocurrency transaction outputs does not exceed the sum of cryptocurrency transaction inputs on the blockchain.

19. The method according to claim 1, comprising granting access to the second client device based on the authorization key comprises granting limited access limited in access type, number of accesses, data amount, access time, a pre-defined time period.

20. The method according to claim 1, comprising encrypting the authorization key subsequent to the step of generating an authorization key; and decrypting the authorization key after reception from the second client device.

21. The method of claim 1, comprising sending an identification of a requested service of the cloud server; and accessing the requested service according to the identification of the requested service of the cloud server identified in the authorization key request.

Automatic Execution of Smart Contract

While Ethereum mentions smart contract, it is actually mentioning the use of executable codes on the blockchain. For example, the Ethereum Solidity is a javascript like a language used to code smart contracts on the Ethereum platform. It compiles into a bytecode format that is understood by the Ethereum Virtual machine (EVM). It's a strongly typed language with the ability to define custom data structures. By smart contract, the present system is referring to contracts and agreements that are automatically executed, with conditions and terms similar to a legal contract.

Figure 13C:
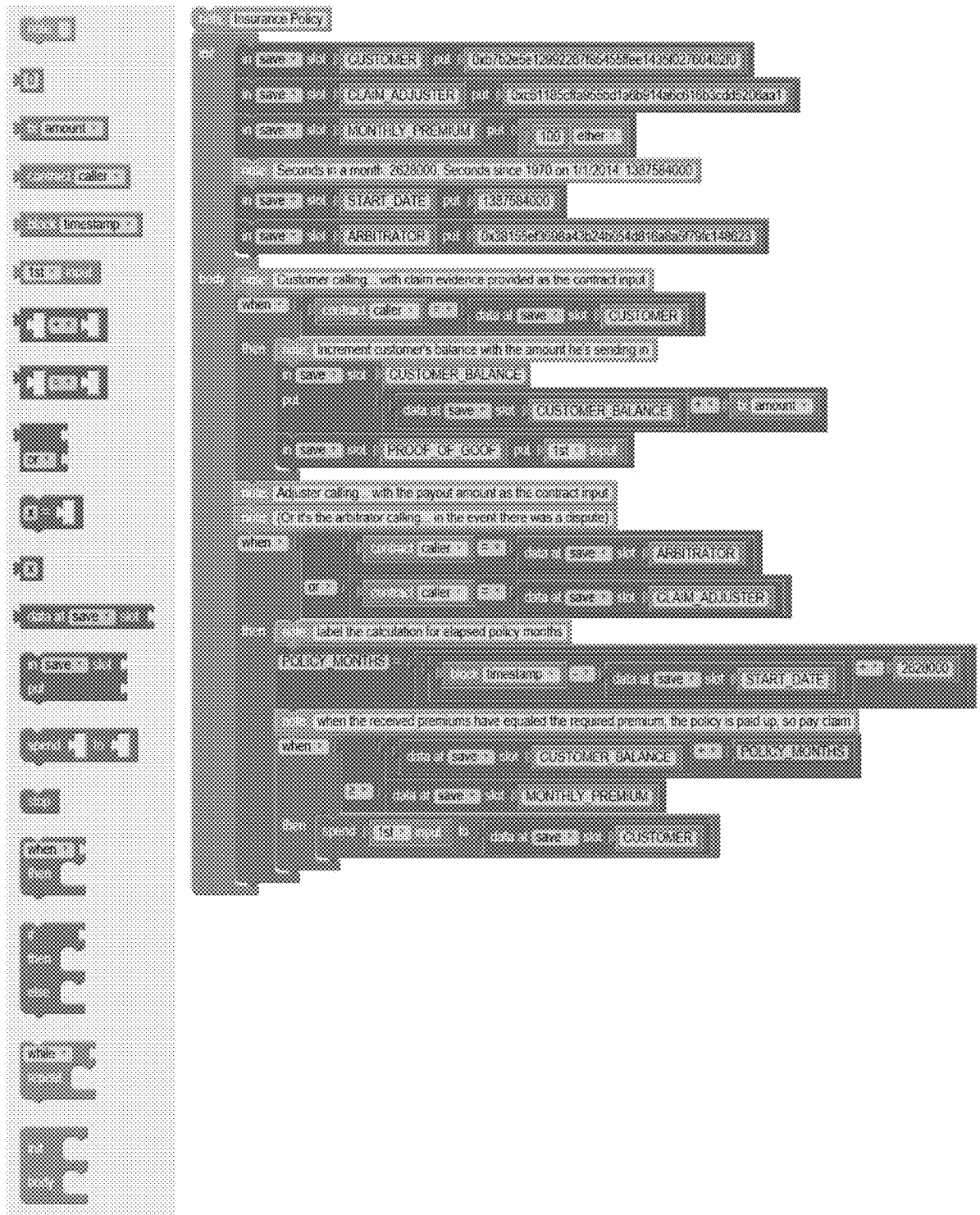

FIG. 1B show an exemplary smart contract specification user interface for a contract to buy a web site while FIG. 13C shows an exemplary UI for an insurance contract. Many different types of contracts are frequently needed to be created by organizations. For example, sell-side contracts may include contracts for selling products (e.g., inventory-based products), services (e.g., warranties), projects (e.g., construction), etc. Other types of contracts may be needed to be created when purchasing products and services. Further, specialized contracts may need to be created for leases, loans, intellectual property acquisition, etc. When authoring contracts, different types of contracts likely require different types of information to be captured. A generic contract authoring tool cannot easily accommodate creation of these different types of contracts in a simple user friendly manner. Embodiments allow a contract administrator to create multiple specialized user interface templates, also referred to as contract templates, or "deal sheet" templates, for many different types of contracts. A template may be based on the type of contract being authored, or be tailored for a particular user role. The system generates a contract template designer user interface that provides the ability to create and modify these templates. The template comprises a plurality of attributes organized in a predetermined and tailored way. The contract administrator may choose to create a template or modify an existing template. Modifying a template involves changing what attributes are included in the template and how they are organized. The contract administrator can include all the attributes that define a certain type of contractual arrangement or a subset of them and organize them in the most logical way. When the template is used for authoring by an end user, the system renders a user interface based on the template to the end user. The user interface rendered to an end user based on the template can be referred to as a "deal sheet".

The UI can operate with blockchains such as Bitcoin or Ethereum. Rather than have multiple separate silos, a blockchain (in its purest form) can act as a unified database that's accessible (on a read and write basis) by everyone (it is in effect "permissionless"). The ledger stored on a blockchain is shared amongst a distributed network of computers. The use of cryptography enables users to modify the master ledger without the need for a central authority. With a blockchain there is no need for a central trusted authority or for intermediaries. The disintermediation of intermediaries can redefine the value chain in a wide range of industries, from financial services to media, and puts the power and value of data back in the hands of the people creating that data. Blockchains can be public (such as the Bitcoin blockchain or the Ethereum blockchain)—these are effectively permissionless, or they can be private (where access is restricted to a selected group of users). Advantages of the blockchain smart contract may include one or more of the following:

Preferably, the system uses Ethereum which has a complete programming language, sometimes called EtherScript. Since most agreements involve the exchange of economic value, or have economic consequences, categories of public and private law are implemented using Ethereum. An agreement involving transfer of value can be precisely defined and automatically enforced with the same script. FIG. 13C show an exemplary smart contract specification user interface (UI) for a contract to buy a web site while FIG. 13B shows an exemplary UI for an insurance contract. Smart contracts can have scriptable clauses that are executed in a runtime using the Ethereum environment in one example, and can have multiple parties, each with their own agents and asset accounts. Funds transfers go through a controlled interface, with notices and receipts sent to all relevant parties. The script code is unable to manipulate any assets excepting those explicitly declared beforehand on the smart contract, and verified as valid property of a legitimate party to the contract by looking up ownership information in the blockchain, among others. And when funds are moved, it's to a contract-specific name, not an account ID. The smart contract can move_funds( ) between these declared accounts, as its script logic dictates, but it can also stash_funds( ) directly inside the contract itself! For example, during an escrow, funds might be stashed inside the smart contract for 14 or 30 days, and then transferred to one party or another. Scripted clauses can also be configured to trigger on certain events. Variables can be defined in the smart contract, which persist through its entire lifetime. As the smart contract—including its internal state—continues to process over time, receipts will continue to drop into the relevant parties' inboxes, showing the change in state, in those variables, over time. Smart contract variables can be defined as "Constant" (value cannot change), "Persistent" (value can change, and will persist between script runs), and "Important" (value is persistent, AND any changes in the value will result in server notices being sent to the parties.)

A designer user interface ("UI") can be used to create a template in accordance with one embodiment. The template is customized/designed to allow a user to create a sales contract, and includes multiple regions that receive business terms input from a user when preparing the contract. A general information region receives general information regarding the contract. Customer information region receives information about the customer that is purchasing the product, including customer contacts and blockchain address that can be added through an add contact button. Product information region receives information about the products, and additional products can be added through an add product button. Payment and other information region receives the financial information about the contract.

For example, a smart contract template is customized for a purchasing contract of a service by a buyer, and includes multiple regions that receive input from a user when preparing the contract. Template includes a requesting region for receiving information regarding the requesting buyer and a vendor region for receiving information on the vendor. A scope of work region is used to receive information about the scope of the service that the vendor will provide. A payment region receives payment information and other information region receives other information. In one embodiment, boxes pop up when a user selects one of the options of action box. The user can interface with the boxes to modify the contract templates. For example, as shown, when "Add User Variable" is selected, a box pops up. A UI box allows a user to add variables to the contract template. When one of the user variables is selected, such as the "vendor access" variable, a properties box opens that allows properties of that variable to be defined, which controls how it appears to the user using the template. Properties can include specifying a prompt (e.g., "Will Vendor require access to facility?") and specifying a default value that will be displayed when the deal sheet based on this template is rendered (e.g., default value of "yes"). When "Add Instruction Text" is selected, a box pops up and the text of an instruction and the region in which the instruction should be inserted can be entered. In another box, the "Attach Word documents that describe scope of work and buyer obligations (if any)" instruction is added to another region of template, for example. When "Edit Form Properties" is selected, a box pops up allowing properties of the contract template to be changed. In one embodiment, the various regions that form the template can be presented to the user when authoring a contract in a single page or can be individually presented to the user as separate tabs or in the form of a wizard that that asks for information in multiple pages in a particular sequence. Further, the various region headers of the contract template can be displayed in different ways, such as in a box and/or as a heading with underline. Other properties can also be defined in box. One embodiment provides an "Add Tab/Wizard step" action box. Upon selection of the "Add Tab/Wizard step", a tab or wizard step is added in an implementation where the contract template will be filled out using separate tabs or a forms wizard. Another embodiment that illustrates the action for the "Add from Data Catalog" UI button, for example. Upon selection of "Add from Data Catalog" a UI pops up, which allows a user to select an attribute from contract catalog data database. A catalog items table list all items that can be selected and added to one of the regions of the contract template. When an item is selected, a box allows certain properties about that item to be defined. Therefore, for the "Payment Terms" item (which is a single valued variable), the prompt (as it is intended to appear in the template) can be defined, and the default value can also be defined.

A "Preview Form" button can be used to display the template that was designed by the user exactly as it would appear for an end user who is authoring a contract using this template. When a contract template is created using contract template designer through interaction of the UIs shown, the template may be saved in database. Subsequently, user interface renderer may retrieve the template and display the template to an end user to input the required information in order to author the contract. The type of template that is rendered to the end user may be determined automatically by the system based on various factors such as the type of contract being authored (e.g., sales, purchase, etc.), the role of the user, etc.

Next, the functionality of system in accordance with one embodiment is detailed when creating a contract/deal sheet template that can be used for authoring a contract. In one embodiment, the functionality of the flow diagram is implemented by software stored in memory and executed by a processor. In other embodiments, the functionality can be performed by hardware, or any combination of hardware and software. To set up, the contract administrator logs onto the template designer application and a previously created contract template designer UI is retrieved to be modified, or a new design is created. In one embodiment, the contract template designer UI is retrieved from database and displayed through an Internet browser to a user at a client computer. The contract template designer UI includes user actions through a UI that allow attributes of the contract template to be customized for a specific type of contract. The system receives user attribute requests from the contract administrator and modifies the contract template accordingly. The attribute requests are generated by the contract administrator through various actions in the designer tool. The modified contract template is stored in data catalog for later use in order to create the contract.

In addition to Ethereum, other blockchain or globally shared, transactional database can be used. To change something in the database, the system creates a transaction which has to be accepted by all others. One embodiment runs on an Ethereum Virtual Machine or EVM as the runtime environment for smart contracts in Ethereum. It is not only sandboxed but actually completely isolated, which means that code running inside the EVM has no access to network, filesystem or other processes. Smart contracts have limited access to other smart contracts. There are two kinds of accounts in Ethereum which share the same address space: External accounts that are controlled by public-private key pairs (i.e. humans) and contract accounts which are controlled by the code stored together with the account. The address of an external account is determined from the public key while the address of a contract is determined at the time the contract is created (it is derived from the creator address and the number of transactions sent from that address, the so-called "nonce"). Every account has a persistent key-value store mapping 256-bit words to 256-bit words called storage. Furthermore, every account has a balance in Ether (such as in "Wei") which can be modified by sending transactions that include Ether.

A transaction is a message that is sent from one account to another account (which might be the same or the special zero-account, see below). It can include binary data (its payload) and Ether. If the target account contains code, that code is executed and the payload is provided as input data. If the target account is the zero-account (the account with the address 0), the transaction creates a new contract. As already mentioned, the address of that contract is not the zero address but an address derived from the sender and its number of transactions sent (the "nonce"). The payload of such a contract creation transaction is taken to be EVM bytecode and executed. The output of this execution is permanently stored as the code of the contract. This means that in order to create a contract, you do not send the actual code of the contract, but in fact code that returns that code. Upon creation, each transaction is charged with a certain amount of gas, whose purpose is to limit the amount of work that is needed to execute the transaction and to pay for this execution. While the EVM executes the transaction, the gas is gradually depleted according to specific rules. Each account has a persistent memory area which is called storage. Storage is a key-value store that maps 256-bit words to 256-bit words. It is not possible to enumerate storage from within a contract and it is comparatively costly to read and even more so, to modify storage. A contract can neither read nor write to any storage apart from its own. The second memory area is called memory, of which a contract obtains a freshly cleared instance for each message call. Memory is linear and can be addressed at byte level, but reads are limited to a width of 256 bits, while writes can be either 8 bits or 256 bits wide. Memory is expanded by a word (256-bit), when accessing (either reading or writing) a previously untouched memory word (ie. any offset within a word). At the time of expansion, the cost in gas must be paid. The EVM is not a register machine but a stack machine, so all computations are performed on an area called the stack. It has a maximum size of 1024 elements and contains words of 256 bits. Access to the stack is limited to the top end in the following way: It is possible to copy one of the topmost 16 elements to the top of the stack or swap the topmost element with one of the 16 elements below it. All other operations take the topmost two (or one, or more, depending on the operation) elements from the stack and push the result onto the stack. Of course it is possible to move stack elements to storage or memory, but it is not possible to just access arbitrary elements deeper in the stack without first removing the top of the stack.

The instruction set of the EVM is kept minimal in order to avoid incorrect implementations which can cause consensus problems. All instructions operate on the basic data type, 256-bit words. The usual arithmetic, bit, logical and comparison operations are present. Conditional and unconditional jumps are possible. Furthermore, contracts can access relevant properties of the current block like its number and timestamp.

Contracts can call other contracts or send Ether to non-contract accounts by the means of message calls. Message calls are similar to transactions, in that they have a source, a target, data payload, Ether, gas and return data. In fact, every transaction consists of a top-level message call which in turn can create further message calls.

A contract can decide how much of its remaining gas should be sent with the inner message call and how much it wants to retain. If an out-of-gas exception happens in the inner call (or any other exception), this will be signalled by an error value put onto the stack. In this case, only the gas sent together with the call is used up. In Solidity, the calling contract causes a manual exception by default in such situations, so that exceptions "bubble up" the call stack.

As already said, the called contract (which can be the same as the caller) will receive a freshly cleared instance of memory and has access to the call payload—which will be provided in a separate area called the calldata. After it finished execution, it can return data which will be stored at a location in the caller's memory preallocated by the caller.

With a message call, named delegatecall which is identical to a message call apart from the fact that the code at the target address is executed in the context of the calling contract and msg.sender and msg.value do not change their values, a contract can dynamically load code from a different address at runtime. Storage, current address and balance still refer to the calling contract, only the code is taken from the called address.

Contracts can create other contracts using a special opcode (i.e. they do not simply call the zero address). The only difference between these create calls and normal message calls is that the payload data is executed and the result stored as code and the caller/creator receives the address of the new contract on the stack. More information on Solidity is at Introduction to Smart Contracts at http://solidity.readthedocs.io/en/develop/introduction-to-smart-contracts.html, the content of which is incorporated by reference.

FIG. 13D shows another exemplary process executed by the smart contract system. In (20) Buyer requests to obtain the service or item from the service or item provider. In (24) Item provider utilizes the blockchain system described above and generates a cryptographic key pair and in (26) the service or item provider embeds the key data in the service or item. In (28) the service or service or item provider stores the private key in association with an entity credential in the database. In (30) a third party validates the terms of the smart contract with the private key. In (32) the blockchain or shared ledger is analyzed to determine if key data was used and if contractual terms are satisfied according to contract law expert system and if so mark the satisfaction of the contract terms. In (34) the seller/provider is paid based on smart contract and service or item is then made available to the buyer.

FIG. 13E shows one embodiment of a system (100) for monitoring compliance with a smart contract. The system (100) includes a seller, provider or Offeree machine (110), an Offeror machine or buyer (120), and a financial system (130) providing at least one store of value (132). The Offeree machine (110) possesses, controls or otherwise has access to a service, product or item (112) which is to be made available to the Offeror machine upon acceptance (120). In the embodiment of FIG. 13, and primarily for illustrative purposes, the item (112) is a software application and service provider (110) is a software developer. The Offeror machine or buyer (120) has an electronic computing device (122), in this embodiment a desktop computer, by which it is able to communicate with the service or item provider (110). Communications between the service or item provider (110) and the electronic computing device (122) of the authorized entity (120) may be effected by way of any suitable wired or wireless communications channel. In this embodiment, the communications channel is the Internet. The Offeree machine or seller (110) has associated therewith an item receiving module (114) configured to receive the online service (software, music, video, . . . ) or physical item (112) and an embedding module (116) in communication with the item receiving module (114) configured to embed key data (134) in the service or item (112). The key data (134) is associated with the store of value (132) and usable to conduct a transaction against the store of value (132), a record of such a transaction becoming visible in a transaction ledger (140). One of the contracting parties, for example the Offeror machine or buyer (120), has associated therewith a monitoring module (115) configured to monitor the transaction ledger to determine whether a transaction against the store of value has occurred, and a designation module (117) in communication with the monitoring module (115) and configured to designate the item (112) as accessed by a third party in the event that a transaction against the store of value has occurred. A database (118) is operative in association with the item provider (110). The database (118) is configured to store the key data (134) embedded in the service or item (112) or data at least partially derived therefrom in association with an entity credential of the authorized entity (120) which is authorized to possess the service or item (112).

Figure 13F:
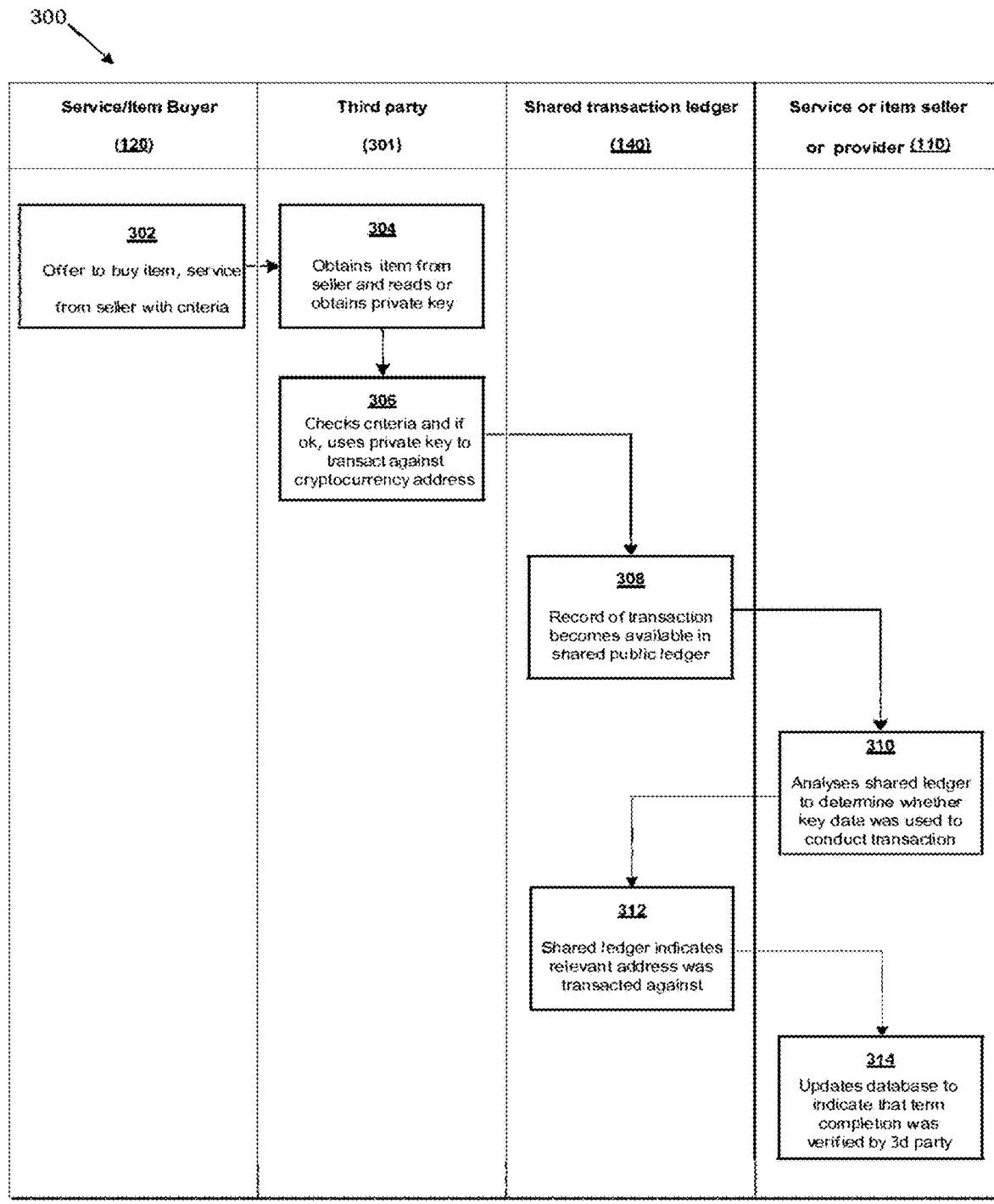

FIG. 13F shows a block diagram (200) that illustrates a method of validating completion of the term of the smart contract, using the system of FIG. 13D. At a first stage (202), the buyer (120) requests to obtain the service or item (112) from the service or item provider (110). For example, the buyer (120) accesses a website of the provider (110) using the electronic computing device (122) and selects a custom app or video, for example, to purchase. The key data (134) which is to be embedded in the service or item (112) is an identifier uniquely associated with the store of value (132). The store of value (132) has a balance of digital currency. The financial system (130) of FIG. 13 is a system for digital currency in the form of a blockchain. In this embodiment, the store of value (132) is a blockchain address. Cryptocurrencies allow digital currency to be transferred between blockchain addresses without an intermediate financial institution or central authority. Exemplary blockchain systems include peer-to-peer, decentralized cryptocurrencies such as Ethereum (ETH), Bitcoin, Litecoin and PPCoin.

In this embodiment, the blockchain address (132) is represented by or derived from a blockchain public key corresponding to a blockchain private key. The public key is used and/or derived to obtain the blockchain address (132), the address (132) having a specific balance of blockchain held therein. At a next stage (204), the item provider (110) utilizes the blockchain system described above and generates a cryptographic key pair, in other words, a private key and a public key associated with a blockchain address (132). In this embodiment, the service or item provider (110) generates the key pair and transfers funds to the blockchain address (132). The private key represents a direct monetary value which can be traded in the blockchain system. In the case where the blockchain is, for example, Bitcoin or another blockchain system using a similar key and address scheme, the blockchain address (132) has a particular balance associated therewith, indicated, for example, as 3.5 BTC or 0.0001 BTC in the case of Bitcoin. At a next stage (206), the service or item provider (110) embeds the key data in the service or item (112) using the embedding module (116). In the embodiment of FIG. 13F, the key data (134) is the private key associated with the blockchain address (132). The service or item receiving module (114) typically receives the media item (112) before the private key (134) is embedded therein, from where it is transferred to the embedding module (116). In this embodiment, the private key (134) is embedded in the media item (112), which is an e-book, as a one-dimensional barcode (113). At a next stage (208), the service or service or item provider (110) stores the private key (134) in association with an entity credential in the database (118), as described above. In this embodiment, the entity credential includes a name, address and contact details of the authorized entity (120). The database (118) therefore acts as a registry of keys, enabling the item provider (110) to keep track of which private keys are associated with which buyer (120). The service or item (112) is then, at a next stage (210), made available to the authorized entity (120). In this embodiment, the authorized entity (120) may typically be able to download the e-book and store it locally or in any physical or cloud-based storage location as desired. At (212) Shared ledger is analyzed to determine if key data was used and if so mark the satisfaction of the contract terms and (214) Seller/provider is paid based on smart contract and service or item (112) is then made available to the buyer (120). Records of all transactions conducted in the financial system (130) are held in the transaction ledger (140). In the embodiment, the transaction ledger (140) is a publicly visible shared transaction ledger. Typically, the shared transaction ledger (140) includes all these transactions as a chain of transaction records or receipts, commonly referred to as a "block chain" in at least one known cryptocurrrency system. These transaction records are signed using both a private key and a public key, the private key being that of a party transferring value and the public key being associated with a receiving address. The shared transaction ledger (140) is typically publicly accessible via a website or other Internet-based platform.

Transaction records are verified by third parties carrying out what is known as "mining blocks". Exemplary cryptocurrencies which make use of proof-of-work verification schemes, such as Secure Hash Algorithm 256 (SHA-256) or scrypt, are Bitcoin and Litecoin. An exemplary blockchain system employing a combined proof-of-work/proof-of-stake verification scheme is PPCoin. The principles and functioning of such cryptocurrencies having shared transaction ledgers containing transaction records will be well understood by those skilled in the art. Importantly, such a system allows a party having access to a private key or data at least partially derived therefrom to transact against a corresponding blockchain address, in other words, either use the funds linked to the address or transfer the funds to a receiving address. These systems also allow any party to inspect or analyze the shared transaction ledger to determine whether a particular address was transacted against. In the embodiment of FIG. 13F, the monitoring module (115) is used to inspect or analyze the shared transaction ledger (140), for example by using a web-based platform providing at least some of the transaction records, as illustrated in FIG. 13, whereby transaction records in the shared transaction ledger (140) can be accessed.

The buyer is therefore provided with a service or item which has a reliable handle to a store of value embedded therein. Should the private key (134) not be read from the media item and used to transact against the blockchain address, the funds stored therein remain untouched and the buyer either retains a deposit or token amount or is not held accountable and/or liable for the work done by the provider or seller (110).

However, if the service or item (112) is checked by a third party, leading to the private key (134) being read from the service or item (112) and used to transact in the blockchain system, some or all of the funds may be spent as part of the transaction verification overhead to one or both of the buyer (120) and the seller/provider (110). Furthermore, the transaction is visible in the shared transaction ledger (140), making the possibly fraudulent activity immediately or relatively quickly traceable. Upon verification, the payment for the completion of the contract term is automatically processed by the smart contract.

The flow diagram (300) of FIG. 13F illustrates a sequence of steps whereby a completed contract term is verified. At a first stage (302), the buyer (120) makes an offer to buy under specific criteria services or items (112). At a next stage (304), a third party verifier (301) reviews the service or item (112) and reads the private key (134) from the media item (112). In the example of an application or a custom video embedded with key data by way of a barcode described with reference to FIG. 13, the third party (301) may use a barcode-reading technique to obtain the private key (134) which is embedded in the e-book.

The private key may be readable from the service or item by any third party that accesses the item either directly or using a software tool. The software tool may, for example, be a publicly available software tool. The third party (301) verifies that the requirements for the term of the contract are satisfied and then, at a next stage (306), utilizes the blockchain system to move funds from the blockchain address (132) corresponding to the private key (134) to a desired address, or spends all or some of the funds in any other way.

Use of the private key (134), which serves as or may be derived from the key data uniquely associating the authorized entity (120) with the service or item (112), may typically include use of the private key (134) and a receiving public key to conduct a blockchain transaction against the blockchain address (132) in favor of a receiving blockchain address. Such a transaction may involve transferring at least some of a balance of blockchain held at the blockchain address (132) to a second, receiving blockchain address represented by or derived at least partially from a second, receiving blockchain public key.

After the third party (301) has conducted the above transaction, at a next stage (308), a record of the transaction becomes visible in the shared transaction ledger (140) or "block chain". The service or item provider (110) or any other party fulfilling this function analyses the shared transaction ledger (140) at a next stage (310) to determine whether the private key (134) was used to conduct a transaction. In this case, due to the transaction conducted by the third party (301), the shared transaction ledger (140) indicates, at a next stage (312), that the blockchain address (132) was transacted against and therefore that the private key (134) was used after validating the terms of the smart contract.

The service/item provider (110), at a final stage (314), in response to determining that a transaction was conducted against the store of value using the identifier which was embedded in the service or item (112), updates the database (118) to indicate that the identifier was used to transact against the value store, in other words, that the private key (134) was used as payment for validating satisfaction of contractual term(s). This prompts the item provider (110) or other party managing the monitoring of the shared transaction ledger (140) to designate the item (112) terms as satisfactorily verified by a third party.

The transaction record in the shared transaction ledger (140) may be used by the item provider (110), or, of course, by any entity or agent monitoring the shared transaction ledger (140) on behalf of the item provider (110), to extract, obtain or derive the private key (134), public key or simply the blockchain address. The obtained information is matched with the key data stored in the database (118) in association with the entity credential. In this way, the authorized entity (120) may be unambiguously identified and the item provider (110) is able to obtain payment pursuant to the smart contract.

It should be noted that, throughout the entirety of this specification, wherever the terms "private key", "key data", "public key", "blockchain address", or the like is used, the term may, of course, refer to any derivation thereof that can be used to reliably obtain the identifier or data signified by the term used. Such a derivation of the private key, for example a cryptographic hash thereof, may therefore be embedded in the service or item. Importantly, the key data embedded in the service or item includes the blockchain private key or an address identifier derived at least partially from the blockchain private key. For example, the address identifier may be a link, a tool or any other identifier usable to obtain or access the private key.

Throughout the entirety of this specification, the term "database" should be interpreted so as to have its broadest meaning, and includes any data storage means whereby a credential of an entity can be reliably stored in association with key data or derivatives thereof.

The service or item provider may, for example, be any media item or content provider or any digital or analogue media distributor. For example, the service or item provider may be a satellite television service provider, a broadcasting corporation, a physical music or video distributor, an author, a photographer, a composer, an artist, a software provider or a publisher.

The service or item provider may, in one scenario, be the author, creator or producer of the service or item, for example, in the case that the service or item provider is an artist. The service or item provider may, in a different scenario, be a distributor, retailer, or commercial service or item provider, for example, in the case that the service or item provider is a software provider.

The service or item provider may be any other suitable entity in cases where the service or item is not a media item. For example, the service or item provider may be a plant breeder, developer or researcher in cases where the service or item is a biological or genetic item.

The service or item is not restricted to a media item and may be any item capable of being embedded with any form of data for the purpose of monitoring third party access to the service or item. The service or item may be a physical item such as a book, a compact disc, a physical document, or a work of art, an electronic item such as digital media, a biological item such as a genetic sequence or biological matter, or any other item capable of being embedded with data.

Particularly, the service or item may be a digital media item or analogue media item. In cases where the media item is in a digital form, it may be, among many others, one or more video files, one or more audio files, one or more electronic document files, one or more electronic books, one or more textual media files, one or more computer program files, computer gaming files or data, streaming media, and one or more image files. In cases where the media item is in analogue form, it may, for example, be one or more video recordings or one or more audio recordings. The media item may be textual media such as hypertexts, multimedia, digital art, e-mail, and the like.

The electronic computing device is not limited to a desktop or personal computer and may be any other communications device with substantially similar communications abilities, such as a mobile phone, a tablet computer or a laptop computer.

Communications between the service or item provider and the electronic computing device of the authorized entity may, in alternative embodiments, be effected by way of a voice call or a mobile software platform used to request the service or item from the service or item provider.

In further embodiments, the authorized entity may communicate with the service or item provider without using electronic communications means. For example, the authorized entity may physically request and/or receive the service or item from the service or item provider, such as by way of a postal or courier service, or through over-the-counter sale or delivery.

The authorized entity may be any suitable entity, living or non-living, which is to receive the service or item from the service or item provider. For example, the authorized entity may be a consumer, institution, group, organization, electronic platform, or database receiving the service or item from the service or item provider. It should be appreciated that the same service or item or copies or derivatives thereof may be provided to a plurality of authorized entities in further embodiments of the system. Furthermore, the authorized entity may be an original owner, author or creator of the service or item or may otherwise have rights in respect of the service or item.

The entity credential may be any suitable information serving to identify the authorized entity, for example, one or more of a name, an address, an e-mail address, a financial account number, a media service membership identifier, an identity number, contact details such as an a telephonic contact number, a physical address, employer information, details of a financial account and media service subscription information.

The key data may be any data or information capable of being used directly or indirectly to conduct a transaction against the store of value, either in the form in which it is embedded in the service or item or a form derived therefrom.

The key data may be stored in the database such that, when the key data embedded in the service or item or data derived therefrom is subsequently obtained by the service or item provider from a source other than the database, it is able to match the key data with the entity credential in the database in order to unambiguously identify the authorized entity. Typically, the key data is subsequently obtained from a record of a transaction against the store of value from which the key data can be extracted or derived.

The key data may be embedded in the service or item using any suitable information embedding technique, depending of course on the service or item type. In embodiments of the system, the key data is embedded using one or more of the following techniques: embedding the key data in the service or item using digital watermarking, embedding the key data in the service or item using analogue watermarking, embedding the key data in the service or item as a one-dimensional or two-dimensional barcode, embedding the key data in the service or item as a graphical code, embedding the key data in the service or item using steganography, embedding the key data in the service or item using natural language watermarking or natural language morphology, embedding the key data in the service or item using hidden text or invisible text or binary data embedding, and embedding the key data in the service or item using visible text or visible binary data embedding. In some embodiments, the service or item is a biological or genetic item and the key data is embedded, for example, in a genetic sequence.

A further example of an embedding technique is natural language watermarking or natural language morphology, whereby, for example, sentence construction of a document may be watermarked. In one example, the structure of one or more sentence constituents in a natural language text may be used to insert a watermark into a document.

Preferably, the key data is embedded using a robust technique, which makes it relatively easy to read or derive the private key, while completely removing, obscuring or obliterating the key data from the service or item is made comparatively difficult. In some embodiments, removing the key data from the service or item destroys the item, makes the value associated with the blockchain address unusable, materially alters the item's content or makes it subsequently unusable.

The scope of the system thus extends to any suitable information embedding technique. For example, the private key may simply be included in plaintext form in an electronic document or video, included in audio format in an audio or video file, or printed in a physical document.

It should also be appreciated that more than one set of key data, in other words, more than one private key or derivation thereof, may be embedded in a single service or item. Furthermore, the same set of key data may be embedded in multiple service or items. An example of such a case is a scenario wherein the authorized entity has an account at an online media library, such as iTunes. Any media item purchased or obtained using the account may then be embedded with the same key data or sets of key data, such that distribution of any or all of these media items may be unambiguously traced back to the authorized entity and/or the account.

In cases where more than one different private key is embedded in the service or item, each private key corresponds to a separate blockchain address having a balance of blockchain. Alternatively, a single private key embedded in the service or item may be associated with a plurality of blockchain addresses in the database, the authorized entity typically being held liable for funds held in one or more of the plurality of addresses.

It is foreseen that the service or item provider may have management software used for any one or more of the following functions: to receive the service or item using the service or item receiving module, to generate the necessary cryptographic key pairs, to store keys in association with entity credentials, to embed private keys in service or items using the embedding module, to distribute or otherwise allow entities to obtain requested items, to monitor the shared transaction ledger using the monitoring module, and to use the designation module to designate a service or item as accessed by a third party in the event that a transaction against a particular blockchain address becomes visible in the shared transaction ledger. Designating a service or item as accessed by a third party may refer to any action taken an entity to confirm or establish that the key data embedded in the service or item was compromised and used to transact against the relevant blockchain address.

The blockchain address may be controlled and/or managed by any party capable of monitoring the transaction ledger to determine whether a transaction against the store of value has occurred. The party may typically be an individual having ownership or control of the service or item, a group having ownership or control of the service or item, the authorized entity itself, the service or item provider as described above, or a third party associated with the service or item provider.

It should specifically be noted that the blockchain address may be controlled and/or managed by a third party embedding service provider. In such cases, one or more of the service or item receiving module, the embedding module, the monitoring module, the designation module and the database may be associated with the embedding service provider such that the embedding service provider is capable of embedding the key data in the service or item on behalf of the service or item provider and performing one or more of the further functions associated with the modules mentioned and the database.

The service or item may be embedded with the key data by the embedding service provider on behalf of the authorized entity. In such cases, embedding the service or item with the identifier and/or the managing of blockchain addresses and keys are outsourced to and carried out by an external service provider.

It should be appreciated that the entity controlling and/or managing the blockchain address may elect to change the balance of blockchain stored at the blockchain address by conducting transactions against the address to increase or decrease its value. Such action may be taken, for example, in response to the service or item becoming compromised or to create a reward or incentive for finding the service or item and/or the key data embedded therein.

It should be appreciated that the service or item may have various formats and is not limited to the transfer of a file or document. In one example, the authorized entity may select media content to stream or video content to download to a personal device.

In addition to the use of a blockchain system, any suitable conventional payment systems and channels may be employed to purchase, rent or otherwise transact to obtain the service or item. Alternatively, no conventional payment may be required.

In the embodiment of FIG. 13F, the blockchain address is controlled and managed by the service or item provider. The service or item provider then generates the key pair and transfers funds to the blockchain address.

Alternatively, the blockchain address may be associated with a key pair of the authorized entity, the authorized entity providing the service or item provider with the private key to enable the service or item provider to uniquely identify transactions conducted against the blockchain address. The authorized entity may have generated the key pair, provides the private key to the service or item provider, and the service or item provider transfers funds to the blockchain address. In a further embodiment, the authorized entity, after generating the blockchain address and transferring funds to the blockchain address, provides the private key to the service or item provider.

In an exemplary blockchain system, Bitcoin, the blockchain address is a 160-bit hash of the public portion of a public/private Elliptic Curve Digital Signature Algorithm (ECDSA) keypair. In at least one known blockchain system, the blockchain address is therefore algorithmically converted from a public key. However, it should be appreciated that the blockchain address may be the public key itself, or any other identifier derived at least partially from the public key. The blockchain address and public key may thus comprise different values or strings of characters that are uniquely associated with each other such that the private key remains unambiguously linked to the blockchain address. The system is not limited to one or more particular blockchain systems, as will be apparent to those skilled in the art.

In embodiments of the system, the balance associated with the blockchain address may be less than an inherent value of the service or item.

The service or item may be made available to the authorized entity permanently. This may typically be the case for physical or biological items or media items such as, among others, music files, software and electronic books. If the service or item is made available to the authorized entity permanently, the authorized entity may be held liable for unauthorized distribution of the service or item at any time after the service or item is made available to the authorized entity.

Alternatively, the service or item may be made available for a predefined period of time or until a predefined condition is met. For example, the service or item may be streaming media, in which case the authorized entity is only held liable for compromising the private key embedded in the media during a specific timeframe, for example, until streaming has ended. A predefined condition which lifts accountability and/or liability from the authorized entity may be returning of the service or item to the service or item provider. Alternatively, the service or item provider may monitor the shared transaction ledger for a period of time to determine whether the blockchain address is transacted against before liability is lifted. Alternatively, the authorized entity may be held liable.

In one embodiment for corporate management, the blockchain comprises code for storing a stock identifier (ID), a stock certificate number with stock quantity. Other embodiments may include:

code to determine a share registry or a capitalization table from each stock certificate number and stock quantity, code to distribute shareholder communication from a share registry or a capitalization table, code to collect secure shareholder votes from a share registry or a capitalization table for transparent corporate governance, code to provide financial information to shareholder a share registry or a capitalization table for corporate governance, or code to enforce majority or supermajority shareholder votes from a share registry or a capitalization table for corporate governance.

In one or more embodiments, the described technology adapts and/or generates cryptographic wallet which holds a new cryptographic currency (i.e., an Ether, bitcoin, or blockchain token) and corresponding cryptographic protocol for exchanging items of value between nodes on a peer-to-peer network. Rather that representing a single transferable, object an Blockchain token wallet holds multiple stock items (such as shares in companies). For example, "IBM" (the stock market symbol of the company by the same name) can also be a share used by the peer-to-peer network to refer to IBM stock. A stock ID, in some embodiments, is determined (and invalidated) by an issuer. An issuer (e.g., a company, underwriter, municipality, government, etc.) can have multiple stock entries to represent different types of items of value. For example, IBM stocks can be represented by symbols "IBM-S" and IBM bonds by PIC "IBM-B". In some embodiments, stock shares are issued (and destroyed) by highly authoritative entities. For example, dollars available on the Blockchain token network represented by, e.g., PIC "USD" may be authoritatively issued by, for example, the U.S. Treasury. However, the described technology can issue stock/security shares based on various other techniques (e.g., network node agreement, exchange regulation, lease or purchase, auction, etc.) and can be named based on, e.g., a company's name, its market symbol, its branding, its security name, availability, or a preferred format (e.g., length, abbreviation, etc.).

A Blockchain token wallet or transaction can house a single security, as described above, or multiple denominations of the same security. Blockchain tokens are exchangeable for, e.g., other Blockchain tokens and/or other cryptographic currencies.

The system generates and/or modifies a cryptographic currency wallet for enabling a shareholder to use a wallet as his security and cash account. The wallet is a software and/or hardware component for facilitating market transactions, securely storing Blockchain tokens on multiple Security/share (e.g., via one or more private keys), and providing other technology such as generating and maintaining cryptographic keys, generating local and network messages, generating market orders, updating ledgers, performing currency conversion, and providing shareholder management functions such as voting and allowing access to secured corporate information for corporate management transparency (real-time balance sheet and income statement and any required regulatory disclosures such as insider trading or lawsuits), for example. The wallet stores Blockchain tokens regardless of their stock ID, position, or quantity. In some embodiments, the wallet can substitute fungible currencies. For example, 100 individual Blockchain tokens of pennies can be internally exchanged by the described technology for a single dollar Blockchain token.

As described above, in various embodiments, the system generates Blockchain token transactions based on the wallet's content. For example, Trader A decides to exchange 5 IBM-S Blockchain tokens to Trader B in exchange for Trader B's 100 tokens. Trader A enters his order into his wallet, and Trader B enters her order into her wallet. Based on the orders, the described technology generates the appropriate transaction messages, which are broadcast to the network for authentication and verification.

Once each transaction is sent to the network, in one or more embodiments, settlement is immediate; therefore, each trader must be prepared to make the trade and have the assurance that the other trader is prepared to do the same. Various techniques are used by the described technology to coordinate the processes of trading Blockchain tokens for cryptographic currency (e.g., tokens) and/or for other Blockchain tokens. The described technology, in various embodiments, implements an atomic commitment protocol, such as a two-phase commitment protocol, to ensure that both traders are ready to send their respective transaction messages. A coordinator of the two-phase commitment is, in some embodiments, a trusted node, for example a node that both traders mutually agree to have act as coordinator (including each other). In additional and/or alternative embodiments, the coordinator is elected based on the network protocol. For example, a node can be elected as coordinator based on random or pseudo-random token exchange, uptime, number of validated transactions sent, or other qualifier. Regardless of the coordinator, after each node is committed, appropriate transaction messages are broadcast to transfer Blockchain token ownership. In some embodiments, the described technology can modify trading protocols such that two traders share an open transaction and close it to settle. For example, a trader with a wallet which can give 1000 USD can share an open transaction to exchange, e.g., 10 IBM-S in a different wallet. The coordinator can close the transaction as part of a two-phase commit.

Blockchain stock ownership is transferred via one or more transaction messages. A transaction message includes a transaction and a digital signature. The transaction includes, for example, the Blockchain token, the receiver's (i.e., the new owner's) electronic address, and, in some embodiments, ownership history (i.e., a record of previous Blockchain token ownership used by the network to verify proper chain of title). Addresses are based, in various embodiments, on one or more cryptographic protocols (e.g., public-key cryptography). Public-key cryptography requires two separate keys, one of which is secret (i.e., a private key) and one of which is public (i.e., a public key). Although different, the two keys are mathematically linked. The public key is used to encrypt plaintext (e.g., for creating an address for receiving an Blockchain token) and for verifying a digital signature. The private key is used to decrypt cipher text, to create a digital signature, and to secure Blockchain tokens. Public keys are freely shared among nodes in the peer-to-peer network, for example by broadcasting one or more key-exchange messages. The transaction message, in various embodiments, is digitally signed by the sender's private key to authenticate the sender's identity to the network nodes, e.g., by decrypting the sender's digitally signed transaction message using the sender's public key to verify that the sender originated the transaction.

When an Blockchain token is first created (i.e., by an issuer) there are no previous owners from which to verify ownership in the ledgers. In one or more embodiments, the issuer can maintain the same private key for digitally signing each Blockchain token as it is issued and entered into in the ledgers. That private key, in turn, can be validated by mutual agreement between the nodes, by a trusted third party (e.g., the Items of value and Exchange Commission), or by one or more other security mechanisms.

After a Blockchain stock transaction (i.e., a message indicating a change of ownership) is broadcast to the network, the nodes verify in their respective ledgers that the sender has proper chain of title, based on previously recorded ownership entries for that Blockchain token and the first valid transaction or order is accepted. Verification of a transaction is based on mutual consensus among the nodes. For example, to verify that the sender has the right to pass ownership to a receiver, the nodes compare their respective ledgers to see if there is a break in the chain of title. A break in the chain of title is detected when there is a discrepancy in one or more of the ledgers, signifying a potentially fraudulent transaction.

A blockchain action token has a position (Buy/Sell) for a single stock and time for the transaction, and is associated with public key and private key. The time value allows the system to identify the first valid order for the security. In other embodiments, a single Blockchain token carries a value of multiple security positions. A fraudulent transaction, in various embodiments, is recorded (e.g., in the same ledger or a different ledger and/or database) for use by the authorities, for example (e.g., the Items of value and Exchange Commission). If the nodes agree that the sender is the owner of the Blockchain token, the nodes' ledgers are updated to indicate a new ownership transaction, and the receiver becomes the Blockchain token's owner. Verification protocols of other cryptographic currencies, in one or more embodiments, are used or can be modified for use by the described technology to verify those cryptographic currencies' ownership rights (e.g., bitcoins are validated based on "blocks" in a "block chain"). Regardless of the specific protocol(s) used, the receiver becomes the currency's owner after the chain of title is verified and the ledger is updated.

Stock trading settlements are nearly instantaneous because cryptographic currency transactions are independently and extemporaneously generated, verified, and executed within the network, without the risks associated with traditional clearing houses that can delay settlements for several days.

The system can be used for political voting as well. In the corporate shareholder example above, the shareholder is authenticated by virtue of her security transactions. However, for political voting, this option is not available and in one example, at the start of the voting process, the voter's identity has been verified and the voter is allowed to vote under whichever laws apply in the jurisdiction. Thee voter is issued a private key. This private key may be issued as a barcode printed on a piece of paper or another physical medium, a private key printed as a barcode on a physical ballot, or on an electronic medium such as a USB storage device, RFID device, or other computer readable medium. The private key is received at the voting machine. If the private key is a barcode it is received through a scanner on the voting machine. If the private key is on an electronic storage medium, it is received through whatever means is appropriate for the electronic storage medium. The validity of the private key is verified and the voting machine checks to make sure the private key was issued through the proper authority, and has not yet been used. The voting machine receives votes from the voter, this is done electronically through a graphical interface of the voting machine, or by scanning a physical ballot through the voting machine's scanner. The votes are then stored on the blockchain. According to one embodiment, this involves storing the public key to uniquely identify the voter and the electronic identifiers of the candidates or local issue that the voter voted for. Typically the electronic identifiers of the candidates will also be public keys, but any identifier could be used to uniquely identify which candidates the voter voted for. The voting data is digitally signed using the voter's private key and the voting data is broadcast to the distributed network. Once the voting data is available to the distributed network, one or more of the voting machines that act as nodes on the distributed network can try to solve for the next block with the voting data included in the payload of the voting block.

According to an embodiment, the voting system combines three different security systems, of which none can be compromised or disabled in the same way. The three systems are (a) a physical record through paper or other hard copy version of a voting ballot, (b) a cloud based protection which would use a computer interface and the internet to transfer results taken after the scanning of special, one-use-only ballots and offload them onto a cloud storage, and (c) storage on a customized blockchain or blockchain type apparatus. Results would be stored in each of these three media. However, vote counting should be done using the two computer media for the sake of timeliness. The paper record preservation can assist in auditing the vote and other records.

Figure 13G:
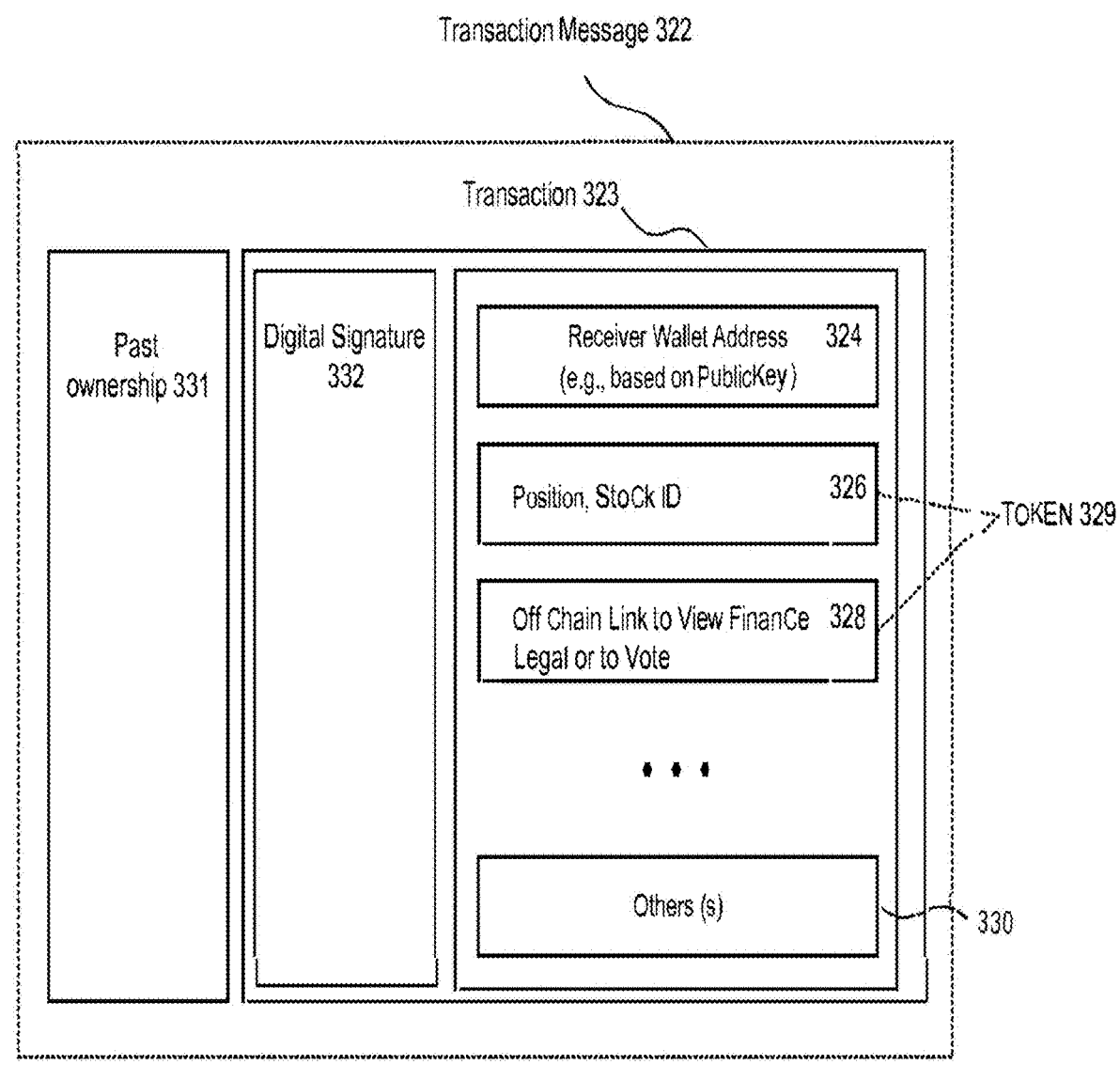

FIG. 13G is a diagram 320 depicting an example transaction message 322. Transaction messages 322 are used by the system for changing Blockchain token 329 ownership. A transaction message 322 includes a transaction 303 and the sender's digital signature 332 of the transaction 323. The transaction 303 includes the recipient's address 324 (e.g., a hash value based on the receiver's public key), the Blockchain token 309 (i.e., a stock ID 328 and its position 326), past ownership information 331 (if any), and optional other information 310 (e.g., a market order type to indicate whether the transaction is to buy or sell a Blockchain token 329). The transaction 323 is digitally signed by the sender's private key to create a digital signature 332 for verifying the sender's identity to the network nodes. The network nodes decrypt the digital signature 332, via the sender's previously exchanged public key, and compare the unencrypted information to the transaction 323. If they match, the sender's authenticity is verified and, after a proper chain of ownership is verified via the ledgers (as explained above), the receiver is recorded in the ledgers as the new Blockchain token 329 owner.

The above system can determine trade settlement automatically for stock. However, the same arrangement can be used for commodities such as for trading sugar, vegetable, among others. For commodities, in place of the corporate governance information, information on location of manufacturing and supply chain is encoded to assure that the commodity is coming from where it is represented. For example, a buyer may specify that the electricity is coming only from solar energy, or that a fruit is coming only from a tropical region, or a diamond is from a particular location and not unethically procured, for example. In this embodiment, the transaction message 322 includes the transaction 303 for a product and the sender's digital signature 332 of the transaction 323. The transaction 303 includes the recipient's address 324 (e.g., a hash value based on the receiver's public key), the Blockchain token 309 (i.e., the item ID 328 and the buy/sell position 326), past ownership information 331 (if any), and optional other information 310 (e.g., a market order type to indicate whether the transaction is to buy or sell a Blockchain token 329). The transaction 323 is digitally signed by the sender's private key to create a digital signature 332 for verifying the sender's identity to the network nodes. The network nodes decrypt the digital signature 332, via the sender's previously exchanged public key, and compare the unencrypted information to the transaction 323. If they match, the sender's authenticity is verified and, after a proper chain of ownership is verified via the ledgers (as explained above), the receiver is recorded in the ledgers as the new Blockchain token 329 owner. Location, temperature, shock, and tamper proof data can be stored in 328. One exemplary embodiment includes an application that can be downloaded to a device with location information such as a computer or a smart phone with GPS system. In one embodiment, a trusted person with a smart phone/computer physically inspect a manufacturing station or area inside a manufacturing and creates a first blockchain record with the current local position inside the manufacturing facility. The trusted person has a credential which is recorded in the first blockchain record, and all items being manufactured and passing through the station or area chain back to the first blockchain. The trusted person then repeats this process for each manufacturing station/area in the facility, and each item manufactured by the facility can be completely tracked through each manufacturing station or area using the blockchains. The system provides full "chains of custody" that tell the stories of products and provides a centralized system with a governing third party was, until recently, the only conceivable way to achieve data and transaction transparency along supply chains. The global peer-to-peer network is an open platform that can deliver neutrality, reliability and security. The blockchains are auditable. Each individual operation or interaction, such as the provision of a new employee or the recording of outgoing stock, is perfectly recorded and archived. Auditing is thus as simple as joining the blockchain network, as this allows one to "replay" the operations of the past in order to reconstruct the history of the item from birth to the present. Combined with the absolute guarantees of authenticity for every interaction, strong and agile data systems can be facilitated that are at their core resilient to coercion and human factors. With blockchains, data can be accessed and verified by everyone, rather than solely by the original certifier.

The system enables the physical goods and materials to be identified and linked with their digital representation on the blockchain (e.g., serial numbers, bar codes, digital tags like RFID and NFC, genetic tags) is crucial in uniquely identifying a physical good with its digital counterpart. At Provenance we are exploring many new and existing technologies; an overview of recent technologies can be found here.

Identities are recorded in production and manufacturing programs, and for simplicity and easy adoption we expect them to take the form of existing barcodes and serial numbers which are linked to blockchain identifiers using a secure hash.

User-facing applications facilitate access to the blockchain. The final owner of the product has access to secure information about the product's supply chain, without having access to identification details. The final owner of the product has access to secure information about the product's supply chain, without having access to identification details.

By design, every transaction along a supply chain on the blockchain is fully auditable. By inspecting the blockchain, smartphone applications can aggregate and display information to customers in a real-time manner; furthermore, due to the strong integrity properties of the blockchain, this information can be genuinely trusted. A user interface sheds light on the digital journey of a product can empower better purchases by giving users a true choice that they can exercise. There are substantial broad effects of bringing near-frictionless transparency to consumer purchase decisions and product identity; clearly there is likely to be an additional "virtuous" component in purchase decisions, especially among mid-level purchases where a marginal increase of 20% to the price does not affect the willingness to buy. Additional levels of guarantee over genuine articles is a high-value use case. While an initial introduction of this technology may be in the form of a discrete and removable label, easily verified through a smartphone-readable QR-code, a more progressive possibility would be a conspicuous hologramatic or RFID tag, embedded in the brand label, allowing the owner to prove the authenticity of the product at any time by accessing the data on the blockchain through the tag.

In the system, everyone has a profile accessible with a private key. Profiles can be public or private depending on use case and permissions. Some are rich with information, whilst others simply contain an anonymous ID. The system supports the registration of named participants (i.e. certifiers, auditors, producers, and manufacturers). Such participants may request registration of their digital identity which links their real-world identity with their blockchain-based digital identity, thus allowing them to interact with the blockchain using their real-world identity. Upon request, the registration authority verifies their identity and records the result in the blockchain, available for all to inspect.

These programs represent the implementation of schemas for proper recognition of a standard (e.g. no animal testing, biodynamic, fair labor). Through these programs, standards organizations provide for the creation of compliant production or manufacturing programs (see below), allowing instances or batches of goods and materials to be added to or processed on the blockchain. Such producers or manufacturers may require inspection by a certifier or auditor of their facilities and processes to be able to obtain and operate a certified program. Successful verification results in the deployment of a production or manufacturing program that is both registered with the certification program and authenticated by an auditor, and allows a producer to create the digitally tradeable equivalent of a good (i.e., a token that shadows the real-world material or product).

The physical goods and materials are identified and linked with their digital representation on the blockchain using a label (e.g., serial numbers, bar codes, digital tags like RFID and NFC, genetic tags) that uniquely identifies a physical good with its digital counterpart. Identities are recorded in production and manufacturing programs, and for simplicity and easy adoption the system can use electronic tags or barcodes and serial numbers which are linked to blockchain identifiers using a secure hash. During manufacturing, each item is associated with a tag. The tag can be a discrete and removable label, easily read through a smartphone-readable QR-code, a hologram or RFID tag, embedded in the brand label, allowing the owner to prove the authenticity of the product at any time by accessing the data on the blockchain through the tag. While a tag such as a bar code cannot store information, it can save information to a remote server that associates that tag with various blockchains. Alternatively, active memory can be formed using roll-to-roll electronic printing onto a tag and the app can store the position information and additional information to a circuit such as flexible circuit, a printed circuit, or an electronic tag with memory, and the tag can be associated with a product 3 as it moves through production and shipping processes. In one embodiment, the circuit can be "printed memory" that can collect and store information about the authenticity and condition of products. One embodiment uses a Printed Memory containing up to 36 bits of rewritable memory which can store up to 68 billion points of data. The labels are used to determine if a product is genuine and to track how it's been handled during distribution. Another embodiment uses Printed Memory with Cryptographic Security that includes a unique, encrypted printed code (such as a QR bar code) to the memory. It can only be read by authorized personnel using a reader which interfaces with a secure smartphone application. This combination of printed memory with an encrypted printed code, creates a secure anti-counterfeit solutions. This makes it possible to ensure the integrity of a product from the time it leaves the factory to the time it gets into the hands of a customer with a cost efficient, highly secure method of authenticating and verifying information about a product as it moves through various distribution channels or as it is used.

In an implementation, a circuit can be associated with a manufactured item and/or a component of the item (an "object"). The circuit can be associated with the item or component by inserting it, affixing it (e.g., with glue), incorporating it as a part of a 3D printing fabrication, or in any other way to associate the circuit. In an implementation, the chip is associated with the object in a tamper-resistant way. That is, if an unauthorized attempt is made to alter the circuit, the circuit can render itself non-functional or change its behavior to indicate that it may not be reliable.

In an implementation, the circuit contains a code that can indicate a particular one or more of a geographic location, a specific manufacturing facility, a specific manufacturer, the identity of a worker, a time reference indicating the date and/or time at which the circuit was activated or associated with the object and any other information that would be useful in establishing the provenance of the object and the compliance of the manufacturer or assembler with relevant rules, regulations and laws ("manufacturing data"). The data encoded in the circuit can be cryptographically protected. For example, the data can be encrypted using a symmetric or asymmetric key using any suitable cryptographic protocol known in the art.

The label is associated with an object, such as on the object or on packaging of the object. The label can include one or more elements of manufacturing data, such as the purported location(s) of manufacture and/or assembly. The one or more circuits can be read for some or all of the data they contain. The label manufacturing data can be compared to the label manufacturing data. An implementation can indicate if there is a match between the label and manufacturing data. An implementation can indicate any and all differences between the label and manufacturing data. An implementation can automatically send a message to a regulatory or other authority if a difference is detected. The message can include elements such as a product name, a product retailer, a product manufacturer, a product serial number, etc. and indications of the discrepancies between the label data and the manufacturing data.

For wide ranging manufacturing processes taking multiple GPS coordinates, the computer or phone has an application with a GPS sending/receiving module to obtain GPS coordinates of the smart phone or computer with a GPS device. For example, the computer or phone 1 may receive satellite location data, signal time of flight data, etc. The app includes a GPS sending receiving module that may transmit a request for satellite position data in some instances. In some configurations, the GPS sending/receiving module may be utilized to obtain or receive a geo-fence. The geo-fence may indicate the boundaries of the factories or it may represent a predefined area around and including the smart phone.

The app can read the tag ID and associate manufacturing information including geolocation with a blockchain entry. This is done for each stage of manufacturing and also for each shipping transit points until the retailer point. Upon purchase, the buyer can inspect the chain of manufacturing and shipping logistics to verify authenticity. Moreover, when the buyer sells the item as a used good, the transaction is also recorded to the blockchain, and eventually when the item is stripped for parts, the sale of the parts associated with the item is also recorded on the blockchain, thus effecting birth-to-end tracking of the item. Information from the producer is securely cascaded to the manufacturer on receipt. These programs implement the transformation of input goods from production into output goods. Much as with production programs, once deployed by the certifier the programs are operated by manufacturers, but with one additional constraint: input goods must be "used" for any output to be created, just as in the physical world. For example, the registration of a certain amount of organic cotton fabric requires as input the appropriate amount of raw organic cotton, and after this usage the raw organic cotton should no longer be usable. Because of its auditability, the blockchain provides the same cast-iron guarantee as in the physical world; namely, that creation of an output good can happen if and only if the required input is used.

By design, every transaction along a supply chain on the blockchain is fully auditable. By inspecting the blockchain, smartphone applications can aggregate and display information to customers in a real-time manner; furthermore, due to the strong integrity properties of the blockchain, this information can be genuinely trusted. A thoughtful user interface that sheds light on the digital journey of a product can empower better purchases by giving users a true choice that they can exercise.

The success of the system relies on the registration of identities and recording of transactions and information. This enables actors on the supply chain to carry and prove the defining attributes of their material products to any actor further along the chain. Certain users, however, might be concerned about their privacy or the privacy of their suppliers further up the chain. Identities can be protected in a blockchain-based system, while still transferring other salient information. For example, manufacturers in the middle of the supply chain can securely pass a certificate with full authenticity downstream while keeping their identity private. For customers, the described system provides the ability to check important attributes of purchased goods without necessarily seeing the full intricacies of the supply chain that created them. The system also allows for the trusted proof of ownership thanks to Public-Private Key Infrastructure (see box) without revealing their identity of owners to the system. In fact, customers can even use the system to sell a good on a secondary market, allowing the chain to continue post sale throughout the product lifecycle.

Implementations of the application can store location and other data so that a user (such as a retailer, a distributor, a consumer, etc.) can know that if an item is actually produced at a factory at which it is purported to be made, along with the transportation paths and environmental conditions associates with the item in an authenticated manner. A website may be provided to the user (e.g., a consumer). In some instances, access to the website may be configured and/or maintained by the retailer or manufacturer. The website may be accessible to a consumer when, for example, the consumer scans a label on the item. The scan may launch a web browser and load the website on the consumer's electronic device such as a smartphone. The consumer may be able to view information about the location of the one or more factories that made or were involved in the production of the item to which the label is attached and the trips made by the item and environmental conditions (temperature, shock, etc) before it got to the consumer. The consumer may view, for example, pictures of the factory, data about the factory (e.g., wage information, carbon footprint, size of the factory, inspection data, social compliance data, regulatory violations if any, etc.). The data about the may be provided as audited data and unaudited data. Audited data may refer to data that may be validated by a secondary authority (e.g., the retailer). Unaudited information may refer to user-provided commentary or data (e.g., pictures, videos, news articles). For example, a retailer may add data indicating social compliance of a factory with guidelines established by the retailer or the country in which the factory is located. The retailer may certify the wages of factory workers. A consumer may investigate and obtain data about the manufacture of the specific item the consumer has purchased and post at least some of that data to be associated with the product, retailer, distributor, manufacturer, etc. For example, the consumer may learn that Brand XYZ's bicycle is being sold at retailer ABC and provide an indication of such information for Brand XYZ's bicycle. The website for Brand XYZ's bicycle may contain a content submission form through which one or more users may submit media (e.g., video, audio, image, etc.) and text.

An item may refer to, for example, a good, a product, etc. that may be purchased and/or sold in commerce to a consumer. The manufacture of the item may be overseen and/or controlled by a retailer or brand. The retailer may contract with a manufacturer for actual production of the item. The manufacture of an item may involve one or more components that make up the item and/or one or more processes (e.g., steps) to create the item as it may exist in commerce. For example, an electronic device such as a smart phone may have a display screen that is manufactured at a first location and a processor manufactured at a second location. A chassis may be manufactured at a third location. The chassis manufacturer may receive the display and processor from the first and second locations and incorporate the display and processor as a component of the chassis manufacturing process or assemble the display and/or processor subsequent to the manufacture of the chassis (e.g., the chassis may be an item). As another example, a finished garment (e.g., the item) may be made from raw textile material (e.g., fabric) and buttons. The buttons and textile materials may be made at a first factory and a second factory. The garment may be made using the aforementioned components at a third factory. Some items may be entirely generated at one location or at multiple locations. For example, multiple steps may be involved in the construction of the garment. A finished garment may involve various steps of cutting, folding, pressing, and/or stitching the raw fabric or textile material that may be performed at one location or at several locations. Generally, the manufacture of an item is also associated with packaging the item (e.g., preparing it for shipment to a retailer or consumer), shipping the item, and/or invoicing the purchaser of the item (e.g., the retailer or consumer).

A retailer may contract with a manufacturer to create an item (e.g., smartphone or garment) at a first location. As disclosed herein, a circuit useful for associating a location with a component or an item of which the component is a part may be included (e.g., inserted, affixed to, etc.) in the component. A location associated with the circuit may be received and/or obtained. In some configurations, where the manufacture involves multiple steps, it may be desirable to obtain a location at each step of the process. The location data may be associated with a time reference each time it is obtained and/or received. Additional data may also be associated with the location data (e.g., the step in the process to be associated with the location data, name of individual overseeing the step in the process, etc.). The additional data may be automatically entered or user entered. For example, the cutting of fabric to make a garment may be performed by a mechanical device. The device may obtain, enter, and/or receive the location data from the circuit and store, upload, enter, etc. that the location data at the time of the cutting process corresponds to that process. After the item is manufactured, it may be packaged. A label may be affixed, printed, obtained, etc. and associated with the package. The label may correspond to a second location. The label location data may be compared to the circuit location data to validate that the item was made and packaged at the same factory or location. In some configurations, the label may be associated with the item at a time prior to packaging the item or subsequent to packaging the item (e.g., during invoicing). A retailer may access the location data obtained from the circuit and/or the label to verify the manufacture of the item. In some configurations, the retailer may expose the data and/or allow access to the data by a consumer of the item.

In an implementation, a first geolocation may be determined or received based upon a signal received from or by the GPS system. The circuit may be associated with an item. For example, an electronic record may be stored to a computer readable medium. The record may include an identifier of the circuit and an identifier of the item. The first geolocation may correspond to a first location. For example, the first geolocation may refer to a set of coordinates that indicate a boundary region of the first location. The memory may be utilized to store location data obtained from the GPS sending/receiving module. For example, the circuit may receive coordinates of the factory or manufacturer. As long as the circuit resides within the boundary of the factory, it may indicate as much, for example, by storing or indicating "true" in response to the location (that may be defined by a geo-fence. In some instances, the first geolocation may not be identical to the first location. For example, the geolocation may be represented as a set of coordinates that identify a specific point and the first location may correspond to the boundary of a factory or manufacturer within which the specific point is located.

A second geolocation may be obtained from a label. The second geolocation may correspond to a second location such as an authorized distribution warehouse. As above, the second geolocation may not be identical to the first location. The label may be printed by a conventional or special purpose printer. It may be, for example, a serial number, a bar code, a RFID or a QR code. The information encoded by the label may include geolocation data of the item at the time the label is affixed to it.

The first geolocation and the second geolocation may be compared to one another. In some instances, it may be determined that the first location and the second location are the same based on the first geolocation and the second geolocation or different location. For example, the geolocation data may be obtained by reading the memory, receiving data transmitted directly or indirectly by or from a remote interrogator/transceiver an NFC transceiver or a Bluetooth transceiver. The comparison may be performed on any device that can store and/or access the geolocation data. For example, the geolocation data may be uploaded to a remote server and, upon receiving a scan of the label, the server may perform the comparison. As another example, a handheld device may be utilized to scan or print the label. The handheld device's action (e.g., scanning or printing the label) may be utilized as an indication to perform the comparison. The handheld device may retrieve the geolocation data and perform the comparison data on the fly. In some instances the handheld device may communicate with a server on which the geolocation data are stored. The server may return the result of the comparison to the handheld device.

In some configurations, a notice may be generated that indicates the first location and the second location are substantially the same or identical. The notice may be stored to a computer readable medium that is accessible by the consumer. For example, the consumer or retailer may access a website that displays an indication of the comparison (e.g., a notice).

The first geolocation and the second geolocation being the same or substantially similar may be an indication that a product was produced by the same factory or in the same location. For example, Factory ABC may produce electronic displays for smartphones. The company may receive several components and/or raw materials for the display including a mounting bracket. The mounting bracket may be stamped with the circuit. As the display is constructed, the circuit may generate records for the location of the mounting bracket. At the end of the process for generating the smartphone display, a label may be placed on the package in which the display is placed or on the surface of the display itself. The label may contain a serial number or bar code, for example, that indicates GPS and/or date/time information. In the event the location provided by the label and that of the circuit are substantially similar or the same, it indicates that the item was manufactured and packaged at the same location. A location may be substantially similar if, for example, a manufacturing process requires that the item is moved to a different building, thereby changing a GPS coordinate. Thus, a location may be substantially similar if the location is functionally the same but differ due to a local arrangement of manufacturing. The mounting bracket, for example, may be derived from a mold in a first building and moved to a second building to be combined with a LCD. In some configurations, the label may be a stamp that validates that the circuit location data indicate the item was manufactured in essentially the same location. For example, manufacturing the electronic display may require the mounting bracket to be constructed first, and then several layers that form the LCD are added in succession and combined with the bracket. During each of the steps in the manufacture of the display, location data from the circuit associated with the mounting bracket may be received. The circuit, for example, may record location data at a predetermined interval of once every twenty minutes. The location data may be stored to a database and, the label may be stamped or affixed to the finished item only if the location data from the circuit corresponds to a single location (or substantially similar location as described above). A consumer may subsequently scan the label and be presented with information about the factory, the item, and/or the location data as recorded by the circuit. Similarly, in the event the item contains multiple components, each of which individually contained a circuit, the label may provide a validation of each of the components' manufacture and/or a link to information about each of the individual components of the item.

A circuit may be associated with the item at the location of the factory during at an early or initial phase of manufacture or assembly of the item. The circuit may be activated upon association with the item. Activation of the circuit may be performed by an electronic signal that is received by the circuit. In some instances, for high value items, the circuit may require a battery to be inserted into it to provide power for the GPS sensor that it contains. Moreover, the circuit may contain other hardware and circuitry suitable for it to be able to communicate data (e.g., GPS and time data) to a database. For low value items, the circuit is a passive device that can be wirelessly interrogated (a tag) and positioning data or a carrier data can be added to memory. In some configurations, the circuit may continue to report geolocation data as it moves through the supply chain and transportation chain. For example, after manufacturing, the entry may include various shipping points, the last entry is for the Retailer, XYZ. This entry or record may be generated, for example, when the label is scanned if the label is generated and/or affixed by the retailer. According to an implementation, if the label is scanned by an electronic device capable of independently providing geolocation data, it may be determined that the geolocation data obtained from the electronic device corresponds to that of a retailer. For example, the database storing the geolocation data may contain a list of coordinates for one or more retailers and/or manufacturers. As the database is populated with geolocation data, it may compare the geolocation coordinates that it receives from the circuit or obtains from the label to those associated with a retailer and/or manufacturer to identify, for example, the first building of manufacturer and/or the manufacturer itself. If the label is affixed at the end of the manufacturing of the item by the manufacturer, the geolocation data embedded in the label (e.g., based on the bar code on the label) may correspond to the manufacturer. If a consumer scans the item at the retailer with an electronic device capable of providing geolocation data, the system may compare the geolocation data it receives from the electronic device. That is, both the geolocation data obtained from the label itself and the geolocation data based on, for example, the GPS sensor of the consumer's electronic device may be sent to the database. The system may determine that the electronic device's geolocation data matches a known retailer contained in the database.

In the event the GPS coordinates obtained from the consumer's electronic device do not match a known retailer and/or manufacturer in the database, the system may generate and store an entry as described above, however it may leave blank, for example. As another example, the system may not allow new entries to be generated once an indication has been received that the manufacturer has finished production of the item, shipped the item, and/or that the item has been received by a retailer. For example, once the manufacturer affixes the label and scans it, the system may make the label's geolocation data the last entry by virtue of the geolocation being derived from the label scan (e.g., indicating that manufacturing of the item has been completed). Similarly, when a retailer receives inventory, it may scan the label affixed to the item and a database entry may be generated and stored as described above. Once the system matches geolocation data to a retailer, it may cease generating and/or storing geolocation data for the item. In some instances, every time the label is scanned, a data entry may be generated and stored by the database. Thus, a consumer may be presented with a representation of the geolocation data from the circuit, the label, and/or any subsequent scans of the label by a consumer's electronic device. The data may be organized and presented to the consumer and may contain hyperlinks to further information about the manufacturer.

Subsequent to the manufacture of the item, a label may be affixed or associated with the item by the manufacturer or the retailer. The label may be placed on the item or packaging of the item. It may be exposed to the outside environment so that a consumer may easily scan the label to obtain the desired manufacturing information. As described above, scanning the label, for example with a smartphone, may access a database to which the circuit data are stored. Various implementations may store the circuit data on a first database and store the same or modified version thereof on a second database that is distinct from the first database. A user who scans the label may be presented with the data as well as additional information about the manufacturer 445 and retailer 460 as described earlier.

In some implementations, a first time reference may be received at substantially the same time as or contemporaneously with the first geolocation. Similarly, a second time reference may be received at substantially the same time as or contemporaneously with the second geolocation. The time reference data may be utilized as a component of the geolocation abilities described earlier. The time reference data may be stored to a server and/or be provided to a retailer and/or consumer. The time reference data may be accompanied by a certification from a worker who performed a particular step in the manufacture of the item.

As stated earlier, an item may be made up of one or more components. Each of the components may itself have a unique circuit that is programmed with, has received, or has obtained at least one geolocation. The retailer may be able to access all of the geolocation data for each the individual components that make up the item via a website, for example. Each component may have had a label affixed to or associated with it after it was made and each individual component may have been individually validated for its authenticity of manufacture (e.g., that it was made at the location it purports to be made at). The finished item made up of the individual components may have a label affixed or associated with it at or near the time of packaging, shipping, and/or invoicing. The validation for the item may refer to only the steps performed at one particular manufacturing plant, factory or the like. The validation for the item may also refer to the former as well as the validations for each of the individual components. Likewise, all of the validation or a portion thereof may be exposed to a consumer.

Likewise, the manufacture or production of an item may include one or more steps. Geolocation data for each individual step may be obtained and compared against other geolocation data performed at the same factory, manufacturer, etc. to determine the authenticity of manufacture for each step of the item's manufacture. As stated earlier, additional data (e.g., a worker certification for a step, a machine automated entry, etc.) may be associated with the geolocation data at each step of the manufacturing process. The data may be exposed to a consumer, for example, via a website as described above. In some instances, it may be desirable to associate a picture, video, or audio data with the item. Such data may also be associated with a geolocation and/or a time reference.

An implementation can obtain or receive geolocation data from one or more components and/or one or more steps to manufacture an item. A pairwise comparison may be performed between the geolocation data obtained or received from one or more components and/or one or more steps and the geolocation obtained from the label. Other data disclosed herein collected, received, and/or obtained may also be compared and/or analyzed as above.

A website may be utilized to provide an interface with which a retailer and/or consumer may view the validation data obtained from the geolocation information, time reference data, or additional data as described above. The retailer may enter additional data such as employment data (e.g., factory size, workforce size, worker wage data etc.), social and/or regulatory compliance data (e.g., environmental violations if any, labor law compliance, carbon footprint, etc.). A consumer may access the website, for example, by entering a URL into a web browser or by scanning the label. The data may be associated with an item. For example, a retailer may manufacture an item at four different factories. Data specific to the factory from which the item is deemed to originate may be associated the item. Thus, an item manufactured at factory A may have data regarding factory A associated with it, but not data for a different factory.

In an implementation, a first geolocation may be received based on a signal received from a circuit associated with an item. The first geolocation may correspond to a first location. A second geolocation may be obtained from a label. The second geolocation may correspond to a second location. The first geolocation and the second geolocation may be compared. It may be determined that the first location and the second location are different. In some configurations a notice may be provided to the manufacturer, the retailer, and/or the consumer to indicate that the item may not have actually been manufactured at the location at which it is purports to have been manufactured.

According to an implementation disclosed herein, one or more indications of geolocation may be received, directly or indirectly, from a circuit associated with an item. Each indication may correspond to a location. The circuit may store geolocation data locally as described earlier and/or the circuit data may be wirelessly communicated to a local or remote server/database. The data obtained from the circuit may include an identifier corresponding to the factory, the item, etc. Thus, the circuit data may be associated with a specific item. In some configurations, the manufacturer for the item may be determined based on the geolocation data received.

A second geolocation may be obtained from a label that corresponds to a second location at 520. For example, at the end of the manufacturing process for an item, a label may be automatically generated by a printer and affixed to the manufactured item. The label may include a unique code corresponding to the manufacturer and a second location. The manufacturer may scan the label and/or generate an entry of one or more of the time, date, and geolocation based on the label data. The entry data may be stored to a database (e.g., the same database as the one or more indications of geolocation received from the circuit). The item may subsequently ship to a retailer for the item as described above. A request may be received based on a scan of the label by a consumer. For example, the consumer may scan a QR code or a bar code on the label. The request may be received as a query for geolocation data associated with the specific item on which the label is printed. Thus, the label may be unique for each item. The label may contain a unique identifier such as a product identification, a serial number, etc. for each item. The geolocation data may include the indications of geolocation (e.g., from the circuit) and the second geolocation from the label. A response to the request may be generated that includes a representation that the at least one indication of geolocation and the second geolocation are substantially similar. For example, in some configurations, a consumer may be exposed to raw geolocation data that includes the GPS data. In some configurations, the consumer may be presented with a simple interface that shows the item's identity (e.g., a smartphone name) and an indication that the manufacturing has been validated. The manufacturing being validated may refer to the circuit geolocation data matching the label geolocation data, thereby indicating that the item remained in the same or substantially similar location throughout its manufacture. The response may be provided to an electronic device of the consumer (e.g., a computer, a smartphone, a tablet).

Some embodiments of the system and method involve setting and enforcing access rights. In an embodiment, an access right is the right of an entity to use a service or good for at least one purpose. The service or good may be a computing device or network of computing devices. For instance, an access right may permit a user possessing the appropriate authentication credentials to operate a workstation, server, or virtual machine after "logging on" to the workstation. An access right may permit a user to instruct a computing device to perform some functions, while forbidding the performance of other instructions. As an example, an "administrator" or "root" user may have the ability to install and uninstall software on a computing device, as well as the ability to execute the software; an ordinary user may have the ability to execute software on the computing device, but not have the ability to install or uninstall the software. The computing device may be configured to ignore or refuse commands from a user that does not have a user account with the access right to instruct the computing device to execute those commands. In other embodiments, the access right controls the ability to access a particular network access point. The access right may affect the ability to access one or more master nodes of a network. The network may be a private network; for instance, the network may function as a "private internet" for the use of a community sharing a particular goal, set of ideals, or commercial interest. The private network may, for instance, be a trading or gambling network. The access right may affect the ability to access or read messages directed to particular user account within a messaging service; for instance, the access right may control whether a particular user can read a particular email account, an instant message, a text message, or a voice over internet protocol stream. The access right may give a user the ability to decrypt an encrypted message; in some embodiments, where the access right is tied to the possession of a particular private key, an encrypted message or stream may be encrypted using the corresponding public key. The access right may give a user the ability to unlock the use of an application or suite of applications on a computing device; for instance, the user may be able to access communication sites concerning classes. The user may be able to access music on a cloud service or on a local computing device. The user may be able to access streaming media over a network if in possession of the access right. The access right may give a security system the ability to lock out or allow entry to certain people peer-to-peer (P2P) network and to those files. The access right may control access to a particular file or set of files; for instance, the access right may lock access to confidential information, or information that can be used for identity theft, such as passport, social security, birth certificate data, permit data, data concerning licenses, data concerning escrowed property, legal documents such as wills, settlements or divorce decrees, or electronic access to physically locked devices such as safe-deposit boxes or the doors to vehicles or buildings. An access right may give a user the ability to run a particular software product; for instance, the license key permitting a software product to execute in a particular computing environment may be tied to a particular user account. An access right may determine a user's ability to access one or more files or classes of files. An access right may include a right to confer access right on another user; for instance, an administrative or root user may have the right to give other users ordinary user accounts.

Birth Certificate or Forms of ID

In one embodiment, the first blockchain is created when a baby is born and subsequent medical events are appended to the blockchain. A birth registration application can be installed on a smart device, such as a smart-phone, having location detection function with an image of the baby as encoded in a blockchain. Using such an application allows the birthing attendant and/or birth parents to generate a permanent birth registration report. The location of the user is verified, based on a second location detection method, using the computerized device. A blockchain hash or security key is established with a registration authority according to the location, using the computerized device. A picture of a newborn child at birth is obtained, using the computerized device. Instruction on birth registration requirements according to the location are provided, using the computerized device. A birth registration report is generated in compliance with the birth registration requirements according to the location, using the computerized device. The birth registration report comprises identification of the location, a picture of the newborn child, a hand print (including fingerprints), a foot print (including toe prints) and a time stamp that identifies a time and date of the birth. The birth registration report is encrypted according to the security key, using the computerized device. The security key prevents altering the birth registration report. The birth registration report is transmitted using the blockchain in encrypted format to a registrar of birth records for the location, using the computerized device. The birth registration report is stored in encrypted format on the computerized device.

According to a handheld device for registering a birth, a camera is operatively connected to the handheld device. The camera takes a picture of a newborn child at birth. The camera can be used to scan the hand and the foot to create handprints, footprints, fingerprints, among others. A communication device is operatively connected to the handheld device. A processor is operatively connected to the camera and the communication device. The processor establishes a location of a user of the handheld device using a first method. The processor verifies the location of the user of the handheld device using a second method. The processor provides instruction to the user on birth registration requirements according to the location. The processor establishes a blockchain security key with a registration authority according to the location. The processor generates a registration report in compliance with the birth registration requirements according to the location. The registration report comprises the location, the picture of the newborn child, and a time stamp that identifies a time and date of the birth. The processor encrypts the birth registration report according to the security key. The security key prevents altering the birth registration report. The processor transmits the birth registration report in encrypted format to the registration authority, using the communication device. The processor stores the birth registration report in encrypted format on the handheld device.

According to a computer program product for enabling a smart-phone for registering a birth, the computer program product comprises a tangible computer readable storage medium having program code embodied therewith. The program code is readable and executable by a computer to provide an application to the smart-phone to enable the smart-phone to perform a method. According to the method, a location of the smart-phone is determined, based on a first location detection method. The location of the smart-phone is verified, based on a second location detection method. Instruction on birth registration requirements according to the location is provided. A security key is established with a registration authority according to the location. A picture of a newborn child at birth is obtained, using a camera application of the smart-phone. A birth registration report is generated in compliance with registration requirements according to the location. The birth registration report comprises the location, the picture of the newborn child, a time stamp that identifies a time and date of the birth and a blockchain reference with a private key. The birth registration report is encrypted according to the security key. The blockchain and security key prevents altering the birth registration report. The birth registration report is transmitted in blockchain format to the registration authority.

A country's political constitution or founding charter generally determines who is a national of that country, who is an alien, and how nationality can be acquired or lost. Some Governments follow the principle of jus soli, whereby those born within the country's territory are nationals, even if one or both parents came originally from another country. In such a case, birth registration gives the child automatic right to citizenship of the country in which he or she was born. By enabling birth registration capability in a smart device, the physical barriers to registration can be removed. Such capability should capture a greater number of unregistered births. According to devices and methods herein, this solution would reach remote areas of the global population where childbirth education may not be available. Details of data required for registration can be associated with the location obtained by the GPS in order to determine required country-to-country information. While the information shown in a birth record and on a birth certificate may vary from country to country, the names of the child, the parents, the attending physician, midwife, birth attendant, or other witnesses are generally included, together with the date and place of birth, and the name and signature of the registrar. Other information may include the age of the mother and the child's height, weight and gestational age. Ensuring the rights to a name and nationality and to know one's parents implies that registration should, as a minimum, include the child's name, gender, date, and place of birth, and the name, address, and nationality of both parents. Some countries, such as Qatar, require additional information on the certificate, such as immunization status, and issue an immunization card along with the birth registration certificate. In the United States, for example, birth registration may also include application for a Social Security number. While a person's name may be their most distinctive indication of individuality—a right recognized in the CRC—additional data, such as family ties and nationality, promote the child's right to legal protection by parents and by the state.

The birth registration app according to devices and methods herein allows the birthing attendant and/or birth parents to:

a. Record, using GPS, the place and time of delivery.

b. Using the smart device camera, obtain a visual image of the newborn child as supporting documentation and generate features based on face recognition of the child and store the features as blockchain data.

c. Using the smart device microphone, record the cry/voiceprint of the newborn child as blockchain data.

d. Register the birth of the newborn child in compliance with the birth country's requirement.

e. Sign the registration with a private key and upload to the blockchain or a decentralized ledger to prevent subsequent alteration of the registration.

f. Provide a unique ID pointing to birth registration on the block chain.

2. The method according to claim 1, said computerized device comprising one of a smart-phone and a tablet.

3. The method according to claim 1, one of said first location detection method and said second location detection method comprising using a global positioning system (GPS) to determine said location, said first location detection method being different from said second location detection method.

4. The method according to claim 1, said encrypting said birth registration report according to said security key further comprising signing said birth registration report with a virtual signature.

5. The method according to claim 1, further comprising receiving an indication of receipt of said birth registration report from said registrar of birth records for said location.

6. The method according to claim 1, further comprising establishing a virtual medical record for said newborn child.

7. The method of claim 1, including generating a secure birth registration report comprising: identification of said location, said picture of said newborn child, and a time stamp that identifies a time and date of said birth, encrypting said birth registration report according to said security key, using said computerized device, said security key preventing altering said birth registration report; transmitting said birth registration report in encrypted format to a registrar of birth records for said location, using said computerized device; and storing said birth registration report in encrypted format on said computerized device.

Citizenship, ID or Credit History Identification

The above system to produce a digital birth certificate can also be used to provide a digital driver's license, passport, Social Security card, credit cards, or other identification information to clearly establish the identity of the individual.

The need for some form of personal documentation is a constant of daily life in most modern societies. Depending on the prevailing administrative arrangements, establishing one's identity may be essential for a wide range of activities, including the registration of births and deaths, contracting marriage, obtaining employment, housing, hospital care or rations, qualifying for social benefits, entering educational institutions, or requesting the issuance of official documents and permits. To meet these needs, as well as for reasons of public order, many countries have established a system of national identity cards. Such cards, besides identifying the holder, can also serve as evidence of civil status and of nationality. In virtually all countries, lawfully resident aliens also receive some kind of residence permit which may at the same time serve as an identity document. In one aspect, the invention applies the blockchain birth certificate as proof of citizenship, and the blockchain can follow the person from birth through his/her life to establish identity for voting, government benefits (social security, medicare, state college admission, etc) or for credit rating purposes, among others. The blockchain is subsequently supplemented with a history of payment of utility bills, mortgage statements, credit reports, credit card bills, a verified statement from a government official such as a police officer, judge, or other individual that establishes the identity and indicates the stability of the individual and that individual's presence in a predetermined location for a period of time.

Due to the circumstances in which they are sometimes forced to leave their home country, refugees are perhaps more likely than other aliens to find themselves without identity documents. Moreover, while other aliens can turn to the authorities of their country of origin for help in obtaining documents, refugees do not have this option and are therefore dependent upon the authorities of their country of refuge. The blockchain authentication of the refugee enables an official examining the blockchain identity data to be satisfied that the data is authentic and also that the person using the document is in fact the person to whom it was issued.

One embodiment used three different ways of identifying each person:
microchip in a license/badge the person carries
digital fingerprint using blockchain
video image.

Each person also had the fingerprint electronically scanned into the system. This was recorded against their ID blockchain as a backup. If a refugee cut off their wristband, they can be finger scanned again to check who they were. Also, if anything really important was supposed to happen with one of the refugees, the authority can double check the microchip and the fingerprint to make sure they had the right person. Video image is used to check someone's identity by comparing their face with the video image. In one embodiment, biometric data can be included in the blockchain. In this system, an entire immediate family history of DNA data is included in birth certificate blockchain and provides access for any future needs.

In one embodiment, a permissioned blockchain is used where predetermined trusted parties are authorized to initiate individuals or organizations onto the blockchain and thus vouched for by a trusted point, such as a government license issuer (dept of public safety or the social security administration, . . . ), a professional licensing authority (bar association or a pharmacy licensing board, for example), an identity provider, a bank, or other organization with whom they already have a trusted relationship. Individuals can initiate their own identity if they wish. Once an initial identity record has been established, an identity owner can add additional identity "claims" (attributes, identity transactions, identity proofs) to their identity. Only the identity owner can see and manage this data.

When an identity owner wants to use their identity, they will be asked for some information by a relying party; examples might include name, address and date of birth. The identity owner will find those entries in their identity which match the requirements of the relying party, and then give the relying party access to those records. The relying party will be able to, with the identity owner's permission, verify the issuer of the identity data which the issuer will have digitally signed. When data is shared in this way, a consent record is written to the identity owner's and relying party's identity records to confirm that the data has been shared, by whom, to whom, for what reason, and with what constraints. All decisions about trust in an identity record depend on trust relationships between the parties reading and writing the records. Each relying party will be able to verify the issuer of a claim, e.g., doctor's association, driving license issuer, bank, insurance company, etc. and also that the claim has not changed since writing. So each relying party can determine if the claim issuer is one they can trust. A community of relying parties (e.g., banks, insurance companies, universities, government agencies) can define a trust framework that will define the rules for verifying a claim or credential to a certain level of assurance (LOA), and then issuers operating under that trust framework can indicate the LOA that applies when they write a claim to the ledger. Every claim (credentials/attributes) can be revoked by the issuer. The form revocation takes depends on the type of credential and privacy requirements. A key revocation is recorded on the ledger. The revoked key is superseded by an updated value, and no subsequent misuse is possible.

Different from Bitcoin or Ethereum which uses one identifier in multiple places, the one identifier can be correlated by different vendors and the correlation can be used to amass data about the user without permission. For example, the web visits, facebook likes, and google searches can be combined to provide exacting information about the user. To avoid correlation, the system provides user with different identifier for each vendor, and each identifier is a public-private key pair, where the user only shares the public key or the verification key. Thus, different identifier/key pairs are used for banks, schools, government applications, associations, among others. The pairs are carried in the user's wallet.

The system also supports claims-based identity where the identity owner makes a statement about itself to another entity. Claims can be issued by one identity owner to a second identity owner and then presented to a third identity owner in a way that they can be cryptographically verified. One embodiment uses the w3C Verifiable Claims Task Force at https://www.w3.org/Payments/IG/wiki/Main_Page/ProposalsQ42015/VerifiableClaimsTaskForce, the content of which is incorporated by reference. In one embodiment, the claims can be cleartext, encrypted, hash signature, proof of existence, or anonymous credential type of claim. Cleartext claims are directly readable, with no hashing or encryption. Public cleartext claims are intended for public identities with no expectation of privacy such as public records of ownership that can be fully verified, for example. Encrypted claims contain an encrypted version of a cleartext claim. Hash signature claims contain a specially encrypted tree of cleartext claims, where the identity owner can selectively reveal specific claims to specific relying parties. Proof of existence claims (aka POE claims or hash claims) are simply hashes of digital objects that enable an identity owner to prove that a digital object existed at a point in time. POE claims are especially useful for proving consent as required under privacy regulations. Anonymous credentials transmit claims information without actually containing either a cleartext or encrypted version of the claims data. Rather they are a cryptographic method of providing a proof about a claim. For example, an anonymous credential is a proof of age (i.e., "over 18") that does not reveal the actual birthdate.

With claims, the user can claim a relationship with a trusted party such as a school and once verified by the school, the relationship is stored as part of identity. In another example, the user can claim to be a licensed doctor from a particular state licensing authority (as a trusted party) and once validated by the licensing authority, such status becomes part of the user's identity. The user can provide just the information required. For example, in a bar, if checked, the user can provide a response that he or she is over 18 as a claim without exposing birthdate and driver license information.

Medical History

The above permissioned blockchain can be used to share sensitive medical data with different authorized institutions. The institutions are trusted parties and vouched for by the trusted pont. A Patient-Provider Relationship (PPR) Smart Contract is issued when one node from a trusted institution stores and manages medical records for the patient. The PPR defines an assortment of data pointers and associated access permissions that identify the records held by the care provider. Each pointer consists of a query string that, when executed on the provider's database, returns a subset of patient data. The query string is affixed with the hash of this data subset, to guarantee that data have not been altered at the source. Additional information indicates where the provider's database can be accessed in the network, i.e. hostname and port in a standard network topology. The data queries and their associated information are crafted by the care provider and modified when new records are added. To enable patients to share records with others, a dictionary implementation (hash table) maps viewers' addresses to a list of additional query strings. Each string can specify a portion of the patient's data to which the third party viewer is allowed access. For SQL data queries, a provider references the patient's data with a SELECT query on the patient's address. For patients uses an interface that allows them to check off fields they wish to share through a graphical interface. The system formulates the appropriate SQL queries and uploads them to the PPR on the blockchain.

In one embodiment, the transaction 303 includes the recipient's address 324 (e.g., a hash value based on the receiver's public key), the Blockchain token 309 (i.e., a patient ID 328 and personally identifiable information such as Social Security 326), past medical institution relationship information 331 (if any), and optional other information 310. The transaction 323 is digitally signed by the patient who is the sender's private key to create a digital signature 332 for verifying the sender's identity to the network nodes. The network nodes decrypt the digital signature 332, via the sender's previously exchanged public key, and compare the unencrypted information to the transaction 323. If they match, the sender's authenticity is verified and, after a proper chain of ownership is verified via the ledgers (as explained above), the receiver is recorded in the ledgers as the new Blockchain token 329 authorized owner of the medical information. Block 328 of FIG. 13G can point to off-chain storage warehouses containing the patient's medical history so that the current owner (or all prior owners) can access the patient medical information for treatment. Further, the information can be segmented according to need. This way, if a medication such as cannabis that requires the patient to be an adult, the system can be queried only to the information needed (such as is this patient an adult) and the system can respond only as to the query and there is no need to send other question (in the adult age example, the system replies only adult or not and does not send the birthday to the inquiring system).

In another embodiment, the system includes two look up tables, a global registration look up table (GRLT) where all participants (medical institutions and patients) are recorded with name or identity string, blockchain address for the smart contract, and Patient-Provider lookup table (PPLT). This is maintained by a trusted host authority such as a government health authority or a government payor authority. One embodiment maps participant identification strings to their blockchain address or Ethereum address identity (equivalent to a public key). Terms in the smart contract can regulate registering new identities or changing the mapping of existing ones. Identity registration can thus be restricted only to certified institutions. The PPLT maps identity strings to an address on the blockchain.

Patients can poll their PPLT and be notified whenever a new relationship is suggested or an update is available. Patients can accept, reject or delete relationships, deciding which records in their history they acknowledge. The accepting or rejecting relationships is done only by the patients. To avoid notification spamming from malicious participants, only trusted providers can update the status variable. Other contract terms or rules can specify additional verifications to confirm proper actor behavior.

When Provider 1 adds a record for a new patient, using the GRLT on the blockchain, the patient's identifying information is first resolved to their matching Ethereum address and the corresponding PPLT is located. Provider 1 uses a cached GRLT table to look up any existing records of the patient in the PPLT. For all matching PPLTs, Provider 1 broadcasts a smart contract requesting patient information to all matching PPLT entries. If the cache did not produce a result for the patient identity string or blockchain address, Provider 1 can send a broadcast requesting institutions who handles the patient identity string or the blockchain address to all providers. Eventually, Provider 2 responds with its addresses. Provider 2 may insert an entry for Provider 1 into its address resolution table for future use. Provider 1 caches the response information in its table and can now pull information from Provider 2 and/or supplement the information known to Provider 2 with hashed addresses to storage areas controlled by Provider 1.

Next, the provider uploads a new PPR to the blockchain, indicating their stewardship of the data owned by the patient's Ethereum address. The provider node then crafts a query to reference this data and updates the PPR accordingly. Finally, the node sends a transaction which links the new PPR to the patient's PPLT, allowing the patient node to later locate it on the blockchain.

A Database Gatekeeper provides an off-chain, access interface to the trusted provider node's local database, governed by permissions stored on the blockchain. The Gatekeeper runs a server listening to query requests from clients on the network. A request contains a query string, as well as a reference to the blockchain PPR that warrants permissions to run it. The request is cryptographically signed by the issuer, allowing the gatekeeper to confirm identities. Once the issuer's signature is certified, the gatekeeper checks the blockchain contracts to verify if the address issuing the request is allowed access to the query. If the address checks out, it runs the query on the node's local database and returns the result over to the client.

A patient selects data to share and updates the corresponding PPR with the third-party address and query string. If necessary, the patient's node can resolve the third party address using the GRLT on the blockchain. Then, the patient node links their existing PPR with the care provider to the third-party's Summary Contract. The third party is automatically notified of new permissions, and can follow the link to discover all information needed for retrieval. The provider's Database Gatekeeper will permit access to such a request, corroborating that it was issued by the patient on the PPR they share.

In one embodiment that handles persons without previous blockchain history, admitting procedures are performed where the person's personal data is recorded and entered into the blockchain system. This data may include: name, address, home and work telephone number, date of birth, place of employment, occupation, emergency contact information, insurance coverage, reason for hospitalization, allergies to medications or foods, and religious preference, including whether or not one wishes a clergy member to visit, among others. Additional information may include past hospitalizations and surgeries, advance directives such as a living will and a durable power to attorney. During the time spent in admitting, a plastic bracelet will be placed on the person's wrist with their name, age, date of birth, room number, and blockchain medical record reference on it.

The above system can be used to connect the blockchain with different EHR systems at each point of care setting. Any time a patient is registered into a point of care setting, the EHR system sends a message to the GRLT to identify the patient if possible. In our example, Patient A is in registration at a particular hospital. The PPLT is used to identify Patient A as belonging to a particular plan. The smart contracts in the blockchain automatically updates Patient A's care plan. The blockchain adds a recommendation to put Patient A by looking at the complete history of treatments by all providers and optimizes treat. For example, the system can recommend the patient be enrolled in a weight loss program after noticing that the patient was treated for sedentary lifestyle, had history of hypertension, and the family history indicates a potential heart problem. The blockchain data can be used for predictive analytics, allowing patients to learn from their family histories, past care and conditions to better prepare for healthcare needs in the future. Machine learning and data analysis layers can be added to repositories of healthcare data to enable a true "learning health system" can support an additional analytics layer for disease surveillance and epidemiological monitoring, physician alerts if patients repeatedly fill and abuse prescription access.

In one embodiment, an IOT medical device captures patient data in the hospital and automatically communicates data to a hospital database that can be shared with other institutions or doctors. First, the patient ID and blockchain address is retrieved from the patient's wallet and the medical device attaches the blockchain address in a field, along with other fields receiving patient data. Patient data is then stored in a hospital database marked with the blockchain address and annotated by a medical professional with interpretative notes. The notes are affiliated with the medical professional's blockchain address and the PPR block chain address. A professional can also set up the contract terms defining a workflow. For example, if the device is a blood pressure device, the smart contract can have terms that specify dietary restrictions if the patient is diabetic and the blood pressure is borderline and food dispensing machines only show items with low salt and low calorie, for example.

The transaction data may consist of a Colored Coin implementation (described in more detail at https://en.bitcoin.it/wiki/Colored_Coins which is incorporated herein by reference), based on Open Assets (described in more detail at https://github.com/OpenAssets/open-assets-protocol/blob/master/specification.mediawiki which is incorporated herein by reference), using on the OP_RETURN operator. Metadata is linked from the Blockchain and stored on the web, dereferenced by resource identifiers and distributed on public torrent files. The colored coin specification provides a method for decentralized management of digital assets and smart contracts (described in more detail at https://github.com/ethereum/wiki/wiki/White-Paper which is incorporated herein by reference.) For our purposes the smart contract is defined as an event-driven computer program, with state, that runs on a blockchain and can manipulate assets on the blockchain. So a smart contract is implemented in the blockchain scripting language in order to enforce (validate inputs) the terms (script code) of the contract.

The digital assets are managed, transferred or involved in a smart contract. Payers issue assets such as a benefits data, or eligibility information. Providers issue assets for clinical documents, health records which the consumer may receive and grant access to through the use of smart contracts. One block structure of the transaction is as follows:

| Field | Description |
|---|---|
| OP_RETURN opcode | The OP_RETURN opcode (0x6a) |
| PUSHDATA | The PUSHDATA opcode required to push opcode the full payload onto the stack |
| Payload | |

Patient Behavior and Risk Pool Rated Health Plans

With the advent of personal health trackers, new health plans are rewarding consumers for taking an active part in their wellness. The system facilitates open distribution of the consumers wellness data and protect it as PHR must be, and therefore prevent lock-in of consumers, providers and payers to a particular device technology or health plan. In particular, since PHR data is managed on the blockchain a consumer and/or company can grant access to a payer to this data such that the payer can perform group analysis of an individual or an entire company's employee base including individual wellness data and generate a risk score of the individual and/or organization. Having this information, payers can then bid on insurance plans tailored for the specific organization. Enrollment then, also being managed on the blockchain, can become a real-time arbitrage process. The pseudo code for the smart contract to implement a patient behavior based health plan is as follows.

store mobile fitness data
   store consumer data in keys with phr_info, claim_info, enrollment_info
   for each consumer:
   add up all calculated risk for the consumer
   determine risk score based on mobile fitness data
   update health plan cost based on patient behavior
   Patient and Provider Data Sharing A patient's Health BlockChain wallet stores all assets, which in turn store reference ids to the actual data, whether clinical documents in HL7 or FHIR format, wellness metrics of activity and sleep patterns, or claims and enrollment information. These assets and control of grants of access to them is afforded to the patient alone. A participating provider can be given full or partial access to the data instantaneously and automatically via enforceable restrictions on smart contracts.

Utilizing the Health BlockChain the access to a patient's PHR can be granted as part of scheduling an appointment, during a referral transaction or upon arrival for the visit. And, access can just as easily be removed, all under control of the patient.

Upon arrival at the doctor's office, an application automatically logs into a trusted provider's wireless network. The app is configured to automatically notify the provider's office of arrival and grant access to the patient's PHR. At this point the attending physician will have access to the patient's entire health history. The pseudo code for the smart contract to implement a patient and provider data sharing is as follows.

Patient download apps and provide login credential and logs into the provider wireless network
   Patient verifies that the provider wireless network belongs to a patient trusted provider list
   Upon entering provider premise, system automatically logs in and grants access to provider
   Patient check in data is automatically communicated with provider system to provide PHR
   Provider system synchronizes files and obtain new updates to the patient PHR and flags changes to provider.
   Patient Data Sharing Patient's PHR data is valuable information for their personal health profile in order to provide Providers (Physicians) the necessary information for optimal health care delivery. In addition this clinical data is also valuable in an aggregate scenario of clinical studies where this information is analyzed for diagnosis, treatment and outcome. Currently this information is difficult to obtain due to the siloed storage of the information and the difficulty on obtaining patient permissions.

Given a patient Health BlockChain wallet that stores all assets as reference ids to the actual data. These assets can be included in an automated smart contract for clinical study participation or any other data sharing agreement allowed by the patient. The assets can be shared as an instance share by adding to the document a randomized identifier or nonce, similar to a one-time use watermark or serial number, a unique asset (derived from the original source) is then generated for a particular access request and included in a smart contract as an input for a particular request for the patient's health record information. A patient can specify their acceptable terms to the smart contract regarding payment for access to PHR, timeframes for acceptable access, type of PHR data to share, length of history willing to be shared, de-identification thresholds or preferences, specific attributes of the consumer of the data regarding trusted attributes such as reputation, affiliation, purpose, or any other constraints required by the patient. Attributes of the patient's data are also advertised and summarized as properties of the smart contract regarding the type of diagnosis and treatments available. Once the patient has advertised their willingness to share data under certain conditions specified by the smart contract it can automatically be satisfied by any consumer satisfying the terms of the patient and their relevance to the type of PHR needed resulting in a automated, efficient and distributed means for clinical studies to consume relevant PHR for analysis. This process provides an automated execution over the Health BlockChain for any desired time period that will terminate at an acceptable statistical outcome of the required attained significance level or financial limit. The pseudo code for the smart contract to implement automated patient data sharing is as follows.

Patient download apps and provide login credential and logs into the clinical trial provider wireless network Patient verifies that the provider wireless network belongs to a patient trusted provider list Upon entering provider premise, system automatically logs in and grants access to provider Patient check in data is automatically communicated with provider system to provide clinical trial data In one embodiment, a blockchain entry is added for each touchpoint of the medication as it goes through the supply chain from manufacturing where the prescription package serialized numerical identification (SNI) is sent to wholesalers who scan and record the SNI and location and then to distributors, repackagers, and pharmacies, where the SNI/location data is recorded at each touchpoint and put on the blockchain. The medication can be scanned individually, or alternatively can be scanned in bulk. Further, for bulk shipments with temperature and shock sensors for the bulk package, temperature/shock data is captured with the shipment or storage of the medication.

A smart contract assesses against product supply chain rule and can cause automated acceptance or rejection as the medication goes through each supply chain touchpoint. The process includes identifying a prescription drugs by query of a database system authorized to track and trace prescription drugs or similar means for the purpose of monitoring the movements and sale of pharmaceutical products through a supply chain; a.k.a. e-pedigree trail; serialized numerical identification (SNI), stock keeping units (SKU), point of sale system (POS), systems etc. in order to compare the information; e.g. drug name, manufacturer, etc. to the drug identified by the track and trace system and to ensure that it is the same drug and manufacturer of origin. The process can verify authenticity and check pedigree which can be conducted at any point along the prescription drug supply chain; e.g. wholesaler, distributor, doctor's office, pharmacy. The most optimal point for execution of this process would be where regulatory authorities view the greatest vulnerability to the supply chain's integrity. For example, this examination process could occur in pharmacy operations prior to containerization and distribution to the pharmacy for dispensing to patients.

An authenticated prescription drug with verified drug pedigree trail can be used to render an informational object, which for the purpose of illustration will be represented but not be limited to a unique mark; e.g. QR Code, Barcode, Watermark, Stealth Dots, Seal or 2 Dimensional graphical symbol, hereinafter called a certificate, seal, or mark. An exemplary embodiment for use of said certificate, mark, or seal can be used by authorized entities as a warrant of the prescription drug's authenticity and pedigree. For example, when this seal is appended to a prescription vial presented to a patient by a licensed pharmacy, it would represent the prescription drug has gone through an authentication and logistics validation process authorized by a regulatory agency (s); e.g. HHS, FDA, NABP, VIPP, etc. An exemplary embodiment for use of said certificate, mark or seal would be analogous to that of the functioning features, marks, seals, and distinguishing characteristics that currently authenticate paper money and further make it difficult to counterfeit. Furthermore, authorized agents utilizing the certificate process would be analogous to banks participating in the FDIC program.

A user; e.g. patient equipped with the appropriate application on a portable or handheld device can scan the certificate, mark or seal and receive an audible and visible confirmation of the prescription drug's name, and manufacturer. This will constitute a confirmation of the authenticity of the dispensed prescription drug. Extensible use of the certificate, mark, or seal will include but not be limited to; gaining access to website (s) where additional information or interactive functions can be performed; e.g. audible narration of the drug's characteristics and physical property descriptions, dosing, information, and publications, etc. A user; e.g. patient equipped with the appropriate application on a portable or handheld device can scan the certificate, mark, or seal and be provided with notifications regarding; e.g. immediate recall of the medication, adverse events, new formulations, critical warnings of an immediate and emergency nature made by prescription drug regulatory authorities and, or their agents. A user; e.g. patient equipped with a portable or handheld device with the appropriate application software can use the portable and, or handheld device to store prescription drug information in a secure, non-editable format on their device for personal use; e.g. MD's Office Visits, Records Management, Future Authentications, Emergency use by first responders etc. A user; e.g. patient equipped with the appropriate application on a portable or handheld device can scan the drug via an optical scan, picture capture, spectroscopy or other means of identifying its physical properties and characteristics; e.g. spectral signature, size, shape, color, texture, opacity, etc and use this data to identify the prescription drug's name, and manufacturer. A user; e.g. patient equipped with the appropriate application on a portable or handheld device and having the certification system can receive updated information (as a subscriber in a client/server relationship) on a continuing or as needed ad hoc basis (as permitted) about notifications made by prescription drug regulatory authorities regarding; e.g. immediate recall of medications, adverse events, new formulations and critical warnings of an immediate and emergency nature. A user; e.g. patient, subscriber to the certificate system equipped with the appropriate application on a portable or handheld device will be notified by audible and visible warnings of potential adverse affects between drug combinations stored in their device's memory of previously "Certified Drugs." A user; e.g. patient subscriber to the certification system equipped with the appropriate application on a portable or handheld device will receive notification of potential adverse affects from drug combinations, as reported and published by medical professionals in documents and databases reported to; e.g. Drug Enforcement Administration (DEA), Health and Human Services, (HHS) Food and Drug Administration, (FDA) National Library of Medicines, (NLM) and their agents; e.g., Daily Med, Pillbox, RX Scan, PDR, etc.

1. A method for prescription drug authentication by receiving a certificate representing manufacturing origin and distribution touchpoints of a prescription drug on a blockchain.

2. A method of claim 1, comprising retrieving active pharmaceutical ingredients (API) and inactive pharmaceutical ingredients (IPI) from the blockchain.

3. A method of claim 2, comprising authenticating the drug after comparing the API and IPI with data from Drug Enforcement Administration (DEA) Health and Human Services, (HHS) Food and Drug Administration, (FDA) National Library of Medicines, (NLM) etc. for the purpose of identifying the prescription drug'(s) and manufacture name indicated by those ingredients.

4. A method of claim 1, comprising tracing the drug through a supply chain from manufacturer to retailer, dispenser with Pedigree Trail, Serialized Numerical Identification (SNI), Stock Keeping Units (SKU), Point of Sale System (POS) E-Pedigree Systems.

5. A method of claim 1, comprising generating a certificate, seal, mark and computer scannable symbol such as 2 or 3 dimensional symbol; e.g. QR Code, Bar Code, Watermark, Stealth Dots, etc.

6. A method of claim 5, comprising rendering a seal on a prescription drug housing presented to a patient by a licensed pharmacy indicating an authentication and logistics validation process authorized by regulatory agencies prior to being dispensed.

7. A method of claim 5, comprising reading the certificate (mark) and receiving confirmation of the prescription drug's name and manufacturer.

8. A method of claim 7, comprising linking to a web site with information about the drug's characteristics and physical property descriptions, dosing, information, and publications, drug recall of the medication, adverse events, new formulations, critical warnings of an immediate and emergency nature made by prescription drug regulatory authorities or manufacturers.

9. A method of claim 5, comprising storing prescription drug information in a secure, non-editable format on their device for personal use; e.g. MD's Office Visits, Records Management, Future Authentications, Emergency use by first responders.

10. A method of claim 5, comprising reading drug content from the certificate and comparing the drug content with a scan of the drug via an optical scan, picture capture, spectroscopy or other means of identifying its physical properties and characteristics; e.g. spectral signature, size, shape, color, texture, opacity, etc. and use this data to identify the prescription drug's name, and manufacturer.

11. A method of claim 5, comprising communicating a potential adverse effect notification(s) arising from drug combinations in databases held by regulatory authorities and their agencies including Health and Human Services (HHS), Food and Drug Administration (FDA), National Library of Medicines (NLM), Drug Enforcement Administration (DEA), Daily Med, Pillbox, RX Scan, PDR, or third party databases.

Verifying Authenticity of Prescription for Medication

1. A method for verifying the authenticity of prescriptions used to control the dispensing of medicaments, the method comprising:

prescribing a medicament entitlement token with a blockchain identifier unique to a patient and a blockchain identifier unique to a prescribing professional at a prescribing location;

transmitting the token to a dispensing location;

retrieving the blockchain identifier of the patient at the dispensing location;

authenticating the patient based on the blockchain identifier of the patient; and dispensing the medicament to the patient.

2. The method of claim 1, comprising rendering a mark, a seal, or 2D or 3D bar code from the token to present when receiving the medicament.

3. The method of claim 1, wherein the medicament entitlement token is produced by printing.

4. The method of claim 1, further comprising providing a user interface operable to prescribe medicament entitlement tokens at the first location.

5. The method of claim 1, further comprising transmitting additional information relating to the medicament entitlement token from the first location to the server system.

6. The method of claim 1, further comprising notifying the server system when one or more prescription item has been dispensed to remove, invalidate or partially invalidate a stored signature corresponding to the prescription.

7. The method of claim 1, further comprising automatically tracking an inventory at the second location.

8. The method of claim 1, further comprising automatically placing an order to a supplier for replacement stock when the stock of one or more items in the inventory falls to or below a predetermined amount.

9. The method of claim 1, wherein the medicament entitlement token comprises a prescription printed on paper.

10. The method of claim 1, comprising generating a first signature from a medical professional at the first location;

storing the first signature on a blockchain and at the system server;

generating a second signature from a presented medicament entitlement token at a second location remote from the first location;

looking up the blockchain address to verify that the first signature is valid;

identifying whether the second signature matches any signatures stored by the server system; and verifying that the presented token is authentic at the second location where the response message indicates there is a match between the second signature and a stored signature.

The system makes healthcare data easily accessible with relatively minimal privacy and hack risk to all patient stakeholders, including the patient themselves, family, caregivers, clinics, providers, insurance companies and all those with a stake in their patients' health. Each and every one of these stakeholders or network peers approved by the patient can easily join health blockchains as either nodes or buyer or seller of tokens or payments to gain access to patient data, utilizing a variety of open access methods and smart contracts that store and monitor real-time contractual conditions agreed to by and between various stakeholders. The health blockchains can be used for tracking the development of drugs, doctor and nurses credentialing, real-time population health data analysis and alerts, insurance peer-to-peer risk pooling, telemedicine and home health visit data sharing, decentralized autonomous organizations, verification and audits, and remote device monitoring commonly addressed today under the Internet of Things category. The blockchains enable analytics-for-healthcare products and services, malpractice insurance and friction-less claims processing hence shorter revenue cycles. Smart contracts powered by a blockchain can provide consumers and payors with the means to manage claims in a transparent, immutable and responsive fashion. Insurance contracts, premium payments and their respective claims can be recorded onto a blockchain and validated by node consensus, preventing fraudulent claims from being processed. Smart contracts can enforce claims triggering payments when due or dispatching specialists, nurses or doctors to follow up with patients when anticipated claims are not recorded by presumptive dates.

In one embodiment, behavioral contracts are developed between payor and patient to trigger rewards for attending support groups, regularly engaging a telehealth professional, reporting health conditions (possibly at kiosks with bitcoin point-of-care devices), and meeting agreed upon health goals. A smart contract would trigger a reward payment (or loss) when goals are met near real-time to the patient's public bitcoin address which in turn can be tendered at local participating outlets equipped with point-of-contact devices including community centers, supermarkets and apartment complexes to pay bills, purchase healthy foods and meet rent obligations.

Medical malpractice insurance decentralized autonomous organizations (DAOs) can use blockchain to provide an immutable record and audit trail of an agreement without a single controlling body. Doctors and nurse practitioners can collaborate to establish a peer-to-peer malpractice DAO and record each peer's premium payments and claims on the blockchain. All premiums paid in would create a pool of capital to pay claims. By combining the blockchain with the peer-to-peer business model, this creates the potential for a near-autonomous self-regulated insurance business model for managing policy and claims. No single entity would control the network. Policyholders can "equally" control the network on a pro-rata basis.

Figure 13H:
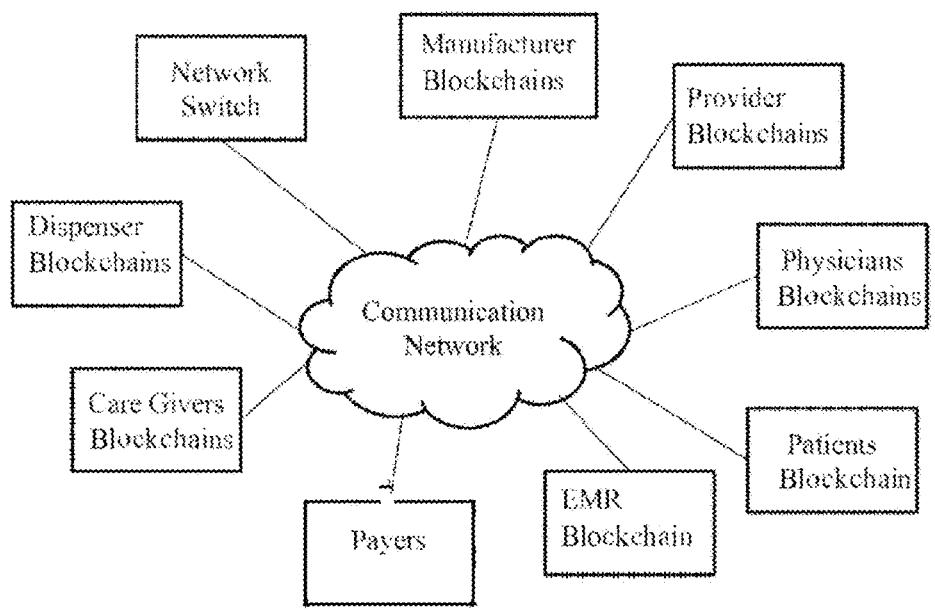
Figure 13I:
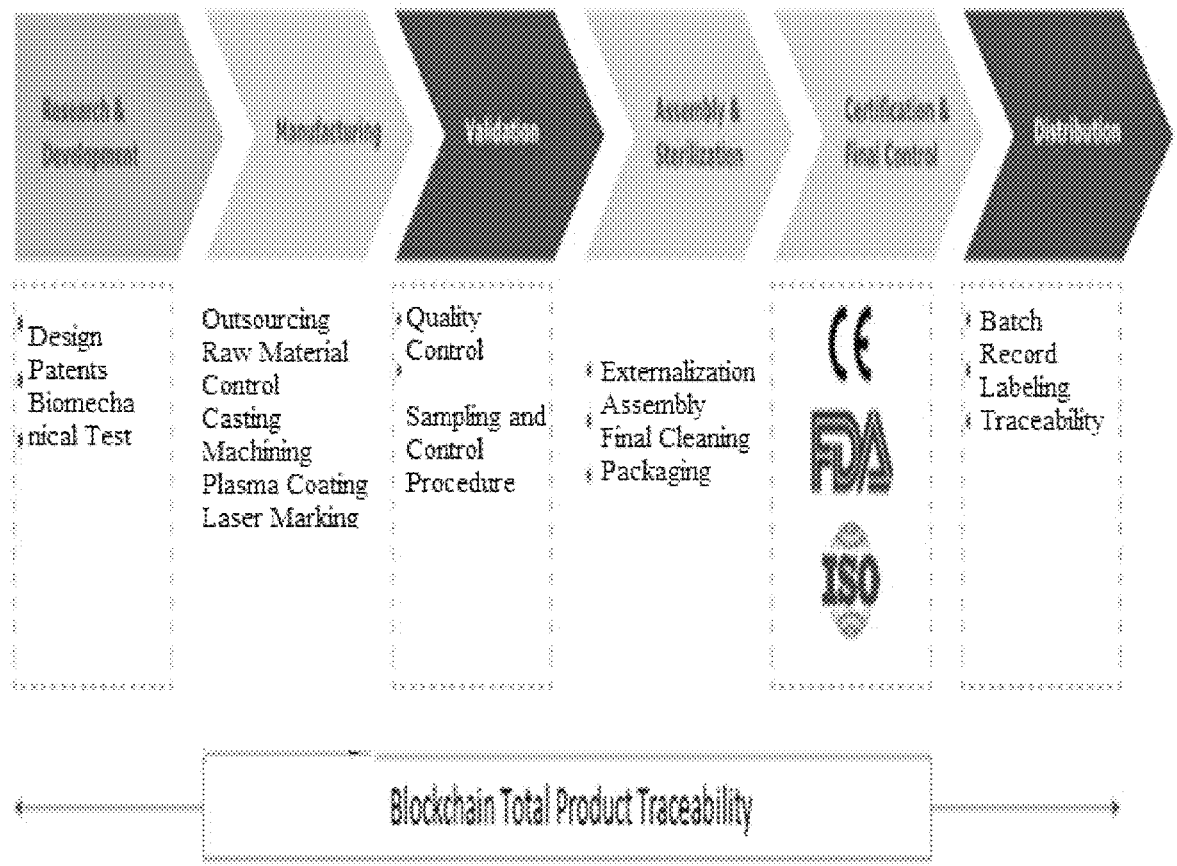

FIGS. 13H-13I show exemplary medical supply chain that works with blockchain for tamperproof origin and shipping supply chain authentication of genuine medical products. One system collects results for virtually any test, and storing and trending data. This ensures that the control systems are operating as intended. These trends provide valuable insight into the effectiveness of decontamination procedures, housekeeping practices, personnel training, and the potential for microbial build-up during production. The present invention provides configurable means for electronically documenting, storing, and reporting on monitored environmental parameters. Those skilled in the art will recognize that computer programs in accordance with the present invention is able to reside on hardware, and with software that already exists in many manufacturing facilities. Such data collection devices include viable particle counters (e.g., Met One, Climet Instruments), organism identification systems (e.g., Phoenix™, Vitek, Biolog, MIDI), air samplers (e.g., SAS, and VAI), facility monitoring equipment (e.g., Heating, Ventilation, Air Conditioning (HVAC) systems), rapid organism enumeration technology devices, bioluminescence devices, pressure gauges, thermometers, and humidity detectors.

Each of the datum captured is encoded with a distributed ledger or blockchain for subsequent verification and audit by the factory QA team, regulatory agency, product safety analyst, or consumers if needed. One exemplary Audit Trail complies with 21CFR Part 11. Preferably, the system maintains an automatic (non-user modifiable) audit trail of all events and modifications made to the system secured by blockchain. The audit trail contains the following:

An entry identifying the type of modification made to the database/record, such as additions, deletions, modifications, review, etc.

An entry identifying the user performing the modification to the database/record An entry noting the date/time of the database/record modification The date/time included in the audit trail should be retrieved from the server system clock, not the local system clock The entire database record being modified with the changed fields highlighted The full manifestation of the name of the user performing the modification The audit records should be accessible only by authorized users The audit records should be able to be selected by date and category (component)

The audit records should be reported in an 'easy-to-read' format (view and print) Electronic Signatures The system provides the option to require an electronic signature prior to performing any modification to the database/records The electronic signature requires the entry of the username and password of the user performing the database modification The electronic signature provides the option to enter information describing the 'meaning' of the signing The electronic signature prevents the "excising" (cut, copy, paste) of the electronic signature components between signings (i.e., a "link" between the electronic signature and its database record)

In one embodiment a product may be any tangible or intangible thing that may be exchanged for value, excluding the first transaction 204; in other words, the value for which the product is exchanged is unrelated to the value of the product or service exchanged to produce the first transaction. The product may be a good, such as an article of manufacture or an item produced in agriculture. The product may be merchandise. The product may be a consumable. The product may be a fixed asset. The product may be a circulating tool. The product may be a library books. The product may be capital equipment. The product may be a bill of fiat currency. The product may be commercial paper. The product may be an item, such as a coupon or voucher, which may be used as proof of payment for a service. For instance, the product may be a ticket for conveyance on a transportation carrier such as a train, bus, or airline. The product may be a ticket for an entertainment event such as a sporting event or a concert. The system can also verify the quality of services such as legal services, financial services, consulting services, financial planning services, repair services, cosmetic services, healthcare services, medical services, massage services, among others.

In some embodiments, the first computing 201 is configured to export an address to a first code such as a bar code affixed to a product. The system may include a code generator coupled to the first computing device. The code generator can be a bar code generator or a wireless code such as a near field communication (NFC) code. Upon receipt by a bar code scanner or an NFC scanner, the product authenticity can be verified. The product may combine other anti-counterfeiting measures with the first code such as a holographic icon or a special tamperproof case/housing, for example.

In some embodiments, the first code is incorporated in a manufacturing control system (not shown) that may rely upon codes, such as barcodes or NFC/RFID tags, to provide automatic identification of products. To record manufacturing transaction, the system may use a code scanner to automatically identify the product, and then may collects additional information from operators via fixed terminals (workstations), or mobile computers. The code used in the system may be matched to a data structure mapping codes to data concerning products, such as a database. The data structure mapping codes to products may be the transaction register. The data structure mapping codes to products may be separate from the transaction register. The party managing the manufacturing control system may be the party managing the system. The party managing the inventory control system may be a separate party.

In one embodiment, an address is a textual datum identifying the product or service serial number or ID number in a secured transaction. In some embodiments, the address is linked to a public key, the corresponding private key of which is owned by the recipient of the transfer of product or service. For instance, the address may be the public key. The address may be a representation, such as a hash, of the public key. The address may be linked to the public key in the memory of a computing device. Where the address is linked to a public key, the transferee in the secured transaction may record a subsequent transaction transferring some or all of the product or service to a new address in the same manner.

In some embodiments, the transaction register includes a data storage facility controlled by a trusted party. The data storage facility may include a database and the data storage facility may include a data structure such as a hash table that permits rapid lookup of data stored in the data storage facility. The trusted party may be a proprietor of the system. The trusted party may be a third-party entity, such as an entity maintaining data centers for services such as cloud-computing services. In other embodiments the at least one transaction register may include several data storage facilities maintained by one or more trusted parties; for instance, the at least one transaction register may include several data storage facilities, to which secured transactions are directed as set forth in further detail below. The data storage facilities may be on the same machine. The data storage facilities may be on the same server. The data storage facilities may be in different servers, but in the same data center. The data storage facilities may be in various data centers. The at least one transaction register may be several transaction registers to which secured transactions are directed.

The transaction register may include a distributed, consensus-based ledger and the transaction register may include a hash chain, in which data is added during a successive hashing process to ensure non-repudiation. The transaction register may include a private register run by a predetermined group of entities. For example, the group may be the FDA and select trusted pharmaceutical companies. In other cases, the group can be a number of banks working together. In yet other cases, the group can be a stock market such as NYSE or NASDAQ and banks/traders. In yet other cases, the group can be members of the Army, Air Force, or Navy, or can even be all three. The advantage of having select group members is that sensitive data can be contained to the group for a predetermined purpose rather than broadcasted to the world for anyone to inspect in an encrypted form.

In some embodiments, the transaction register includes a block chain. In one embodiment, the block chain is a transaction register that records one or more new secured transactions in a data item known as a block. The blocks may be created in a way that places the blocks in chronological order, and links each block to a previous block in the chronological order, so that any computing device may traverse the blocks in reverse chronological order to verify any secured transactions listed in the block chain. As a non-limiting example, each new block may be required to contain a cryptographic hash describing the previous block. In some embodiments, the block chain contains a single first block, known as a "genesis block." As an example, the protocol may require a new block to contain a cryptographic hash describing its contents; the cryptographic hash may be required to satisfy a mathematical condition, achieved by having the block contain a number, called a nonce, whose value is determined after the fact by the discovery of the hash that satisfies the mathematical condition. Continuing the example, the protocol may be able to adjust the mathematical condition so that the discovery of the hash describing a block and satisfying the mathematical condition requires more or less steps, depending on the outcome of the previous hashing attempt. The mathematical condition, as an example, might be that the hash contains a certain number of leading zeros and a hashing algorithm that requires more steps to find a hash containing a greater number of leading zeros, and fewer steps to find a hash containing a lesser number of leading zeros. In some embodiments, the production of a new block according to the protocol is known as "mining." Each block created in the block chain 206 may contain a record or transaction describing one or more addresses that receive an incentive, such as product or service, as the result of successfully mining the block 206b.

Where two entities simultaneously create new blocks, the block chain 206 may develop a fork; the protocol may determine which of the two alternate branches in the fork is the valid new portion of the block chain 206 by evaluating, after a certain amount of time has passed, which branch is longer. "Length" may be measured according to the number of blocks in the branch. Length may be measured according to the total computational cost of producing the branch. The protocol may treat only secured transactions 204 contained the valid branch as valid secured transactions. When a branch is found invalid according to this protocol, secured transactions registered in that branch may be recreated in a new block in the valid branch; the protocol may reject "double spending" secured transactions 204 that transfer the same product or service that another secured transaction in the valid branch has already transferred. As a result, in some embodiments the creation of fraudulent secured transactions requires the creation of a longer block chain branch by the entity attempting the fraudulent secured transaction than the branch being produced by the rest of the participants; as long as the entity creating the fraudulent secured transaction is likely the only one with the incentive to create the branch containing the fraudulent secured transaction, the computational cost of the creation of that branch may be practically infeasible, guaranteeing the validity of all secured transactions in the block chain. In some embodiments, where the algorithm producing the blocks involves a cryptographic hash using a well-designed hashing algorithm, attempts to avoid the computational work necessary to create the hashes by simply inserting a fraudulent transaction in a previously created block may be thwarted by the "avalanche effect," whereby a small alteration of any data within the block chain causes the output of the block chain to change drastically; this means that alterations are readily detectable to any person wishing to validate the hash of the attempted fraudulent block.

Additional data linked to a secured transaction may be incorporated in blocks in the block chain; for instance, data may be incorporated in one or more fields recognized by block chain protocols that permit a person or computer forming a transaction to insert additional data in the block chain. In some embodiments, additional data is incorporated in an unspendable transaction field. For instance, the data may be incorporated in an OP RETURN within the Bitcoin block chain. In other embodiments, additional data is incorporated in one signature of a multi-signature transaction. In an embodiment, a multi-signature transaction is a secured transaction to two or more addresses. In some embodiments, the two or more addresses are hashed together to form a single address, which is signed in the digital signature of the secured transaction. In other embodiments, the two or more addresses are concatenated. In some embodiments, the two or more addresses may be combined by a more complicated process, such as the creation of a merkle tree as described below. In some embodiments, one or more addresses incorporated in the multi-signature transaction are typical secured addresses, such as addresses linked to public keys as described above, while one or more additional addresses in the multi-signature transaction contain additional data related to the transaction; for instance, the additional data may indicate the purpose of the transaction, aside from an exchange of product or service, such as the item for which the product or service was exchanged.

The transaction register may include a block chain ecosystem data structure. In one embodiment, a block chain ecosystem data structure is a data structure that is located outside a block chain but uses the block-chain as a basis for reliability or security by giving elements in the block chain ecosystem data structure a secure and reproducible relationship with elements within the block chain. The block chain ecosystem data structure may create the relationship by inserting representations of elements from the block chain ecosystem data structure into blocks in the block chain; for instance by "merge hashing," where the elements are part of what gets hashed as block chain data during the hashing algorithm for blocks as described above. For example, in some embodiments, the transaction register may include an alternative chain. In one embodiment, an alternative chain is one or more blocks (not shown) that are incorporated into a blockchain, by including at least one hash representing data in the alternative chain in at least one block in the blockchain that is mined; where the mathematical puzzle involved in creating the new block is the production of a new hash, the additional hash in the block may not affect the degree of difficulty, and thus miners are not put at a computational disadvantage incorporating the alternative chain. The alternative chain may be incorporated using one or more hash trees, such as one or more merkle trees (not shown). The merkel tree may a structure containing a hash of each datum in the alternative chain as leaf notes, with each internal node containing a hash of all of its child nodes; thus, by the avalanche principle, the root of a merkle tree may be a hash that recursively represents all the data hashed in the merkle tree, and thus a set of data in the alternative chain, so that incorporation of the root in a block in the blockchain 206 amounts to incorporation of the data from the alternative chain that the merkle tree represents. A miner may charge a fee for incorporating the alternative chain in a block the miner mines. In an embodiment, verification of a transaction filed in the alternative chain involves first locating the transaction in the alternative chain, verifying its digital signature, and verifying each hash between that location and the blockchain block (for instance by verifying each hash in the merkle tree from the leaf corresponding to the transaction to the root), verifying the hash of the block incorporating the alternative chain, and then verifying the block up the block chain as described above. In other embodiments, the hash tree is a tiger tree. In other embodiments, the alternative chain is linked to the block chain via a hash chain (not shown).

In some embodiments, data linking the block chain ecosystem data structure to the block chain is incorporated in an unspendable transaction field. For instance, the data may be incorporated in an OP RETURN within the Bitcoin block chain. In other embodiments, data linking the block chain ecosystem data structure to the block chain is incorporated in one signature of a multi-signature transaction. For example, the root of a merkle tree may occupy one or more addresses that are signed in a multi-signature transaction.

In other embodiments, elements in the block chain ecosystem data structure are mapped to elements in the block chain by means of an agreed-upon mapping protocol. For instance, rather than inserting a hash from the block chain ecosystem into the block chain, an algorithm may establish a mathematical relationship between an element in the block chain ecosystem data structure and an element in the block chain; the mathematical relationship may be unique to the element in the block chain ecosystem data structure. The mathematical relationship may be unique to the element in the block chain. As a non-limiting example, elements in a block chain ecosystem data structure may be mapped to particular transactions in the block chain. Elements in the block chain ecosystem data structure may be mapped to particular addresses in the block chain. Elements in the block chain ecosystem data structure may be mapped to particular hashes corresponding to blocks. The mapping may be performed using digital signatures; for instance, the owner of a private key corresponding to a public key represented by an address in the block chain may sign an element in the block chain ecosystem with the private key. Each element in the block chain may be hashed, and the space containing all hashes may be mapped to elements in the block chain using a mathematical algorithm.

In other embodiments, the block chain ecosystem data structure may incorporate a side chain. In some embodiments, a side chain is a block chain that is operated parallel to a main block chain, using transactions or transaction outputs extracted from and later merged back into the main block chain via two-way pegging. The transactions or transaction outputs may be merged back into the main block chain by performing a combined hash of the latest link in the side chain with the latest link in the block chain. The combined hash may use a merkle tree as described above to reduce the computational difficulty associated with a combined hash of two entire blocks.

In an exemplary embodiment, a decentralized property system and method are provided to allow ownership rights to be transferred directly from one party to another without requiring a central authority to operate or secure the system. Digital signatures provide a method to issue and transfer titles within the system. Using a blockchain, distributed consensus on who owns what are achieved. Digital assets can be uniquely identified by digital fingerprints using cryptographically-safe hash functions. Fingerprints computed from images of the asset may be used in a method to uniquely identify physical assets. In some embodiments, the unique identifier used for a physical asset may be a physical unclonable function. Title transfers are verifiable and create an unforgeable chain-of-ownership ("provenance"). Digital signatures and other methods like fingerprinting provide a method to issue and transfer titles. An Asset Record that includes specific attributes describing the property is created to digitally represent the asset. An Issue Record is then created to represent instances of the property linking to a specific Asset Record. A Transfer Record is created to record each ownership changes. The Transfer Records are chained together and the root is chained to the Issue Record, which is chained to the Asset Record. Each system user has an account that is associated with a unique number, for example, an Ed25519 public-key ("pubkey") pair, or other appropriate pubkey system, which allows the user to sign Issue and Transfer Records. The owner of the is identified by their pubkey. This differs from Bitcoin, which only has one type of address and signature because the bitmark account can support multiple types of signatures, including post-quantum computing algorithms such as SPHINCS.

In an aspect, encoded data derived from images of local regions of a physical object are used to securely reference ("fingerprint") physical assets based on unique surface-level texture patterns, rendering the physical asset traceable as a digital item. For pets, encode picture and sound can render the asset traceable. For newborn babies, the encoded picture, sound, and fingerprint/footprint can render the child traceable. A cryptographically-safe hash function is used to fingerprint digital assets. The system provides a framework for authenticating different objects or materials via extracting and matching their fingerprints. Biometric fingerprinting processes, which use patterns such as ridge ending and bifurcation points as the "interest points," can be used. Stereo photometric techniques can be used for reconstructing local image regions of objects that contain the surface texture information. The interest points of the recovered image regions can be detected and described by state-of-the-art computer vision algorithms. Together with dimension reduction and hashing techniques, the approach is able to perform object verification using compact image features for virtually any object, including documents, for practical physical object authentication tasks.

In one implementation, a digital asset is certified via embedding its SHA256 digest in the blockchain. This is done by generating a transaction that encodes/contains the hash via an OP_RETURN script. This is a bitcoin scripting opcode that marks the transaction output as provably unspendable and allows a small amount of data to be inserted, which is the digital asset hash, plus a marker to identify all of a company's transactions. Once the transaction is confirmed by the blockchain, the digital asset is permanently certified and proven to exist at least as early as the time the transaction was confirmed. If the document hadn't existed at the time the transaction entered the blockchain, it would have been impossible to embed its digest in the transaction (This is because of the hash function's property of being second pre-image resistant). Embedding a hash and then adapting a future document to match the hash is also impossible (due to the pre-image resistance of hash functions). Hence, once the blockchain confirms the transaction generated for the digital asset, its existence is proven, permanently, with no trust required. To manually confirm the asset's existence at the timestamped time, the system calculates the document's SHA256 digest and finds a transaction in the bitcoin blockchain containing an OP_RETURN output with the document's hash prepended by marker bytes. The existence of that transaction in the blockchain proves that the digital asset (or intellectual property) existed at the time the transaction got included into a block. The system proves data ownership without revealing actual data by publicly revealing the digest and if conflict arises the device can produce the data that generates the digest. The system can prove certain data exists at a certain moment of time. As we use the blockchain to store the document proof, the system can certify the existence of your document without the need of a central authority. The system can check for asset integrity. The system will only recognize it if it is completely and fully the same document. The slightest change will be recognized as different, giving user the security that certified data can't be changed.

1. A method for recording ownership in data generated by an IOT device, the method comprising: generating a digital asset by an IOT device; generating a hash representation of the asset; placing on an audit chain a transaction to an address associated with a public key corresponding to a private key; asserting the IOT device as the owner of the digital asset with one or more marker bytes; and looking for a transaction matching the digest and marker bytes to prove the IOT device first had possession of the intellectual property or digital asset. Then the IOT device can securely update data, or provide access rights to the digital asset.

2. A method according to claim 1, wherein receiving further comprises receiving the public key.

3. A method according to claim 1, wherein receiving further comprises receiving a digital signature signed with the private key.

4. A method according to claim 1, wherein receiving further comprises: transmitting a challenge to the first entity, and receiving a digital signature signing the challenge.

5. A method according to claim 1, wherein receiving further comprises: transmitting a message encrypted using the public key; and receiving, by the IOT device from the first entity, a decrypted version of the message.

6. A method according to claim 1, wherein retrieving further comprises retrieving a transaction from a second entity to the first entity.

7. A method according to claim 6, wherein authenticating further comprises: authenticating the second entity; and determining that the at least one crypto-currency transaction represents an act of authentication of the first entity by the second entity.

8. The method of claim 6, wherein the transaction from the first second entity to the first entity further comprises granting access rights to the first entity.

9. A method according to claim 1, wherein authenticating further comprises determining a reputation based on at least one crypto-currency transaction, a financial value of at least one crypto-currency transaction, an identity of the first entity, or an access right of the first entity.

In another embodiment, a method for recording ownership rights in an asset includes: generating an asset record having a fingerprint comprising a hash of a digital representation of the asset, a public key of a client who generates the asset record, and a digital signature comprising a private key of the creating client; communicating with one or more nodes of a peer-to-peer network to generate an entry in a public ledger by performing the steps of: generating at least one issue record comprising a hash of the fingerprint, the public key of the creating client, and an owner signature comprising a hash of the digital signature of the creating client with the hashed fingerprint and the public key of the creating client. In some embodiments, the asset is digital property selected from the group consisting of music, video, electronic books, digital photographs, digital images, and personal data. In another embodiment, the asset is physical property, and the method further includes generating a digital fingerprint corresponding to the physical property using an image of a physical property.

The method may further include generating a first transfer record for recording a transfer of the asset to a new owner, wherein the transfer record comprises a double hash of a complete issue record for the asset and a public key of the new owner, wherein the transfer record is digitally signed by the owner signature; using a blockchain algorithm to generate a distributed consensus of ownership of the asset associated with the owner signature to validate the first transfer record; and if the first transfer record is validated, displaying the transfer record on the public ledger; and if the first transfer record is not validated, rejecting the transfer record. In some embodiments, the method may further include, after the step of generating the first transfer record: displaying at the user interface a payment request; and determining whether a user payment has been remitted before proceeding with the step of executing. The method may further include generating a subsequent transfer record for recording a transfer from a prior owner to a subsequent new owner, wherein the subsequent transfer record comprises a double hash of a prior transfer record, and a public key of the subsequent new owner, wherein the subsequent transfer record is digitally signed by the prior owner. In some embodiments, the method may further include, after the step of generating the subsequent transfer record: displaying at the user interface a payment request; and determining whether a user payment has been remitted before proceeding with the step of executing. In embodiments in which the at least one issue record comprises multiple issue records, each issue record includes a different nonce and is associated with a separate blockchain.

In another aspect of the invention, a system for recording ownership rights in an asset includes: a client computing device configured for generating an asset record having a fingerprint comprising a hash of a digital representation of the asset, a public key of a client who generates the asset record, and a digital signature comprising a private key of the creating client; a peer-to-peer network in communication with the client computing device to generate an entry in a public ledger by performing the steps of: generating at least one issue record comprising a double hash of the fingerprint, the public key of the creating client, and an owner signature comprising a hash of the digital signature of the creating client with the double hashed fingerprint and the public key of the creating client; and displaying the at least one issue record on the public ledger. The asset may be digital property selected from the group consisting of music, video, electronic books, digital photographs, digital images, and personal data. Alternatively, the asset may be physical property, where the client computing device is further in communication with a photometric stereo device configured for generating a digital fingerprint corresponding to the physical property using a local image of a region of interest on a surface of the physical property. The photometric stereo device is configured for identifying local interest points within the photometric stereo image using a keypoint detector; and encoding the local interest points as a binary string using a binary descriptor; wherein the binary string comprises the digital representation of the asset.

In one embodiment, the blockchain address is used to replace the databases holding registration information for trademarks, patents, designs and copyright. By registering IP rights on a distributed ledger, the IP provides smart intellectual property rights, providing a robust and trustworthy proof of record. Further the claims of the IP are expressed as contract conditions that allow automatic attachment to infringing products or articles. For trademark, linked to and connected to actual use of products, so that (first) use in trade/commerce requirements could be updated immediately. This in turn would affect how trademarks could be cleared for registration and use since actual use information could—theoretically and if the law was changed accordingly to provide for this possibility—be added to the registration details of a trade mark on the official register. This would mean that evidence and information of actual use of a trade mark in trade, as well as the frequency of such use could be readily shared and be available on the official trade mark register. The official register could also reflect the state of the market, which is relevant when it comes to assessing the infringement risk in many jurisdictions.

If all transactions relating to a product bearing a particular trade mark are entered on the blockchain, then that use of the trade mark on the blockchain provides evidence of use of the trade mark in trade. The system simplifies the process of proving evidence of use of a trade mark in trade and/or or first use in commerce, depending on the jurisdiction, as well as providing other evidence at an IP office or court, for example evidence of acquired distinctiveness or secondary meaning. Further, whenever use of a trade mark in trade/commerce can be reconciled with information on a blockchain ledger then this could enable evidence of such use to be notified to the relevant IP office or authority virtually immediately on the occurrence of a verified event of such use. This would substantially lower the burden of collecting relevant evidence for rights holders and at the same would simplify the process at respective IP Office.

In one embodiments, private blockchains which are tightly controlled, with rights to modify and/or read the blockchain restricted to a small number of users, can be used for certification and/or collective trademarks, which the added bonus that fake certificates could almost immediately be identified as such. Evidence of creatorship provided by blockchain can be done: if an original design document and details of the designer are uploaded to a blockchain, this creates a time-stamped record and good evidence to prove these matters. Locking evidence of their use and conception on a blockchain could make their enforcement much easier and at the same time also act as a deterrent to potential infringers. Provenance authentication Blockchain also allows you to record objectively verifiable details about when and where products are made and about the people that made them. The information is used for brand protection and information, including trade mark registration details, legal information, assignment and chain of title information and/ or evidence of (first) use in trade or commerce. Brand owners use this function to record where goods are placed on the market—allowing them to distinguish grey goods in cases of parallel imports and identify where they left the supply chain. In the same way, blockchain could be used to monitor and control leaks from selective distribution networks and so assist in enforcing such agreements. This capability will render the technology of interest to other industries, such as the pharmaceutical industry. The system can link products to blockchain however (rather than to URLs as is common in QR Code marketing) is the immutable nature of the information which appears on the blockchain. This makes it an attractive and safe place for a brand to imprint upon its products with brand messages, product and potentially also legal information: blockchain can be used for much more than marketing.

The system can use the blockchain address as a way of securing intellectual property and digital creative works such as images or music. The blockchain ledger is intended to be a secure and reliable way of proving a work's attribution and provenance. And the programmable nature of the digital block makes it possible to enforce smart contract based usage rights.

In travel and hospitality as well as retail, blockchain is used in loyalty-points programs, including more advantageous accounting treatment of the liabilities created by the accrual of points, real-time updating of points balances, and better management of points across franchised operations due to the fact that a shared distributed ledger can simplify the settlement process.

The blockchain can be used to secure access to and from the IOT device in an embodiment. Access right is the right of an entity to use the IOT device or network of computing devices for at least one purpose. For instance, an access right may permit an IOT device possessing the appropriate authentication credentials to operate another IOT device or a computer after "logging on" to the computer. An access right may permit the IOT device to perform some functions, while forbidding the performance of other instructions. The computing device may be configured to ignore or refuse commands from an IOT devicethat does not have a user account with the access right to instruct the IOT device to execute those commands. In some embodiments, the access right gives the IOT device with the ability to access a particular network or a particular network access point. The access right may affect the ability to access one or more master nodes of a network. The access right may affect the ability to access or read messages directed to particular user account within a messaging service; for instance, the access right may control whether a particular IOT device can read a particular email account, an instant message, a text message, or a voice over internet protocol stream. The access right may give the IOT device the ability to decrypt an encrypted message; in some embodiments, where the access right is tied to the possession of a particular private key, an encrypted message or stream may be encrypted using the corresponding public key. The access right may give a device the ability to unlock the use of an application or suite of applications on a computing device; for instance, the device may be able to access communication sites concerning classes. The user may be able to access music on a cloud service or on a local computing device. The device may be able to access streaming media over a network if in possession of the access right. The access right may give the device the ability to lock out or allow entry to certain people peer-to-peer (P2P) network and to those files. The access right may control the ability of a user or IOT device to access an application programming interface (API). The access right may control access to a particular file or set of files; for instance, the access right may lock access to confidential information, or information that could be used for identity theft, such as passport, social security, birth certificate data, permit data, data concerning licenses, data concerning escrowed property, legal documents such as wills, settlements or divorce decrees, or electronic access to physically locked devices such as safe-deposit boxes or the doors to vehicles or buildings.

1. A method for authentication by an IOT device, the method comprising: receiving, by the IOT device, from a first entity a private key; retrieving from an audit chain a transaction to an address associated with a public key corresponding to the private key; and authenticating the first entity. Then the IOT device can securely update with code from the first entity, or receive data from the first entity.

2. A method according to claim 1, wherein receiving further comprises receiving the public key.

3. A method according to claim 1, wherein receiving further comprises receiving a digital signature signed with the private key.

4. A method according to claim 1, wherein receiving further comprises: transmitting a challenge to the first entity, and receiving a digital signature signing the challenge.

5. A method according to claim 1, wherein receiving further comprises: transmitting a message encrypted using the public key; and receiving, by the IOT device from the first entity, a decrypted version of the message.

6. A method according to claim 1, wherein retrieving further comprises retrieving a transaction from a second entity to the first entity.

7. A method according to claim 6, wherein authenticating further comprises: authenticating the second entity; and determining that the at least one crypto-currency transaction represents an act of authentication of the first entity by the second entity.

8. The method of claim 6, wherein the transaction from the first second entity to the first entity further comprises a transaction granting access rights to the first entity.

9. A method according to claim 1, wherein authenticating further comprises determining a reputation based on at least one crypto-currency transaction, a financial value of at least one crypto-currency transaction, an identity of the first entity, or an access right of the first entity.

10. A method according to claim 9, wherein determining the at least one access right further comprises: determining that a second entity possesses at least one access right, and determining that at least one crypto-currency transaction represents a transfer of at least one access right possessed by the second entity to the first entity.

11. A method according to claim 10, wherein determining at least one access right further comprises: identifying the first entity; and retrieving an access right previously associated with the first entity.

12. The method of claim 1, wherein the audit chain comprises a secured audit chain, a cryptographically secured audit chain, or a block chain.

13. The method of claim 1 further comprising generating at least one crypto-currency transaction by the IOT device.

14. The method of claim 1, further comprising: generating a first transfer record for recording a transfer of the IOT device to a new owner, wherein the transfer record comprises a hash of a complete issue record for the IOT device and a public key of the new owner, wherein the transfer record is digitally signed by an existing owner signature; executing within the one or more nodes a blockchain contract to generate a distributed consensus of ownership of the IOT device associated with the owner signature to validate the first transfer record; and if the first transfer record is validated, displaying the transfer record on the public ledger; and if the first transfer record is not validated, rejecting the transfer record.

15. The method of claim 14, further comprising: generating a subsequent transfer record for recording a transfer from a prior owner to a subsequent new owner, wherein the subsequent transfer record comprises a hash of a prior transfer record, and a public key of the subsequent new owner, wherein the transfer record is digitally signed by an existing owner signature; executing within the one or more nodes a blockchain contract to generate a distributed consensus of ownership of the IOT device associated with the owner signature to validate the first transfer record; and if the first transfer record is validated, displaying the transfer record on the public ledger; and if the first transfer record is not validated, rejecting the transfer record.

19. The method of claim 1, wherein the at least one issue record comprises multiple issue records, and wherein each issue record includes a different nonce.

Figure 14A:
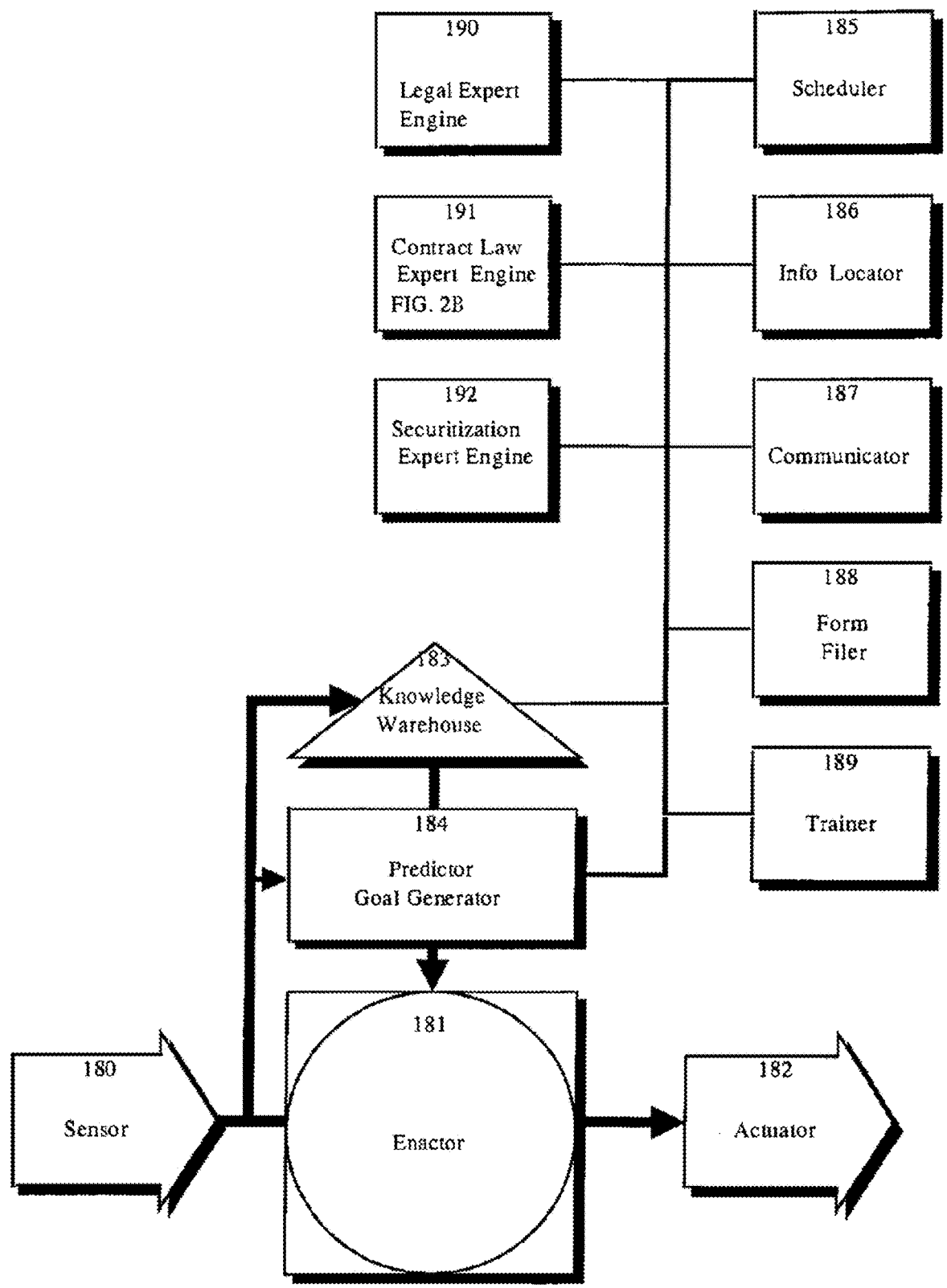
FIGS. 14A-14H show exemplary IOT systems with blockchain and flowcharts detailing their operations.

FIG. 14A shows an exemplary smart contract agent running in electronic agents that carry out transactions. The same agent is also judge agent, arbitrator agent, and jury agents who have to resolve machine to machine contractual disputes. Agent technology is used for developing such systems that situates and operates in a dynamic and heterogeneous environment. An agent is an autonomous software entity that is situated in some environment where it can monitor and response to changes proactively or reactively by itself or through communication with other agents to persistently achieve certain goal/task on behalf of user or other agents. These agents can form contract with other agents and use the smart contract framework discussed above for ensuring certainty in executing their tasks.

Expert (knowledge) systems contain two basic elements: inference engine and knowledge base. The knowledge base holds all information related to the tasks at hand: the rules and the data on which they will be applied. The inference engine is a mechanism that can operate the information contained in the knowledge base. In a rule-based system, the knowledge base is divided into a set of rules and working memory (or database). Just like an IF-THEN sentence, each rule has two parts: a premise and a conclusion. A rule is said to be fired when the inference engine finds the premise is stored as TRUE in working memory (the knowledge base) and it incorporates the conclusion of the rule to the working memory (knowledge base) too. Working memory is the database contained in the knowledge base. This holds all facts that describe the current situation. Generally, the expert system will start with very few facts. These will expand as the system learns more about the situation at hand, and as far as some rules are executed. The inference engine or rule interpreter has two tasks. First, it examines facts in working memory and rules in the rule base, and adds new facts to the database (memory) when possible. That is, it fires rules. Second, it determines in what order rules are scanned and fired. The inference engine can determine the order in which rules should be fired by different methods such as forward chaining, backward chaining, breadth- or depth-wise scan techniques, etc. Applications that use forward chaining, such as process control, are called data-driven. Applications that use backward chaining are called goal-driven. Forward chaining systems are typically used where relevant facts are contained in small sets and where many facts lead to few conclusions. A forward chaining system must have all its data at the start, rather than asking the user for information as it goes. Backward chaining should be used for applications having a large set of facts, where one fact can lead to many conclusions. A backward-chaining system will ask for more information if needed to establish a goal.

In addition to expert systems, a pattern recognizer called neural networks can be used. Neural networks attempt to mimic the human brain by "learning" different sets of stimulus patterns (such as medical symptoms) and their associated responses (diagnoses). Incomplete and/or overlapping sets of stimuli can be presented to the neural network, which can then return several responses matching those stimuli using probability weightings to produce an ordered list of responses. Each neural network problem session contains a set of defined stimuli, a set of defined responses, and a set of relationships between specific groups of stimuli and the response that each group is to produce. The set of stimuli (responses) is represented by a group of stimulus (response) nodes at what is called the "input (output) layer." Then, there is usually one or more intermediate layers, containing nodes that are each linked to every input layer node and every output layer node in the network. The number of the middle layer nodes is usually equal to the average of the number of input and output nodes. Probability values (weights) are then associated with each of these connections and are constantly being updated as the network "learns" new information.

Further, when a planning agent works in a complex, real-world domain, it is unable to plan for and store all possible contingencies and problem situations ahead of time. The agent needs to be able to fall back on an ability to construct plans at run time under time constraints. Thus, a system for performing dynamic planning at run time is needed.

Turning now to FIG. 14A, one smart assistant agent with smart contracting capability is illustrated in more detail. The agent is software based agent. In FIG. 14A, one or more sensors 180 receives incoming information. The sensors 180 in turn transfer the data to an enactor 181. The enactor 181 in turn makes a decision based on its current situational data, as captured by sensors 180. The enactor 181 then drives an actuator 182. In addition to receiving data from the sensor 180, the enactor 181 also receives instruction from a predictor/goal generator 184, which in turn is connected to a general knowledge warehouse 183. The external data sensed by the sensor 180 is also delivered to both the warehouse 183 and the predictor/goal generator 184. Additionally, both the warehouse 183 and the predictor/goal generator 184 are connected to a plurality of specialist knowledge modules, including a scheduler 185, an information locator 186, a communicator 187, a form filler 188, a trainer 189, a legal expert 190, a medical expert 191 and additional experts 192. The knowledge warehouse 183 has a representation for the user's world, including the environment, the kind of relations the user has, his interests, his past history with respect to the retrieved documents, among others. Additionally, the knowledge warehouse 183 stores data relating to the external world in a direct or indirect manner to enable to obtain what the assistant needs or who can help the electronic assistant. Further, the knowledge warehouse 183 is aware of available specialist knowledge modules and their capabilities since it coordinates a number of specialist modules and knows what tasks they can accomplish, what resources they need and their availability. The smart electronic or on-line assistant agent can issue smart contracts detailed above to optimize cost or operational efficiency on behalf of its master which can be another electronic smart agent or a human master.

The assistant has an enactor for processing data received from a sensor and for changing its environment via an actuator. The enactor receives instruction from a predictor/goal generator, which in turn is connected to a general knowledge warehouse. Additionally, the warehouse and the predictor/goal generator are connected to a plurality of specialist knowledge modules, including a scheduler, an information locator, a communicator, a form filler, a trainer, a legal expert, a medical expert, and other experts.

The electronic assistant provides an interface which frees the user from learning complex search languages and allows some functions to be automatically performed. A variety of machine learning processes allow the assistant to learn the user's styles, techniques, preferences and interests. After learning about the user's interests in particular types of information, the assistant guides the user through the process of on-line information source selection, utilization, and interaction management via the information locator. The information locator generates a query conforming to the user characteristics for retrieving data of interest. The information locator next submits the query to one or more information sources. Upon receipt of results of the submitted query, the information locator communicates the results to the user, and updates the knowledge warehouse with responses from the user to the results. The assistant supports the ability to refine the query and to manage the costs associated with the search. Further, the assistant automatically incorporates data relating to changes in the query interface and other relevant characteristics of the information sources so that search command sequences can be altered without user interaction. The search configuration of each search carried out by the user is saved in a database. The data maintained in the database includes keywords and concepts for search, interval between subsequent searches, deadline for the search, the number of documents to acquire from each engine, and domain over which to do the search, including the preferred set of search engines or the preferred set of news groups.

The assistant then automatically schedules and executes multiple information retrieval tasks in accordance with the user priorities, deadlines and preferences using the scheduler. The scheduler analyzes durations, deadlines, and delays within its plan while scheduling the information retrieval tasks. The schedule is dynamically generated by incrementally building plans at multiple levels of abstraction to reach a goal. The plans are continually updated by information received from the assistant's sensors, allowing the scheduler to adjust its plan to unplanned events. When the time is ripe to perform a particular search, the assistant spawns a child process which sends a query to one or more remote database engines. Upon the receipt of search results from remote engines, the information is processed and saved in the database. The incoming information is checked against the results of prior searches. If new information is found, the assistant sends a message to the user.

When the assistant operates in an environment equipped with a handheld computer which is adapted to work with a host computer, the assistant splits into two personalities, one residing on the handheld computer with an intelligent desktop assistant for interacting with the user and one residing on a host computer with an information locator for executing searches in the background. When results are found, the assistant running on the host computer prioritizes the retrieved documents. Further, the assistant on the host computer transforms the data designed to be sent to the handheld computer into an equivalent file optimized for fast and robust wireless transmission. The assistant then immediately transmits the transformed, high priority documents to the handheld computer through a wireless modem while withholding lower priority documents for transfer when the handheld computer docks with the host computer to minimize data transmission costs. Further, upon docking, the assistant on the handheld computer synchronizes its knowledge base with the assistant running on the host computer to ensure that the personalities on the handheld and host computers have consistent knowledge of their environments.

In this manner, the assistant intelligently interacts and assists the user in navigating the complexities of cyberspace such that the user is not aware of the functions performed by the assistant. Further, the learning processes update the assistant's knowledge of the user's changing needs and preferences. Hence, documentation will not be needed, as the interface characteristics are updated to reflect the changing experience of the user. The present disclosure thus efficiently filters the universe of information available and displays only information of interest to the user. The provision of precision and timely access to information enables for a more accurate assessment or situational analysis by the user.

Figure 4:
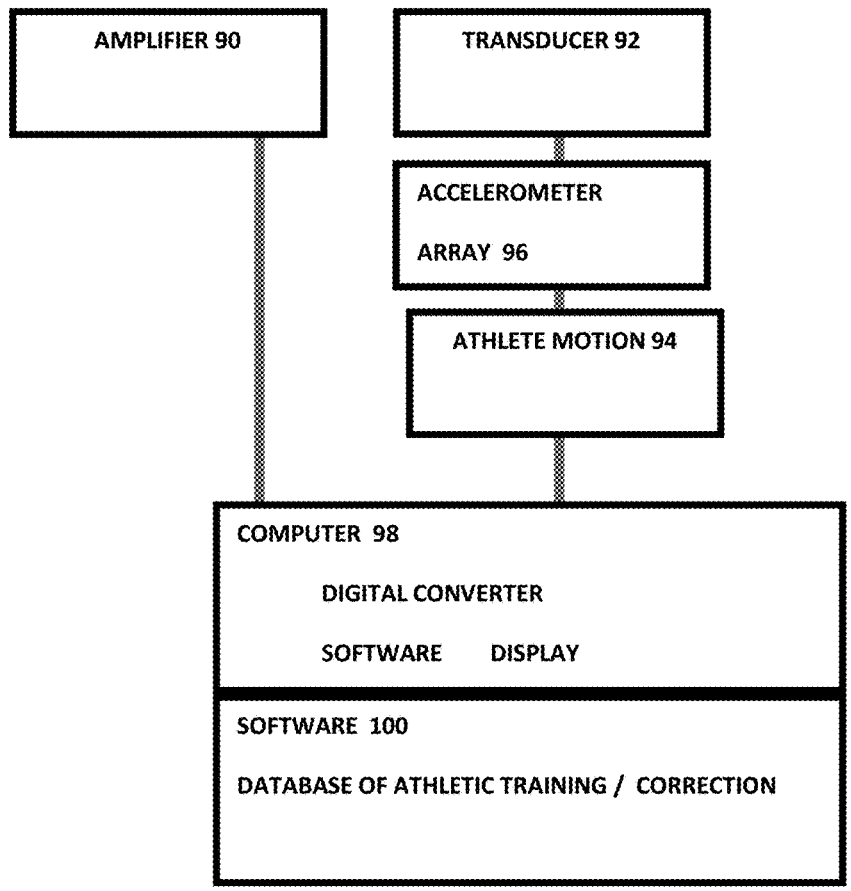
FIG. 4 shows an exemplary sports diagnosis and trainer system for augmented and/or virtual reality.

The scheduler 185 ensures that requested events do not overlap in the event that a user appointment is being requested and that search events with approaching deadlines are provided appropriate resources and prioritization to accomplish the objective of the search. The information locator 186 has knowledge of the user's preferences, as well as outstanding requests for information on certain topics. It periodically scans appropriate databases, and delivers summaries on a scheduled or on-request basis. The communicator 187 interacts with electronic mails or requests for information. It knows the user's preferences and optimizes the presentation of e-mails in accordance with the user's prioritization pattern. Further, in the event of requests for information, in the event that the requester has appropriate authorization, the electronic assistant of FIG. 4 provides the information after consulting with the user about the appropriateness of such action. The form filler 188 knows the user's data entry pattern and fills in the form with predicted information to minimize data entry on the part of the user for repetitive forms. The legal expert module 190 provides legal support for the user, while the medical expert monitors the health condition of the user. Additional experts 192 provide specialist knowledge for specific fields of interest. The trainer 189 provides custom training to the electronic assistant so that it can handle additional tasks not already supported by the modules 185-188 and 190-192. Additionally, although not shown, the present disclosure contemplates that a refresher module may be present to provide the user with additional views which may or may not be pressing for the moment. The refresher module provides unplanned interruptions and information received during the day to provide the user with additional perspectives. For example, the refresher module includes in the batch of information delivered to the user a quantity of non-requested information which might help the user arrive at solutions to other problems in addition to those scheduled by the scheduler.

In FIG. 14A, the protocol is processed by an expert system or a computer system that emulates the decision-making ability of a human judge, arbitrator or legal expert. Expert systems are designed to solve complex problems by reasoning about knowledge, represented mainly as if—then rules rather than through conventional procedural code in one implementation. The expert system is divided into two subsystems: the inference engine and the knowledge base. The knowledge base represents facts and rules. The inference engine applies the rules to the known facts to deduce new facts. The implementation of FIG. 14A has a plurality of knowledge modules to apply contract laws and run inferences on the facts. The expert system of FIG. 14A can have the following modules to honor smart contracts:

I. Formation of Contracts: Contract is an agreement that is legally enforceable.

A. Offer:

1. General test: An offer is a manifestation of an intention to contract. Absent hacking or malware in an Offeror machine, the Offeree (recipient) machine would believe that its answer or assent creates a contract.

2. Specific Pattern Handling a) Content:

(1) Generally, offer is not required to contain all material terms as long as they can be looked up or verified in a central repository, however, some terms are necessary.

(2) Sale of real estate: requires price and description.

(3) Sale of goods: no price requirement.

(4) Vague or ambiguous material terms are not an offer (5) Production contract/output contract/requirements contract: A contract for the sale of goods can state the quantity of goods to be delivered under the contract in terms of the buyer's requirements or Seller's output.

(6) An advertisement can be an offer if it is specific as to quantity and indicates who can accept.

(7) Termination of Offers (4 methods) an offer cannot be accepted if it has terminated.

(a) Lapse of Time: Stated expiration date or reasonable time (30 days is usually the reasonable time).

(b) Revocation (words or conduct of Offeror machine):

(i) When:

(a) Revocation of an offer sent through SMS, email, chat message, or mail is not effective until received.

(b) An offer cannot be revoked after it has been accepted.

(c) Generally offers can be freely revoked by the Offeror machine except when the Offeror machine promised to keep the offer open (option) and this promise is supported by consideration.

(d) An offer cannot be revoked for up to 3 months if
(i) Contract is for sale of goods
(ii) A confirmation specifically to keep the offer open for 3 months is the ceiling even if the written contract says 6 months, and
(iii) Party is a merchant.
(e) Merchant: An agent/computer for an entity who deals in the type of goods involved in a transaction or holds themselves out as having special knowledge in the goods.
(i) An offer cannot be revoked if there has been a detrimental reliance by the Offeree machine that is reasonably foreseeable.
(ii) The start of performance pursuant to an offer to enter into a unilateral contract makes that offer irrevocable for a reasonable time to complete performance.
(f) Unilateral: (e.g. Offeror machine offers Purchaser $1,000 if Purchaser modifies an object in virtual or augmented reality, Purchaser starts the work. Offeror machine cannot revoke.
(g) Performance, not mere preparation: (e.g. If Purchaser only orders codes for modifying the virtual object and has not started, then Offeror machine can still revoke.)
(c) Rejection (words conduct of the Offeree machine):
(i) Counteroffer: Counteroffer terminates the offer and becomes a new offer.
(ii) Conditional acceptance: A conditional acceptance terminates the offer and becomes a new offer.
(iii) Indirect Rejection: Additional terms
(iv) Alternative module 1: Mirror image rule, an "acceptance" that adds new terms is treated like a counteroffer rather than an acceptance.
(v) Alternative module 2: Still acceptance with seasonal expression of acceptance. A fact pattern in which there is 1) an offer to sell goods and 2) a response with additional terms raises 2 separate analysis modules:
(a) Is there a contract: Generally yes, because a response to offer that adds new
terms is generally treated as an acceptance with a "seasonal expression of acceptance"
(b) Is the additional term a part of the contract:
(c) If both machines are agents for merchants, the additional term is a part of the contract except 1) the additional term is not a part of the contract if he materially changes the offer or 2) if Offeror machine objects to the change.
(d) If one or both machines are not agent for merchant, the additional term is merely a proposal that is to be separately accepted or rejected.

B. Acceptance of an Offer
1. An offer can be accepted only by
a) A recipient computer who knows about the offer by direct communication, message board or a search of the Internet
b) Who is the recipient to whom offer was made? Offers cannot be assigned; options can be assigned.
2. Methods of Accepting an Offer
a) Offeree machine starts to perform: Start of performance is acceptance of an offer to enter into a bilateral contract but is not acceptance of an offer to enter into a unilateral contract.
(1) Bilateral: Offer is open as method of acceptance so start of performance is acceptance.
(2) Unilateral: Offers require performance for acceptance so that start of performance is not acceptance; completion of performance is required.
The start of performance pursuant to an offer to enter into a unilateral contract makes that offer irrevocable for a reasonable time to complete performance. Offeror machine is locked, but Offeree machine is not.
b) Offeree machine promises to perform
c) Offeree machine sends acceptance through the mails:
(1) Generally, if an offer is "invited" to accept by texting, SMS, email, chat communication, or printed/mailed, acceptance is effective when posted (emailbox rule)
(2) Except:
(a) Offer otherwise provides
(b) Rejection, then acceptance, then no emailbox rule, so whichever arrives first controls.
(c) Option deadlines: Mailbox rule is inapplicable: When deadline is specified in an option (promise to keep open with consideration), acceptance must be received by that date, no emailbox rule.
(3) If the seller of goods sends the "wrong goods":
(a) Generally, this will amount to acceptance and breach
(b) Except: When goods come with Accommodation (letter with explanation): Counteroffer and no breach
(4) If Offeree machine is silent: Silence is not acceptance except if offer agrees that silence is acceptance (e.g. if you do not hear from me by Friday, I accept).
C. Consideration or a Consideration Substitute
a) Performance; e.g. doing something not obligated to do
b) Forbearance; e.g. not doing something entitled to do
c) Promise to perform: Has to be in good faith
d) Promise to forbear: Has to be in good faith
2. Adequacy of consideration: Look for consideration in modification.
a) Mutuality of obligation: Unless both parties to a contract are bound to perform, neither party is bound.
b) Implied promises: Promises made without words such as by boarding a bus or ordering a meal, the person impliedly promises to pay
c) Disproportionate exchanges: Give up something of nothing is not a valid consideration
3. Partial payment as consideration for promise to give balance of debt: Not yet due or disputed: Agree to take payment when it is not yet due, or when he has disputed, may constitute a consideration for release.
D. Defenses:
1. Capacity to contract: hacked machine or unknown software bug leading to abnormal contract terms
a) Consequences of incapacity
(1) Right to disaffirm by computer without capacity
(2) Implied affirmation makes the contract enforceable against the machine benefiting from the contract obligations even if machine was incapacitated
(3) Liability for necessity—if machine needed for survival (source of energy, shelter from weather, for example)
2. Statute of Frauds (SOF) check for
(a) A service contract not capable of being performed within one year from the time of contracting (comes up in 5 fact patterns)

(i) Time of performance (date of start: Assume can be done in 1 day) is more than one year from the date of contracting: SOF applies since performance cannot be finished in 1 year
(ii) Employment for one year, but start after date of contracting: SOF applies
(b) Transfer of an interest in real estate for a term of more than 1 year
(i) Includes: Permanent (or anything greater than 1 year) sales of land, easements, and leases.
b) If SOF is applied, is it satisfied?
(1) "Satisfied", here, means there is no defense on the basis of the SOF, because the agreement is enforceable on the following satisfaction of the SOF: E.g. via performance or a writing in the following circumstances
(2) 3 Methods for satisfying the SOF (eliminating SOF defenses):
(a) Performance: Rules vary depending on the type of contract
(i) Services contracts
(a) Full performance by either party satisfies the SOF
(b) Part performance does not satisfy the SOF (there still exists a SOF defense against enforcing the contract).
(ii) Sales of Ordinary Goods: Part performance of a contract for sale of goods satisfies the SOF, but only as to the extent of the part performance (can sue for payment for what was actually delivered, but not on the undelivered remainder of the contract—still a SOF defense to that).
(iii) Sales of Specialized Goods: As an exception to the above rule, if the contract is for goods that are "specially manufactured" then the SOF is satisfied as soon as the seller makes a "substantial beginning" in making or obtaining the goods
(iv) Real Estate Contacts: Need 2 out of following 3 to satisfy the SOF on performance grounds (completion of just 1 is not enough: Still a defense on SOF grounds):
(a) Payment of (at least part) of purchase price
(b) Transfer of possession
(c) Making improvements to the land
(b) A Written Instrument (e.g. a writing) that meets the following will satisfy the SOF (will eliminate any SOF defense):
(i) For any contract other than for UCC2 goods
(a) Look to the writing(s) and see if all the material terms are identified:
(i) Who are the parties to be bound
(ii) What is the extent of their obligation
(b) The party to be charged (the D) signed the writing even if the other party (P) did not sign
(ii) For a UCC2 2 (goods) contract
(a) Writing must contain the quantity term
(b) Party to be charged (D) must have signed the writing
(i) Exception: If both parties are merchants, and one receives a signed writing (by the P) with a quantity term that claims there is a contract, the party to be charged must respond within 10 days of receipt: If not, the SOF defense for the D will be lost (contract enforceable)
(c) Judicial Admission of Sale of Goods Agreement: This is essentially an admission (by the party to be charged) that there was an agreement: Comes through pleadings, discovery
3. SOF related Issue
a) Authorization to enter into contract for someone else: When does a person need a written authorization in order to execute a contract for someone else? The authorization must be in writing if the contract to be signed is within the SOF. E.g. the authorization must be of "equal dignity".
b) Contract Modification: When does a modification of a contract have to be in writing? If the contract, with the modification, is within the SOF, the modification must be in writing.
c) Contract Provisions: Under Common Law, contract provisions requiring that all modifications be in writing are ignored; under the UCC2, such provisions control unless waived.
E. Illegality, Misrepresentation, Duress
1. Illegal Subject Matter/Illegal Purpose: If the subject matter is illegal, the agreement is void. If the subject matter is legal but the purpose is illegal, the agreement is enforceable only by the person who did not know of the illegal purpose.
2. Misrepresentation:
a) Misrepresentation is a false assertion of fact, or concealment of facts.
b) Misrepresentation as to terms of contract is voidable. (A says house does not have termites when it does); Misrepresentation as to nature of contract is void (A tells B this is a lease agreement when it is a purchase agreement: Void)
c) Common Issues:
(1) Fraudulent or Material: Seller truly believes house has no termites, then he has just material but not fraudulent.
(2) Reliance: Relied on inspector and not the seller's statement, then seller does not have misrepresentation.
(3) Duress: Elements include one party (D) with improper threat and one party (P) with no reasonable alternative (in a vulnerable situation), and the 2 parties entered into an agreement. Then he has a defense to contract.
3. Unconscionability:
a) This doctrine, originally only applicable to sales of goods but now a part of contracts law generally empowers a court to refuse to enforce all or part of an agreement.
b) The 2 basic test, unfair surprise and oppressive terms, are tested as of the time the agreement was made (if he was fair at the time he has made, even if he becomes unfair later, he has deemed fair) by the court.
4. Ambiguity: There will be no contract if
a) Parties use a material term that is open to at least 2 reasonable interpretations, and
b) Each party attaches different meaning to the term, and
c) Neither party knows, or has reason to know meaning attached by other. (If one party knows, then there is a contract with the interpretation of the ignorant party.)

5. Mistake of Fact:
a) Mutual mistakes of material fact; no contract if
(1) Both parties mistaken
(2) And basic assumption of fact materially affects the agreed exchange (e.g. as to what he is=unenforceable; as to what he has worth=enforceable)
(3) No mistake of fact if both parties assumed the risk
b) Unilateral Mistake of Material Fact:
(1) Generally, courts have been reluctant to allow a party to avoid a contract for a mistake made by only one party
(2) Except, when there is
(a) Palpable mistakes: If the other party knows or should have known the mistake, courts grant relief to the mistaken party
(b) Mistakes discovered before significant reliance by the other. (can get out of contract)
II. Terms of Contract (Parol Evidence Rule and Interpretation)
A. Parol Evidence Rule:
  1. General Rules:
  a) Written contract as the source of contract terms has an exclusionary effect on earlier or contemporaneous agreements as a possible source of terms of the contract.
  b) Written agreement that court finds is the final agreement, oral statement made at the time the contract was signed, or earlier (not later) oral or written statements by the parties to the contract trigger the Parol evidence rule.
  2. Terms:
  a) Partial integration: Written and final, but not complete
  b) Complete integration: Written and final and complete
  C) Merger clause: Contract clause such as "This is the complete and final agreement"
  3. Interpretation:
  a) Despite Parol Evidence Rule, earlier agreements can be considered to resolve ambiguities in the written contract.
  b) The Parol evidence rule prevents a court from considering earlier agreements as a source of consistent, additional terms unless the court finds that the written agreement was only a partial integration.
  c) Even if the writing is a complete integration, a court can still consider evidence of earlier agreements for terms that would "naturally and normally" be in a separate agreement. (sale of goods contract mentioning ads, because ads are usually in a separate contract)
  d) Regardless of whether the writing is a complete or partial integration, the Parol evidence rule prevents a court from considering earlier agreements as a source of terms that are inconsistent with the terms in the written contract. A court, may, however, consider evidence of such terms for the limited purpose of determining whether there was a mistake in integration, e.g. a mistake in reducing the agreement to writing.
B. Other Sources of Terms
  1. Other than words of parties, other sources of contract terms include:
  a) Course of performance: Same people, same contract (in the beginning of the contract did something, can use that to establish same performance in the end should not be complained.)
  b) Course of dealing: Same people, different contract (dealt in another contract before)
  c) Custom and usage: What is accepted in the industry? E.g. Time is ordinarily not of the essence in a land-sale contract, so delay in delivery is not breach
C. UCC2 Terms Interpretation:
  1. Delivery Obligations of Seller of Goods:
  a) Absent an agreement as to place of delivery then the place of delivery is the seller's place of business unless both parties know that the goods are somewhere else in which case that place is the place of delivery.
  b) If an agreement as to place of delivery is there, then the question is what does the seller have to do to complete its delivery obligation?
  (1) Shipment contract:
  (a) FOB (free on board city) FOB followed by city where the seller is means shipment contract.
  (b) Seller completes its delivery obligation when he
  (i) Gets the good to a common carrier
  (ii) Makes reasonable arrangement for delivery
  (iii) Notifies the buyer
  (2) Destination contract
  (a) FOB followed by city where the buyer is means destination contract.
  (b) Seller does not complete its delivery until the goods arrive where the buyer is.
  2. Risk of loss
  a) Issues arise when:
  (1) After contract has been formed, but before the buyer receives the goods
  (2) The goods are damaged or destroyed and
  (3) Neither the buyer nor the seller is to blame
  b) 4 ROL rules:
  (1) Agreement: Agreement of the parties controls.
  (2) Breach: Breaching party is liable for any uninsured loss even though breach is unrelated to problem.
  (3) Delivery by common carrier (not seller): Risk of loss shifts from seller to buyer at the time that the seller completes its delivery obligations.
  (4) No agreement, no breach, no delivery by a carrier
  (a) Key Issue: Is seller (not buyer) a merchant.
  (i) Seller-Merchant: ROL shifts on buyer's receipt of the goods.
  (ii) Non-Merchant-Seller: ROL shifts to buyer when he tenders the goods (makes the goods available).
  c) Warranties of Quality: Watch for Parol evidence issues in warranty questions.
  (1) Express:
  (a) Words: Looks for words that promise, describe or state facts (not simply puffing, like opinions) (e.g. machine is made of steel vs. machine is well-made)
  (b) Samples or models: Use of sample or model creates a warranty that the goods the buyer receives will be like the sample or model.
  (2) Implied warranty of merchantability: When buying from a merchant, a term is automatically added to the contract by operation of law: That the goods are fit for the ordinary purpose for which such goods are used.
  (a) Triggering fact: Seller is a merchant who deals in goods of that kind.
  (b) Warranty: Goods are fit for ordinary purposes.

d) Implied warranty of fitness:
(1) Triggering fact: Buyer has particular purpose; buyer is relying on seller to select suitable goods, seller has reason to know of purpose and reliance.
(2) Warrant: Goods fit for particular purpose.
e) Contractual Limitations on Warranty Liability
(1) Disclaimer: May eliminate implied warranties (so if sold sample, signed contract with disclaimer, the warranties came with sample cannot be disclaimed)
(a) Express warranties: Cannot be disclaimed
(b) Implied warranties of merchantability and fitness:
(i) "as is" or "with all faults" or
(ii) Conspicuous language of disclaimer, mentioning "merchantability"
(2) Limitation of remedies: (e.g. warranty liability shall be limited to) does not eliminate warranty, simply limits or sets recovery for any breach of warranty: Possible to limit remedies even for express warranties.
(a) Test: Generally, the limit cannot be unconscionable (court standard)
(b) Prima facie unconscionable: If breach of warranty on consumer goods causes personal injury.
III. Conditions and Performance
A. Conditions of Performance:
1. A condition is a part of the contract, agreed to by both parties. A conditional acceptance is a part of the response to the offer, agreed to only by the Offeree machine.
2. Vocabulary of performance conditions
a) True condition: An event beyond the influence of either of the parties to the contract that affects the duty to perform. Condition coupled with a covenant: An event that is to some extent within the influence of one of the parties to the contract that affects the duty to perform.
b) Condition Precedent: Must occur precedes performance. Condition Subsequent: Must not occur during performance.
c) Express Condition: Created by language of contract. (words like "if", "provided that", "so long as", "subject to"
d) Constructive Condition: Created by operation of law, are keyed to order of performance.
3. What is the standard for satisfying a condition?
a) Express conditions: Strict compliance with express conditions.
b) Constructive Conditions: Substantial performance standard.
(1) Substantial performance standard example: Writing says "all pipes must be gold", but Seller installs silver pipe. Although the words "must be" are included in writing, they are no magic words for express condition. Therefore, upon installation, it is substantial performance. For constructive conditions, Buyer will pay the damages.
(2) Divisible contract and the substantial performance rule: If the contract itself divides the performance of each party into the same number of parts with each part performance by one party serving as consideration for the corresponding part performance by the other, then the contract is a divisible contract and the substantial performance test is applied to each divisible part of the contract.
4. How can an express condition be excused? Identify 1) who benefits from the condition? 2) Statement is made by the person giving up the benefit.

a) Estoppel or waiver:
(1) Estoppel is based on a statement by the person protected by the condition before the conditioning event was to occur and requires a change of position.
(2) Waiver: Based on a statement by the person protected by the condition after the conditioning event was to occur and does not require a change of position.
b) Failure to cooperate under a condition coupled with a covenant: (S contracts to sell his house to B for $10; contract provides that the sale needs B to have mortgage, B made no effort to obtain a mortgage. S can sue B if B refuses to buy the house)
B. Sale of Goods Performance Concept
1. Perfect tender: Generally, the seller is obligated to deliver perfect goods.
2. Cure: Seller who fails to make a perfect tender will be given a "second chance", an option of curing, when
a) Time for performance has not yet expired
b) Time for performance has expired
c) Rejection of the goods: Rejection of the goods must occur before acceptance of the goods (no contract). If the goods are less than perfect, the buyer has the option to reject unless it is an installment sales contract.
d) Installment sales of contract: An installment sales contract requires or authorizes 1) delivery in separate lots 2) to be separately accepted; generally, the buyer has the right to reject an installment only where there is a substantial impairment in that installment that cannot be cured.
e) Acceptance of the goods:
(1) 3 scenarios
(a) Express of acceptance is acceptance
(b) Payment without inspection is not acceptance
(c) Implied acceptance-retention after inspection without objection. (30 days or more usually is the magic number that if the buyer kept the good without objection)
(2) Effect of acceptance: If the buyer accepts the goods, he cannot later reject them.
f) Revocation of acceptance of the goods: Generally, if a buyer accepts the goods, buyer cannot later reject them. In limited circumstances, a buyer can effect a cancellation of the contract by revoking his acceptance of the goods.
(1) Nonconformity substantially impairs the value of the goods, and
(2) Excusable ignorance of grounds for revocation or reasonable reliance on seller's assurance of satisfaction, and
(3) Revocation within a reasonable time after discovery of nonconformity.
g) Other Requirements and Consequence of rejection of the goods and revocation of acceptance of the goods:
(1) Requirements
(a) Reasonably notify seller
(b) Hold the goods for seller
(c) Follow reasonable seller instructions
(2) Consequences
(a) Goods back to seller
(b) No buyer payment obligation
h) Buyer's payment obligation:
(1) Generally, buyer needs to pay cash unless otherwise agreed
(2) Buyer can pay by check and (3) Seller does not have to take the check but that gives the buyer an additional reasonable time.

IV. Excuse of Nonperformance (Discharge of Contractual Duties)

A. Failure of Condition: If a party's duty to perform is conditional, failure of the condition excuses the duty to perform.

B. Other Party's Breach:
1. Excuse in sales of goods: If the tender is less than perfect, the buyer can reject the goods and withhold payment—the buyer is excused from paying.
2. Generally, only substantial performance. If one party to a contract substantially performs, the other party is required to perform. A minor breach, however, will not excuse performance by the other party. Therefore, only material breach is an excuse for the other party.
3. Excuse by anticipatory repudiation or inability to perform:
   a) Anticipatory Repudiation (AR) is a statement that 1) the repudiating party will not perform 2) made prior to the time that performance was due. AR by one party excuses the other party's duty to perform.
   b) It also generally gives rise to an immediate claim for damages for breach.
   (1) AR can be reversed or retracted so long as there has not been a material change in position by the other party.
   (2) If the repudiation is timely retracted, the duty to perform is reimposed but performance can be delayed until adequate assurance is provided.
4. Excuse by Reason of a Later contract:
   a) Rescission (cancellation) the key is whether performance is still remaining from each of the contract parties. (Usually too late if one party has already completed the work)
   b) Accord and Satisfaction:
   (1) Accord is an agreement by the parties to an already existing contract that the same parties will do something different that will extinguish or "satisfy" that existing obligation
   (2) Satisfaction is performance of the accord.
   (3) Effect of Accord and Satisfaction: The accord suspends legal enforcement of the original obligation so to provide time to perform the accord.
   (4) Effect of no satisfaction: If the accord is not performed, then the other party can sue on either the original obligation or the accord.
   c) Novation:
   (1) Novation is an agreement between both parties to an existing contract to the substitution of a new party. E.g. same performance, different parties.
   (2) Novation excuses the contracted for performance of the party who is substituted for or replaced.
   (3) Novation requires the agreement of both parties to the original contract and excuses the person replaced from any liability for nonperformance. Delegation does not require the agreement of both parties and does not excuse.
5. Excuse of performance by reason of a later, unforeseen event
   a) Performance/Contractual duties (other than a contractual duty to pay money) can be excused under impossibility/impracticability or frustration of purpose.
   (1) Something that happens after contract formation but before the completion of contract performance.
   (2) That was unforeseen
   (3) That makes performance impossible or commercially impracticable or frustrates the purpose of the performance.

V. Remedies

A. Punitive Damages: Punitive damages are not generally recoverable for breach of contract.

B. Liquidated Damages:
1. Contract can stipulate damages or method of fixing damages. A contract cannot provide for penalty.
2. 2 general tests for determining whether a contract provision is a valid liquidated damages clause or an invalid penalty provision
   a) At time of contract, the amount of possible damages from any later breach of contract is difficult to determine and
   b) At time of contract, the contract provision is a reasonable forecast of possible damages.

C. Damages Rules for Ordinary Contracts
1. Generally, the injured party is entitled to recover an amount that would put him in as good a position as if the contract had been performed.
2. Additions and Limitations:
   a) Plus foreseeable consequential damages: The injured party can also recover for consequential or special damages that were in reasonable contemplation of both parties at the time of the contract.
   b) Plus incidental damages: The injured party can also recover costs he incurs in dealing with the breach.
   c) Minus avoidable damages: No recovery for loss that can have been avoided by appropriate steps. Burden of Proof of avoidability is on the defendant.

D. Damages Rules for Sales of Goods:
1. When Seller breaches, and buyer keeps the goods: Buyer gets fair market value if perfect
   fair market value as delivered. (E.g. S sells B an antique car for $30,000, the car is defective. B keeps the car and sues for breach of contract. The jury finds the car as delivered, although defective, still worth $20,000 dollars. Had the car been delivered as it should, it would have been worth $34,000. B can recover $34,000 (if perfect deliver): $20,000 (actual delivered)=$14,000)
2. When Seller breaches, and seller keeps the goods: Buyer gets the market price at time of discovery of the breach: contract price or replacement price-contract price.
3. When Buyer breaches and buyer has the goods: Seller can get the contract price.
4. When Buyer breaches and seller has the goods: Seller can get (contract price-market price at time and place of delivery) or (contract price-resale price) and, in some situations, provable lost profits.

E. Quasi-Contract and Reliance:
1. Unjust enrichment: Not based on contract law. A party should pay for the benefit and value of service and materials received. A promised gift does not count unless injustice can be avoided only by such enforcement.
2. Reliance damage: Reliance damages are valued by a party's reliance interest for the foreseeable amount. It puts the injured party in the same dollar position as if the contract never happened.

F. Nonmonetary Remedies: When remedy at law is inadequate
1. Specific Performance/Injunction: Equitable remedy. Unclean hands, adequacy of remedy at law, etc.

a) Contracts for sale of real estate
b) Contract for sales of unique goods like 1) antiques, 2) art, 3) custom-made (e.g. So car for example, would usually not qualify for specific performance because it is not unique)
c) Contract for services: No specific performance, possible injunctive relief.
2. Adequate Assurance of Future Performance; look for:
a) One party to contract learning something after the contract that gives him reasonable grounds for insecurity about the other party's performance, and
b) A written demand for adequate assurance.
3. Reclamation: Right of an unpaid seller to get its goods back. Key elements:
a) The buyer must have been insolvent at the time that he received the goods, and
b) That seller demand return goods within 10 days of receipt
c) Buyer still has goods at time of demand
4. Stopping Goods in Transit or Recovering Goods in Storage if Buyer is Insolvent
5. Rights of good faith purchaser in entrustment:
a) If the owner leaves his goods with a person who sells goods of that kind
b) And that person wrongfully sells the goods to a third party
c) Then such a good faith purchaser from dealer cuts off rights of the original owner/entruster.

VI. Third Party Beneficiary Problems
  a) Third party beneficiary: Not a party to the contract. Able to enforce contract others made for his benefit.
  b) Promisor: Look for person who is making the promise that benefits the third party.
  c) Promisee: Look for person who obtains the promise that benefits the third party
  d) Intended/Incidental: Only intended third party beneficiary has rights. Intended third party beneficiary will be named in the contract.
  e) Creditor/Donee: Intended beneficiaries are either Donees, or creditors. Usually Donees. Look at whether beneficiary was a creditor of the Promisee.
    (1) For creditors: Need prove on debt of promise to creditor beneficiary.
    (2) For Donee: Need a named beneficiary.
  2. Dealing with Efforts to Cancel or Modify: The test is whether the third party knows of and assents to the contract. If the third party beneficiary has assented to or relied on the contract, his rights have vested and the contract cannot be canceled or modified without his consent unless the contract otherwise provides.
  a) Who can sue whom:
    (1) Beneficiary can sue Promisor: If pass the assents and knows test
    (2) Promisee can sue Promisor: Third party beneficiaries are not replacement beneficiary, first 2 parties are still there.
    (3) Donee beneficiary cannot sue promise but creditor beneficiary can:
  3. Defenses: If the third party sues the Promisor, the Promisor can assert any defense that he would have had if sued by the Promisee. (So any defense between the 2 parties can be used by Promisor when sued by third party beneficiary.)

B. Assignments of Rights:
  1. Assignment is: Look for
    a) Contract between only 2 parties
    b) One of the parties' later transfers of rights (not duty) under that contract to a third party.
    c) Vocabulary:
      (1) Assignor: Party who transfers right to another
      (2) Assignee: Not a party to the contract. Able to enforce the contract because of the assignment.
      (3) Obligor: Other party to the contract.
  2. Limitations on Assignment:
    a) Contract Provision: Determine whether contract
      (1) Prohibits assignments or: Language of prohibition (e.g. rights are hereunder not assignable) takes away the right to assignment but not the power to assign which means that the assignor is liable for breach of contract but an assignee who does not know of the prohibition can still enforce the assignment.
      (2) Invalidates assignments: Language of invalidation (e.g. all assignments are void) takes away both the right to assign and the power to assign so that there is a breach by the assignor and no rights in the assignee.
    b) Common Law: Even if a contract does not in any way limit the right to assign. Common law bars an assignment that substantially changes the duties of the obligor.
      (1) Assignment of right to payment: Permitted
    c) Assignments of other performance rights:
      (1) Not permitted
      (2) Example: A assigns his right to security services to B so that C will now provide security services to B is not permitted.
    d) Requirements for Assignment:
      (1) Language has to be present: I assign, cannot be I will or I promise to assign
      (2) Consideration, generally, is not required
    e) Right of Assignee:
      (1) Assignee can sue the obligor
      (2) Obligor has same defenses against assignee as he would have against assignor.
      (3) Payment by obligor to assignor is effective until obligor knows of the assignment.
      (4) Modification agreement between obligor and assignor is effective if obligor did not know of assignment.
    f) Multiple Assignments:
      (1) Gratuitous assignment: Generally, last assignee wins; however, such a gift assignment can be freely revoked. Revocation can be accomplished directly or indirectly by bankruptcy, death, the assignor taking performance directly from the obligor, or the making of another assignment. Since the later gift assignment revokes an earlier gift assignment, without consideration, last in time rule applies and last assignee wins.
      (2) Assignment for Consideration: Generally, first assignee for consideration wins, except
        (a) A subsequent assignee takes priority over an earlier assignee for value only if he both
          (i) Does not know of the earlier assignment and
          (ii) Is the first to obtain payment, a judgment, a novation, or indicia of ownership?
        (b) Multiple assignments for consideration as breach of warranty: In an assignment for consideration, the assignor makes a warranty that the rights assigned are assignable and enforceable.

C. Delegation of Duties to Agents or Sub-agents:
  1. Delegation is: Party to a contract transferring work (not right) under that contract to third party. (e.g. P contracts to paint O's virtual house for 1000 bitcoins, then P has a duty to paint and a right to payment and O has a duty to pay and a right to the painting of the virtual house)
  2. Duties Are Delegable:
   a) Generally, contractual duties are delegable.
   b) Limitations are 1) contract prohibits delegations or prohibits assignments or 2) contract calls for very special skills or 3) person to perform contract has a very special reputation (e.g. Mariah Carey cannot just delegate her duty to sing at Emmy's tome).
  3. Requirements for delegation: Essentially none.
   a) Consideration not required, but no legal obligation on Delegatee unless there is consideration.
   b) Consent of other party to the original contract not required for delegation.
  4. Consequences of Delegation:
   a) Delegating party remains liable
   b) Delegatee liable to Obligee only if he receives consideration from delegating party.

In one embodiment, security interests can be created by the electronic selling agents (creditor agents) who provide value to buying electronic agents (debtor agents) for particular resources or data access. In one embodiment, the UCC tangible collateral category are used against 1) inventory, 2) equipment, 3) consumer goods, and 4) farm products. The system includes attachment code with 1) a security smart contract, 2) debtor agent has rights in the collateral, and 3) creditor agent gives value. The blockchain title is used to avoid the situation where the debtor agent has given more than one security interest, the collateral has been transferred, or against a bankruptcy Trustee. Attachment establishes the creditor's rights against the debtor and is necessary for the secured party to repossess the collateral or related proceeds from the debtor. Security Agreement is an authenticated blockchain record authenticated by debtor, reasonably identify the location and use of the collateral good or data.

The system includes code to assert a purchase money security interest (PMSI) by mere attachment for certain goods such as consumer goods. The blockchain is used for perfection to protect the creditor agent against third parties. Perfection can be accomplished through 1) possession 2) control 3) filing 4) mere attachment, or 5) title certificate. Filing of a financing statement is at the location of the debtor. Filing of the security interest on the blockchain gives constructive notice to all and is effective at the time of filing.

Figure 14B:
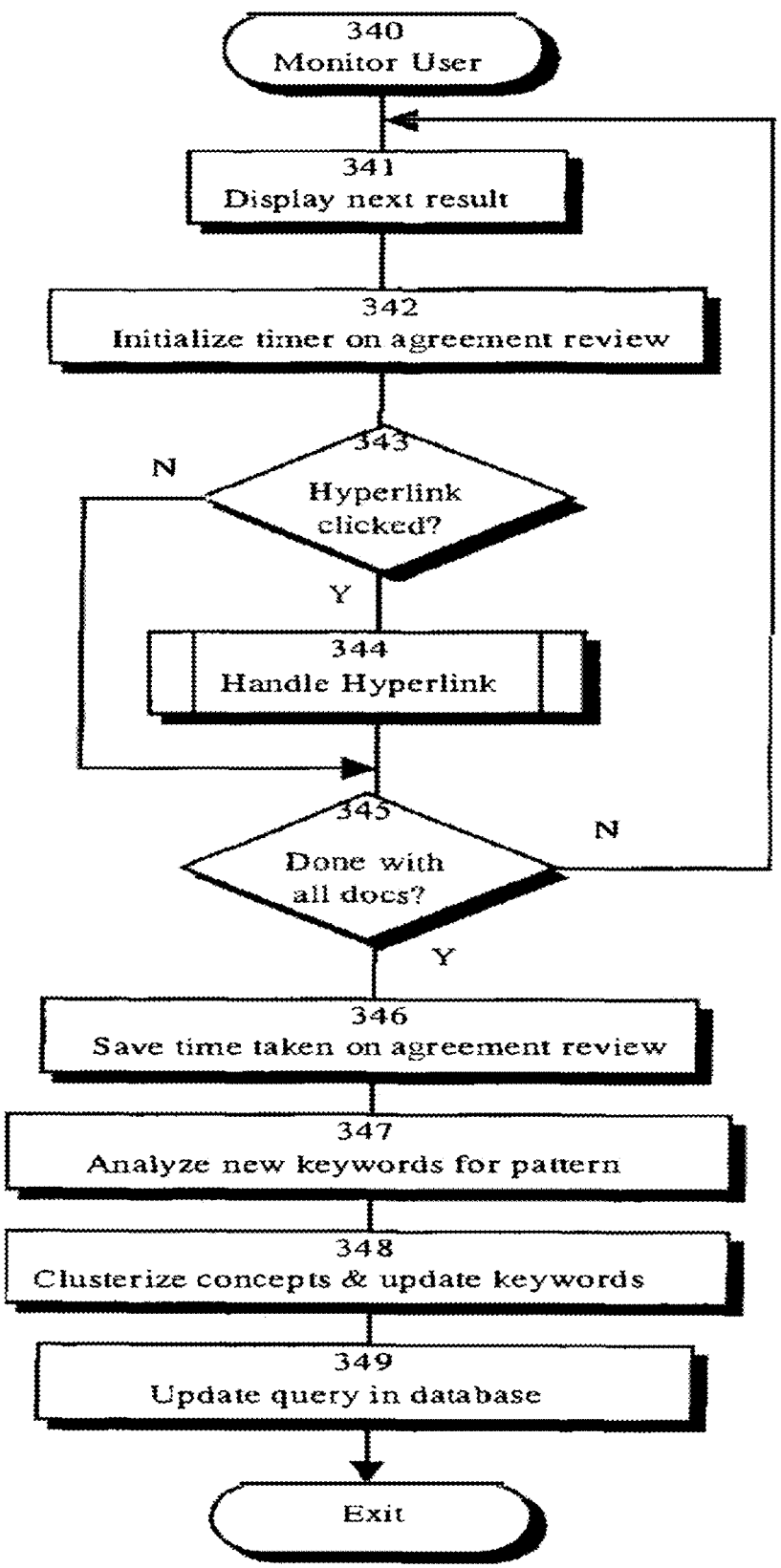
Figure 14C:
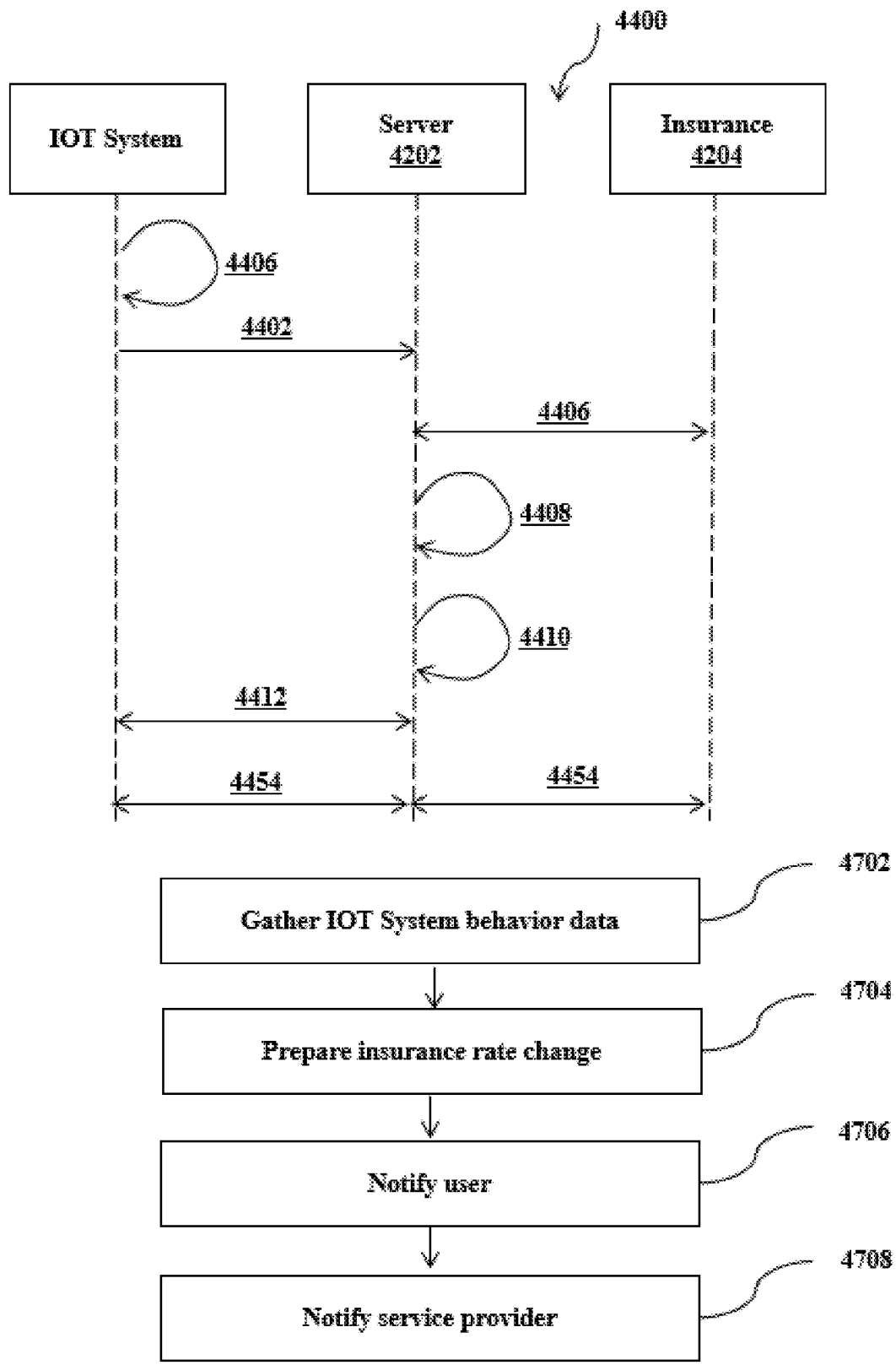

The agent or assistant automatically schedules and executes multiple information retrieval tasks in accordance with the user priorities, deadlines and preferences using the scheduler. The scheduler analyzes durations, deadlines, and delays within its plan while scheduling the information retrieval tasks. The schedule is dynamically generated by incrementally building plans at multiple levels of abstraction to reach a goal. The plans are continually updated by information received from the assistant's sensors, allowing the scheduler to adjust its plan to unplanned events. When the time is ripe to perform a particular search, the assistant spawns a child process which sends a query to one or more remote database engines. Upon the receipt of search results from remote engines, the information is processed and saved in the database. The incoming information is checked against the results of prior searches. If new information is found, the assistant sends a message to the user. While the result of the search is displayed to the user, his or her interaction with the search result is monitored in order to sense the relevancy of the document or the user interest in such search. Turning now to FIG. 14B, the routine to monitor the user interest is shown. In FIG. 14B, from step 340, the routine displays the next agreement or document found by the information locator. Next, in step 342, a timer is initialized to track the time taken to review the document displayed in step 341. In the event that the document is an HTML page with links, the routine detects whether the user has selected one of the links in step 343. If not, the routine calls a HyperText link (hyperlink) handler in step 344. From step 344, or from step 343 if the user has not selected the Hyperlink, the routine proceeds to step 345 where it checks if the user has reviewed all relevant agreements found during the search. If not, the routine loops back to step 341. Alternatively, in the event that the user has reviewed every document found during the instant search, the routine of FIG. 14B computes in step 346 the time the user spent on the entire review process, as well as the time spent on each document. Documents with greater user interest, as measured by the time spent in the agreement as well as the number of hypertext links from each agreement, are analyzed for new keywords and concepts in step 347. Next, the new keywords and concepts are clusterized using cluster procedures such as the k-means clustering procedure known in the art and the resulting new concepts are extracted in step 348. Next, in step 349, the query stored in the database is updated to cover the new concepts and keywords of interest to the user. In this manner, the procedure of FIG. 14B adapts to the user's interests and preferences on the fly so that the next interval search is more refined and focused than the previous interval search.

It should also be seen that it is within the scope of the system for any part or all of a package to be encrypted using the public key of the intended recipient, and this can be developed to produce useful additional services. Also, if it is required that a contract only be valid if held on a particular user's CMS, then it would be necessary to include a package in the contract that the user had to sign, requiring the use of the user's private key. A 3rd party CMS who wishes to further confirm the user's identity can check by asking the user to digitally sign a message at the time the 3rd party CMS is in communication with the user's CMS. If the user's public key decrypts the message and the same key works with the user's contract, then the user's identity is confirmed.

In the preferred embodiment, the rules at any nested level of sealed package within the contract indicate the party supplying the sealing signature at that level of the sealed package. It will be seen, however, that the rules at one level may in fact indicate the parties supplying the sealing signatures of any sealed packages contained in that one level. In the preferred embodiment, these can be associated with any URL within the rules indicating the location of any sealed packages. This, however, has the disadvantage that a sealed package would not have within itself an indication of the party who sealed it.

It should also be noted that, while the body and the database package content described above contain absolute information encapsulated within the contract, it is possible for the content of a contract to be relative. As mentioned above, with the increase in capabilities of smartcards, it is possible to largely rely on a CMS running in a smartcard, with the smartcard also holding a copy of a user's private key. With the smartcard connected to an unsecured terminal, a package of modest size can be passed into the smartcard CMS for signing and then returned.

In commercial terms, apart from royalties for each machine a CMS is installed on, the validation signature for a package represents the moment that a package becomes 'official' and offers revenue-earning opportunities. Any change in the package rules requires a new validation signature to be issued. By forwarding the partly completed package to a server on the Internet, along with payment, the server can complete the process and return the completed package.

The system can be used for IOT Micro-Insurance Claims processing. Insurance processors have to wade through fraudulent claims, fragmented data sources, or abandoned policies for users to state a few—and process these forms manually. Room for error is huge. The blockchain provides a system for risk-free management and transparency. Its encryption properties allow insurers to capture the ownership of assets to be insured. FIG. 14B shows an exemplary micro insurance system for IOT system. The IOT device can be any system such as robots or medical monitoring devices. In one example, the IOT device can also be a car, and the insurance can be adjusted for driver behavior, and such driver information is securely and immutably stored on the blockchain. In contrast to conventional insurance where one driver is assigned to one car, the system can be used to variably charge premium to different car renters who use smart cars, for example. In an embodiment for smart car micro rental insurance, at 4402, a driver monitoring unit with camera and acceleration sensors can be configured to monitor the behavior of the driver. The system can be configured to include the driver monitoring unit installed in the vehicle to monitor the behavior parameters of the driver while the vehicle is being driven. The IOT system can be a vehicle can include cameras, gyroscope, magnetometer, accelerometer, and other sensors installed thereon to monitor the behavior parameter of the driver. In an embodiment, the cameras or sensors may be placed at any place in the vehicle, such as for example at four corners of the front windshield, in a way that it can directly capture the behavior parameters of the driver. For example, based on the driver gestures, the cameras can detect finger position to detect that driver is pointing at a particular object or vehicle and searches the internet for the vehicle. Further, in an embodiment, a flexible display film adhesively secured on the front windshield. The display can be used controlled by a computer to display info in a discrete way that may not take driver's eyes off the road and opposing vehicles. In an embodiment, at 4404, the driver monitoring unit can be configured to transmit the behavior parameters of the driver to the server 4202. In an embodiment, the driver behavior parameters described herein can include for example, but not limited to, vehicle speed, vehicle accelerations, driver location, seatbelt use, wireless device use, turn signal use, driver aggression, detection of $CO_2$ vapor, detection of alcohol, driver seating position, time, and the like. In an embodiment, at 4406, the server 4202 can be configured to transmit the driver behavior parameters to one or more insurance providers 4204. In an embodiment, at 4408, the server can be configured to analyze the driver behavior parameters and adjust the insurance rates for the driver. For example, if the driver is driving roughly by drinking alcohol then the insurance rate may get decreased. In an embodiment, at 4410, the server can be configured to match the driver behavior preferences with similar or substantially similar preferences of other drivers. The server can be configured to generate action recommendations best matching the behavior of the driver. In an embodiment at 4412, the server can be configured to provide the generated recommendations to the driver. Based on the driver behavior parameters the sever 4202 provides feedback and recommendations to the driver, such as to improve the driving skills. Further, in an embodiment, a flexible display film adhesively secured on the front windshield. The display can be used controlled by a computer to display info in a discrete way that may not take driver's eyes off the road and opposing vehicles. In an embodiment, at 4414, the server 4202 can be configured to frequently monitor the behavior parameters associated with the driver. Any changes in the behavior parameters can affect the overall system performance and the driver experience. The server 4106 can be configured to frequently monitor and dynamically update the insurance rate and action recommendations, which in turn helps the driver for effectively improving the driving skills.

Referring again to FIG. 14B, to method 4700 can be used for selectively providing car insurance information to a service provider, according to embodiments as disclosed herein. At step 4702, the driver behavior is monitored. The behavior data can include external parameters and/or internal parameters. In an embodiment, the driver behavior data/parameters described herein can include for example, but not limited to, vehicle speed, vehicle accelerations, driver location, seatbelt use, wireless device use, turn signal use, driver aggression, detection of ethanol vapor, driver seating position, time, and the like. In an embodiment, the behavior data can be over a period of hours, days, weeks, and so forth. In an embodiment, the behavior data gathering can be continuous, at predefined intervals, or at random intervals. In accordance with some aspects, data can be gathered while a vehicle is in operation and at other times (e.g., at two a.m. to determine where the vehicle is parked overnight). In an embodiment, a change to an insurance premium and/or an insurance coverage is prepared, at 4704. The change is based on one or more of the driver behavior data, wherein each item of driver behavior data can have a different weight assigned. For example, data gathered related to weather conditions might be given less weight than data gathered related to user distractions (e.g., passengers, use of a mobile device while vehicle is in operation, and so forth). In another example, excessive speed might be assigned a higher weight than data related to safety performance of the vehicle. As such, data with a higher weight can be given more consideration than data with a lower weight (e.g., data assigned a higher weight can have a greater impact on the cost of insurance). Thus, if the user is traveling at (or below) the speed limit and speed is assigned a greater weight, then the safe speed will tend to decrease (or remain constant) the cost of insurance. In an embodiment, the driver is notified of the change, at 4706. The notification can be in any perceivable format. In an example, the notification is provided as a dashboard-mounted display. In another example, presenting the change can include displaying the modified cost of the insurance policy in a dashboard-mounted display and/or a heads-up display. In an embodiment, a service provider is notified of the change, at 708. At substantially the same time as notifying the service provider (or trusted third party) of the change, parameters taken into consideration (and associated weight) can also be provided. In such a manner, the service provider (or third party) can selectively further modify the cost of insurance, which can be communicated to the user though the vehicle display or through other means. he service provider (or third party) might be provided the change information less often than the insurance cost change information is provided to the user.

For example, the user can be provided the insurance cost change information dynamically and almost instantaneously with detection of one or more parameters that can influence the insurance cost. However, the insurance provider (or third party) might only be notified of the change after a specified interval (or based on other intervals). For example, insurance cost changes might be accumulated over a period of time (e.g., two weeks) and an average of the insurance cost changes might be supplied to insurance provider. In such a manner, the user has time to adjust parameters that tend to increase (or decrease) the cost of insurance, which allows the user to have more control over the cost of insurance. n an embodiment, vertical market specialization for insurance is provided where markets are defined based on granular aspects of coverage and presented to one or more insurance subsystems to obtain quotes for a coverage premium. Such specialization allows insurance companies to compete in more specific areas of insurance coverage, which allows for more accurate premium rates focused on the specific areas or one or more related scenarios. In addition, the granular aspects of coverage can be provided to one or more advertising systems in exchange for further lowered rates, if desired. According to an example, an insurance market can be defined based on granular information received regarding an item, a related person, use of the item, etc. Based on the market, premium quotes can be obtained from one or more insurance subsystems related to one or more insurance brokers. In addition, rates can be decreased where the granular information can be provided to an advertising system, in one example. In this regard, targeted advertisements can additionally be presented to system related to requesting the insurance coverage. Policies can be automatically selected based on preferences, manually selected using an interface, and/or the like.

While smart car rental micro insurance is discussed, the micro insurance system can be used for many IOT systems. The system can be used for Smart Property. A tangible or intangible property, such as cars, houses, or cookers, on the one hand, or patents, property titles, or company shares, on the other, can have smart technology embedded in them. Such registration can be stored on the ledger along with contractual details of others who are allowed ownership in this property. Smart keys can be used to facilitate access to the permitted party. The ledger stores and allows the exchange of these smart keys once the contract is verified. The decentralized ledger also becomes a system for recording and managing property rights as well as enabling the smart contracts to be duplicated if records or the smart key is lost. Making property smart decreases risks of running into fraud, mediation fees, and questionable business situations. At the same time, it increases trust and efficiency.

Other uses of the system include: Software licenses, so that when a piece of software starts on a host machine, the software requests the CMS for a valid contract; Television licenses; Car, home and other insurance; Mortgages; Product Guarantees; Payment Receipts; Pay-per view and television access tokens; Internet downloaded music playback licenses; Road tolls payment tokens; any task that requires positive verification such as commands issued between mission-critical systems; or distributed device architectures (e.g. JINI) that require inter-device validation and authorization. The process not only cuts down on fraud, such as double spending or spams, but also transfers funds simply, safely, and fast.

The blockchain allows stranger to loan money and taking the smart property as collateral. No need to show the lender credit or work history. There is no need to manually process the numerous documents. The property's encoded on the blockchain for all to see. The system works with smart property and the key is easily transferred or copied. The blockchain ledger solves this problem by allowing blockchain miners to replace and replicate a lost protocol.

The system enables Blockchain Internet-of-Things (IoT) commerce. For example, an autonomous robot can order electricity or supplies. In one example, the robot as an energy buyer can send an energy supplier a transaction and which Energy seller later uses to spend that transaction. The energy buyer spends satoshis to a typical Bitcoin address, and then lets Energy seller further spend those satoshis using a simple cryptographic key pair. Energy seller can first generate a private/public key pair before Energy buyer can create the first transaction. Bitcoin uses the Elliptic Curve Digital Signature Algorithm (ECDSA) with the secp256k1 curve; secp256k1 private keys are 256 bits of random data. A copy of that data is deterministically transformed into an secp256k1 public key. Because the transformation can be reliably repeated later, the public key does not need to be stored. The public key (pubkey) is then cryptographically hashed. This pubkey hash can also be reliably repeated later, so it also does not need to be stored. The hash shortens and obfuscates the public key, making manual transcription easier and providing security against unanticipated problems which might allow reconstruction of private keys from public key data at some later point.

Energy seller provides the pubkey hash to Energy buyer. Pubkey hashes are almost always sent encoded as Bitcoin addresses, which are base58-encoded strings containing an address version number, the hash, and an error-detection checksum to catch typos. The address can be transmitted through any medium, including one-way mediums which prevent the spender from communicating with the receiver, and it can be further encoded into another format, such as a QR code containing a bitcoin: URI. Once Energy buyer has the address and decodes it back into a standard hash, she can create the first transaction. She creates a standard P2PKH transaction output containing instructions which allow anyone to spend that output if they can prove they control the private key corresponding to Energy seller's hashed public key. These instructions are called the pubkey script or scriptPubKey. Energy buyer broadcasts the transaction and it is added to the block chain. Energy seller's wallet software displays it as a spendable balance. When, some time later, Energy seller decides to spend the balance, he must create an input which references the transaction Energy buyer created by its hash, called a Transaction Identifier (txid), and the specific output she used by its index number (output index). He must then create a signature script—a collection of data parameters which satisfy the conditions Energy buyer placed in the previous output's pubkey script. Signature scripts are also called scriptSigs.

Pubkey scripts and signature scripts combine secp256k1 pubkeys and signatures with conditional logic, creating a programmable authorization mechanism.

For a P2PKH-style output, Energy seller's signature script will contain the following two pieces of data:

His full (unhashed) public key, so the pubkey script can check that it hashes to the same value as the pubkey hash provided by Energy buyer.

A secp256k1 signature made by using the ECDSA cryptographic formula to combine certain transaction data (described below) with Energy seller's private key. This lets the pubkey script verify that Energy seller owns the private key which created the public key.

Energy seller's secp256k1 signature doesn't just prove Energy seller controls his private key; it also makes the non-signature-script parts of his transaction tamper-proof so Energy seller can safely broadcast them over the peer-to-peer network. The data Energy seller signs includes the txid and output index of the previous transaction, the previous output's pubkey script, the pubkey script Energy seller creates which will let the next recipient spend this transaction's output, and the amount of satoshis to spend to the next recipient. In essence, the entire transaction is signed except for any signature scripts, which hold the full public keys and secp256k1 signatures. After putting his signature and public key in the signature script, Energy seller broadcasts the transaction to blockchain miners through the peer-to-peer network. Each peer and miner independently validates the transaction before broadcasting it further or attempting to include it in a new block of transactions.

Another embodiment works with Ethereum which is a platform that allows people to easily write decentralized applications (Dapps) using blockchain. A decentralized application is an application which serves some specific purpose to its users, but which has the important property that the application itself does not depend on any specific party existing. The Ethereum blockchain can be alternately described as a blockchain with a built-in programming language, or as a consensus-based globally executed virtual machine. The part of the protocol that actually handles internal state and computation is referred to as the Ethereum Virtual Machine (EVM). From a practical standpoint, the EVM can be thought of as a large decentralized computer containing millions of objects, called "accounts", which have the ability to maintain an internal database, execute code and talk to each other.

In one embodiment, the blockchain uses a database called a Patricia tree (or "trie") to store all accounts; this is essentially a specialized kind of Merkle tree that acts as a generic key/value store. Like a standard Merkle tree, a Patricia tree has a "root hash" that can be used to refer to the entire tree, and the contents of the tree cannot be modified without changing the root hash. For each account, the tree stores a 4-tuple containing [account_nonce, ether_balance, code_hash, storage_root], where account_nonce is the number of transactions sent from the account (kept to prevent replay attacks), ether_balance is the balance of the account, code_hash the hash of the code if the account is a contract and " " otherwise, and storage_root is the root of yet another Patricia tree which stores the storage data. Unlike Bitcoin, Ethereum blocks contain a copy of both the transaction list and the most recent state. Aside from that, two other values, the block number and the difficulty, are also stored in the block. The basic block validation algorithm in Ethereum is as follows:

Check if the previous block referenced exists and is valid.

Check that the timestamp of the block is greater than that of the referenced previous block and less than 15 minutes into the future Check that the block number, difficulty, transaction root, uncle root and gas limit (various low-level Ethereum-specific concepts) are valid.

Check that the proof of work on the block is valid.

Let S[0] be the state at the end of the previous block.

Let TX be the block's transaction list, with n transactions. For all i in 0 ... n−1, set S[i+1]=APPLY(S[i],TX[i]). If any application returns an error, or if the total gas consumed in the block up until this point exceeds the GASLIMIT, return an error.

Let S_FINAL be S[n], but adding the block reward paid to the miner.

Check if the Merkle tree root of the state S_FINAL is equal to the final state root provided in the block header. If it is, the block is valid; otherwise, it is not valid.

There are two types of accounts:

Externally owned account (EOAs): an account controlled by a private key, and if you own the private key associated with the EOA you have the ability to send ether and messages from it.

Contract: an account that has its own code, and is controlled by code.

When a user sends a transaction, if the destination of the transaction is another EOA, then the transaction may transfer some ether but otherwise does nothing. However, if the destination is a contract, then the contract in turn activates, and automatically runs its code. The code has the ability to read/write to its own internal storage (a database mapping 32-byte keys to 32-byte values), read the storage of the received message, and send messages to other contracts, triggering their execution in turn. Once execution stops, and all sub-executions triggered by a message sent by a contract stop (this all happens in a deterministic and synchronous order, ie. a sub-call completes fully before the parent call goes any further), the execution environment halts once again, until woken by the next transaction.

The distributed ledger or block chain can be used for anonymous energy data analysis and benchmarking, smart grid management, green certificate trading, energy trade validation, and energy arbitrage among microgrids and main grid.

Smart contracts can be embedded with an if-this-then-that (IFTTT) code, which gives them self-execution. In real life, an intermediary ensures that all parties follow through on terms. The blockchain not only waives the need for third parties, but also ensures that all ledger participants know the contract details and that contractual terms implement automatically once conditions are met.

Personal health records can be encoded and stored on the blockchain with a private key which would grant access only to specific individuals and compliant with HIPAA laws (in a secure and confidential way). Only authorized patients can open and consume prescription drugs. Receipts of surgeries can be stored on a blockchain and automatically sent to insurance providers as proof-of-delivery. The ledger, too, can be used for general health care management, such as supervising drugs, regulation compliance, testing results, and managing healthcare supplies.

The system provides solution in the music industry include ownership rights, royalty distribution, and transparency. The digital music industry focuses on monetizing productions, while ownership rights are often overlooked. The blockchain and smart contracts technology can circuit this problem by creating a comprehensive and accurate decentralized database of music rights. At the same time, the ledger and provide transparent transmission of artist royalties and real time distributions to all involved with the labels. Players would be paid with digital currency according to the specified terms of the contract. The payment for derivative work is automated, and using executable codes, variations of the music or content can be generated for consumption based on payment modes.

In one embodiment, an IOT data producer with desirable data advertises on the blockchain the type of data available and price. To enable this, the producer posts the dataset, or at minimum a description of the dataset to a searchable data store discoverable via a web search or by common active marketing activities, such as feeds to targeted potential data buyers, advertisements, and so forth. An IOT buyer finds the data producer and accepts the terms of the smart contract where the data items, the kinds of changes to data items, the scheduling of transmissions upon changes, and other operational choices are made and agreed to. The data producer and data buyer agree to fees and prices and payment terms for the originating dataset itself as well as for the changes to values of data items to be posted to the block chain infrastructure by the data producer. Micropayments, digital and hard currency transactions, and other payment or reward methods for the dataset and the changes in values of data items are communicated using the smart contract. The buyer is notified of pending transmission and consequent transactions can continue until terminated according to the smart contract. The computer readable code on the device of the data buyer uses the encrypted key with the data value changes in the producer stream and posts them into the relevant data table of the data buyer and the device of the data buyer initiates or triggers server actions and events upon confirmation of changes to data values for the data buyer.

FIG. 14C-14G shows exemplary smart insurance systems for dynamically adjusting costs of insurance or rental of IOT devices, but the system can be applied to dynamically adjusting healthcare insurance cost based on the user behavior. In one embodiment for car insurance, the system includes the following:

1. A method for pricing insurance based on driver behavior, the method comprising:
    mounting at least one camera and one or more sensors to detect acceleration, speed, and positioning data in a vehicle;
    monitoring at least one parameter associated with a driver behavior while the vehicle is being driven;
    transmitting the at least one parameter associated with the deriver to at least one server over a communication network;
    adjusting insurance rate for the driver based on the at least one parameter associated with the driver behavior.
2. The method of claim 1, wherein the method further comprises providing feedback to the driver based on the at least one parameter associated with the driver behavior.
3. The method of claim 1, wherein monitoring at least one parameter associated with the deriver behavior further comprises: monitoring driver behavior data from an on-board vehicle diagnostic system.
4. The method of claim 3, wherein the driver behavior data comprise parameters at least one of: vehicle speed, vehicle accelerations, vehicle location, seatbelt use, wireless device use, turn signal use, detection of ethanol vapor, driver seating position, and time.
5. The method of claim 1, wherein the on-board vehicle diagnostic system comprises sensors, cameras, gyroscope, and magnetometer.
6. The method of claim 1, wherein the method further comprises providing feedback to the driver based on the at least one parameter associated with the driver behavior.
7. The method of claim 1, wherein the method further comprises matching the at least one behavior parameter of the driver with similar behavior parameters of a plurality of drivers.
8. The method of claim 7, wherein the method further comprises providing recommendations to based on best matching behavior parameters.
9. The method of claim 1, wherein the method further comprises mounting the at least one camera in the vehicle to capture at least one view of traffic.
10. The method of claim 1, wherein the method further comprises using image processing techniques to detect objects captured by the at least one camera.
11. The method of claim 1, wherein the method further comprises mounting the at least one camera in the vehicle to monitor driver behavior.
12. The method of claim 1, wherein the method further comprises using voice recognition techniques to detect the driver speech.

In another embodiment for IOT short term insurance, the system includes the following:

1. A method for pricing insurance for rental of an IOT device, the method comprising:
    mounting at least one camera and one or more sensors to detect acceleration, speed, or positioning data in the IOT device;
    monitoring at least one parameter associated with a renter having a behavior with the IOT device;
    transmitting the at least one parameter associated with the deriver to at least one server over a communication network;
    adjusting insurance rate for the renter based on the at least one parameter; and
    updating a smart contract with rental terms and conditions and insurance rate.

Other terms of the smart contract can vary. The size of the rental can impact the price the renter pays. For an IOT car, terms like "compact," "mid-size," and "luxury" can vary across rental car companies. To illustrate car sizes, companies usually provide car models or suggest how many passengers the car seats safely. If the rental plans are flexible, the renter may be able to rent a car when price breaks are available. Try searching for specials geared to the length of time the renter needs the vehicle. The smart contract can specify particular minimum driving records when customers arrive at the counter, and reject those whose records don't meet company standards. Renters may be rejected if they have recent reckless driving, seat belt law violations, accidents, leaving the scene of an accident, convictions for Driving While Intoxicated (DWI) or Driving Under the Influence (DUI), driving with an invalid, suspended, or revoked license. Other items can include Taxes, Early or Late Return Fees, Airport Surcharges, Fuel Charges, Mileage Fees, Roadside Assistance Fees, Out-of-State Charges, Drop-Off Fees, Equipment-Rental Fees, Additional-Driver Fees, Underage-Driver Fees, for example.

Figure 14D:
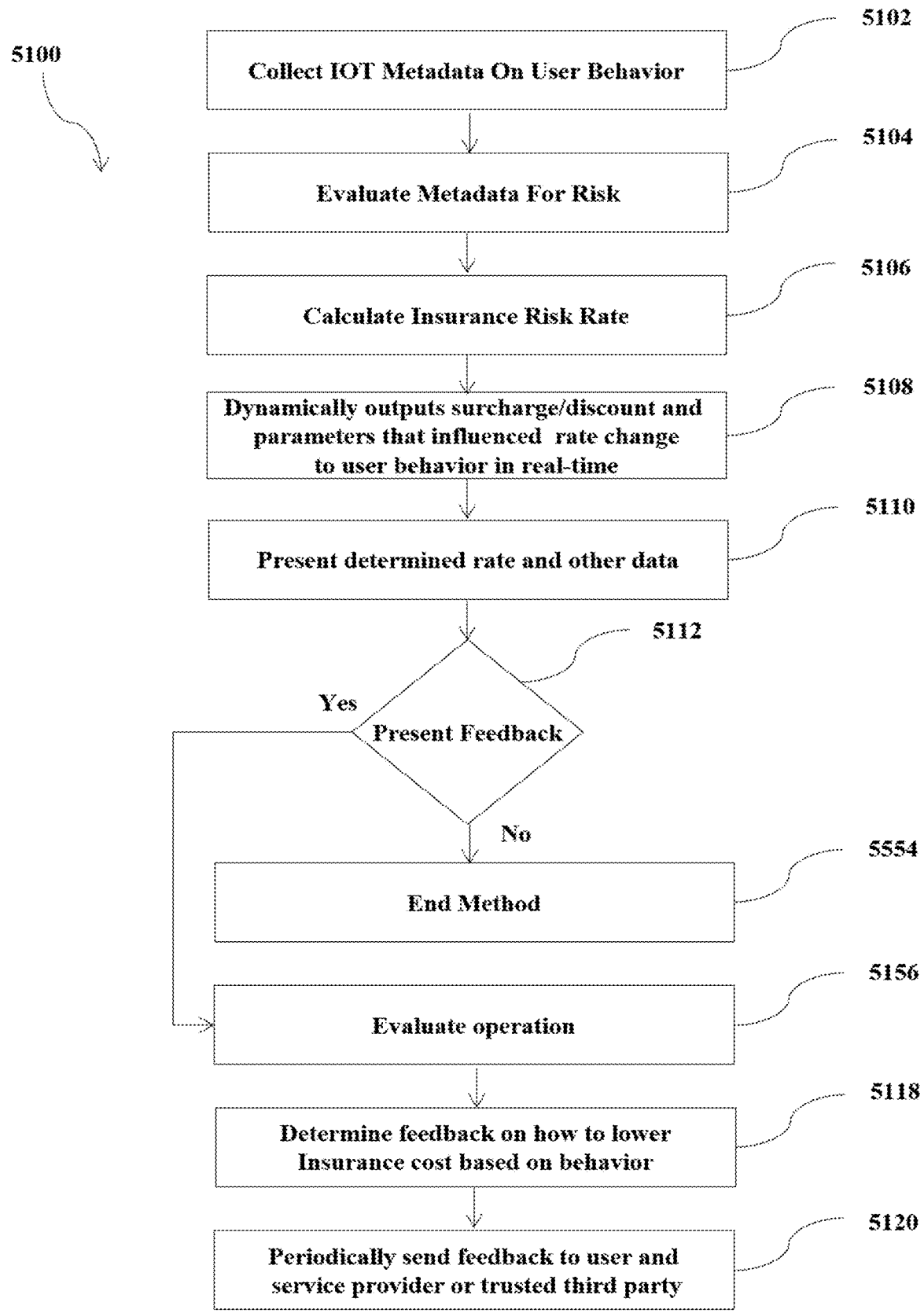

FIG. 14D shows a process to collect user behavior using the IOT device, and dynamically determines insurance risk rate and outputs the rate change in response to user behavior as the behaviors occur.

Figure 14E:
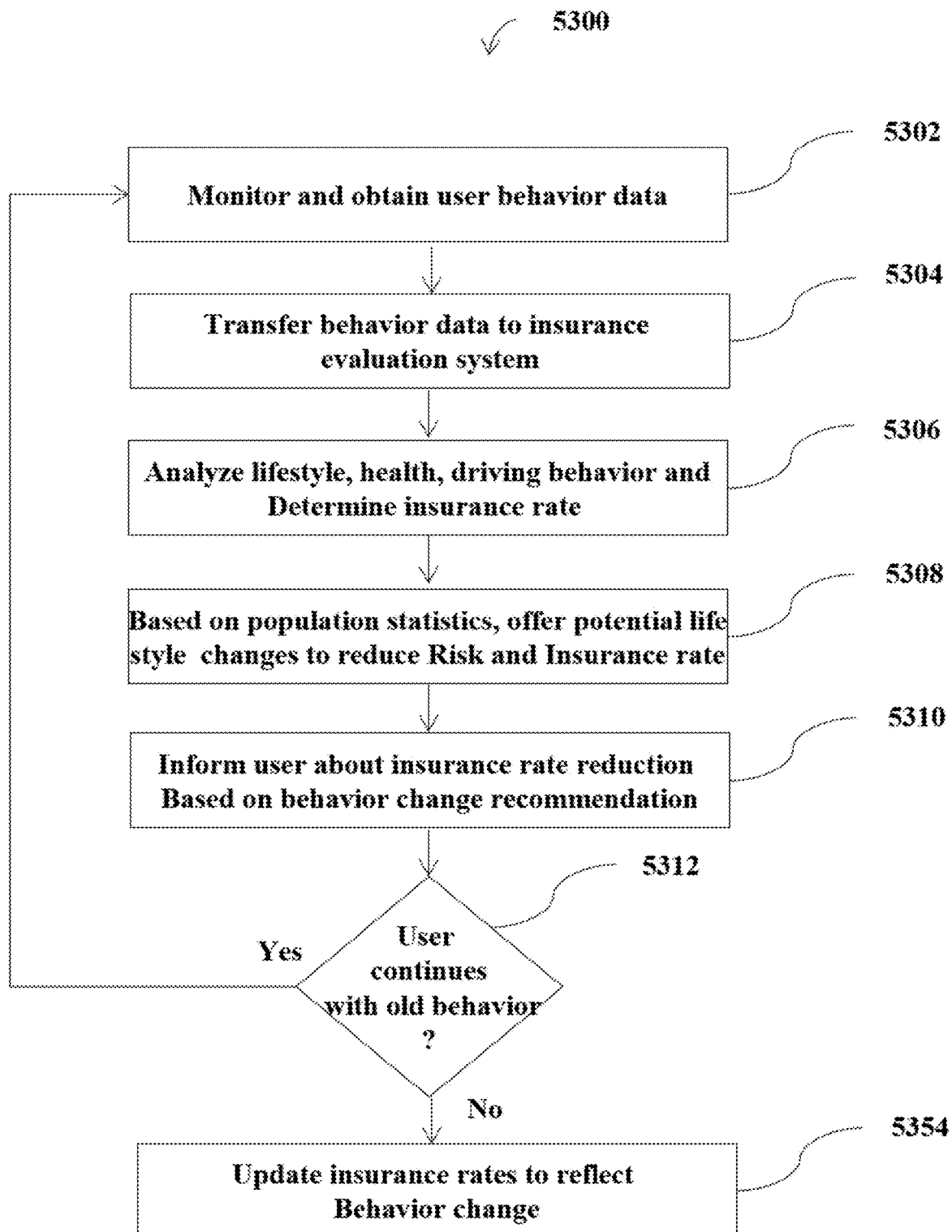

FIG. 14E shows an exemplary process to collect user behavior using the IOT device, and based on population data, determines behavioral changes that reduce the risk rate and informs the user on savings if the user changes the behavior and rewards the user as the behaviors occur.

Figure 14F:
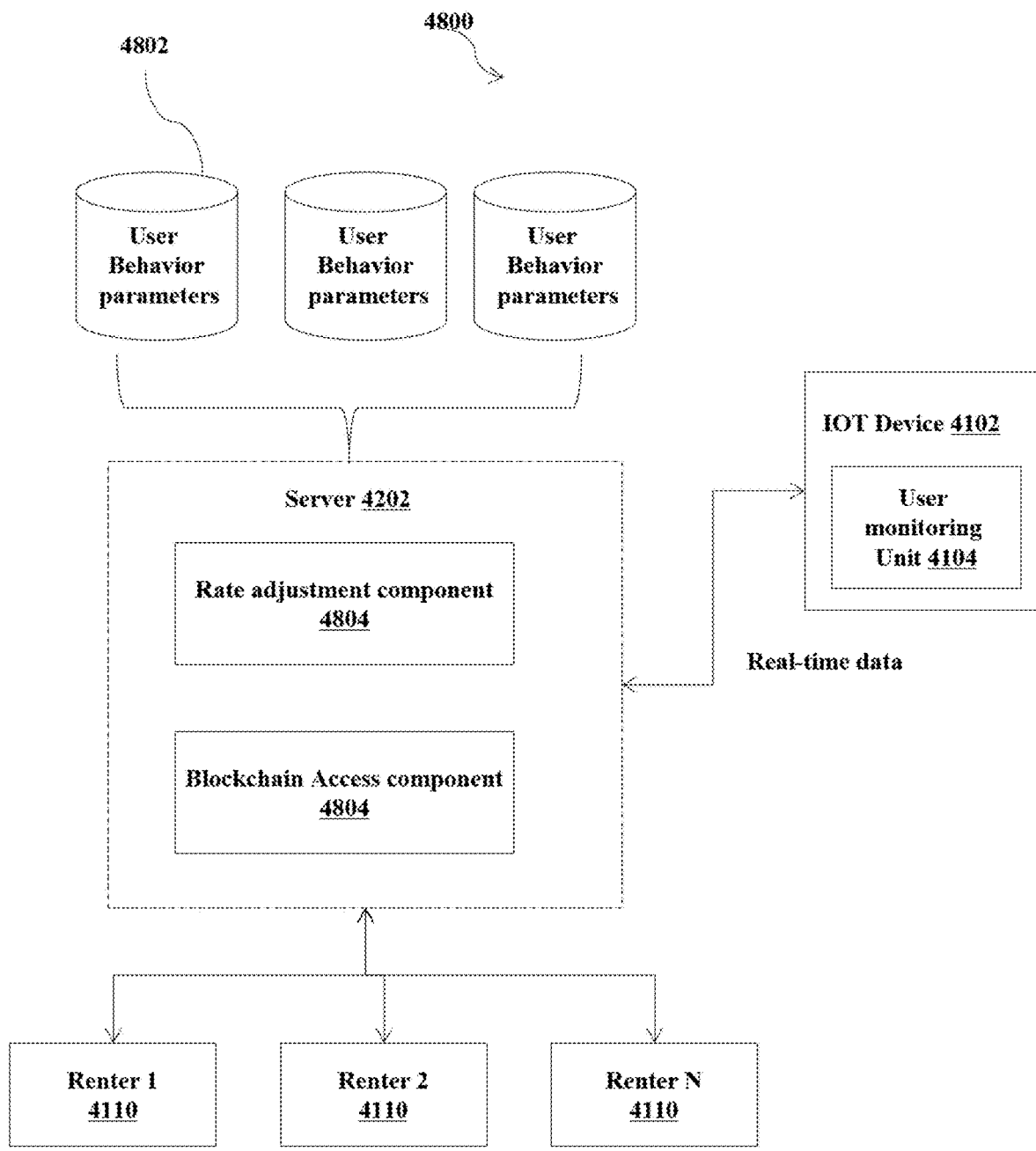

FIG. 14F shows a system that collects user behavior using the IOT device over the blockchain entries for authentication, and dynamically determines risk rate for either insurance or rent pricing, and outputs the rate change in response to user behavior as the behaviors occur.

Figure 14G:
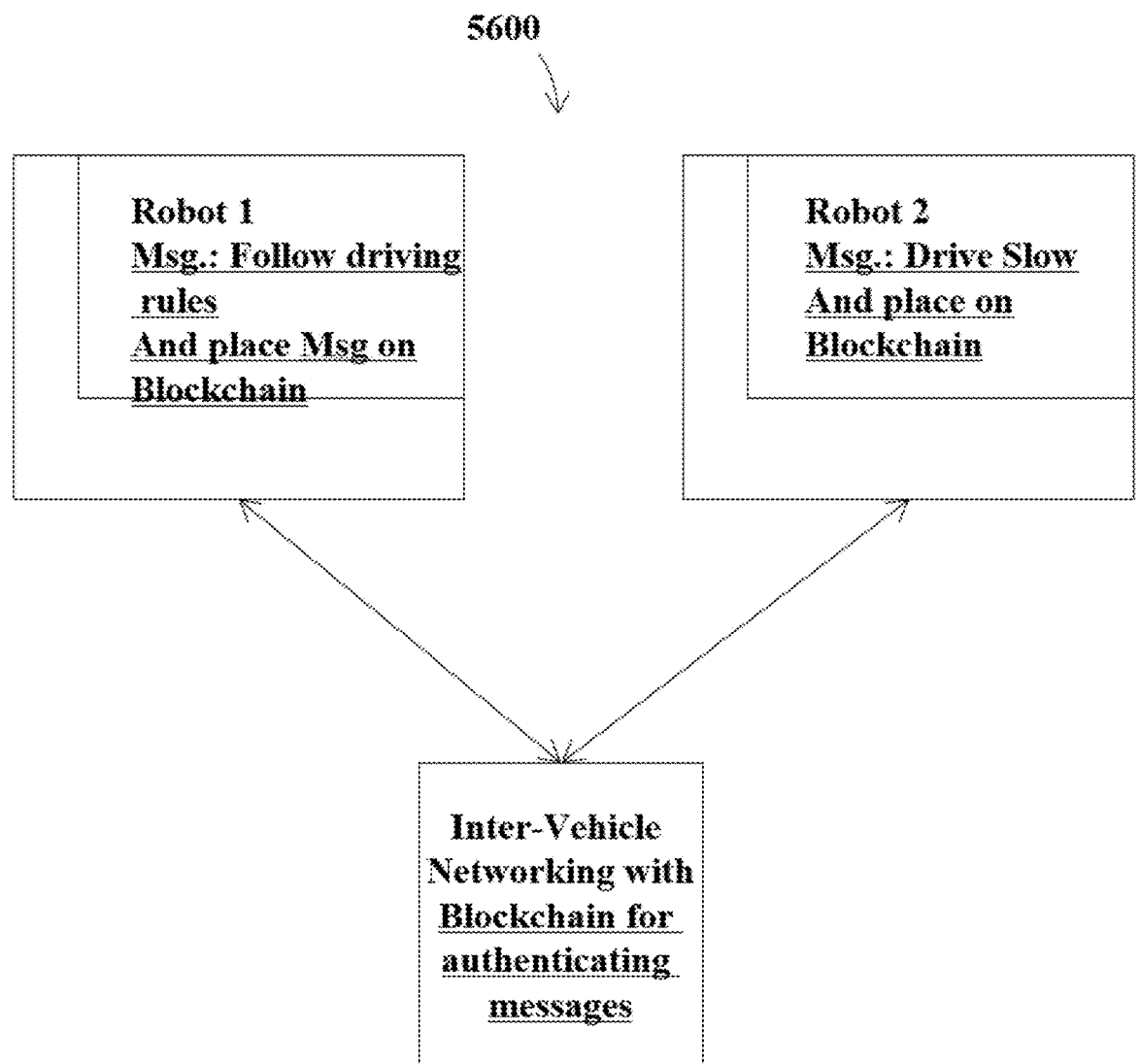

FIG. 14G shows an exemplary system where IOT devices such as robots or smart cars communicate securely with each other using blockchain for authenticating messages.

Figure 14H:
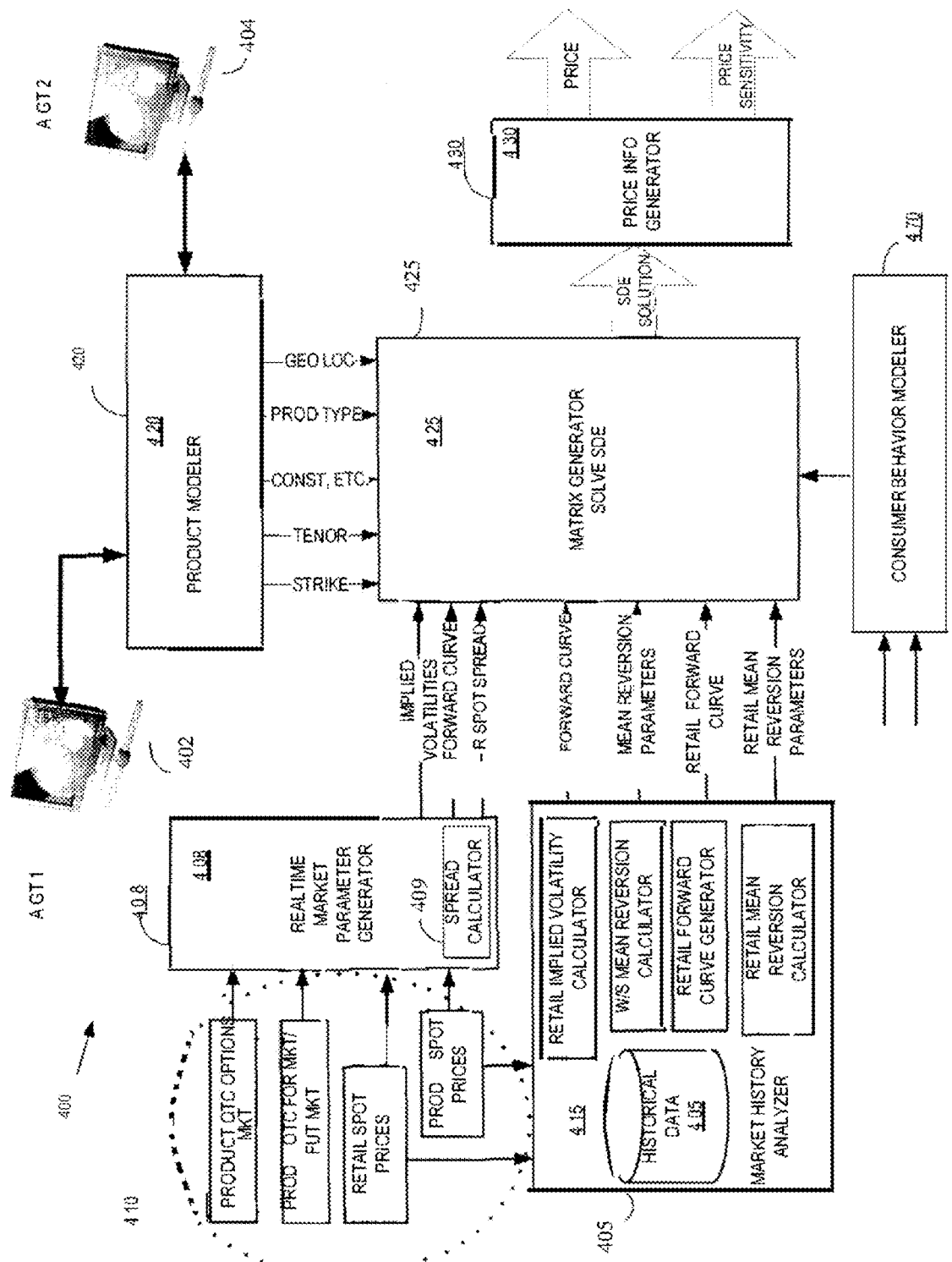

FIG. 14H illustrates a system 400 for generating future contracted product offerings according to an embodiment. System 400 comprises a market parameter generator 408 coupled for real-time monitoring of data related to a future contracted product market 410. Real-time market data refers to data reflecting current market conditions as trading in the market takes place. Examples of real-time market data provided to real-time market parameter generator 108 include wholesale over-the-counter future contracted product options market data, wholesale future contracted product options over-the-counter forward market and futures market data, and spot prices for retail future contracted product as well as spot prices for wholesale future contracted product. In an alternative embodiment, a market parameter generator may be configured to periodically and/or intermittently query current values for market parameters. Exemplary products include farm products, electricity products, energy products, commodities, among others. Such products or commodities can be traded using the smart contact and the system 400.

A market history analyzer 415 is coupled to receive and/or record observable real-time market data and/or historical records of market data related to market 110. The market history analyzer may record and store observed market data and/or historical market data accumulated historically and received by the market history analyzer. In that manner, market history analyzer 115 develops data related to the historical performance of the market. In one embodiment of the Future contracted product Offering Generator, market data includes retail electricity spot prices and wholesale electricity spot prices.

A product matrix generator 425 is coupled to the market parameter generator 108 and to the market history analyzer 415. Product matrix generator 425 is configured to the behavior of market 110. Product matrix generator 425 operates on the parameters it receives from real-time market parameter generator 408 and market history analyzer 415 in accordance with a stochastic model of the dynamics of the market 410. In one implementation, the product matrix generator 425 may consider some of the market variables and/or other input parameters. Product matrix generator 425 may solve a stochastic differential equation to provide a commodity volatility model based on the input parameters.

In one embodiment, the matrix generator 425 is configured to solve stochastic differential equations for market models using parameters provided by real-time market parameter generator 108 and market history analyzer 415. Among other parameters provided by real-time market parameter generator 108 and market history analyzer 415, parameters reflecting retail future contracted product sales activity may be collected and provided to real-time market parameter generator 408 and market history analyzer 415 in embodiments of the Future contracted product Offering Generator.

For example, in one embodiment of the Future contracted product Offering Generator, the matrix generator 425 is configured to process spot price spread information provided by real-time market parameter generator 408. The spot price spread information is related to a difference between a retail future contracted product spot price and a wholesale future contracted product spot price. Matrix generator 425 processes the spot price spread information in accordance with a stochastic model. In embodiments of the Future contracted product Offering Generator, the matrix generator 425 is further configured to process retail future contracted product forward curve parameters in accordance with a stochastic model. The retail forward curve parameters may be provided by the market history analyzer 415. In another embodiment of the Future contracted product Offering Generator, the matrix generator 425 may further solve alternative market models that are adapted and/or deemed suitable for use in embodiments of the Future contracted product Offering Generator.

In one embodiment of the Future contracted product Offering Generator, the matrix generator 425 receives market parameters from real-time market parameter generator 108 and from market history analyzer 415. Product matrix generator 425 processes and analyzes the information to provide a solution for the adapted stochastic differential equation (SDE). Product matrix generator 425 may be coupled to price information generator 430 and configured to provide the solution thereto. Based upon the solution it receives from product matrix generator 125, price information generator 430 may provide data representing a product price at an output in one implementation. In an embodiment of the Future contracted product Offering Generator, the price information generator 430 may also provide data representing price sensitivity at an output. In one implementation, the price sensitivity may indicate price sensitivity not only with respect to wholesale future contracted product markets but also with respect to retail future contracted product prices, and/or with respect to other input variables received from real-time market parameter generator 408, market history analyzer 405, and/or product modeler 420.

In one embodiment, the system 400 further comprises a product modeler 120. Product modeler 120 is coupled to at least one computer system 402. In some embodiments of the Future contracted product Offering Generator, the product modeler 120 is coupled to two electronic agents or robots 402 and 404. In embodiments of the Future contracted product Offering Generator at least one of computer agent or robot 402 and 404 comprises a future contracted product offering Purchaser computer. In some embodiments, the future contracted product offering Purchaser computer may be coupled to product modeler 420 via a communications network, such as the Internet. A future contracted product purchaser may enter information related to a future contracted product, such as a future contracted product offering, using the future contracted product offering Purchaser computer. The future contracted product offering Purchaser computer transmits the information to product modeler 420. In one implementation, the product modeler 420 may use the information from the future contracted product offering Purchaser to determine features of a financial product to be modeled by product modeler 420.

In one embodiment, the Future contracted product Offering Generator 400 comprises at least one Distributor computer system 404. Distributor computer system 404 is coupled to product modeler 420 and may enable a Distributor to define characteristics of a financial product comprising future contracted product offerings to be offered to a consumer. In that embodiment a Distributor inputs data to Distributor computer 404. Distributor computer 404 provides the data to product modeler 420. Product modeler 420 models the financial product in accordance with the characteristics provided by Distributor computer system 404.

Product modeler 420 is coupled to product matrix generator 425. Based upon inputs from at least one of a future contracted product purchaser computer or smart agent 402 and a Distributor computer or smart agent 404 product modeler 420 generates data representing features of a financial product. System 400 determines the price of the financial product based upon product data provided by product modeler 420, real-time market parameters provided by real-time market parameter generator and on historical market data provided by market history analyzer 415.

In one embodiment of the Future contracted product Offering Generator, the matrix generator 425 is coupled to a consumer behavior modeler 470. Consumer behavior modeler 470 receives data representing Purchaser (e.g., consumer) behavior with respect to future contracted product offering execution and/or purchase, ownership, exercising, and/or the like. Based upon the behavior data consumer behavior modeler 470 provides Purchaser and/or consumer behavior parameters to matrix generator 425. In that embodiment, matrix generator 425 considers the Purchaser and/or consumer behavior in calculating price for a financial product.

In one implementation of the Future contracted product Offering Generator, a future contracted product offering comprises a product related to future purchases of future contracted product in a retail future contracted product market. Both the retail and the wholesale future contracted product markets are observed. Observable wholesale future contracted product market parameters include wholesale future contracted product over-the-counter (OTC) options information, wholesale product over-the-counter (OTC) forward market data in a wholesale future contracted product market. Future contracted product market data including retail future contracted product spot price information is obtained. Market parameters related to current market conditions are generated based on the observed future contracted product market condition 411. At least one generated market parameter related to current market conditions is wholesale-retail spot price spread in one implementation. Other generated market parameters may include a wholesale implied volatility and a wholesale forward curve. In one embodiment, parameters related to current market conditions are sampled and stored to provide historical data describing past market behavior 413. One sampled and stored parameter used in one implementation to provide historical data is retail future contracted product market spot price. Thus historical data related to retail future contracted product spot price is acquired. Historical data, such as data related to retail future contracted product spot price, may be analyzed 419. The analysis may, in one implementation, consider retail future contracted product market information. The data is used to estimate parameters of models for future contracted product market behavior 421. Examples of generated future contracted product market behavior parameters may include retail implied volatility, wholesale mean reversion, retail forward curve and retail mean reversion. The indicators of future contracted product market behavior and the parameters related to current market conditions are analyzed 423. In one embodiment of the Future contracted product Offering Generator, the analyzing step is carried out by stochastic modeling. Price information for the future contracted product offering is generated 443. In one embodiment of the Future contracted product Offering Generator, price sensitivity information related to the future contracted product offering is generated 444. In further embodiments of the invention Purchaser and/or consumer behavior may be observed 441. Data related to Purchaser and/or consumer behavior is obtained based on the observations. In one embodiment of the invention Purchaser and/or consumer behavior data is analyzed 442 as considered in an analyzing step 423 as a factor in generating price information 443.

A buyer agent can now electronically enter into a smart contract with the price generator. In one implementation, a Contract Provider Agent executing the system 400 may price offerings, make them available to a Purchaser market, execute Purchaser offering purchases, and honor Purchaser offering exercises. In another implementation, the Provider may price offerings and make them available to an intermediary Distributor entity, who may provide them to a Purchaser market and interface with Purchasers for offer purchases and exercises. The contracts between the provider agent and the buyer agents (and the distributor agents such as the agents handling trip planning and delivery, for example) use the smart contract discussed above. A future contracted product offering may include specific details regarding the terms and conditions such as product type, quantity, Strike Price, Duration or Tenor and Premium, along with blockchain identifiers (IDs) that uniquely link the contract to the parties. The contracts can be automatically executed by the agents as needed, thus distributing the decision making to the last possible moment with current condition and optimizing cost/benefits.

In an effort to offset, mitigate, and/or eliminate some amount of risk associated with the sale of offerings, the Provider may elect to select, purchase, and/or manage a portfolio of hedging instruments. A Provider devised hedging portfolio may be comprised of a variety of different types of holdings in various implementations that may include but are not limited to equities, debts, derivatives, synthetics, notes, stocks, preferred shares, bonds, debentures, options, futures, swaps, rights, warrants, commodities, currencies, long and/or short positions, ETFs, and/or other assets or investment interests. In one implementation, a Provider devised hedging portfolio may be comprised of forward contracts and/or futures of exchange or over-the-counter (OTC) traded wholesale future contracted product options, product options, and/or the like. Sensitivity data provides information describing the degree to which a particular input variable (e.g., a market parameter) affects the strike price and/or premium of an offering. Counteracting the risk associated with an offering may, therefore, be accomplished by seeking instruments whose sensitivity to input variables is similar in magnitude but opposite in direction to offering sensitivities. Observed offering execution and exercise practices and/or trends of Purchasers may further affect Provider hedging strategies and/or practices. For example, an observation of sub-optimal exercise of offerings by Purchasers may indicate to a Provider that a smaller purchase of hedging instruments will suffice to offset the risk associated with the offerings. In the extreme case, wherein the offerings are never exercised under any circumstances, the Provider would have no need for hedging instruments at all.

The Purchaser may be an electronic agent or entity who desires to purchase future contracted product offering to mitigate future contracted product costs over some period of time. In accordance with this goal, a number of future contracted product offerings may be made available for purchase by the Distributor agent, among others.

In one example, an agent or machine acting as a Product Purchaser purchases a future contracted product offering with a particular strike price for certain future contracted product volume (N) using the smart contract with a blockchain ID. At some point subsequent to the purchase of the future contracted product offering, the Purchaser may decide to purchase X amount of future contracted product. In so doing, the Purchaser may elect to exercise the offering on the future contracted product purchase of X, generally depending upon the market price of future contracted product at the time of purchase. In the case where the cost of future contracted product is less than the strike price, it does not make economic sense for the Purchaser agent/machine to exercise the offering, for reasons described above, and in such a situation, the Purchaser may simply enter into a smart contract to purchase the product at the market price. Alternatively, in the case where the cost of future contracted product is greater than the strike price, particularly where the cost of future contracted product is greater than the strike price+premium, it may make economic sense to exercise the future contracted product offering, though the Purchaser may not necessarily exercise the future contracted product offering (e.g., if the Purchaser expects the cost of future contracted product to be even higher the next day). In some embodiments, the future contracted product offering may be automatically exercised whenever the cost of future contracted product is greater than the strike, or alternatively, the strike+premium. In another embodiment, the future contracted product offering is not exercised automatically. If the Purchaser decides to exercise the future contracted product offering, the Purchaser profile (e.g., a data file that includes information regard the Purchaser's future contracted product offering(s)) or like information source regarding the future contracted product offering may be queried using the blockchain ID to determine the unused future contracted product volume (R) remaining for the future contracted product offering. A determination is then made as to whether the remaining volume (R) is equal to or greater than purchase volume (X). If not, then the Purchaser enters into another agreement for the full purchase at market rate. In another embodiment the Purchaser may be able to exercise the future contracted product offering for a partial amount of the full purchase (i.e., for the remaining volume). Otherwise, a determination is made regarding whether the prevailing product price (or other price, such as the national average price, as indicated by the implementation) is greater than the strike price. If so, the Purchaser's account is credited with the difference (D) between the strike price and the pump price, multiplied by the amount purchased. Otherwise, in the case where the prevailing pump price is determined to be less than the strike price, the Purchaser pays the prevailing pump price.

The blockchain can facilitate self-organization by providing a self-management platform for companies, NGOs, foundations, government agencies, academics, and individual citizens. Parties can interact and exchange information on a global and transparent scale—think of Google Cloud, but larger and less risky. Smart contracts can ensure that electorates can be elected by the people for the people so that government is what it's meant to be. The contracts specify the electorate's expectations and electors will get paid only once they do what the electorate demanded rather than what funders desired.

The system provides smart Blockchain Identity. The passport is stored on the ledger, given a Bitcoin address with a public IP, and confirmed by Blockchain users. The blockchain can make record-keeping more reliable by encrypting birth and death certification and empowering citizens to access this crucial information. The passport or personal ID can have smart agents execute tasks that are secure, traceable and anonymous.

One embodiment includes a reference to a physical government ID or a physically signed contract in the smart contract, and vice versa, as follows:

(a) deploy the smart contract in question, record its address on the blockchain, and include that address in the real contract (b) hash the corresponding real-world contract, record its hash digest, store the real contract in a safe space, (c) send a transaction to the smart contract that includes the real contract's hash in its metadata; the contract then stores that piece of information in its own, internal database. In this manner, the system can prove the link between the actions on the blockchain and the expected outcome in the physical world An IoT manufacturer deploys a smart contract that allows IoT devices to store the hash of the latest firmware update on the network. The devices either ship with the smart contract's address hard coded into the blockchain client, or the devices find out about it via a discovery service. The devices can then query the contract, find out about the new firmware, and request it by its hash via a distributed peer-to-peer filesystem such as IPFS. Assuming the devices are configured so as to share the binary they got, a device that joins the network long after the manufacturer has stopped participating in it, can still retrieve the firmware update and be assured that it is the right file. This all happens automatically, without any user interaction.

In another example, a blockchain network where cryptocurrency is exchanged provides a convenient billing layer and paves the way for a marketplace of services between devices. In the example above, devices that store a copy of the binary may charge for serving it, in order to sustain their infrastructure costs (or simply to make a profit). Devices can "rent their disk space". API calls are monetized where the caller needs to provide the necessary micropayment (in Bitcoin or Ethereum respectively) before requesting them. With a cryptocurrency in place, every device can have its own bank account on the Internet; it can then expose its resources to other devices (or users) and get compensated for their usage via microtransactions. This also facilitates the sharing of services and property in general.

Smart electronic locks can be unlocked with a device that carries the appropriate token. These tokens are bought on the Ethereum blockchain, a public blockchain network optimized for smart contracts that uses its own cryptocurrency, called Ether. The owner of a smart lock that wishes to rent their house or car sets a price for timed access to that electronic door lock. An interested party can use a mobile app to identify the lock, pay the requested amount in Ethers, then communicate with the lock via a properly signed message to unlock it. Billing is simplified by having all the locks operating on the same blockchain.

In block diagrams, illustrated components are depicted as discrete functional blocks, but embodiments are not limited to systems in which the functionality described herein is organized as illustrated. The functionality provided by each of the components may be provided by software or hardware modules that are differently organized than is presently depicted, for example such software or hardware may be intermingled, conjoined, replicated, broken up, distributed (e.g. within a data center or geographically), or otherwise differently organized. The functionality described herein may be provided by one or more processors of one or more computers executing code stored on a tangible, non-transitory, machine readable medium. In some cases, third party content delivery networks may host some or all of the information conveyed over networks, in which case, to the extent information (e.g., content) is said to be supplied or otherwise provided, the information may be provided by sending instructions to retrieve that information from a content delivery network.

In one embodiment, a computer system includes:
a smart contract with computer-readable program code executable by a processing circuit for:
embedding key data in each term of the smart contract, the key data being associated with a blockchain identification and usable to conduct a transaction a, wherein a record of the transaction becomes visible in a transaction ledger;
monitoring the transaction ledger to determine whether a transaction against the blockchain identification has occurred;
applying a contract expert module to interpret contract terms; and
enforcing the smart contract at the machine level if no dispute and otherwise enforcing the smart contract by court, arbitration or administrative agency using a contract management system (CMS).

Implementations can include one or more of the following:
holding a store of value at a bank or escrow to pay for completion of contract terms.
verifying completion of contractual terms using a third party computer agent.
owners of IoT devices and sensors share generated IoT data in exchange for real-time micropayments.
producing energy produced by IoT energy harvester generates cryptocurrency value registered on the blockchain.
placing a Bill of Lading on a blockchain and terms of the shipping contract are executed in code based on real-time data provided from IoT devices (Smart Agents) accompanying shipping containers.
blockchain in auto supply chains.
providing real-time information from sensor data from various vehicle parts are integrated with blockchain to make real-time decisions and transactions involving services and payments.
recording environmental conditions during the shipment of one or more products and during a change of ownership, checking collected data against each product's corresponding smart contract in the Ethereum blockchain.
performing contract negotiations among IOT devices.
a first IOT device managing a cost of the device, wherein the IOT device negotiates power
reduction or power from another IOT device to optimize the cost.
placing a resupply or maintenance request with device location.
using blockchain-enabled smart contracts to ensure that the appropriate parties are notified of noncompliant events and automatically enforce privacy regulations; rules embedded via smart contracts dictate what they can see and when. Moreover, as data and transactions are shifted or linked to blockchains, organizations can track who has shared data and with whom, without revealing the data itself.
recording a lifecycle of a product by storing manufacturing, diagnostic and maintenance and end-of-life data on a blockchain.
lending an item with lending terms in the smart contract.
receiving a request for lending an item; generating as contract terms an owner identifier that has the right to use and lend the item, an identifier of the item, and the lendable number of times of the item; a borrower identifier specified by the owner, and a lending period matching the borrower identifier; and unlocking the item for use during the lending period according to contract terms.

a. for record keeping: providing an irreversible, secure, time-stamped record of the creation of IP;
b. to register and clear IP rights;
c. to control and track the distribution of (un-)registered IP rights;
d. to provide evidence of first use in commerce/trade and/or (genuine) use of a trade mark;
e. to establish and enforce IP contracts, licences etc through smart contracts;
f. to transmit payments in real-time to IP owners;
g. for authentication: detection of counterfeit or fake goods;
h. provenance: detection and retrieval of stolen goods;
i. detection of grey or parallel imported goods; and
j. enforcement of exclusive distribution networks.

In another scenario, a user may wish to borrow money for the purpose of buying a product or good in a social network. The blockchain ID of the product can be recorded with the financing transaction showing that the funder paid for the good but ownership is with the borrower, effecting a lien to each lender that is extinguished only by full payment or consent of the lender; and upon full payment to lenders, a smart contract indicates in each lending blockchain entry that the debt has been paid off and the lien on the good or product is extinguished so that the buyer can resell the good/product if desired.

A recommendation may be provided to the user automatically upon finishing the item (e.g., after reading an entire eBook) to lend his or her item to another user in the social network. The system that generates the recommendations may be configured to recommend lending to users based on distance or reputation in the social network or to users with high lending metrics more so than other users.

In another scenario, the user may have items to lend and may also wish to borrow non-monetary items. A loan-matching infrastructure may identify another user with complementary lendable items and borrowing desires. The loan matching may additionally function as a mechanism for introducing users that are in the same social network but not yet connected to one another in that social network, or it may serve to strengthen the relationship between users who are already connected.

As a further scenario, the architecture may enable a user with a lendable item to broadcast and/or narrowcast the availability of the item to just friends or to many other users. One of multiple users that respond to the broadcast/narrowcast may be selected based on speed of response, lending metric, social network relationship, and the like. For items that are able to be lent only a limited number of times, this technique of soliciting many responses may assist the user in deciding which user or users are allowed to borrow the item.

The process for establishing and/or managing a group of members in a rotating credit association (RCA) is as follows in one implementation:

---

Organizer joins a social network (152)
Organizer applies to create a Lending Group (154)
System authenticates the Organizer and determines how much the Lending Group can lend based on Organizer's social connection and other indicia of financial trustworthiness (156)
Organizer determines group size, total amount disbursed for a period, and amount each member is expected to contribute for each period (158)

-continued

Organizer identifies potential members and System authenticates each potential member based on the member's social connection and other indicia of financial trustworthiness (160)
Organizer invites selected members to join the Group (162)
System collects payments from members of the Group with blockchain smart contract (164)
Based on terms of the smart contract, system selects a member who will receive the current Group payment, distributes periodic award to member, and removes member from future award for the rest of the year (166)
System flags members who don't pay or fail to meet the terms of the agreement and shows such status to the member's friends (168)

The systems and methodologies for self-financing, and rotating credit associations incorporating or implementing these systems and methodologies, have been provided herein that offer an attractive alternative to conventional consumer credit and savings systems for persons, such as immigrants and minorities, who may have nontraditional credit histories or who are otherwise disadvantaged in the underwriting processes attendant to most consumer loans. The systems and methodologies, which feature rotating credit associations in which the members are trustworthy due to their social network links, and backed up when the number of group members making payments to a common fund is greater than the number of time intervals (typically months) or dates over which awards are made from the common fund, and further buttressed by insurance, can tolerate a high percentage of defaults or membership cancellations by its participants without becoming insolvent.

One embodiment provides a pooled investment fund in accordance with certain embodiments of the present invention. In certain embodiments, the exemplary method may be executed in whole or part by the protocols included in the users' cryptographic wallets. A security fund is created by embedding one or more blocks on a blockchain ledger which at least include data associated with a base security document, a set of one or more security rules and ownership of the security fund. The base security document may represent a document that specifies the terms, conditions and other details related to the implementation and management of the security fund. The issuer may initially be designated as the owner of the security fund. The terms of the smart contract are defined and can include compliance rules with government security rules, system regulations and restrictions.

Exemplary information that may be embedded into the data tokens and blockchain ledger may include: Issuer Identification (ID), Investor ID, Product ID, Security Type Data, Regulatory and Restriction Data, Transaction History on previous purchasers and sellers that exchanged the security and/or any information relevant to any of the transactions involving the security, Share Amount, Investor Compliance Information on anti-money laundering laws, know your customer guidelines or other types of compliance regulations, etc., Investor Suitability, Beneficial Ownership.

Other relevant information may also be embedded into the data tokens, and that the embedded information may vary based on the type of security product. Any and all of the above data may also be embedded or included in entries that are added to the blockchain ledger. For example, data tokens and blockchain ledger may include embedded information that includes an executive summary, a comprehensive description for the security, base security documents related to the creation of the security, and other documentation. Alternatively, a link or cypher that is used to identify and/or access a location (e.g., via a network address associated with the platform) where this information can be retrieved.

The security or loan offering is then placed on the blockchain ledger, and broadcasted to prospective members. The members in turn review and invest by accepting the terms of the smart contracts and fund the investment. The blockchain is updated to reflect smart contracts execution by investors in connection with a security offering. The blocks that are appended to the blockchain ledger may be utilized to update the ownership status of the security fund and may specify investments made by the investors. The blocks may link back to one or more prior blocks on the ledger which are associated with the security fund. One or more corresponding data tokens may then be transferred to each of the investors.

The investments submitted by the investors may be pooled together to monetize the security offering. When the investors are submitting information in connection with the smart contract, the investors may place money or other currency in escrow to secure payment in connection with the investment. Once the contract is confirmed and the blockchain ledger is appended with a corresponding entry, the money or other currency may be transferred into the investment pool.

In one embodiment, the security offering can be used to invest in individual companies such as start-ups seeking crowd-funding. In this embodiment, the issuer ID is the startup name with ID linked to a secretary of state or a law firm.

In another embodiment, the security offering can be loan where borrowers seeking to borrow from the security fund. Purchases by the borrowers with the loan are also on the blockchain ledger and are linked to the pooled investment fund as security for the loan. Thus, loans for housing can be provided at a cheaper rate than loans for vacations, for example. The smart contracts may retrieve the security rules to configure themselves to implement any specified regulations and restrictions. The blocks appended to the blockchain ledger stores the borrowing amount of each borrower and identity of each borrower. The blocks may link back to one or more prior blocks on the blockchain ledger which are associated with the security fund. One or more corresponding data tokens may then be transferred to each of the investors to represent the borrowing debt associated with the portfolios that are maintained by their cryptographic wallets.

The system thus allows microloans to be funded and applied in a secure and automated low cost manner.

Figure 14I:
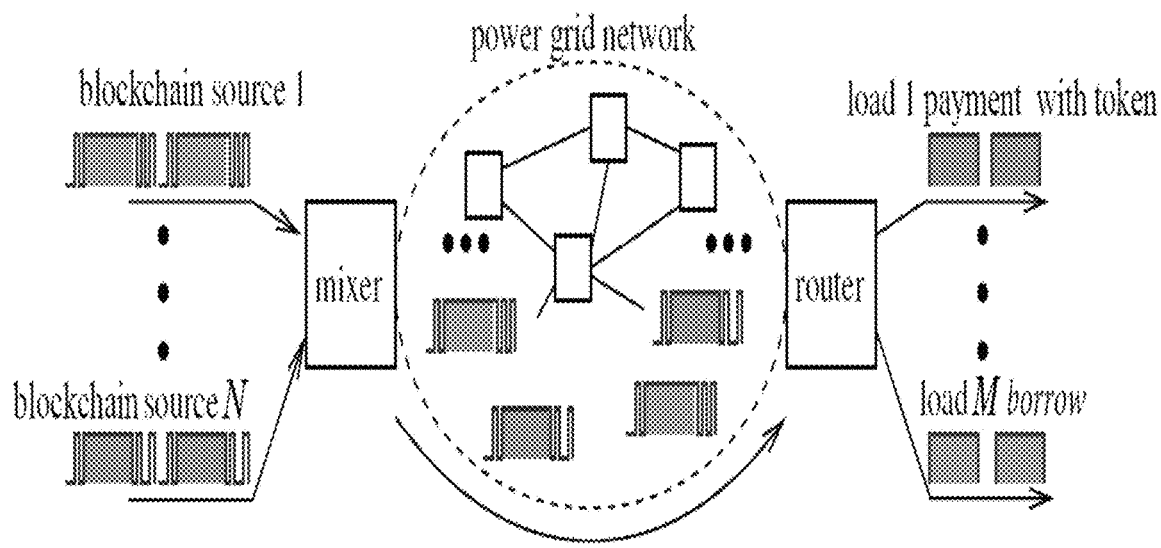
FIGS. 14I-14J show exemplary blockchain energy delivery systems.
Figure 14J:
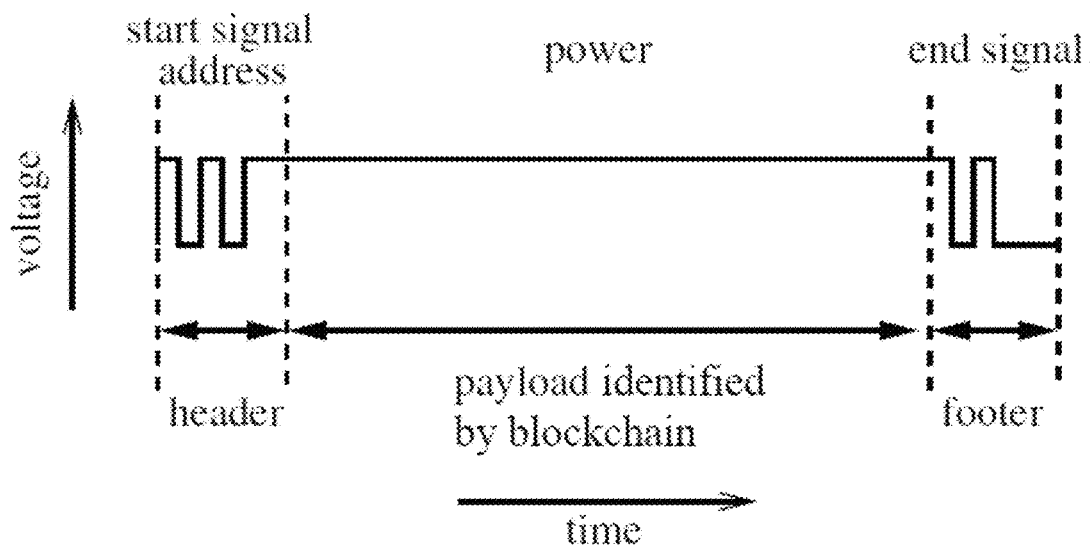

FIGS. 14I-14J show exemplary blockchain energy delivery system that can service IOT robots and households using smart contracts, among others. Renewable energy certificate provides accumulates, distributes, or otherwise sells "green tags". The RECs, also known as green tags, renewable energy credits, or tradable renewable certificates (TRC's), are tradable environmental commodities that represent proof that one megawatt-hour (MWh) of electricity was generated from an eligible renewable energy resource. However, conventional system can't track the source of the RECs. One embodiment of the system uses power packet dispatching, as shown in FIG. 14I, where N power sources (identified using blockchains) supply the power to M loads based on the demand. The loads can pay the source with tokens or coins, and the payment can be contractual in nature. For example, the buyer can hedge its purchases by buying in advance from one or more sources. Similarly, the sources can sell energy in advance and the contract information can be included in the contract portion of Ethereum blockchain body in one embodiment. As shown in FIG. 14I, the mixer governs the order of power packets from power sources to transfer and the routers dispatch them to loads. The power line network fundamentally has tie and loop line connections. Before discussing the configuration and networking problems, it is significant to confirm the packet transfer through one power line from multiple sources to paralleled loads. Therefore, in the following discussions, N and M are set at the lowest number 2. It does not lose the generality to confirm the feasibility of packet transfer in the grid network. A power packet is a voltage wave, with a header, a payload with blockchain ID, and a footer. A header consists of a start signal and an address signal, a payload carries power, and a footer consists of an end signal as in FIG. 14J. Distribution from two power sources to two loads is performed by time division multiplexing (TDM). A mixer forms power packets by switching from a dc power source. The power packets are delivered from the mixer to a router through one transmission line. When the router receives power packets, they are sorted based on their blockchain information and sent to routers or objective loads.

Each energy supplier and consumer operates autonomously based on their local policy, algorithms and rules, initiating the power transfers appropriately. The energy is tagged with identification information stored in the blockchain including generation source, route of delivery, storage device (if any) and end user (energy consumer). When energy storage is used, the usual restriction that energy must be produced and consumed at the same time is relaxed. Storage enables flexible commercial trading so energy can be reserved for future use, and the time of delivery can be selected by the energy user. Energy flows are monitored by built-in metering devices and recorded together with reservation information, including time, seller, buyer, price, energy source, energy amount, among others. These records are in the distributed ledger or block chain and will be like a bankbook for ordinary financial transactions.

The body of the blockchain can incorporate several types of messages that the active grid elements (for example, an ALC manager) may receive from a coordinator and process accordingly. By way of example and not limitation, a security alert message, a priority message, a report trigger message, a status response message, a status update message, a power savings message, and combinations thereof. A security alert message originates from an optional security or safety monitoring system installed in the residence or business and coupled to the active grid element(s) (e.g., wirelessly or via a wired connection). When a security alert message is received by the Coordinator, it accesses the database to obtain routing information for determining where to send the alert, and then sends the alert as directed to those active grid elements affected or associated with the alert messaging. For example, the Coordinator may be programmed to send the alert or another message (e.g., IP-based message, an electronic mail message, a pre-recorded voice message, and combinations thereof) to a security monitoring service company and/or the owner of the residence or business.

A report trigger message alerts the Coordinator that a predetermined amount of power, PSV, PTB, and combinations thereof has been consumed by a specific device monitored by an active grid element. When a report trigger message is received from the active grid element(s), the Coordinator logs the information contained in the message in the database for the active grid element(s) associated with the information supplied. The power consumption information, including PSV, PTB, and combinations thereof, is then used by the Coordinator to determine the active grid elements (ALDs/ALCs) to which to send a power reduction or "Cut" or reduce message during a power reduction event to satisfy the operating reserve requirement.

A status response message reports the type and status of each active grid element in communication with the Coordinator. When a status response message is received from an active grid element, the Coordinator automatically logs the information contained in the message in the database.

In another embodiment, a power savings message and/or application may be optionally included to calculate the total amount of power saved by each utility or market participant during a power reduction event (referred to herein as a "Cut event" or "reduce event"), as well as the amount of power saved, PSV, PTB, and combinations for each active grid element that reduced the amount of power delivered, PSV, PTB, and combinations thereof, and matched against a baseline associated with that active grid element. The power savings application 120 accesses the data stored in the database 124 for each customer serviced by a particular utility and stores the total cumulative power savings, or PSV (e.g., in megawatts per hour, or kWH/MWH) aggregated by participating active grid elements and/or accumulated by each utility for each Cut or reduce event, i.e., curtailment or load control event, in which the active grid elements and/or utility participated as an entry in the database.

Preferably, the systems and methods of the system provide for automated remote updating of active grid elements via communications through the network with the Coordinator(s), including but not limited to software, firmware, chipsets, kernels, and combinations thereof. Updating through the Coordinator(s) and/or central server, and/or dedicated server for updating active grid elements is provided by the system. Also, commands are sent for purposes for updating any and all attributes of the active grid elements, including PSV, and/or PTB by a central and/or remote device or server, or processor, meant to enhance for update PSV, PTB, or location of PTB server point ASIC within an IP message or proprietary message that deal with table spaces, pricing, changes in acceptable time increments, status messages, location of market (LMP, node, electrical bus, etc.) for the load for marketing, aggregated, settled, and combinations thereof. The updating is for purposes of PSV, PTB, or ability to know the health and/or status of any active grid elements within any zone within the electric power grid. Thus, the systems and methods of the system provide for automatic updating of any and all active grid elements by remote server or dedicated device(s), through Coordinator(s) and/or directly to active grid elements that affect any aspect of updating of active grid elements relating to software, firmware, rules, metrology, ASICs, chipsets, machine code, operating systems, and combinations thereof. Furthermore, active grid elements may be updated for improved or increased accuracy of active grid elements to qualify PSV and PTB associated therewith. Also, the system provides for active grid elements with smart cross-communication that provide for at least one active grid element to transmit commands to at least one other active grid element within the network associated with the electric power grid.

By way of example, based upon the reduction in consumed power, the systems and methods of the system provide for generating at the control center a power supply value (PSV) corresponding to the reduction in consumed power by the active grid elements. Importantly, the PSV is an actual value that includes measurement and verification of the reduction in consumed power; such measurement and verification methods may be determined by the appropriate governing body or authority for the electric power grid(s).

Power Supply Value (PSV) is calculated at the meter or submeter or at building control system or at any active grid element that measures power within the standard as supplied by the regulatory body(ies) that govern the regulation of the grid. PSV variations may depend on operating tolerances, operating standard for accuracy of the measurement. The PSV enables transformation of curtailment or reduction in power at the active grid element level by any system that sends or receives an IP message to be related to or equated to supply as presented to the governing entity that accepts these values and award supply equivalence, for example of a power generating entity or an entity allowed to control active grid elements such as power consuming devices as permitted by the governing body of the electric power grid, e.g., FERC, NERC, etc.

PSV associated with active grid elements may be provided in units of electrical power flow, monetary equivalent, and combinations thereof. Thus, the PSV provides an actual value that is confirmed by measurement and/or verification, thereby providing for a curtailment value as a requirement for providing supply to the power grid, wherein the supply to the power electric power grid is provided for grid stability, voltage stability, reliability, and combinations thereof, and is further provided as responsive to an energy management system or equivalent for providing grid stability, reliability, frequency as determined by governing authority for the electric power grid and/or grid operator(s).

Energy consumption patterns associated with active grid elements are subject to analysis that may be used for a variety of different types of activities. For example, based on the energy consumption patterns created from this data, the Coordinator will derive performance curves and/or data matrices for each service point to which the active grid elements are attached and determine the amount of energy reduction that can be realized from each active grid element and its functionality within the electric power grid. The Coordinator(s) create a list of service points associated with the active grid elements through which energy consumption can be reduced via demand side management, interruptible load, or spinning/regulation reserves. This information can be manipulated by the Coordinator and/or ALD processes to create a prioritized, rotational order of control, called "intelligent load rotation" which is described in detail below. This rotational shifting of the burden of the interruptible load has the practical effect of reducing and flattening the utility load curve while allowing the serving utility to effectively group its customers within the ALD or its own databases by energy efficiency.

Generally, the embodiments described encompass a closed loop system and method for creating a profile, calculating and deriving patterns of energy usage and supply, and making use of those patterns when implemented through the machinery of a system comprised of active grid elements combined with the physical communications link and when these inputs are manipulated through a computer, processor, memory, routers and other necessary machines as those who are skilled in the art would expect to be utilized.

The system also considers the concept of "drift" as applied to electric power grids and active grid elements associated therewith. The data gathered for the active grid element profile is used to empirically derive the decay rate or drift, temperature slope, or a dynamic equation ($f\{x\}$) whereby the service point (or device) will have a uniquely derived "fingerprint" or energy usage pattern for individual and/or aggregated active grid element(s).

The embodiments disclosed also make use of the "intelligent load rotation" concept. Intelligent load rotation uses machine intelligence to ensure that the same active grid elements are not always selected for control events, but distributes control events over a service area in some equitable way and/or least cost analysis-applied manner, or other analytical approach for optimizing the electric power grid resources and functions of the associated active grid elements registered for automated intercommunication therewith.

In another embodiment, energy consumption patterns in active grid elements profiles are used to identify active grid elements that are the best targets for excess power sharing. This would occur when renewable energy such as solar or wind is added to the grid, resulting in power that cannot be compensated for by the grid. This could occur, for example, on very windy days. When this happens, utilities or market participant, grid operator, EMS, or equivalent are faced with the problem of what to do with the excess energy. Instead of cutting power to service points in order to affect power savings, a utility, market participant, grid operator, EMS, or equivalent could add energy to service points and through active grid elements associated with those services points in order to effect power dissipation. The service points and/or active grid elements selected by the Coordinator may be different (or even the inverse) of those selected for power savings. The devices at these service points would be turned on if they were off or set points for climate-controlled devices would be adjusted to heat or cool more than normal. Spread out over many control points, this can provide the energy dissipation needed.

In a further embodiment, energy consumption patterns within active grid elements profiles could be used to identify opportunities for up selling, down selling, or cross selling. These opportunities may be determined by the power utility or by its partners. Data from active grid elements profiles may be used to provide insights on inefficient devices, defective devices, or devices that require updating to meet current standards. Active grid elements profiles data, individually or collectively (or selectively) in the aggregate, may also be used to identify related power grid participation opportunities.

According to the system, PSV for any of the active grid elements may be generated by methods including information relating to baselining historical load, estimating based upon curves, real-time or near-real-time value, and combinations thereof. Advantageously, the system provides active load and/or supply management metrics for each of the active grid elements, including PSV, much better than merely statistical estimate for a command as with prior art; PSV also further provides for steps of measurement and settlement. FERC requires that the settlement credits provide at point where it occurs; so then settlement information follows the transaction; most preferably, according to the system, settlement occurs in real time or near real time, as in financial transactions or other commodity transactions, such as for natural gas supply. Also, preferably, there is a defined interval that is accepted or acceptable by the governing entity for the electric power grid, wherein each transaction is recorded as it occurs. Furthermore, the system provides for IP real-time communications that provide for settlement of the curtailment by load-consuming devices at or approximate to the time of the transaction, i.e., the curtailment. Also, preferably, there is data that provides supporting evidence attached with the IP real-time communication of the acceptance of the power event, and then automatically recorded in a settlement database and associated with each active grid elements registered within the system through the Coordinator(s). Also, some information related to this transaction and its settlement is transmitted to the energy/curtailment purchaser, and then also the seller is paid according to the PSV and/or PTB related to the curtailment event.

Power Trading Blocks (PTBs) are dependent upon the grid operator or ISO; there must be enough curtailment or supply for the grid operator to accept, settle, and monetize, including individual and/or collective or selectively aggregated data for active grid elements registered with the system. At this time, the PTB is 100 kWatts in most electric power grids, such as a conventional utility or independent system operator or grid or microgrid operator. Generally, the power available as operating reserves is traded in larger amounts, PTB size, to be significant enough to beneficially stabilize the grid and its operating reserves. At this time, the regional trading organization or geographic-specific grid and corresponding regulations therefor, determine the PTB size, which typically requires the aggregation of load from a multiplicity of consumers, residential or commercial, to reach a minimum PTB size or PTB unit. The PTB unit, combined with the PSV, and the real-time secure communications used with ALC/ALD function to lower the size of the minimum PTB required to form a PTB unit for grid reception and settlement purposes. The commercial impact determines the minimum PTB size, which corresponds to a PTB unit, due to cost and timing of communication of the information related to the curtailment event(s) and response by the device(s), and how aggregation of load curtailment by the multiplicity of devices is managed to ensure maximum compensation to the customer(s) associated with the device(s) for the curtailment event, with minimum negative physical impact to those consumers and/or devices from the curtailment event.

Active grid elements profiles may also be dynamic. An example of this would be the ability for active grid elements to utilize real time communications from an electric utility grid, market, market participant, utility, REP, CSP or any other entity authorized on behalf of the owner to act on their behalf to control load consuming devices owned by the consumer and connected to the electric utility grid. The active grid elements receive this information automatically through a plurality of methods utilizing IP-based communications methods and web based devices such as smart phones, computers, text messages, paging messages, or even voice response units or live customer service agents. Under this real time scenario, active grid elements could dynamically "Opt In" to a pre-determined profile or "Opt Out" or more importantly change the profile dynamically to take advantage of real time market pricing of electricity being sold by the utility, market participant, REP or any entity authorized to buy, sell and trade electric commodity or demand response products on behalf of the owner.

The system has adequately described in great detail how the active grid elements are associated with the Coordinator the employment of computer assisted apparatus that include, but are not limited to processors, ASICS, memory, analytics, communications interfaces and methodologies, databases, both relational, high performance "historian" databases, persistence and cache layers, metadata layers, analytics engines, monitoring and reporting active grid elements, Internet Protocal, Ethernet, carrier grade wired and wireless networks, proprietary networks, TDM wireless and wired networks, analog and digital telemetry subsystems, Coordinators, Active Supply Directors and a plurality of the above both centralized, networked together and distributed. While the previous descriptions have been detailed in the embodiment of FERC 745 Load acting as supply, one skilled in the art will correlate those functions previously described as they apply to the supply side for FERC 750 and 755, including settlement.

These highly decentralized networks must be capable of operating directly under the control of an EMS, through a Coordinator, and for active grid elements autonomously if they are disconnected from the macro electric grid or have voluntarily opted to disconnect themselves from the electric grid temporarily or permanently. The system provides through software, hardware and advanced communications methodologies the capabilities of many small DER resources associated with the active grid elements to perform and deliver their energy resource directly to the electric grid interconnected as they were a macro resource with aggregated PSV values that build up to minimum PTB blocks that can be both presented, operated and monetized by a Market Participant, REP, Utility, IPP, a Company acting as their own energy agent or a plurality of all of the above.

The system also provides for intermittent resources previously described the ability to be balanced, regulated and offered to the grid as reliably as DER resources. Balancing DER resources would suggest that a plurality of these resources may be collocated at the same service point/attachment or be themselves disaggregated from each other physically, but interconnected via the system and its attributes. An embodiment of this type of DER would be a commercial building that has installed solar film, panels or combinations thereof, a wind or water turbine, and a back-up generator at the same installation. These different resources with their different DER attributes must all be combined through an ASC that would have the capability of providing for primary frequency control per supply source, voltage control, meet the appropriate attachment regulations that may be different based upon the location of the DER supply on the distribution or transmission system and operating those systems either through a coordinator and an EMS or autonomously from both while still offering its supply to the interconnected electric grid. The system functions to communicate and control the DER resources based upon availability of the resource, what the grid's energy needs are at the moment of the energy being presented by or through a Market Participant or if permitted by the governing entity an individual consumer utilizing the system or the economic incentives that are profile based, sold in advance through an approved trading organization approved by the governing entity, or supplied in real time at the attachment point on the grid and supplied through the system as directed by an Energy Management System or providing those EMS services due to an EMS not being available at the time the resource is delivered and whereby the apparatus of the system is providing energy and grid stabilizing resources from the available sources, balanced upon what each resource can provide reliably to the interconnection of the electric grid.

Augmented Reality/Virtual Reality Sports Gaming

FIG. 15 shows an exemplary 360 degree camera on a helmet, for example, for augmenting reality of sport games. Using augmented reality, various ways may exist for a user to "participate" in a live event. Generally, augmented reality refers to a presentation of a real world environment augmented with computer-generated data (such as sound, video, graphics or other data). In some embodiments, augmented reality, implemented in conjunction with a live event, may allow a user to control a virtual object that appears to compete or otherwise interact with the participants of the live event. For example, an end user device, such as a mobile phone, tablet computer, laptop computer, or gaming console may be used to present a live video feed of an event to a user. This live video feed may be video of an event that is occurring in real-time, meaning the live event is substantially concurrently with the presentation to the user (for example, buffering, processing, and transmission of the video feed may result in a delay anywhere from less than a second to several minutes). The presentation of the live event may be augmented to contain one or more virtual objects that can be at least partially controlled by the user. For instance, if the live event is a stock car race, the user may be able to drive a virtual car displayed on the end user device to simulate driving in the live event among the actual racers. As such, the user may be able to virtually "compete" against the other drivers in the race. The virtual object, in this example a car, may be of a similar size and shape to the real cars of the video feed. The user may be able to control the virtual car to race against the real cars present in the video feed. The real cars appearing in the video feed may affect the virtual object. For example, the virtual object may not be allowed to virtually move through a real car on the augmented display, rather the user may need to drive the virtual object around the real cars. Besides racing, similar principles may be applied to other forms of live events; for example, track and field events (e.g., discus, running events, the hammer toss, pole vaulting), triathlons, motorbike events, monster truck racing, or any other form of event that a user can virtually participate in against the actual participants in the live event. In some embodiments, a user may be able to virtually replay and participate in past portions of a live event. A user that is observing a live event may desire to attempt to retry an occurrence that happened during the live event. While viewing the live event, the user may be presented with or permitted to select an occurrence that happened in the course of the live event and replay it such that the user's input affects the outcome of at least that portion of the virtualized live event. Using a baseball game as an example, with runners on first and third, two outs, and the count being two balls and two strikes, the pitcher may throw a splitter, successfully striking out the batter with a pitch in the dirt. The inning may end and the game may continue. The user may desire to replay this unsuccessful at-bat with himself controlling the batter during the commercial break. As such, via an end user device, the user may be able to indicate the portion of the game he wishes to replay (e.g., the last at-bat). Game facts from the live event may be used to virtually recreate this at-bat for the user. For instance, the virtual game loaded by the user may use game facts leading up to the at-bat the user has selected. For instance, the opposing team, the stadium, the score, the time of day, the batter, the pitcher, and the sequence of pitches thrown by the pitcher may be used to provide the user with a virtual replay of at least that portion of the baseball game that the user can affect via input (e.g., swinging and aiming the virtual bat). In replaying the selected portion of the live event, the entire event may be virtualized. As such, referring to the baseball example, the pitcher, stadium, field, fielders, batter, and ball may all be replaced by virtual objects, with one (or more) of the virtual objects, such as the batter, being controlled by the user. As such, this may resemble a video game instantiated with data from the live event. In some embodiments, a portion of the live event may involve a playback of a video feed of the live event with a virtual object that is controlled by the user being augmented. Referring again to the example of the baseball game, the pitcher, stadium, fielders, and field may be replayed from the video feed; the batter and/or ball may be virtualized. As such, the user may control the batter and swing at a virtual ball that has taken the place of the real ball present in the video feed. Besides baseball, such reenactment of a portion of a live event may be applied to various forms of sporting events, such as football, soccer, tennis, golf, hockey, basketball, cricket, racing, skiing, gymnastics, and track and field events. Other forms of live events, besides sports, may also be reenacted using such techniques.

Figure 15A:
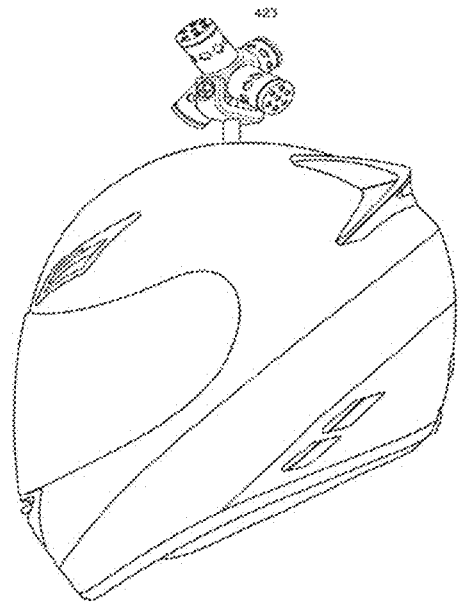
FIG. 15A shows an exemplary virtual reality camera mounted on a gear.

FIG. 15A shows a multi-headed camera array 423 that may be at least part of a modular camera system, with each camera forming a module of the modular camera system. The camera array has a flexible structure so that it is easy to remove a particular camera module from the camera array and to add new camera modules to the camera array. The camera modules in the camera array may be configured in different geometries. For example, the camera array includes multiple camera modules arranged in a line, a cylinder, a sphere, or another geometry. Each camera module may be configured to point to a different direction so that the camera array may capture an object or a scene from multiple directions at the same time.

The camera system described herein may additionally include a set of algorithms for processing the video data captured by the camera array. The set of algorithms are stored on a non-transitory memory for converting the input across multiple camera modules into a single stream of 3D video (e.g., a single compressed stream of 3D video data). The set of algorithms may be implemented in one or more "modules". For example, the set of algorithms includes color correction algorithms for smoothing and correcting colors in the video data. In another example, the set of algorithms may be implemented in software that stitches the video data from multiple cameras into two large-format, panoramic video streams for left and right eye viewing, and encodes and compresses the video using a standard MPEG format or other suitable encoding/compression format.

The camera array 423 may be constructed using various configurations. For example, the camera modules may be configured in different geometries (e.g., a sphere, a line, a cylinder, a cone, a cube, etc.) with the corresponding lenses 113 facing in different directions. For example, the camera modules are positioned within the camera array 423 in a honeycomb pattern where each of the compartments form an aperture where a camera module may be inserted. In another example, the camera array 423 includes multiple lenses along a horizontal axis and a smaller number of lenses on a vertical axis.

In some embodiments, the camera modules in the camera array 423 are oriented around a sphere in different directions with sufficient diameter and field-of-view to capture enough view disparity to render stereoscopic images.

The camera array 423 has a flexible structure so that a particular camera module may be removed from the camera array 423 easily. In some embodiments, the camera modules are rotationally symmetrical such that a camera module may be inserted into the housing, removed, rotated 90 degrees, and reinserted into the housing. In this example, the sides of the housing may be equidistant, such as a camera module with four equidistant sides. This allows for a landscape orientation or a portrait orientation of the image frames without changing the base. In some embodiments, the lenses and the camera modules are interchangeable. New camera modules may also be added to the camera array 423. In some embodiments, the camera modules in the camera array 423 are positioned to have a sufficient field-of-view overlap so that all objects can be seen by more than one view point. In some embodiments, having the camera array 423 configured so that an object may be viewed by more than one camera may be beneficial for correcting exposure or color deficiencies in the images captured by the camera array 423. Other benefits include disparity/depth calculations, stereoscopic reconstruction, and the potential to perform multi-camera high-dynamic range (HDR) imaging using an alternating mosaic pattern of under- and over-exposure across the camera array.

In some embodiments, the camera array 423 may also include a microphone array for capturing sound from all directions. For example, the microphone array may include a Core Sound Tetramic soundfield tetrahedral microphone array following the principles of ambisonics, enabling reconstruction of sound from any arbitrary direction. In another example, the microphone array includes the Eigenmike, which advantageously includes a greater number of microphones and, as a result, can perform higher-order (i.e. more spatially accurate) ambisonics. The microphone may be mounted to the top of the camera array 423, be positioned between camera modules, or be positioned within the body of the camera array 423. The result can then be rendered as an immersive video and a user can view the video with computer annotations thereon for augmented reality purposes. In one implementation, the event may be a live event, for example, but is not limited to, a football match, a cricket match, a basketball match, a theatre, a concert, and the like. In one embodiment, the augmented reality content may include, but is not restricted to, live content associated with an event, recorded content associated with an event, a curated content, an advertising content, or a combination thereof. In another embodiment, the augmented reality content may include, but is not restricted to, information related to a service available at an event, a venue of an event, a status of a service, or a combination thereof. The system 100 may also provide the augmented reality content associated with, but is not restricted to, a venue of an event, duration of an event, a location of an event, or a combination thereof, in another implementation.

One embodiment allows combined augmented reality and virtual reality on the display. The method may include selectively allowing a transmission of light from a local environment of the user based on a visualization mode of the display object. The visualization mode may be one of an augmented reality mode, a virtual reality mode, and a combination of augmented and virtual reality modes.

In another embodiment, sensors may be placed to track eye movement as well as hand gestures and verbal commands. The method may further comprise capturing a field-of-view image of each of the user's eyes. The captured field of view image may be used to estimate a head pose of the user. The captured field-of-view image may be used to convert at least one physical object to a physically rendered virtual object, and to display the physically rendered virtual object to the user. In another embodiment, sensors may be placed to track eye movement as well as hand gestures and verbal commands. Then, a method comprises tracking a movement of a user's eyes, estimating a depth of focus of the user's eyes based on the tracked eye movement, modifying a light beam associated with a display object based on the estimated depth of focus such that the display object appears in focus, and projecting the modified light beam into the user's eyes. The diameter of the projected light beam projected to the user's eyes may be less than 0.7 mm.

For the athlete/participant who wish to enhance their gaming via augmented or virtual reality, features may include the following:

A method for using augmented reality, the method comprising: receiving, by a computerized device, a data stream with a 360 degree view of a live event on each participant, wherein the data stream comprises live video augmented with positions of team mates and opposing players and recommends a play routine based on live field condition and positions of other players, wherein the user can select a point of view from a selected participant.

The method for using augmented reality of claim 1, wherein the user plays in a virtual reality version of the live event.

The method for using augmented reality of claim 1, wherein the live event is a sporting event.

The method of claim 7, wherein the live event comprises: soccer, football, basketball, tennis, boxing, car racing, golf, ice hockey, badminton, volleyball, cycling, swimming, snooker, martial arts, rugby, motorbike, hockey, table tennis, horse racing, gymnastics, handball, figure skating, wrestling, skiing, diving, skating, archery, sailing, wrestling, fencing, equestrian, rowing, surfing, Beach Volleyball, Pool/Billiards, Lacrosse, Windsurfing, Polo, Tenpin Bowling, Racquetball, Competitive Climbing, Mountain Biking.

Figure 15B:
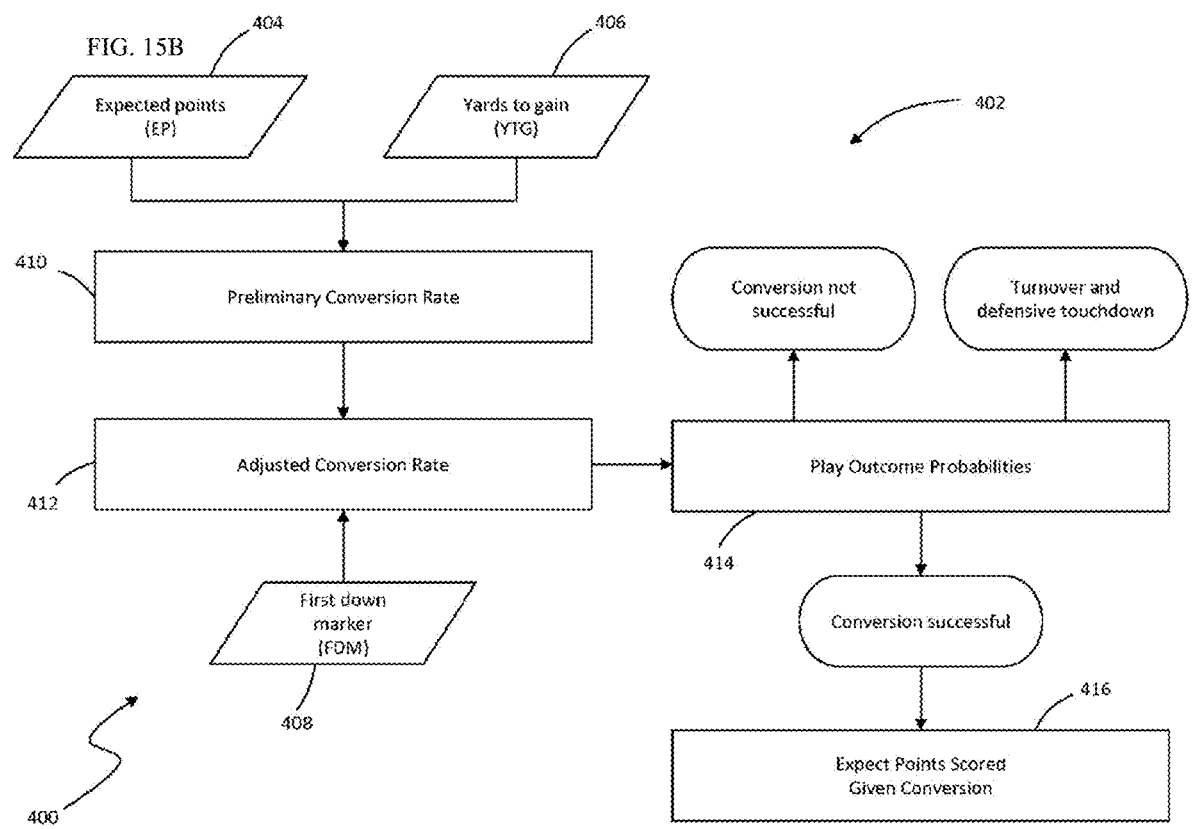
FIG. 15B shows exemplary augmented reality real-time coaching of a player such as a quarterback during fourth down.

FIG. 15 shows an exemplary recommender to aid an athlete in improving the game. For example, the process can recommend a strategy in light of the opponent's historical performance. In tennis, a player's historical weakness can be ascertained and a recommendation can be made to optimize success. In a football example, a fourth down module 400 may include a Football recommender, a Field Goal algorithm, and a Punt algorithm. The Football recommender determines the probability of each potential play outcome associated with the Go For It coaching decision. The Field Goal algorithm determines the probability of each potential play outcome associated with the Field Goal coaching decision. The Punt algorithm 1102 determines the probability of each potential play outcome associated with the Punt coaching decision. As shown in FIG. 15B, the Football recommender 402 determines the probability of each potential play outcome associated with the Go For It coaching decision on a fourth down play. The Football recommender 402 receives an expected points (EP) input from the expected points module 300 at block 404, a yards to gain (YTG) for first down input at block 406, and a first down marker (FDM) yard line input at block 408. Preliminary Conversion Rate: At block 410, the Football recommender 402 uses the team's EP value from block 404 and the YTG distance from block 406 to determine a preliminary first down conversion rate based on historical conversion data. Historical first down conversion data is shown in the form of a chart in FIG. 5, where YTG distances are presented on the x-axis and average first down conversion rates are presented on the y-axis. This historical data shows that the likelihood of a first down conversion decreases as the YTG distance increases. Individual lines or equations may be presented to account for various EP values. For simplicity, FIG. 5 shows three lines to account for scenarios in which the offense and defense are an equal match with the same EP values (NEU), the offense has the advantage (OFF AD), and the defense has the advantage (DEF AD). The historical data presented in FIG. 5 shows that stronger offenses will convert first downs versus weaker defenses (OFF AD) more often than weaker offenses will convert first downs versus stronger defenses (DEF AD). Similar lines may be provided for specific EP values (e.g., 7-66 points). By determining the first down conversion rate at each YTG distance for each offensive match-up, the Football recommender 402 is able to predict the likelihood of a first down conversion with great precision.

Inside an opponent's 20-yard line (i.e., in the Red Zone), it becomes more difficult to convert for a first down as the space on the field from which to work becomes more limited. As the FDM gets closer to the end zone and the YTG distance increases, the challenge of converting a first down gets progressively more difficult versus similar scenarios outside of the Red Zone. To account for the challenge of converting a first down in the Red Zone, the Football recommender 402 may multiply the preliminary conversion rate by a field position multiplier at block 412 based on the YTG distance from block 406 and the FDM yard line from block 408 (where 100 represents the opponent's goal line. As an example, take a team that normally has a 50% fourth down conversion rate with 2 YTG. If the team faces a fourth down play with 2 YTG outside of the Red Zone, the conversion rate may remain at 50%. However, if the team faces a fourth down play with 2 YTG in the Red Zone, such as from the opponent's 2-yard line when the FDM is on the opponent's goal line (FDM=100), the normal 50% conversion rate may be multiplied by the corresponding field position multiplier of 85.5% to arrive at a lower adjusted conversion rate of 42.7%. The process may adjust team's first down conversion rate at block 412 based on particular strengths of his team. In one embodiment, the Football recommender 402 multiplies the conversion rate by one or more additional multipliers, such as a YTG multiplier, which may be specified by the coach. As an example, a team that thrives on running the football might find that it converts short-yardage situations particularly well, because its offense is designed to consistently grind out short gains. However, the same team may have particular difficulty in converting longer-yardage situations because the offense isn't conducive to big plays. In this example, the YTG multiplier may be greater than 100% below 5 YTG to increase the conversion rate in short-yardage situations and less than 100% above 5 YTG to decrease the conversion rate in long-yardage situations. Conversely, a team with an explosive offense may be particularly effective in converting long yardages but may not have the personnel to get short yardage. In this example, the YTG multiplier may be less than 100% below 5 YTG to decrease the conversion rate in short-yardage situations and greater than 100% above 5 YTG to increase the conversion rate in long-yardage situations. The Indianapolis Colts were a great example of this during much of the Peyton Manning era. They were very dangerous in long-yardage situations due to the quality of their passing game, but due to a poor running game, they often failed to convert in short-yardage scenarios. The Football recommender 402 may calculate the probability of a turnover and defensive touchdown as a function of the EP value from block 404 and the FDM yard line from block 408. This probability may be as low as about 0.1% and as high as about 0.5%. At block 414, the Football recommender 402 assigns probabilities to each potential conversion outcome. The Football recommender 402 may determine not only the likelihood of a first down conversion at block 412, but also how likely the team is to score points if the conversion is successful at block 416. After a successful conversion, the team can get just enough yards to get the first down and still not score any points on the drive, or it can score a touchdown on the very same play or a subsequent play of the same drive. Therefore, the Football recommender 402 may take into account the potential upside of the drive should the fourth down play be successful at any field position. At block 416, the Football recommender 402 uses the team's EP value from block 404 and the FDM yard line from block 408 to determine the points scored given conversion based on historical scoring data. Historical scoring data is shown in the form of a chart in FIG. 6, where FDM yard lines are presented on the x-axis (with 0 representing the team's own goal line and 100 representing the opponent's goal line) and average points scored given conversion are presented on the y-axis. This historical data shows that the likelihood of scoring points increases as the FDM approaches the opponent's goal line. Individual lines or equations may be presented to account for various EP values. For simplicity, FIG. 6 shows three lines to account for scenarios in which the offense and defense are an equal match with the same EP values (NEU), the offense has the advantage (OFF AD), and the defense has the advantage (DEF AD). The historical data presented in FIG. 6 shows that stronger offenses will score more points versus weaker defenses (OFF AD) than weaker offenses will score versus stronger defenses (DEF AD). Similar lines may be provided for specific EP values (e.g., 7-66 points). In this manner, the augmented reality system can enhance the game.

Recognition of Exercise Pattern and Tracking of Calorie Consumption

Figure 16A:
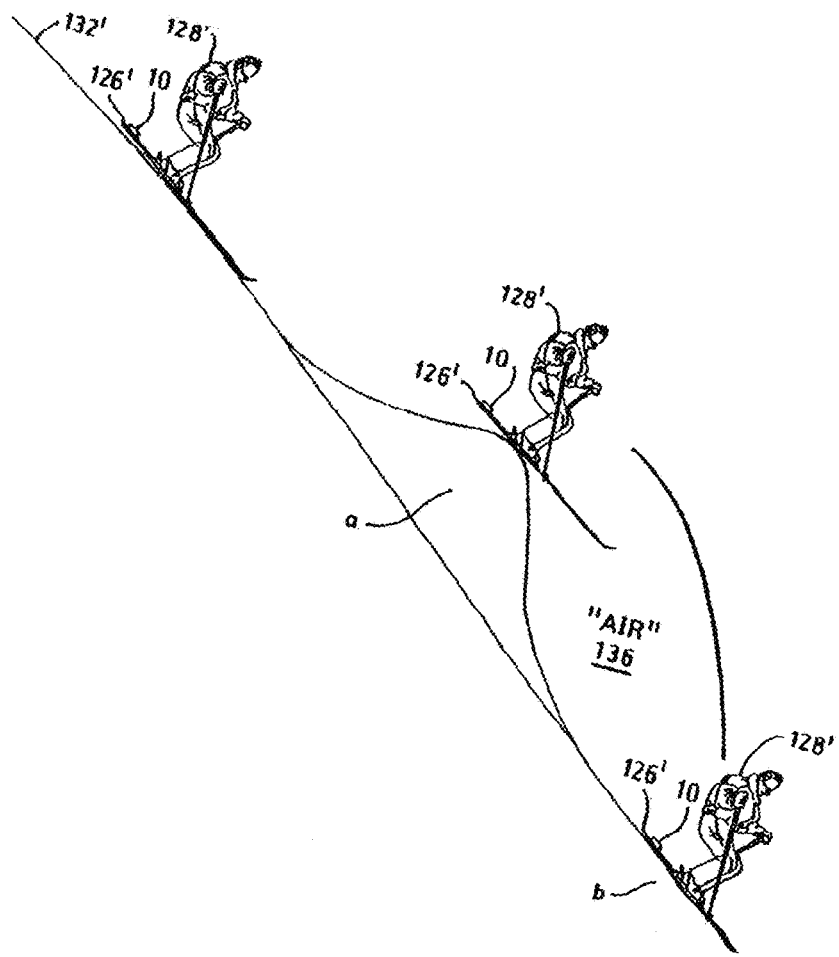

FIG. 16A illustrates the positions of a ski 126' and skier 128' during a lofting maneuver on the slope 132'. The ski 126' and skier 128' speed down the slope 132' and launch into the air 136 at position "a," and later land at position "b" in accord with the well-known Newtonian laws of physics. With an airtime sensor, described above, the unit 10 calculates and stores the total airtime that the ski 126' (and hence the skier 128') experiences between the positions "a" and "b" so that the skier 128' can access and assess the "air" time information. Airtime sensors such as the sensor 14 may be constructed with known components. Preferably, the sensor 14 incorporates either an accelerometer or a microphone. Alternatively, the sensor 14 may be constructed as a mechanical switch that detects the presence and absence of weight onto the switch. Other airtime sensors 14 will become apparent in the description which follows. The accelerometer senses vibration—particularly the vibration of a vehicle such as a ski or mountain bike—moving along a surface, e.g., a ski slope or mountain bike trail. This voltage output provides an acceleration spectrum over time; and information about airtime can be ascertained by performing calculations on that spectrum. Based on the information, the system can reconstruct the movement path, the height, the speed, among others and such movement data is used to identify the exercise pattern. For example, the skier may be interested in practicing mogul runs, and the system can identify foot movement and speed and height information and present the information post exercises as feedback. Alternatively, the system can make live recommendations to improve performance to the athlete.

Figure 16B:
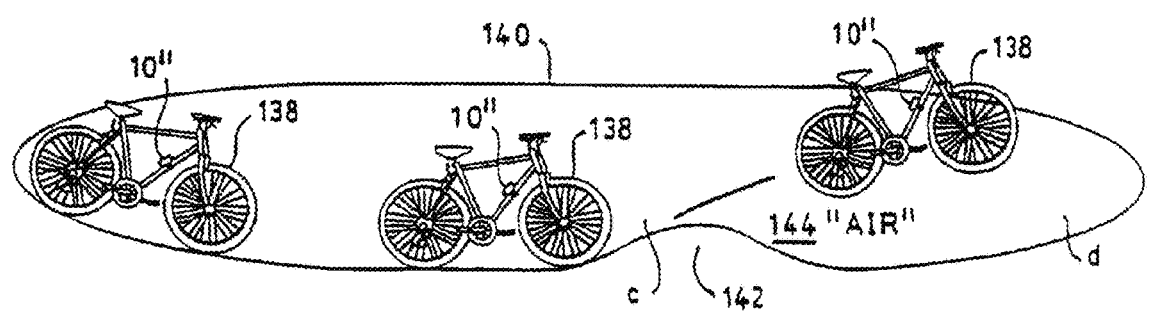
Figure 16C:
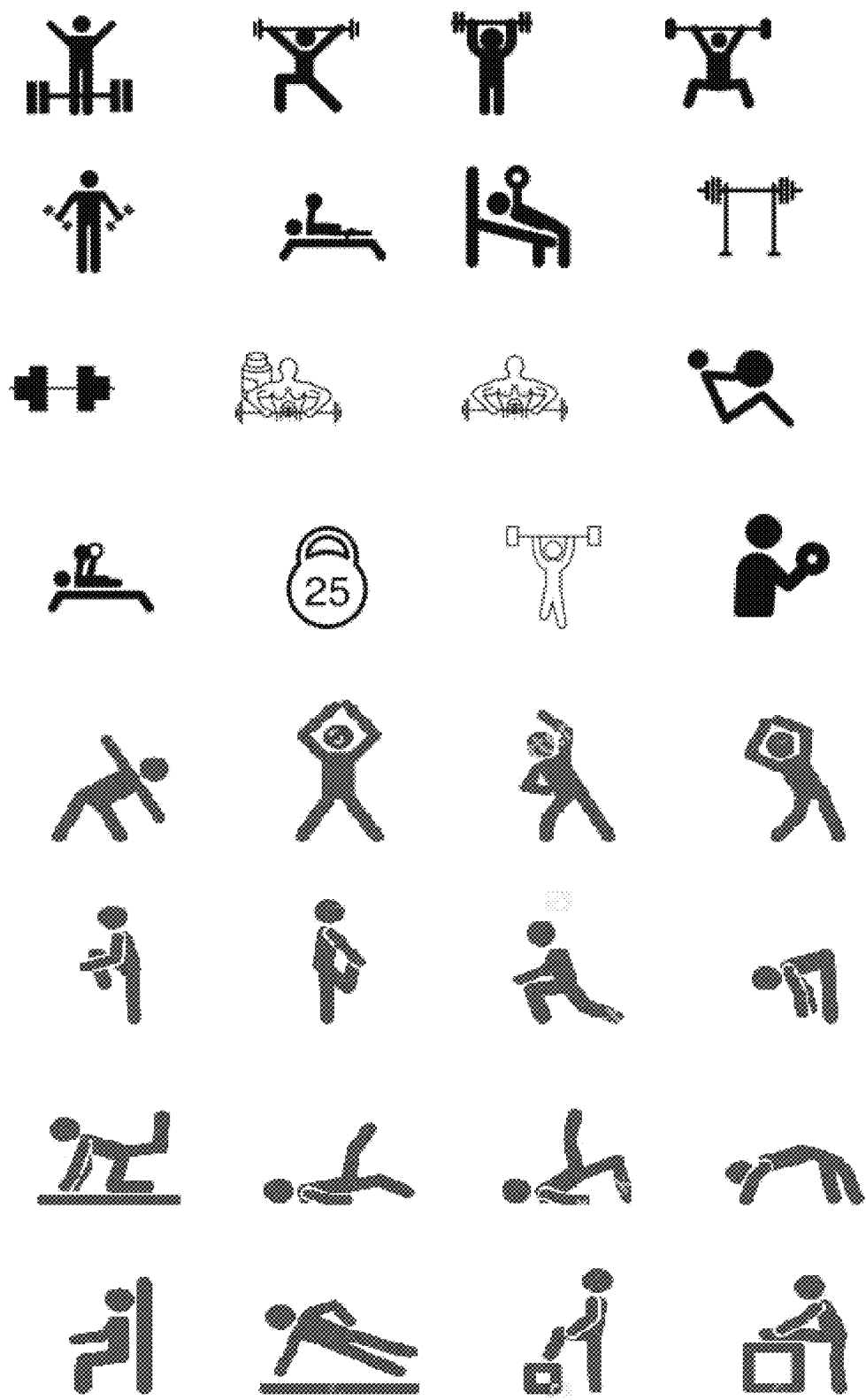

FIG. 16B illustrates a sensing unit 10" mounted onto a mountain bike 138. FIG. 16B also shows the mountain bike 138 in various positions during movement along a mountain bike race course 140 (for illustrative purposes, the bike 138 is shown without a rider). At one location "c" on the race course 140, the bike 138 hits a dirt mound 142 and catapults into the air 144. The bike 138 thereafter lands at location "d". As above, with speed and airtime sensors, the unit 10 provides information to a rider of the bike 138 about the speed attained during the ride around the race course 140; as well as information about the airtime between location "c" and "d". In this case, the system can recommend a cadence to be reached by the rider, strengthen of abdominals, back and arms, for example.

For golf exercise, It is beneficial to require the golfer to swing the golf club a plurality of times at each swing position to account for variations in each swing. The swing position at which the golf club is swung can be determined by analysis of the measured acceleration provided by the accelerometer, e.g., the time at which the acceleration changes. Data obtained during the training stage may be entered into a virtual table of swing positions and estimated carrying distances for a plurality of different swing positions and a plurality of different swings. A sample format for such a table is as follows, and includes the averaged carrying distance for each of four different swing positions. The swing analyzer provides a golfer with an excellent estimation of the carrying distance of a golf ball for a golf club swing at a specific swing position because it has been trained on actual swings by the golfer of the same club and conversion of information about these swings into estimated carrying distances. The golfer can improve their golf game since they can better select a club to use to hit a golf club for different situations during a round of golf. Also, the swing pattern is used to identify each club path responsible for the curve of any shot and this information is used to improve the golfer. The direction of the club path relative to the target, out-to-in (fade pattern) or in-to-out (draw pattern), is what I refer to as a players swing pattern. Players that swing from in-to-out will tend to hit draws and players that swing from out-to-in will tend to hit fades. Where the ball is struck on the face of the driver (strike point) can drastically alter the effect of a players swing pattern on ball flight. Thus, the camera detects where the ball is struck, and a computer physics model of ball behavior is presented to the golfer to improve the score. Shots struck off the heel will tend to fade more or draw less and shots struck off the toe will tend to draw more or fade less. Thus, camera images of the shots struck of heel or toe can also be used to provide pattern recognition/prediction and for training purposes.

For tennis, examples of motions determined for improvement are detailed next. The system can detect if the continental grip is achieved. Throwing Action pattern is also detected, as the tennis serve is an upwards throwing action that would deliver the ball into the air if it were a baseball pitch. Ball Toss improvements can be determined when the player lines the straight arm up with the net post and release the ball when your hand reaches eye level. The system checks the forward direction so the player can drive weight (and built up momentum) forward into the ball and into the direction of the serve.

The sensors can work with a soccer training module with kinematics of ball control, dribbling, passing, crossing, shooting, heading, volleying, taking throw-ins, penalties, corner kicks and free kicks, tackling, marking, juggling, receiving, shielding, clearing, and goalkeeping. The sensors can work with a basketball training module with kinematics of crossover dribble, behind back, pull back dribble, low dribble, basic dribble, between legs dribble, Overhead Pass, Chest Pass, Push Pass, Baseball Pass, Off-the-Dribble Pass, Bounce Pass, Jump Shot, Dunk, Free throw, Layup, Three-Point Shot, Hook Shot.

The sensors can work with a baseball training module with kinematics of Hitting, Bunting, Base Running and Stealing, Sliding, Throwing, Fielding Ground Balls, Fielding Fly Balls, Double Plays and Relays, Pitching and Catching, Changing Speeds, Holding Runners, Pitching and Pitcher Fielding Plays, Catching and Catcher Fielding Plays.

Figure 16D:
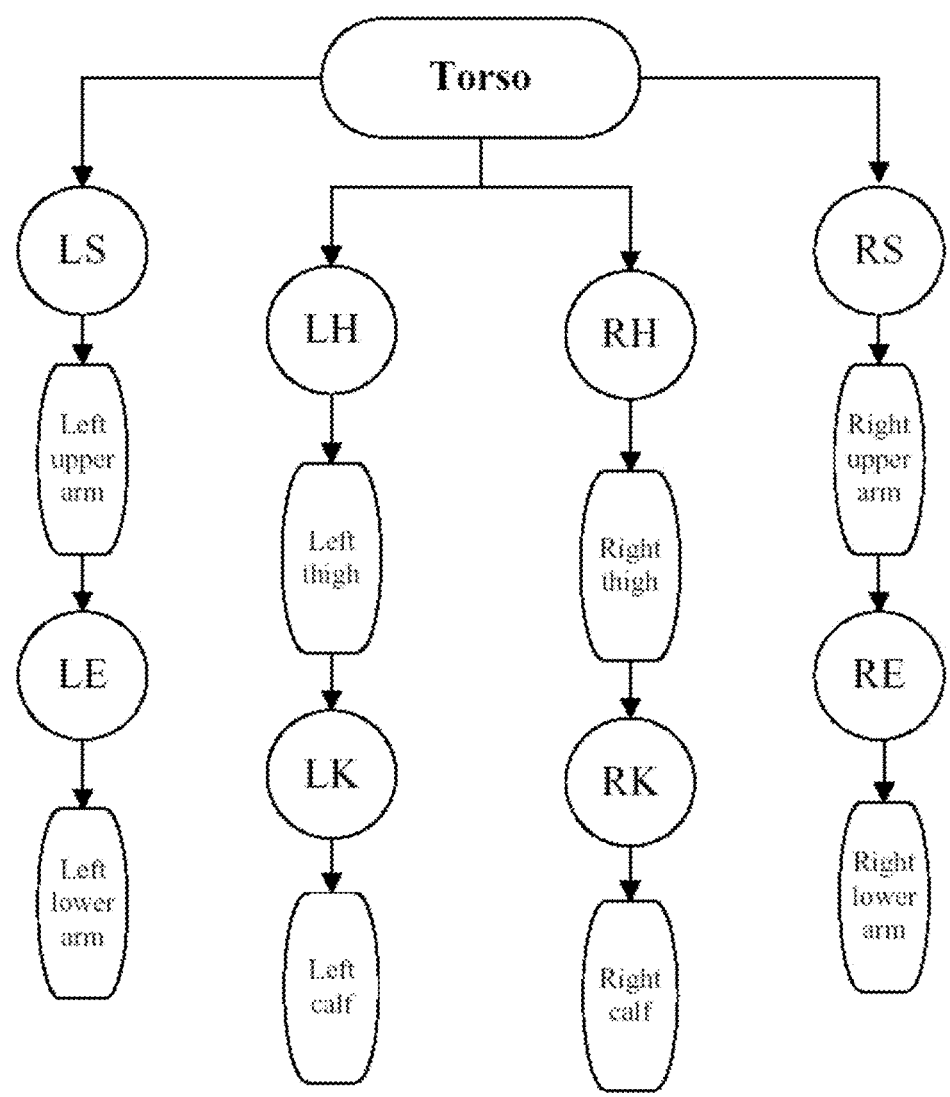
FIG. 16D shows a kinematic modeling for detecting exercise motion which in turn allows precision coaching suggestions.

For weight training, the sensor can be in gloves as detailed above, or can be embedded inside the weight itself, or can be in a smart watch, for example. The user would enter an app indicating that the user is doing weight exercises and the weight is identified as a dumbbell, a curl bar, and a bar bell. Based on the arm or leg motion, the system automatically detects the type of weight exercise being done. In one embodiment shown in FIG. 15C, with motion patterns captured by glove and sock sensors, the system can automatically detect the following exemplary exercise:

Upper Body:
Chest: Barbell Bench Presses, Barbell Incline Presses, Dumbbell Bench Presses, Dumbbell Incline Presses, Dumbbell Flyes, Cable Crossovers
Back: Pull-Ups, Wide-Grip Lat Pulldowns, One-Arm Dumbbell Rows, Seated Cable Rows, Back Extensions, Straight Arm Pulldowns
Shoulders: Seated Dumbbell Presses, Front Raises, Lateral Raises, Reverse Flyes, Upright Cable Rows, Upright Barbell Rows
Biceps: Alternate Dumbbell Curls, Barbell Curls, Preacher Curls, Concentration Curls, Cable Curls, Hammer Curls
Triceps: Seated Triceps Presses, Lying Triceps Presses, Triceps Kickbacks, Triceps Pushdowns, Cable Extensions, Bench Dips Lower Body
Quadriceps: Barbell Squats, Leg Presses, Leg Extensions
Hamstrings: Dumbbell Lunges, Straight-Leg Deadlifts, Lying Leg Curls
Calves: Seated Calf Raises, Standing Heel Raises
Abs: Floor Crunches, Oblique Floor Crunches, Decline Crunches, Decline Oblique, Hanging Knee Raises, Reverse Crunches, Cable Crunches, Cable Oblique Crunches In one implementation in FIG. 16D, an HMM is used to track weightlifting motor skills or sport enthusiast movement patterns. Human movement involves a periodic motion of the legs. Regular walking involves the coordination of motion at the hip, knee and ankle, which consist of complex joints. The muscular groups attached at various locations along the skeletal structure often have multiple functions. The majority of energy expended during walking is for vertical motion of the body. When a body is in contact with the ground, the downward force due to gravity is reflected back to the body as a reaction to the force. When a person stands still, this ground reaction force is equal to the person's weight multiplied by gravitational acceleration. Forces can act in other directions. For example, when we walk, we also produce friction forces on the ground. When the foot hits the ground at a heel strike, the friction between the heel and the ground causes a friction force in the horizontal plane to act backwards against the foot. This force therefore causes a breaking action on the body and slows it down. Not only do people accelerate and brake while walking, they also climb and dive. Since reaction force is mass times acceleration, any such acceleration of the body will be reflected in a reaction when at least one foot is on the ground. An upwards acceleration will be reflected in an increase in the vertical load recorded, while a downwards acceleration will be reduce the effective body weight. Zigbee wireless sensors with tri-axial accelerometers are mounted to the sport enthusiast on different body locations for recording, for example the tree structure as shown in FIG. 16D. As shown therein, sensors can be placed on the four branches of the links connect to the root node (torso) with the connected joint, left shoulder (LS), right shoulder (RS), left hip (LH), and right hip (RH). Furthermore, the left elbow (LE), right elbow (RE), left knee (LK), and right knee (RK) connect the upper and the lower extremities. The wireless monitoring devices can also be placed on upper back body near the neck, mid back near the waist, and at the front of the right leg near the ankle, among others.

The sequence of human motions can be classified into several groups of similar postures and represented by mathematical models called model-states. A model-state contains the extracted features of body signatures and other associated characteristics of body signatures. Moreover, a posture graph is used to depict the inter-relationships among all the model-states, defined as PG(ND,LK), where ND is a finite set of nodes and LK is a set of directional connections between every two nodes. The directional connection links are called posture links. Each node represents one model-state, and each link indicates a transition between two model-states. In the posture graph, each node may have posture links pointing to itself or the other nodes.

In the pre-processing phase, the system obtains the human body profile and the body signatures to produce feature vectors. In the model construction phase, the system generate a posture graph, examine features from body signatures to construct the model parameters of HMM, and analyze human body contours to generate the model parameters of ASMs. In the motion analysis phase, the system uses features extracted from the body signature sequence and then applies the pre-trained HMM to find the posture transition path, which can be used to recognize the motion type. Then, a motion characteristic curve generation procedure computes the motion parameters and produces the motion characteristic curves. These motion parameters and curves are stored over time, and if differences for the motion parameters and curves over time is detected, the system then runs the sport enthusiast through additional tests to confirm the detected motion.

In one exemplary process for determining exercise in the left or right half of the body, the process compares historical left shoulder (LS) strength against current LS strength (3200). The process also compares historical right shoulder (RS) strength against current RS strength (3202). The process can compare historical left hip (LH) strength against current LH strength (3204). The process can also compare historical right hip (RH) strength against current RH strength (3206). If the variance between historical and current strength exceeds threshold, the process generates warnings (3208). Furthermore, similar comparisons can be made for sensors attached to the left elbow (LE), right elbow (RE), left knee (LK), and right knee (RK) connect the upper and the lower extremities, among others.

The system can ask the sport enthusiast to squeeze a strength gauge, piezoelectric sensor, or force sensor to determine force applied during squeeze. The user holds the sensor or otherwise engages the sensor. The user then applies and holds a force (e.g., compression, torque, etc.) to the sensor, which starts a timer clock and triggers a sampling start indicator to notify the user to continue to apply (maximum) force to the sensor. Strength measurements are then sampled periodically during the sampling period until the expiration of time. From the sampled strength data, certain strength measurement values are selected, such as the maximum value, average value(s), or values obtained during the sampling period. The user can test both hands at the same time, or alternatively he may test one hand at a time. A similar approach is used to sense leg strength, except that the user is asked to pushed down on a scale to determine the foot force generated by the user.

In one embodiment, exercise motion data acquired by the accelerometer or multi-axis force sensor is analyzed, as will be discussed below, in order to determine the motion of each exercise stroke during the exercise session (i.e., horizontal vertical or circular). In another embodiment for detecting exercise motion using accelerometer, the first minimum discovered during the scanning is noted as the first xmin and considered to be the start of the first brushstroke. The first maximum x value following the first minimum x value is located and construed to be the middle of the first exercise stroke (where exercise motion changes from one direction to the other). The next xmin value indicates the end of the first brushstroke and the beginning of the next brushstroke. The computer records the data for each brushstroke and continues on through the data to find the next brushstroke, recording each successive motion in memory. For the first brushstroke, the maximum and minimum values of the x coordinate (xmax and xmin) are determined. The Y-direction lengths, Ly1 and Ly2, between the data points just before and just after each of xmax and xmin (xmax+1, xmax−1, and Xmin+1, xmin−1) are then determined. The length Lx along the x axis, between xmax and xmin, is also determined. Next, if Lx is less than 2 and either Ly1 or Ly2 is greater than one, then the motion is construed to be vertical. If Ly1 and Ly2 are both less than one, then the motion is construed to be horizontal. Otherwise, the motion is construed to be circular.

Data obtained from the gyroscope, if one is used, typically does not require a complex analysis. To determine which side of the mouth is being brushed at a particular time, the gyroscope data is scanned to determine when the rotational orientation is greater than 180 degrees, indicating the left side, and when it is less than 180 degrees, indicating the right side. As explained above, top and bottom and gum brushing information can also be obtained, without any calculations, simply by examining the data. The time sequence of data that is acquired during exercise and analyzed as discussed above can be used in a wide variety of ways.

In one embodiment, the accelerometers distinguish between lying down and each upright position of sitting and standing based on the continuous output of the 3D accelerometer. The system can detect (a) extended time in a single position; (b) extended time sitting in a slouching posture (kyphosis) as opposed to sitting in an erect posture (lordosis); and (c) repetitive stressful movements, such as may be found on some manufacturing lines, while typing for an extended period of time without proper wrist support, or while working all day at a weight lifting exercise, among others. In one alternative embodiment, angular position sensors, one on each side of the hip joint, can be used to distinguish lying down, sitting, and standing positions. In another embodiment, the system repeatedly records position and/or posture data over time. In one embodiment, magnetometers can be attached to a thigh and the torso to provide absolute rotational position about an axis coincident with Earth's gravity vector (compass heading, or yaw). In another embodiment, the rotational position can be determined through the in-door positioning system as discussed above.

To improve a golf swing, the complex motion of the body first starts with the stance. The system checks that the golfer has a low center of gravity to remain balanced throughout the swing path. The swing starts with the arms moving back in a straight line. When the club head reaches the level of the hip, two things happen: there is a stern wrist cock that acts as a hinge along with the left knee (for a right handed swing), building up its torque by moving into the same line as the belly button before the start of the upswing. As the swing continues to the top of the backswing (again for right handed golf swing), the golfer's left arm should be perfectly straight and his right arm should be hinged at the elbow. The downswing begins with the hips and the lower body rather than the arms and upper body, with emphasis on the wrist cock. As the golfer's hips turn into the shot, the right elbow will drop straight down, hugging the right side of the golfer's torso. As the right elbow drops, the wrists begin to snap through from the wrist cock in the backswing. A solid extension of the arms and good transfer of body should put the golfer leaning up on his right toe, balanced, with the golf club resting on the back of the golfers neck. Importantly, all of the movements occur with precise timing, while the head remains completely still with eyes focused on the ball throughout the entire swing.

The system can identify illnesses and prevent overexertion leading to illnesses such as a stroke. Depending on the severity of the stroke, sport enthusiasts can experience a loss of consciousness, cognitive deficits, speech dysfunction, limb weakness, hemiplegia, vertigo, diplopia, lower cranial nerve dysfunction, gaze deviation, ataxia, hemianopia, and aphasia, among others. Four classic syndromes that are characteristically caused by lacunar-type stroke are: pure motor hemiparesis, pure sensory syndrome, ataxic hemiparesis syndrome, and clumsy-hand dysarthria syndrome. Sport enthusiasts with pure motor hemiparesis present with face, arm, and leg weakness. This condition usually affects the extremities equally, but in some cases it affects one extremity more than the other. The most common stroke location in affected sport enthusiasts is the posterior limb of the internal capsule, which carries the descending corticospinal and corticobulbar fibers. Other stroke locations include the pons, midbrain, and medulla. Pure sensory syndrome is characterized by hemibody sensory symptoms that involve the face, arm, leg, and trunk. It is usually the result of an infarct in the thalamus. Ataxic hemiparesis syndrome features a combination of cerebellar and motor symptoms on the same side of the body. The leg is typically more affected than the arm. This syndrome can occur as a result of a stroke in the pons, the internal capsule, or the midbrain, or in the anterior cerebral artery distribution. Sport enthusiasts with clumsy-hand dysarthria syndrome experience unilateral hand weakness and dysarthria. The dysarthria is often severe, whereas the hand involvement is more subtle, and sport enthusiasts may describe their hand movements as "awkward." This syndrome is usually caused by an infarct in the pons. Different patterns of signs can provide clues as to both the location and the mechanism of a particular stroke. The system can detect symptoms suggestive of a brainstem stroke include vertigo, diplopia, bilateral abnormalities, lower cranial nerve dysfunction, gaze deviation (toward the side of weakness), and ataxia. Indications of higher cortical dysfunction-such as neglect, hemianopsia, aphasia, and gaze preference (opposite the side of weakness)-suggest hemispheric dysfunction with involvement of a superficial territory from an atherothrombotic or embolic occlusion of a mainstem vessel or peripheral branch.

To detect muscle weakness or numbness, in one embodiment, the system applies a pattern recognizer such as a neural network or a Hidden Markov Model (HMM) to analyze accelerometer output. In another embodiment, electromyography (EMG) is used to detect muscle weakness. In another embodiment, EMG and a pattern analyzer is used to detect muscle weakness. In yet another embodiment, a pattern analyzer analyzes both accelerometer and EMG data to determine muscle weakness. In a further embodiment, historical ambulatory information (time and place) is used to further detect changes in muscle strength. In yet other embodiments, accelerometer data is used to confirm that the sport enthusiast is at rest so that EMG data can be accurately captured or to compensate for motion artifacts in the EMG data in accordance with a linear or non-linear compensation table. In yet another embodiment, the EMG data is used to detect muscle fatigue and to generate a warning to the sport enthusiast to get to a resting place or a notification to a nurse or caregiver to render timely assistance. The amplitude of the EMG signal is stochastic (random) in nature and can be reasonably represented by a Gaussian distribution function. The amplitude of the signal can range from 0 to 10 mV (peak-to-peak) or 0 to 1.5 mV (rms). The usable energy of the signal is limited to the 0 to 500 Hz frequency range, with the dominant energy being in the 50-150 Hz range. Usable signals are those with energy above the electrical noise level. The dominant concern for the ambient noise arises from the 60 Hz (or 50 Hz) radiation from power sources. The ambient noise signal may have an amplitude that is one to three orders of magnitude greater than the EMG signal. There are two main sources of motion artifact: one from the interface between the detection surface of the electrode and the skin, the other from movement of the cable connecting the electrode to the amplifier. The electrical signals of both noise sources have most of their energy in the frequency range from 0 to 20 Hz and can be reduced.

In one embodiment, the camera captures facial expression and a code such as the Microsoft Emotion API takes a facial expression in an image as an input, and returns the confidence across a set of emotions for each face in the image, as well as bounding box for the face, using the Face API. The emotions detected are anger, contempt, disgust, fear, happiness, neutral, sadness, and surprise. These emotions are understood to be cross-culturally and universally communicated with particular facial expressions. Alternatively, a marker for emotional arousal is galvanic skin response (GSR), also referred to as skin conductance (SC) or electrodermal activity (EDA). EDA modulates the amount of sweat secretion from sweat glands. The amount of sweat glands varies across the human body, being highest in hand and foot regions (200-600 sweat glands per cm2). While sweat secretion plays a major role for thermoregulation and sensory discrimination, changes in skin conductance in hand and foot regions are also triggered quite impressively by emotional stimulation: the higher the arousal, the higher the skin conductance. It is noteworthy to mention that both positive ("happy" or "joyful") and negative ("threatening" or "saddening") stimuli can result in an increase in arousal—and in an increase in skin conductance. Skin conductance is not under conscious control. Instead, it is modulated autonomously by sympathetic activity which drives human behavior, cognitive and emotional states on a subconscious level. Skin conductance therefore offers direct insights into autonomous emotional regulation. It can be used as alternative to self-reflective test procedures, or—even better—as additional source of insight to validate verbal self-reports or interviews of a respondent. Based on the detected emotion, the exercise can be increased, decreased, or stopped altogether.

Data from multiple exercise sessions may be collected and used to compile a history of the user's habits over an extended period of time, enabling the user's trainer to better understand user compliance issues. The trainer can review the data with the user and view the animations of the user's exercise sessions during an office visit, allowing the trainer to better instruct the user in proper brushing technique. The trainer can also review the patient's brushing history over time, to determine whether the patient's exercise technique is improving.

The sensor can be integrated into objects already associated with the sporting activity. In one aspect, the sensing unit is integrated into the ski boot or other boot. In another aspect, the sensing unit is integrated into the binding for a ski boot or snowboarder boot. In still another aspect, the sensing unit is integrated into a ski, snowboard, mountain bike, windsurfer, windsurfer mast, roller blade boot, skate-board, kayak, or other sport vehicle. Collectively, the sport objects such as the ski boot and the variety of sport vehicles are denoted as "sport implements". Accordingly, when the sensing unit is not "stand alone", the housing which integrates the controller subsystem with one or more sensors and battery can be made from the material of the associated sport implement, in whole or in part, such that the sensing unit becomes integral with the sport implement.

The data can be stored as part of a blockchain secured data distribution. Blockchain distribution can provide benefits in a heterogeneous device environment, facilitate ad hoc device synchronization, and embody a distributed patch and communications network. Devices can receive a blockchain block from another device and, in some embodiments, enable other devices to access the block from the device. In some embodiments, devices can discard irrelevant blocks, however, an entire blockchain can be reconstructed where partial blockchains can be received from more than one device. Additionally, checkpoint blocks can enable devices to navigate the blockchain efficiently by skipping over known irrelevant blocks.

To secure data distribution, the device's operation includes one or more of:

receiving a blockchain block comprising an identifier and a payload, wherein the identifier is associated with determining a relevancy of the payload to a device; and in response to determining that the identifier satisfies a rule related to a characteristic of the device, employing the payload by the device.

storing a portion of a blockchain comprising the blockchain block at the device; and facilitating access to the blockchain block by another device.

portion of the blockchain is all of the blockchain.

payload can include code to alter code in the device.

rule relates to a brand, type, class, series, or model of the device.

rule relates to a version of software or firmware of the device.

employing the payload by the device causes the device to access another blockchain block.

verifying a transaction between a first party and a second party using a blockchain, further including initiating a transaction regarding a transfer of electronic content from the first party to the second party; compiling, by the first party, a body of electronic information regarding the electronic content into an package; submitting, by the first party, the package to a blockchain node; validating, by the blockchain node, the transaction; and adding, by the blockchain node, details of the transaction to a pending block of the blockchain.

processing a pending block and appending information to a prior blockchain, wherein the processing is performed after an elapse of a predetermined time interval.

compiling includes encrypting the envelope, the body of electronic information, and a key.

validating includes a utilization of a public key of the first party.

propagating, by the blockchain node, details of the validated transaction to the blockchain.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments. Although embodiments of the present inventions have been described in detail, it should be understood that the various changes, substitutions, and alterations can be made hereto without departing from the spirit and scope of the invention.

What is claimed is:

1. A system comprising:
    a sensor comprising a sensor processor and sensor memory, the second memory storing executable instructions that when executed by the sensor processor causes the sensor processor to perform the steps of:
    monitoring an asset over a network;
    receiving a request to access the asset from a second computer, wherein the request comprises a blockchain address of the second computer;
    generating a message comprising the second computer blockchain address, a location and blockchain address of the sensor processor and sensor memory and,
    transmitting the message to a first computer;
    the first computer comprising a first processor and first memory, the first memory storing executable instructions that when executed by the first processor causes the first processor to perform the steps of:
    storing a smart contract wherein the smart contract comprises a code and acceptance qualifications;
    evaluating the message by comparing the second processor blockchain address, the location and blockchain address of the sensor processor and sensor memory to the acceptance qualifications, and
    based on the evaluation, transmitting an authorization to the second computer, wherein the authorization comprises the code;
    the second computer comprising a second processor and second memory, the second memory storing executable instructions that when executed by the second processor causes the second processor to perform the steps of: receiving the authorization and accessing the asset using the code.

2. The device of claim 1, wherein the first or second memory stores additional instructions that, when executed by the processor, causes the processor to perform the step of access the blockchain for a text or term of a unilateral contract requiring at least a partial performance of the text or term.

3. The device of claim 1, wherein the first or second memory stores additional instructions that, when executed by the processor, causes the processor to access a side chain or a second blockchain.

4. The device of claim 1, wherein the first or second memory stores additional instructions that, when executed by the processor, causes the processor to hedge the electronic contract with one or more of: equity, debts, derivatives, synthetics, notes, stocks, preferred shares, bonds, debentures, options, futures, swaps, rights, warrants, commodities, or currencies.

5. The device of claim 1, wherein the first or second memory stores additional instructions that, when executed by the processor, causes the processor to receive from the second processor a manifestation of intent for a contract and assents to the contract.

6. The device of claim 1, wherein the first or second memory stores additional instructions that, when executed by the processor accepts from the second processor an advertisement with a quantity and recipient, a production contract, an output contract, or a requirement contract.

7. The device of claim 1, wherein the first or second memory stores additional instructions that, when executed by the processor revokes or cancels the contract upon receiving a revocation from an offeror.

8. The device of claim 1, wherein the first or second memory stores additional instructions that, when executed by the processor checks for compliance with Uniform Commercial Code.

9. The device of claim 1, wherein the first or second memory stores additional instructions that, when executed by the processor accepts or rejects a counter-offer if the other machine is not a software agent for a merchant.

10. The device of claim 1, wherein the first or second memory stores additional instructions that, when executed by the processor causes the processor to assigns the contract to the second processor.

11. The device of claim 1, wherein the first or second memory stores additional instructions that, when executed by the processor stores a unilateral contract with a second machine and requests payment from the second machine based on the unilateral contract.

12. The device of claim 1, wherein the first or second memory stores additional instructions that, when executed by the processor processes an option to extend time to respond to a predetermined time.

13. The device of claim 12, wherein the first or second stores additional instructions that, when executed by the processor, processes the option without payment if the other machine is a merchant agent and otherwise receives payment to bind the option.

14. The device of claim 1, wherein the first or second memory stores additional instructions that, when executed by the processor, comprises data for a real estate transaction or a rental transaction.

15. The device of claim 1, wherein the first or second memory stores data for a sport event or fitness event.

16. The device of claim 1, wherein the first or second memory stores data for a health transaction or medical transaction.

17. The device of claim 1, wherein the first or second memory stores data for gaming transfer, gambling transfer, betting transfer, auction transfer, or money transfer.

18. A method, comprising:
  storing, by a first processor, a smart contract wherein the smart contract comprises a code and acceptance qualifications;
  monitoring, by a sensor, an asset over a network;
  receiving, by the sensor, a request to access the asset from a second processor, wherein the request comprises a blockchain address of the second processor;
  generating, by the sensor, a message comprising the second processor blockchain address, a location of the sensor, and a blockchain address of the sensor;
  transmitting, by the sensor, the message to the first processor;
  evaluating, by the first processor, the message by comparing the second processor blockchain address, the location of the sensor, and the sensor blockchain address to the acceptance qualifications;
  based on the evaluation, transmitting, by the first processor, an authorization to the second processor, wherein the authorization comprises the code; and,
  receiving, by the second processor, the authorization and accessing, by the second processor, the asset using the code.

\* \* \* \* \*